United States Patent
Muto et al.

(10) Patent No.: US 8,097,759 B2
(45) Date of Patent: Jan. 17, 2012

(54) INFLAMMATORY CYTOKINE RELEASE INHIBITOR

(75) Inventors: Susumu Muto, Tokyo (JP); Tatsuo Nagano, Tokyo (JP); Tomomi Sotome, Tokyo (JP); Akiko Itai, Tokyo (JP)

(73) Assignee: Institute of Medicinal Molecular Design, Inc., Tokyo (JP)

( * ) Notice: Subject to any disclaimer, the term of this patent is extended or adjusted under 35 U.S.C. 154(b) by 0 days.

(21) Appl. No.: 12/830,018

(22) Filed: Jul. 2, 2010

(65) Prior Publication Data

US 2010/0274051 A1   Oct. 28, 2010

Related U.S. Application Data

(60) Continuation of application No. 11/835,978, filed on Aug. 8, 2007, now abandoned, which is a division of application No. 10/433,619, filed as application No. PCT/JP01/11084 on Dec. 18, 2001.

(30) Foreign Application Priority Data

Dec. 18, 2000 (JP) .................. 2000-383202

(51) Int. Cl.
*C07C 233/64* (2006.01)
*A61K 31/166* (2006.01)

(52) U.S. Cl. ........................ 564/179; 514/622

(58) Field of Classification Search ................... None
See application file for complete search history.

(56) References Cited

U.S. PATENT DOCUMENTS

| | | | |
|---|---|---|---|
| 3,331,874 A * | 7/1967 | Stecker | 564/214 |
| 3,332,996 A * | 7/1967 | Troshen et al. | 564/166 |
| 3,382,145 A | 5/1968 | Chupp et al. | |
| 3,419,585 A * | 12/1968 | Early et al. | 564/174 |
| 3,681,458 A | 8/1972 | Ruschig et al. | |
| 3,823,236 A | 7/1974 | Buchel et al. | |
| 3,906,023 A | 9/1975 | Buchel et al. | |
| 3,906,034 A | 9/1975 | Franz et al. | |
| 4,287,191 A | 9/1981 | Coburn et al. | |
| 4,358,443 A | 11/1982 | Coburn et al. | |
| 4,560,549 A | 12/1985 | Ritchey | |
| 4,659,710 A | 4/1987 | Sato et al. | |
| 4,659,738 A * | 4/1987 | Miller et al. | 514/514 |
| 4,661,630 A | 4/1987 | Harigaya et al. | |
| 4,690,924 A | 9/1987 | Sato et al. | |
| 4,725,590 A | 2/1988 | Ritchey | |
| 4,742,083 A | 5/1988 | Ritchey | |
| 4,786,644 A | 11/1988 | Glamkowski et al. | |
| 4,939,133 A | 7/1990 | Connor et al. | |
| 4,952,588 A | 8/1990 | Glamkowski et al. | |
| 4,966,906 A | 10/1990 | Glamkowski et al. | |
| 5,126,341 A | 6/1992 | Suzuki et al. | |
| 5,589,514 A | 12/1996 | Naik et al. | |
| 5,776,977 A | 7/1998 | Naik et al. | |
| 5,905,090 A | 5/1999 | Bertolini et al. | |
| 5,958,911 A | 9/1999 | Evans et al. | |
| 6,022,884 A | 2/2000 | Mantlo et al. | |
| 6,117,859 A | 9/2000 | Evans et al. | |
| 6,159,988 A | 12/2000 | Naik et al. | |
| 6,174,887 B1 | 1/2001 | Haruta et al. | |
| 6,225,329 B1 | 5/2001 | Richter et al. | |
| 6,262,044 B1 | 7/2001 | Møller et al. | |
| 6,410,586 B1 | 6/2002 | Møller et al. | |
| 6,414,013 B1 | 7/2002 | Fancelli et al. | |
| 6,465,455 B1 | 10/2002 | Brown et al. | |
| 6,492,425 B1 | 12/2002 | Callahan et al. | |
| 6,566,394 B1 | 5/2003 | Takeuchi et al. | |
| 6,653,309 B1 | 11/2003 | Saunders et al. | |
| 6,787,652 B1 | 9/2004 | Dow et al. | |
| 6,815,384 B2 | 11/2004 | Ishikawa | |
| 7,626,042 B2 | 12/2009 | Muto et al. | |
| 2002/0002199 A1 | 1/2002 | Jeppesen et al. | |
| 2002/0019412 A1 | 2/2002 | Andersen et al. | |
| 2002/0165398 A1 | 11/2002 | Jeppesen et al. | |
| 2003/0069267 A1 | 4/2003 | Moller et al. | |
| 2003/0083386 A1 | 5/2003 | Yuan et al. | |
| 2004/0048891 A1 | 3/2004 | Kato et al. | |
| 2004/0087650 A1 | 5/2004 | Saunders et al. | |
| 2004/0122244 A1 | 6/2004 | Suzuki et al. | |

(Continued)

FOREIGN PATENT DOCUMENTS

DE    1 017 606    10/1957

(Continued)

OTHER PUBLICATIONS

Jackson et al., "IMP Dehydrogenase, An Enzyme Linked with Proliferation and Malignancy" *Nature* vol. 256, pp. 331-333, 1975.

Pankiewicz et al., "The Practical Synthesis of a Methylenebisphosphonate Analogue of Benzamide Adenine Dinucleotide: Inhibition of Human Inosine Monophosphate Dehydrogenase (Type I and II)" *J. Med. Chem.* vol. 40, pp. 1287-1291, 1997.

Yamada et al., "IMP Dehydrogenase: Inhibition by the Anti-Leukemic Drug, Tiazofurin" *Leukemia Research* vol. 13, No. 2, pp. 179-184, 1989.

English language translation of FR 2088225, published Jan. 7, 1972.

Aisen, "Journal of Pain and Symptom Management," 2002, vol. 23, No. 4, p. S35-40.

(Continued)

*Primary Examiner* — Brian J Davis
(74) *Attorney, Agent, or Firm* — Greenblum & Bernstein, P.L.C.

(57) ABSTRACT

A medicament having inhibitory activity against NF-κB activation, which comprises a compound represented by the following general formula (I) or a pharmacologically acceptable salt as an active ingredient:

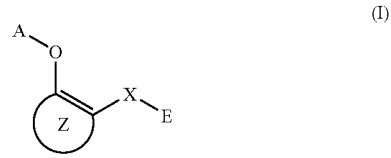

(I)

wherein X represents a connecting group, A represents hydrogen atom or acetyl group, E represents an aryl group or a heteroaryl group, and ring X represents an arene or a heteroarene.

3 Claims, No Drawings

U.S. PATENT DOCUMENTS

| | | | |
|---|---|---|---|
| 2004/0157844 A1 | 8/2004 | Dow et al. |
| 2004/0259877 A1 | 12/2004 | Muto et al. |
| 2006/0014811 A1 | 1/2006 | Muto et al. |
| 2006/0019958 A1 | 1/2006 | Muto et al. |
| 2006/0035944 A1 | 2/2006 | Muto et al. |
| 2006/0089395 A1 | 4/2006 | Muto et al. |
| 2006/0100257 A1 | 5/2006 | Muto et al. |
| 2006/0111409 A1 | 5/2006 | Muto et al. |
| 2006/0122243 A1 | 6/2006 | Muto et al. |
| 2007/0042997 A1 | 2/2007 | Itai et al. |
| 2007/0185110 A1 | 8/2007 | Muto et al. |
| 2008/0090779 A1 | 4/2008 | Muto et al. |
| 2008/0249071 A1 | 10/2008 | Muto et al. |
| 2008/0311074 A1 | 12/2008 | Muto et al. |
| 2008/0318956 A1 | 12/2008 | Muto et al. |
| 2010/0113770 A1 | 5/2010 | Muto et al. |
| 2010/0274051 A1 | 10/2010 | Muto et al. |

FOREIGN PATENT DOCUMENTS

| | | |
|---|---|---|
| DE | 996074 | 6/1965 |
| EP | 0 081 782 | 6/1983 |
| EP | 0198456 | 10/1986 |
| EP | 0221211 | 5/1987 |
| EP | 0221346 | 5/1987 |
| EP | 0317991 | 5/1989 |
| EP | 0452873 | 10/1991 |
| EP | 0483881 | 5/1992 |
| EP | 0551849 | 7/1993 |
| EP | 0 931 544 | 7/1999 |
| EP | 1 008 346 | 6/2000 |
| EP | 1018514 | 7/2000 |
| EP | 1088819 | 4/2001 |
| EP | 1 113 000 | 7/2001 |
| EP | 1205478 | 5/2002 |
| EP | 1219596 | 7/2002 |
| EP | 1314712 | 5/2003 |
| EP | 1344525 | 9/2003 |
| EP | 1352650 | 10/2003 |
| FR | 1481713 | 6/1966 |
| FR | 2088225 | 1/1972 |
| GB | 1 079 177 | 8/1967 |
| GB | 1099865 | 7/1969 |
| GB | 2031410 | 4/1980 |
| JP | 37-000225 | 1/1962 |
| JP | 37000225 * | 1/1962 |
| JP | 52-110835 | 9/1977 |
| JP | 57-112360 | 7/1982 |
| JP | 62-30780 | 2/1987 |
| JP | 62-081359 | 4/1987 |
| JP | 62-99329 | 5/1987 |
| JP | 10-87491 | 4/1988 |
| JP | 63-104912 | 5/1988 |
| JP | 2-138260 | 5/1990 |
| JP | 4-217981 | 8/1992 |
| JP | 4-2179166 | 8/1992 |
| JP | 6-009476 | 1/1994 |
| JP | 8-175990 | 7/1996 |
| JP | 9-169747 | 6/1997 |
| JP | 9-227561 | 9/1997 |
| JP | 10-45738 | 2/1998 |
| JP | 11-21225 | 1/1999 |
| JP | 11-021243 | 1/1999 |
| JP | 11-217361 | 8/1999 |
| JP | 2000-80041 | 3/2000 |
| JP | 2000-169479 | 6/2000 |
| JP | 2001-114768 | 1/2001 |
| JP | 2001-522834 | 11/2001 |
| JP | 2002-506072 | 2/2002 |
| JP | 2004-501146 | 1/2004 |
| WO | 93/24115 | 12/1993 |
| WO | 96/17832 | 6/1996 |
| WO | 97/09315 | 3/1997 |
| WO | 98/20864 | 5/1998 |
| WO | 98/32017 | 7/1998 |
| WO | 99/24404 | 5/1999 |
| WO | 99/40907 | 8/1999 |
| WO | 99/46236 | 9/1999 |
| WO | 99/46244 | 9/1999 |
| WO | 99/46267 | 9/1999 |
| WO | 99/51580 | 10/1999 |
| WO | 99/55663 | 11/1999 |
| WO | 99/65449 | 12/1999 |
| WO | 00/01349 | 1/2000 |
| WO | 00/03991 | 1/2000 |
| WO | 00/35442 | 6/2000 |
| WO | 01/00213 | 1/2001 |
| WO | 01/10865 | 2/2001 |
| WO | 01/12588 | 2/2001 |
| WO | 01/44217 | 6/2001 |
| WO | 01/68648 | 9/2001 |
| WO | 01/98290 | 12/2001 |
| WO | 02/16633 | 2/2002 |
| WO | 02/76918 | 3/2002 |
| WO | 02/28819 | 4/2002 |
| WO | 02/49632 | 6/2002 |
| WO | 02/051397 | 7/2002 |
| WO | 02/067919 | 9/2002 |
| WO | 02/076926 | 10/2002 |
| WO | 03/103647 | 12/2003 |
| WO | 03/103648 | 12/2003 |
| WO | 03/103654 | 12/2003 |
| WO | 03/103655 | 12/2003 |
| WO | 03/103656 | 12/2003 |
| WO | 03/103657 | 12/2003 |
| WO | 03/103658 | 12/2003 |
| WO | 03/103665 | 12/2003 |
| WO | 2004/006906 | 1/2004 |
| WO | 2005/007151 | 1/2005 |

OTHER PUBLICATIONS

Baud, et al., "Trends in Cell Biology," 2001, vol. 11, No. 9, p. 372-377.
Daidone, et al., "Farmaco," 1989, vol. 44, No. 5, p. 465-473.
Djuric, et al., "The Journal of Medicinal Chemistry," 2000, vol. 43, No. 16, p. 2975-2981.
Dou, et al., "Proceedings of the National Academy of Sciences of the United States of America," 2003, vol. 100, No. 2, p. 721-726.
Dumas, et al., "Bioorganic and Medicinal Chemistry Letters," 1999, vol. 9, No. 17, p. 2531-2536.
Eldar-Finkelman, "Trends of Molecular Medicine," 2002, vol. 8, No. 3, p. 126-132.
Frame, et al., "The Biochemical Journal," 2001, vol. 359, No. PT1, p. 1-16.
Hoshi, et al., "Proceedings of the National Academy of Sciences of the United States of America," 1996, vol. 93, No. 7, p. 2719-2723.
Hsi, et al., "The Journal of Organic Chemistry," 1972, vol. 37, No. 22, p. 3427-3431.
Hunt, et al., "The Journal of the Chemical Society ," 1956, p. 3099-3107.
Inaba, et al., "Chemical and Pharmaceutical Bulletin," 2000, vol. 48, p. 131-139.
Ishige, et al., "Yakugaku Zasshi," 1999, vol. 119, No. 7, p. 510-518.
Kang, et al., "Neuroreport," 2001, vol. 12, No. 7, p. 1449-1452.
Karin, et al., "Proceedings of the National Academy of Science of the United States of America," 1998, vol. 95, No. 16, p. 9067-9069.
Karttunen, et al., "Proceedings of the National Academy of Sciences of United States of America," 1991, vol. 88, No. 9, p. 3972-3976.
Kaytor, et al., "Current Opinion of Neurobiology," 2002, vol. 12, No. 3, p. 275-278.
Kim, et al., "The Journal of Clinical Investigation," 2001, vol. 108, No. 3, p. 437-446.
Klosa, "Journal fuer Praktische Chemie," 1964, vol. 25, No. 1-2, p. 48-55 together with English language Abstract(Chemical Abstract) of the same.
Konta, et al., "The Journal of Biological Chemistry," 2001, vol. 276, No. 16, p. 12697-12701.
Ladva, et al., "Indian Journal of Chemistry, Section B," 1996, vol. 35B, No. 10, p. 1062-1066.
Lee, et al., "Proceedings of the National Academy of Science of the United States of America," 1998, vol. 95, No. 16, p. 9319-9324.
Mailliot, et al., "Annals of the New York Academy of Science," 2000, vol. 920, p. 107-114.

Mattson, et al., "The Journal of Clinical Investigation," 2001, vol. 107, No. 3, p. 247-254.

Mattson, et al., "Cell and Tissue Research," 2000, vol. 301, No. 1, p. 173-187.

Millet, et al., "The Journal of Biological Chemistry," 2000, vol. 275, No. 20, p. 15114-15121.

Mori, et al., "Yakugaku Zasshi," 1975, vol. 95, No. 12, p. 1477-1482, together with an English language abstract of the same.

Noble, et al., "Neuron," 2003, vol. 38, No. 4, p. 555-565.

Ohsugi, et al., "Yakugaku Zasshi," 1976, vol. 96, No. 2, p. 165-169, together with an English language abstract of the same.

Palanki, et al., "Current Medicinal Chemistry," 2002, vol. 9, No. 2, p. 219-227.

Phlel, et al., "Nature," 2003, vol. 423, No. 6938, p. 435-439.

Piu, et al., "Molecular and Cellular Biology," 2001, vol. 21, No. 9, p. 3012-3024.

Robert-Piessard, et al., "Pharmaceutical Science," 1997, vol. 3, No. 5/6, p. 295-299.

Sato, et al., "The Journal of Biological Chemistry," 2002, vol. 277, No. 44, p. 42060-42065.

Umezawa, "Surgery Frontier," 2002, vol. 9, No. 2, p. 88-91, together with English language translation of the same.

Upadhyay, et al., "Indian Journal of Heterocyclic Chemistry," 1991, vol. 1, No. 2, p. 71-74.

Waisser, et al., "Archiv der Pharmazie," 1998, vol. 331, No. 1, p. 3-6.

Wajant, "Cellular Signaling," 2001, vol. 13, No. 6, p. 389-400.

West, et al., "Analytical Biochemistry," 1990, vol. 190, No. 2, p. 254-258.

Won, et al., "Neuroscience," 1999, vol. 94, No. 1, p. 83-91.

Xu, et al., "The Journal of Neuroscience," 2001, vol. 21, No. 1, RC118, 5 pages.

Yamamoto, et al., "The Journal of Clinical Investigation," 2001, vol. 107, No. 2, p. 135-142.

Burton D. Clark et al., "Genomic Sequence for Human Prointerleukin 1 Beta: Possible Evolution from a Reverse Transcribed Prointerleukin 1 Alpha Gene", Nucleic Acids Research, vol. 14, No. 20, pp. 7897-7913 (1986).

S.A. Nedospasov. et al., "Tandem Arrangement of Genes Coding for Tumor Necrosis Factor (TNF-α) and Lymphotoxin (TNF-β) in the Human Genome", Cold Spring Harbor Symposia on Quantitative Biology, vol. 51, pp. 611-624 (1986).

Inder M. Verma e al., "Rel/NF-κB/IκB family: Intimate Tales of Association and Dissociation", Genes & Development, vol. 9, pp. 2723-2735 (1995).

Joseph A. DiDonato et al., "A Cytokine-Responsive IκB Kinase that Activates the Transcription Factor NF-κB", Nature, vol. 388, pp. 548-554 (1997).

Catherine H Régnier et al., "Identification and Characterization of an IκB Kinase", Cell, vol. 90, pp. 373-383 (1997).

John D. Woronicz et al., "IκB Kinase-β: NF-κB Activation and Complex Formation with IκB Kinase-α and NIK", Science, vol. 278, pp. 866-869 (1997).

Ebrahim Zandi et al., "The IκB Kinase Complex (IKK) Contains Two Kinase Subunits, IKKα and IKKβ, Necessary for IκB Phosphorylation and NF-κB Activation", Cell, vol. 91, pp. 243-252 (1997).

Elizabeth Kopp et al., "Inhibition of NF-κB by Sodium Salicylate and Asprin", Science, vol. 265, pp. 956-959 (1994).

Min-Jean Yin et al., "The Anti-Inflammatory Agents Asprin and Salicylate Inhibit the Activity of IκB Kinase-β", Nature, vol. 396, pp. 77-80 (1998).

Robert I. Scheinman et al., "Role of Transcriptional Activation of IκBα in Mediation of Immunosuppression by Glucocorticoids", Science, vol. 270, pp. 283-286 (1995).

Sunil K. Manna et al., "Immunosuppressive Leflunomide Metabolite (A77 1726) Blocks TNF-Dependent Nuclear Factor-êB Activation and Gene Expression[1]", Journal of Immunology, vol. 164, pp. 2095-2102 (1999).

Robert W. Sullivan et al., "2-Chloro-4(trifluoromethyl)pyrimidine-5-N-(3',5'-bis(trifluoromethyl)phenyl)- carboxamide: A Potent Inhibitor of NF-κB- and AP-1-Mediated Gene Expression Identified Using Solution-Phase combinatorial Chemistry", J. Med. Chem., vol. 41, pp. 413-419 (1998).

Naoki Matsumoto et al., "Synthesis of NF-κB Activation Inhibitors Derived from Epoxyquinomicin C", Bioorganic & Medicinal Chemistry Letters, vol. 10, pp. 865-869 (2000).

Takashi Okamoto, "NF-κB-mediated Mechanism of Action of Antirheumatic Drugs, Specifically DMARDs", 18th Meeting of Japanese Inflammatory Society, pp. 57, (2000).

Mark J. Macielag et al., "Substituted Salicylanilides as Inhibitors of Two-Component Regulatory Systems in Bacteria", J. Med. Chem., vol. 41, pp. 2939-2945 (1998).

Me Zwaagstra et al. , "Synthesis of Carboxylated Flavonoids as New Leads of $LTD_4$ Antagonists" Eur. J. Med. Chem., vol. 31, pp. 861-874 (1996).

Zh. Org. Khim., vol. 16, pp. 2185-2188 (1980), accompanied by a partial English translation;Satoshi Yamamoto et al., "Synthesis and Biological Activity of Novel 1,3-Benzoxazine Derivatives as $K^+$Channel Openers", Chem Pharm. Bull., vol. 44, No. 4, pp. 734-745 (1996).

Michael S. South et al., "Reactions of a 4-(Trifluoromethyl)thiaxole Dianion", J. Heterocyclic Chem., vol. 28, pp. 1017-1024 (1991).

Yoshio Tajika, "Studies on the Synthesis of the 2-Aminothiazole Derivatives. IV. Reaction of the 1,1'-Dithiodiformamidine Hydrohalide With the Ketones", Yakugaku Zasshi, vol. 81, pp. 1456-1459 (1961).

Nihon Kagaku Zasshi, vol. 83, pp. 209-211 (1962).

Yasuo Yura et al., "Studies on Acetylenic Compounds. XXII.[1)] Ring Closure. (4). New Synthesis of Thiazoles and Imidazole", Chem. Pharm. Bull., vol. 10, pp. 376-382 (1962).

Enrique Diéz-Berra et al., "On the π-π Interaction in the Benzylation of Ketones", Tetrahedron, vol. 53, No. 33, pp. 11437-11448 (1997).

Caroline S. Hill et al., Functional Analysis of a Growth Factor-Responsive Transcription Factor Complex, Cell, vol. 73, pp. 395-406 (1993).

Babita Madan et al., "2'-Hydroxychalcone Inhibits Nuclear Factor-κB and Blocks Tumor Necrosis Factor-α- and Lipopolysaccharide-Induced Adhesion of Neutrophils to Human Umbilical Vein Endothelial Cells" Molecular Pharmacology, vol. 58, No. 3., pp. 526-534 (2000).

Yin, et al., "Cell," 1998, vol. 93, No. 5, p. 875-884.

Yuan, et al., "Science," 2001, vol. 293, p. 1673-1677.

Matsuzaki, et al., "Amer. J. Reproductive Immunol.," 1986, vol. 40, p. 291-294.

Uchiide, et al., "Nikkei Medical," 2002, No. 415, p. 28, with English translation.

Uchiide, et al., "Fertility and Sterility," 2002, vol. 78, No. 4, p. 782-786.

Chegini, "Frontiers in Bioscience," 2002, vol. 7, p. e91-115.

Berking, et al., "American Journal of Pathology," 2001, vol. 158, No. 3, pp. 943-953.

Singh, et al., "Histology and Histopathology," 2000, vol. 15, pp. 843-849.

Recio, et al., "Cancer Research," 2002, vol. 62, No. 22, pp. 6724-6730.

Chemical Abstract of B. Madan et al. "2'-Hydroxychalcone Inhibits Nuclear Factor-κB and Blocks Tumor Necrosis Factor α and Lipopolysaccharide-Induced Adhesion of Neutrophils to Human Umbilical Vein Endothelial Cells", Molecular Pharmacology, 2000, 58(3), 526-534.

Chemical Abstract of C. W. Chung et al. "Primary Sensitization Potentials of Some Halogenated Salicylanilides and their Cross-Sensitivity in Guinea-Pigs", Food and Cosmetics Toxicology, 1977, 15 (4), 325-30.

Chemical Abstract of D. Lehmann et al. "Inhibition of the Progression of Multiple Sclerosis by Linomide is Associated with Upregulation of CD4+/CD45RA+ Cells and Downregulation of CD4+/CD45RO+ Cells", Clinical Immunology and Immunopathology, 1997, 85 (2), 202-209.

Chemical Abstract of M. Katunani et al. "JTE-607, a Novel Inflammatory Cytokine Synthesis inhibitor without Immunosuppression, Protects from Endotoxin Shock in Mice", Inflammation Research, 1999, 48 (8), 461-468.

Extended European Search Report for EP 07 01 5427, Jul. 29, 2009.

Database Crossfire Beilstein XP002536489 (Abstract), Database Accession Nos. 2818733 and 2819714, 1964.

Database Crossfire Beilstein XP002536490 (Abstract), Database Accession No. 2698830, 1965.
Database Crossfire Beilstein XP002536491 (Abstract), Database Accession No. 3372658, 1959.
Partial European Search Report for EP 07 01 5427, Mar. 26, 2009.
Tavares et al., "Immunoglobulin E-mediated anaphylaxis activates nuclear factor κB in rat small intestine," *Inflamm. Res.*, vol. 47, pp. 265-269, 1998.
Coward et al., "Asthma, adenosine, mast cells and theophylline," *Clinical and Experimental Allergy*, vol. 28, Supplement 3, pp. 42-46, 1998.
Piscopo et al., {Biological activity of 4-hydroxyisophthalic acid derivatives. III. Variously substituted anilides with antimicrobial activity, Bollettino—Societa Italiana di Biologia Sperimentale, (1985), 61(2), 199-204}.

Marking et al., {Comparative toxicity of 29 nitrosalicylanilides and related compounds to eight species of fish, Invest. Fish Contr. (1970), No. 36-38, 37, 11 pp.}.
Lang et al., {Cyclic salicylanilides as antibacterial agents, Journal of the Society of Cosmetic Chemists (1966), 17, 355-60}.
Schraufstaetter et al., {A new molluscicide. I. Relations between structure and activity, Zeitschrift fuer Naturforschung (1961 ), 16b, 95-108}.
Orzalesi et al., Bollettino Chimico Farmaceutico, 1967, 106(2), p. 88-93 (Abstract).
"Colitis" on Medscape Reference; Drugs, Diseases & Procedures at <http://emedicine.medscape.com/article/927845-overview#a0104>, visited at Sep. 15, 2011.

* cited by examiner

INFLAMMATORY CYTOKINE RELEASE INHIBITOR

CROSS-REFERENCE TO RELATED APPLICATIONS

The present application is a Continuation of U.S. application Ser. No. 11/835,978, filed Aug. 8, 2007, which is a Divisional of U.S. application Ser. No. 10/433,619, which is a National Stage of PCT/JP2001/011084, filed Dec. 18, 2001, which was not published in English under PCT Article 21(2), and which claims priority of Japanese Application No. 2000-383202, filed Dec. 18, 2000. The entire disclosures of application Ser. Nos. 11/835,978 and 10/433,619 are considered as being part of this application, and the entire disclosures of application Ser. Nos. 11/835,978 and 10/433,619 are expressly incorporated by reference herein in their entireties.

FIELD OF INVENTION

The present invention relates to pharmaceutical compositions having inhibitory activity against the production and release of inflammatory cytokines such as interleukin (IL)-1, IL-6, IL-8 and tumor necrosis factor (TNF-α), and having inhibitory activity against the activation of NF-κB.

BACKGROUND ART

Inflammation is a basic defense mechanism to various infestations, where inflammatory cytokine such as interleukin (IL)-1 and TNF-α (tumor necrosis factor) are known to play important roles. Due to the progress of gene analysis of inflammatory cytokines and inflammatory cell adhesion factors, it has been revealed that these cytokines are controlled by a common transcription factor (also called as transcription regulatory factor). This transcription factor is a protein called as NF-κB (also described as NF κB, Clark B. D., et al., Nucl. Acids Res., 14, 7898 (1984); Nedospasov S. A., et al., Cold Spring Harb. Symp. Quant. Biol., 51, 611 (1986)).

This NF-κB is a hetero dimer (also called as complex) of p65(also called as Rel A) and p50(also called as NF-κB-1), usually binds to I-κB when external stimulation does not exist, and exists in cytoplasm as an inactive type. I-κB is phosphorated by various external stimulations such as oxidative stress, cytokine, lipopolysaccharide, virus, UV, free radical, protein kinase C to become ubiquitin, and then decomposed by proteasome (Verma I. M., Stevenson J. K., et al., Genes Dev., 9, 2723-2735 (1995)). NF-κB separated from I-κB immediately move into nucleus, and plays a role as a transcription factor by binding to promoter region which has recognition sequence of NF-κB.

In 1997, phosphoenzyme (called as IκB kinase abbreviated as "IKK"), which participates in phosphorylation of I-κB, was identified (DiDonation J., Hayakawa M., et al., Nature, 388, 548-554 (1997); Regnier C. H., Song H. Y., et al., Cell, 90, 373-383 (1997)). IKK-α (also called as IKK1) and IKK-β (also called as IKK2) which resemble each other and exist among a class of IKK, and they are known to form a complex to bind directly to IκB and phosphorize IκB (Woronicz J. D., et al., Science, 278, 866-869 (1997); Zandi, E., et al., Cell, 91, 243-252 (1997)).

Recently, a mechanism except cyclooxygenase inhibition is suggested for aspirin which is a widely used anti-inflammatory agent, which is known to be based on inhibition of NF-κB activation (Kopp E., et al., Science, 265, 956-959 (1994)). Moreover, it was revealed that aspirin regulates release and activation of NF-κB by binding reversibly to IKK-β which is I-κB kinase competing with ATP and by inhibiting phosphorylation of I-κB (Yin M. J., et al., Nature, 396, 77-80 (1998)). However, since huge amount of aspirin needs to be administered to sufficiently suppress NF-κB activation, and as a result, since possibility of side effects such as gastrointestinal disorders by prostaglandin synthesis inhibition and increase of bleeding tendency by anticoagulation is expected with high probability, aspirin is not suitable for long term application.

Besides aspirin, some pharmaceuticals are known to have inhibitory action against NF-κB activation. Glucocorticoids (steroid hormones) such as dexamethasone supprress NF-κB activation by binding to their receptors (called as glucocorticoid receptor, Scheinman R. L., et al., Science, 270, 283 (1995)). However, long term use is not suitable, because they have serious side effects such as aggravation of an infectious disease, generation of peptic ulcer, degradation of bone density, and central action. Leflunomide as an immunosuppressive agent, as an isoxazole-type agent, also has NF-κB inhibitory action (Manna S., et al., J. Immunol., 164, 2095-2102 (1999)), however, the drug is also not suitable for long term use due to serious side effects. Furthermore, substituted pyrimidine derivatives (Japanese Patent Publication of International Application (Kohyo) (Hei) 11-512399, J. Med. Chem., 41, 413 (1998)), xanthine derivatives (Japanese Patent Unexamined Publication (KOKAI) No. (Hei) 9-227561), isoquinoline derivatives (Japanese Patent Unexamined Publication (KOKAI) No. (Hei) 10-87491), indan derivatives (WO00/05234), epoxyquinomycin C, D, and their derivatives (Japanese Patent Unexamined Publication (KOKAI) No. (Hei) 10-45738, Bioorg. Med. Chem. Lett., 10, 865-869 (2000)) are known as inhibitors against NF-κB activation. However, mechanism of inhibition against NF-κB activation and participating receptors or proteins have not been revealed.

DISCLOSURE OF THE INVENTION

Compounds having specific inhibitory action against IKK-β, found by using IKK-β as a target which directly induces phosphorylation of IKK-β, are expected to have inhibitory action against production and release of the target inflammatory cytokine and inhibitory action against production of inflammatory cell adhesion molecules, without affecting other signal transfer pathway, that is, without serious side effects. NF-κB activation is induced by the aforementioned external stimulation, and as a result, proteins such as inflammatory cytokine are expressed. Among the inflammatory cytokines, TNF-α and interleukine (IL)-1 whose gene expression itself is considered to be regulated positively by NF-κB to form positive feedback loop (TNF-α→NF-κB→TNF-α) and is considered to participate in chronicity of inflammation (18th Meeting of The Japanese Inflammatory Society, Symposium "Mechanism of Antirheumatic Pharmaceutical composition and New Development" Tokyo, 2000). Accordingly, the compounds which specifically inhibit IKK-β as a target are expected to be useful drugs for inflammatory diseases advanced in a chronic stage and diseases caused by TNF-α and IL-1.

Therefore, an object of the present invention is to provide medicaments useful for preventive and/or therapeutic treatment of inflammatory disorders, autoimmune disease such as chronic arthrorheumatism, and bone disease such as osteoporosis, in which inflammatory cytokine is participated. Another object of the present invention is to provide an inhibitor against release of an inflammatory cytokine which avoids side effects by specifically inhibiting IKK-β, and has inhibitory activity against NF-κB activation.

The inventors of the present invention carried out search for compounds having inhibitory action against NF-κB activation by selective inhibition of IKK-β by using computerized molecular design technology to solve the aforementioned object. Appropriate protein kinases with high homology with IKK-β were selected from the kinases whose structures are registered in PDB (Protein Data Bank), and three-dimensional structure model of IKK-β was constructed by applying the homology modeling technique employing the chosen kinase as a template, and then binding mode of aspirin to the ATP binding region of IKK-β and characteristic intermolecular interactions were analyzed by using automatic search program for binding modes of a drug molecule to a protein. On the basis of the results obtained, an automatic search program of a ligand from a three-dimensional compound database based on the tree-dimensional structure of the protein was carried out, and compounds potentially be specific inhibitors against IKK-β were selected by a virtual screening out of compounds registered in a database of commercial compounds. Further, inhibitory activity of those compounds against NF-κB activation was confirmed by a reporter assay method under TNF-α stimulation. Among them, the compounds with potent activities were further studied on the binding mode to IKK-β and interactions. On the basis of these results, the present invention was achieved by further carrying out search from compound databases of analogous compounds and syntheses The medicament of the present invention is:
(1) that having inhibitory action against NF-κB activation which comprises as an active ingredient a substance selected from the group consisting of a compound represented by the general formula (I) and a pharmacologically acceptable salt thereof, and a hydrate thereof and a solvate thereof:

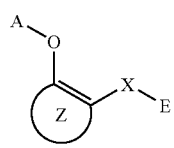
(I)

wherein X represents a connecting group whose number of atoms in the main chain is 2 to 4 (said connecting group may be substituted),
A represents hydrogen atom or acetyl group,
E represents an aryl group which may be substituted or a hetero aryl group which may be substituted,
ring Z represents an arene which may have one or more substituents in addition to the group represented by formula —O—A wherein A has the same meaning as that defined above and the group represented by formula —X—E wherein each of X and E has the same meaning as that defined above, or a hetero arene which may have one or more substituents in addition to the group represented by formula —O—A wherein A has the same meaning as that defined above and the group represented by formula —X—E wherein each of X and E has the same meaning as that defined above.

Among them, preferred medicaments include:
(2) the medicament having inhibitory action against NF-κB activation which comprises as an active ingredient a substance selected from the group consisting of the compound and a pharmacologically acceptable salt thereof, and a hydrate thereof and a solvate thereof, wherein X is a group selected from the following connecting group a which may be substituted:

[Connecting groups α]: The groups of the following formulas:

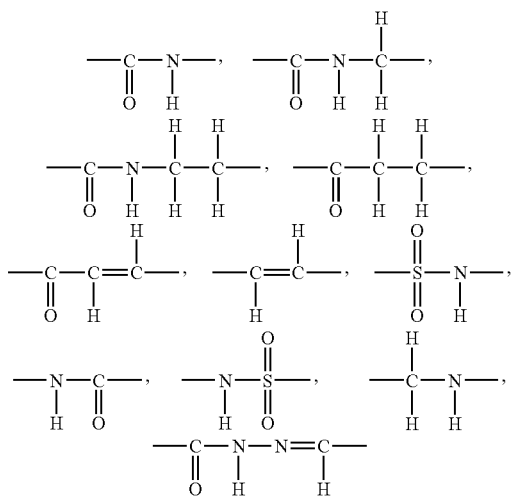

wherein the bond at the left end binds to ring Z and the bond at the right end binds to E;
(3) the medicament having inhibitory action against NF-κB activation which comprises as an active ingredient a substance selected from the group consisting of the compound and a pharmacologically acceptable salt thereof, and a hydrate thereof and a solvate thereof, wherein X is a group which may be substituted and represented by the following formula:

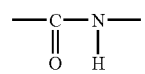

wherein the bond at the left end binds to ring Z and the bond at the right end binds to E;
(4) the medicament having inhibitory action against NF-κB activation which comprises as an active ingredient a substance selected from the group consisting of the compound and a pharmacologically acceptable salt thereof, and a hydrate thereof and a solvate thereof, wherein X is a group represented by the following formula:

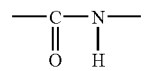

wherein the bond at the left end binds to ring Z and the bond at the right end binds to E;
(5) the medicament having inhibitory action against NF-κB activation which comprises as an active ingredient a substance selected from the group consisting of the compound and a pharmacologically acceptable salt thereof, and a hydrate thereof and a solvate thereof, wherein A is a hydrogen atom;
(6) the medicament having inhibitory action against NF-κB activation which comprises as an active ingredient a substance selected from the group consisting of the compound and a pharmacologically acceptable salt thereof, and a hydrate thereof and a solvate thereof, wherein ring Z is a $C_6$ to $C_{10}$ arene which may have one or more substituents in addition to the group represented by formula —O—A wherein A has the same meaning as that defined in the general formula (I) and the group represented by formula —X—E wherein each of X and E has the same meaning as that defined in the general formula (I), or a 6 to 13-membered hetero arene which may have one or more substituents in addition to the group represented by formula —O—A wherein A has the same meaning as that defined in the general formula (I) and the group represented by formula —X—E wherein each of X and E has the same meaning as that defined in the general formula (I);

(7) the medicament having inhibitory action against NF-κB activation which comprises as an active ingredient a substance selected from the group consisting of the compound and a pharmacologically acceptable salt thereof, and a hydrate thereof and a solvate thereof, wherein ring Z is selected from the following ring group B which may have one or more substituents in addition to the group represented by formula —O—A wherein A has the same meaning as that defined in the general formula (I) and the group represented by formula —X—E wherein each of X and E has the same meaning as that defined in the general formula (I):

[Ring Group β] benzene ring, naphthalene ring, pyridine ring, indole ring, quinoxaline ring, carbazole ring;

(8) the medicament having inhibitory action against NF-κB activation which comprises as an active ingredient a substance selected from the group consisting of the compound and a pharmacologically acceptable salt thereof, and a hydrate thereof and a solvate thereof, wherein ring Z is a benzene ring which may have one or more substituents in addition to the group represented by formula —O—A wherein A has the same meaning as that defined in the general formula (I) and the group represented by formula —X—E wherein each of X and E has the same meaning as that defined in the general formula (I);

(9) the medicament having inhibitory action against NF-κB activation which comprises as an active ingredient a substance selected from the group consisting of the compound and a pharmacologically acceptable salt thereof, and a hydrate thereof and a solvate thereof, wherein ring Z is a benzene ring which may further have one or more substituents selected from the following substituent group γ-1z in addition to the group represented by formula —O—A wherein A has the same meaning as that defined in the general formula (I) and the group represented by formula —X—E wherein each of X and E has the same meaning as that defined in the general formula (I):

[substituent group γ-1z] a halogen atom, nitro group, cyano group, hydroxy group which may be substituted, amino group which may be substituted, hydrocarbon group which may be substituted, heterocyclic group which may be substituted, acyl group which may be substituted, ureido group which may be substituted, thioureido group which may be substituted, diazenyl group which may be substituted;

(10) the medicament having inhibitory action against NF-κB activation which comprises as an active ingredient a substance selected from the group consisting of the compound and a pharmacologically acceptable salt thereof, and a hydrate thereof and a solvate thereof, wherein the following partial structural formula (Iz-1) including ring Z in the general formula (I):

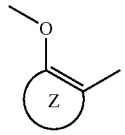

(Iz-1)

is a group represented by the following formula (Iz-2)

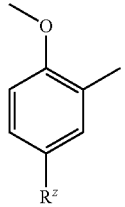

(Iz-2)

wherein $R^z$ represents hydrogen atom, a halogen atom, nitro group, cyano group, hydroxy group which may be substituted, an amino group which may be substituted, a hydrocarbon group which may be substituted, a heterocyclic group which may be substituted, an acyl group which may be substituted, an ureido group which may be substituted, a thioureido group which may be substituted, or a diazenyl group which may be substituted;

(11) the medicament having inhibitory action against NF-κB activation which comprises as an active ingredient a substance selected from the group consisting of the compound and a pharmacologically acceptable salt thereof, and a hydrate thereof and a solvate thereof, wherein $R^z$ is hydrogen atom, a halogen atom, nitro group, cyano group, a $C_1$ to $C_6$ alkoxy group which may be substituted, a di($C_1$ to $C_6$ alkyl)-amino group, a $C_6$ to $C_{10}$ aryl-carbonyl-amino group, a $C_1$ to $C_6$ alkyl group which may be substituted, a $C_1$ to $C_6$ halogenated alkyl group which may be substituted, a $C_2$ to $C_6$ alkenyl group which may be substituted, a $C_2$ to $C_6$ alkynyl group which may be substituted, a $C_7$ to $C_{16}$ aralkyl group which may be substituted, a 5 to 6 membered heteroaryl group which may be substituted, a carbamoyl group which may be substituted, a sulfamoyl group which may be substituted, a $C_1$ to $C_6$ alkyl-carbamoyl group which may be substituted, a $C_1$ to $C_6$ alkoxy-carbamoyl group which may be substituted, a 5 membered heteroaryl-sulfonyl group which may be substituted, a 6 membered nonaromatic heteroyclic-sulfonyl group which may be substituted, or a diazenyl group which may be substituted;

(12) the medicament having inhibitory action against NF-κB activation which comprises as an active ingredient a substance selected from the group consisting of the compound and a pharmacologically acceptable salt thereof, and a hydrate thereof and a solvate thereof, wherein $R^z$ is hydrogen atom, a halogen atom, nitro group, cyano group, methoxy group, dimethylamino group, benzoylamino group, methyl group, tert-butyl group, 1-hydroxyethyl group, 1-(methoxyimino)ethyl group, 1-[(benzyloxy)imino]ethyl group, trifluoromethyl group, pentafluoroethyl group, phenyl group, 4-(trifluoromethyl)phenyl group, 4-fluorophenyl group, 2,4-difluorophenyl group, 2-phenylethen 1-yl group, 2,2-dicyanoethen-1-yl group, 2-cyano-2-(methoxycarbonyl)ethen-1-yl group, 2-carboxy-2-cyanoethen-1-yl group, ethynyl group, phenylethynyl group, (trimethylsilyl)ethynyl group, phenyl group, 2-phenethyl group, 2-thienyl group, 3-thienyl group, 1-pyrrolyl group, 2-methylthiazol-4-yl group, 2-pyridyl group, N-[3,5-bis(trifluoromethyl)-phenyl]carbamoyl group, dimethylcarbamoyl group, dimethylsulfamoyl group, acetyl group, isobutyryl group, methoxycarbonyl group, piperidinocarbonyl group, 4-benzylpiperidino group, (pyrrol-1-yl)sulfonyl group, 3-phenylureido group, (3-phenyl)thioureido group, (4-nitrophenyl)diazenyl group, or {[(4-pyridin-2-yl)sulfamoyl]phenyl}diazenyl group;

(13) the medicament having inhibitory action against NF-κB activation which comprises as an active ingredient a substance selected from the group consisting of the compound and a pharmacologically acceptable salt thereof, and a hydrate thereof and a solvate thereof, wherein $R^z$ is a halogen atom:

(14) the medicament having inhibitory action against NF-κB activation which comprises as an active ingredient a substance selected from the group consisting of the compound and a pharmacologically acceptable salt thereof, and a hydrate thereof and a solvate thereof, wherein E is a $C_6$ to $C_{10}$ aryl group which may be substituted or a 5 to 13 membered heteroaryl group which may be substituted;

(15) the medicament having inhibitory action against NF-κB activation which comprises as an active ingredient a substance selected from the group consisting of the compound and a pharmacologically acceptable salt thereof, and a hydrate thereof and a solvate thereof, wherein E is a $C_6$ to $C_{10}$ aryl group which may be substituted;

(16) the medicament having inhibitory action against NF-κB activation which comprises as an active ingredient a substance selected from the group consisting of the compound and a pharmacologically acceptable salt thereof, and a hydrate thereof and a solvate thereof, wherein E is a phenyl group which may be substituted;

(17) the medicament having inhibitory action against NF-κB activation which comprises as an active ingredient a substance selected from the group consisting of the compound and a pharmacologically acceptable salt thereof, and a hydrate thereof and a solvate thereof, wherein E is a phenyl group substituted with two $C_1$ to $C_6$ halogenated alkyl groups and said phenyl group may further have one or more substituents in addition to the two $C_1$ to $C_6$ halogenated alkyl groups;

(18) the medicament having inhibitory action against NF-κB activation which comprises as an active ingredient a substance selected from the group consisting of the compound and a pharmacologically acceptable salt thereof, and a hydrate thereof and a solvate thereof, wherein E is a phenyl group substituted with two $C_1$ to $C_6$ halogenated alkyl groups;

(19) the medicament having inhibitory action against NF-κB activation which comprises as an active ingredient a substance selected from the group consisting of the compound and a pharmacologically acceptable salt thereof, and a hydrate thereof and a solvate thereof, wherein E is 3,5-bis(trifluoromethyl)phenyl group or 2,5-bis(trifluoromethyl)phenyl group;

(20) the medicament having inhibitory action against NF-κB activation which comprises as an active ingredient a substance selected from the group consisting of the compound and a pharmacologically acceptable salt thereof and a hydrate thereof and a solvate thereof, wherein E is 3,5-bis(trifluoromethyl)phenyl group;

(21) the medicament having inhibitory action against NF-κB activation which comprises as an active ingredient a substance selected from the group consisting of the compound and a pharmacologically acceptable salt thereof, and a hydrate thereof and a solvate thereof, wherein E is a phenyl group substituted with one $C_1$ to $C_6$ halogenated alkyl group and said phenyl group may further have one or more substituents, except a $C_1$ to $C_6$ halogenated alkyl group, in addition to the $C_1$ to $C_6$ halogenated alkyl group;

(22) the medicament having inhibitory action against NF-κB activation which comprises as an active ingredient a substance selected from the group consisting of the compound and a pharmacologically acceptable salt thereof, and a hydrate thereof and a solvate thereof, wherein E is a phenyl group substituted with one $C_1$ to $C_6$ halogenated alkyl group and said phenyl group may further have one or more substituents selected from the following substituent group γ-1e in addition to the $C_1$ to $C_6$ halogenated alkyl group:

[Substituent group γ-1e] a halogen atom, nitro group, cyano group, hydroxy group which may be substituted, a hydrocarbon group which may be substituted, a heterocyclic group which may be substituted, sulfanyl group which may be substituted;

(23) the medicament having inhibitory action against NF-κB activation which comprises as an active ingredient a substance selected from the group consisting of the compound and a pharmacologically acceptable salt thereof, and a hydrate thereof and a solvate thereof, wherein E is a phenyl group substituted with one $C_1$ to $C_6$ halogenated alkyl group and said phenyl group may further have one or more substituents selected from the following substituent group γ-2e in addition to the $C_1$ to $C_6$ halogenated alkyl group:

[Substituent group γ-2e] a halogen atom, nitro group, cyano group, a $C_1$ to $C_6$ alkyl group which may be substituted, a 5 to 6 membered nonaromatic heterocyclic group which may be substituted, a $C_1$ to $C_6$ alkoxyl group which may be substituted, a $C_1$ to $C_6$ alkyl-sulfanyl group which may be substituted;

(24) the medicament having inhibitory action against NF-κB activation which comprises as an active ingredient a substance selected from the group consisting of the compound and a pharmacologically acceptable salt thereof, and a hydrate thereof and a solvate thereof, wherein E is 2-(trifluoromethyl)phenyl group, 3-(trifluoromethyl)phenyl group, 4-(trifluoromethyl)phenyl group, 2-fluoro-3-(trifluoromethyl)phenyl group, 2-chloro-4-(trifluoromethyl)phenyl group, 2-fluoro-5-(trifluoromethyl)phenyl group, 2-chloro-5-(trifluoromethyl)phenyl group, 3-fluoro-5-(trifluoromethyl)phenyl group, 3-bromo-5-(trifluoromethyl)phenyl group, 4-chloro-2-(trifluoromethyl)phenyl group, 4-fluoro-3-(trifluoromethyl)phenyl group, 4-chloro-3-(trifluoromethyl)phenyl group, 2-nitro-5-(trifluoromethyl)phenyl group, 4-nitro-3-(trifluoromethyl)phenyl group, 4-cyano-3-(trifluoromethyl)phenyl group, 2-methyl-3-(trifluoromethyl)phenyl group, 2-methyl-5-(trifluoromethyl)phenyl group, 4-methyl-3-(trifluoromethyl)phenyl group, 2-methoxy-5-(trifluoromethyl)phenyl group, 3-methoxy-5-(trifluoromethyl)phenyl group, 4-methoxy-3-(trifluoromethyl)phenyl group, 2-(methylsulfanyl)-5-(trifluoromethyl)phenyl group, 2-(1-pyrrolizino)-5-(trifluoromethyl)phenyl group, or 2-morpholino-5-(trifluoromethyl)phenyl group;

(25) the medicament having inhibitory action against NF-κB activation which comprises as an active ingredient a substance selected from the group consisting of the compound and a pharmacologically acceptable salt thereof, and a hydrate thereof and a solvate thereof, wherein E is 2-chloro-5-(trifluoromethyl)phenyl group, 4-chloro-3-(trifluoromethyl)phenyl group, 2-methoxy-5-(trifluoromethyl)phenyl group, or 3-methoxy-5-(trifluoromethyl)phenyl group;

(26) the medicament having inhibitory action against NF-κB activation which comprises as an active ingredient a substance selected from the group consisting of the compound and a pharmacologically acceptable salt thereof, and a hydrate thereof and a solvate thereof, wherein E is 2-chloro-5-(trifluoromethyl)phenyl group;

(27) the medicament having inhibitory action against NF-κB activation which comprises as an active ingredient a substance selected from the group consisting of the compound and a pharmacologically acceptable salt thereof, and a hydrate thereof and a solvate thereof, wherein E is a phenyl group which may have one or more substituent except a $C_1$ to $C_6$ halogenated alkyl group;

(28) the medicament having inhibitory action against NF-κB activation which comprises as an active ingredient a substance selected from the group consisting of the compound and a pharmacologically acceptable salt thereof, and a hydrate thereof and a solvate thereof. wherein E is a phenyl group which may have one or more substituents selected from the following substituent group γ-3e:

[Substituent group γ-3e] a halogen atom, nitro group, hydroxy group which may be substituted, hydrocarbon group which may be substituted, acyl group which may be substituted;

(29) the medicament having inhibitory action against NF-κB activation which comprises as an active ingredient a substance selected from the group consisting of the compound and a pharmacologically acceptable salt thereof, and a hydrate thereof and a solvate thereof, wherein E is a phenyl group which is substituted with one or more substituents selected from the following substituent group γ-4-e;

[Substituent group γ-4e] a halogen atom, nitro group, hydroxy group, a $C_1$ to $C_6$ alkyl group which may be substituted, a $C_6$ to $C_{10}$ aryl group which may be substituted, a $C_1$ to $C_6$ alkylene group which may be substituted, a $C_1$ to $C_6$ alkoxy group which may be substituted, a $C_1$ to $C_6$ alkyl-carbonyl group which may be substituted, a $C_1$ to $C_6$ alkoxy-carbonyl group which may be substituted;

(30) the medicament having inhibitory action against NF-κB activation which comprises as an active ingredient a substance selected from the group consisting of the compound and a pharmacologically acceptable salt thereof, and a hydrate thereof and a solvate thereof, wherein E is phenyl group, 3-chlorophenyl group, 4-chlorophenyl group, 2,5-dichlorophenyl group, 3,4-dichlorophenyl group, 3,5-difluorophenyl group, 3,5-dichlorophenyl group, 3,4,5-trichlorophenyl group, pentafluorophenyl group, 3,5-dinitrophenyl group, 3,5-dichloro-4-hydroxyphenyl group, 2,5-dimethoxyphenyl group, 3,5-dimethoxyphenyl group, 3,5-dimethylphenyl group, 2,5-bis[(1,1-dimethyl)ethyl]phenyl group, 3,5-bis[(1,1-dimethyl)ethyl]phenyl group, 5-(1,1-dimethyl)ethyl-2-methoxyphenyl group, 3,5,5,8,8-pentamethyl-5,6,7,8-tetrahydronaphthalen-2-yl group, biphenyl-3-yl group, 4-methoxybiphenyl-3-yl group, 3-acetylphenyl group, or 3,5-bis (methoxycarbonyl)phenyl group;

(31) the medicament having inhibitory action against NF-κB activation which comprises as an active ingredient a substance selected from the group consisting of the compound and a pharmacologically acceptable salt thereof, and a hydrate thereof and a solvate thereof, wherein E is 2,5-bis[(1,1-dimethyl)ethyl]phenyl group, 3,5-bis[(1,1-dimethyl)ethyl]phenyl group, or 5-(1,1-dimethyl)ethyl-2-methoxyphenyl group;

(32) the medicament having inhibitory action against NF-κB activation which comprises as an active ingredient a substance selected from the group consisting of the compound and a pharmacologically acceptable salt thereof, and a hydrate thereof and a solvate thereof, wherein E is a 5 to 13 membered heteroaryl group which may be substituted;

(33) the medicament having inhibitory action against NF-κB activation which comprises as an active ingredient a substance selected from the group consisting of the compound and a pharmacologically acceptable salt thereof, and a hydrate thereof and a solvate thereof, wherein E is a thienyl group which may be substituted, a pyrazolyl group which may be substituted, an oxazolyl group which may be substituted, a thiazolyl group which may be substituted, a thiadiazolyl group which may be substituted, a pyridyl group which may be substituted, a pyrimidinyl group which may be substituted, an indolyl group which may be substituted, a quinolyl group which may be substituted, or a carbazolyl group which may be substituted;

(34) the medicament having inhibitory action against NF-κB activation which comprises as an active ingredient a substance selected from the group consisting of the compound and a pharmacologically acceptable salt thereof, and a hydrate thereof and a solvate thereof, wherein E is a thiazolyl group which may be substituted;

(35) the medicament having inhibitory action against NF-κB activation which comprises as an active ingredient a substance selected from the group consisting of the compound and a pharmacologically acceptable salt thereof, and a hydrate thereof and a solvate thereof, wherein E is a thiazolyl group which may have one or more substituents selected from the following substituent group γ-5e:

[Substituent group γ-5e] a halogen atom, cyano group, a hydrocarbon group which may be substituted, a heteroring group which may be substituted, an acyl group which may be substituted;

(36) the medicament having inhibitory action against NF-κB activation which comprises as an active ingredient a substance selected from the group consisting of the compound and a pharmacologically acceptable salt thereof, and a hydrate thereof and a solvate thereof, wherein E is a thiazolyl group which may have one or more substituents selected from the following substituent group γ-6e:

[Substituent group γ-6e] a halogen atom, cyano group, a $C_1$ to $C_6$ alkyl group which may be substituted, a $C_1$ to $C_6$ halogenated alkyl group which may be substituted, a $C_6$ to $C_{10}$ aryl group which may be substituted, a $C_7$ to $C_{16}$ aralkyl group which may be substituted, a 6 membered nonaromatic heteroring group, a $C_1$ to $C_6$ alkyl-carbonyl group which may be substituted, a $C_6$ to $C_{10}$ aryl-carbonyl group which may be substituted, a $C_1$ to $C_6$ alkoxy-carbonyl group which may be substituted;

(37) the medicament having inhibitory action against NF-κB activation which comprises as an active ingredient a substance selected from the group consisting of the compound and a pharmacologically acceptable salt thereof, and a hydrate thereof and a solvate thereof, wherein E is 5-bromo-4-[(1,1-dimethyl)ethyl]thiazol-2-yl group, 5-bromo-4-(trifluoromethyl)thiazol-2-yl group, 5-cyano-4-[(1,1-dimethyl)-ethyl]thiazol-2-yl group, 4-[(1,1-dimethyl)ethyl]thiazol-2-yl group, 5-phenyl-4-(trifluoromethyl)thiazol-2-yl group, 4-(1,1-dimethyl)ethyl-5-ethylthiazol-2-yl group, 5-methyl-4-phenylthiazol-2-yl group, 4-isopropyl-5-phenylthiazol-2-yl group, 4-benzyl-5-phenylthiazol-2-yl group, 4-(1,1-dimethyl)ethyl-5-[(2,2-dimethyl)-propionyl]thiazol-2-yl group, 5-acetyl-4-phenylthiazol-2-yl group, 5-benzoyl-4-phenylthiazol-2-yl group, 4-(1,1-dimethyl)ethyl-5-(ethoxycarbonyl)-thiazol-2-yl group, 5-ethoxycarbonyl-4-(trifluoromethyl)thiazol-2-yl group, 5-ethoxycarbonyl-4-phenylthiazol-2-yl group, 4-(1,1-dimethyl)ethyl-5-piperidino-thiazol-2-yl group, 4-(1,1-dimethyl)ethyl-5-morpholinothiazol-2-yl group, 4-(1,1-dimethyl)ethyl-5-(4-phenylpiperidin-1-yl) thiazol-2-yl group, 4-(1,1-dimethyl)ethyl-5-(4-methylpiperidin-1-yl)thiazol-2-yl group, 4,5-diphenylthiazol-2-yl-group, 4-phenylthiazol-2-yl group, 4,5-dimethyl thiazol-2-yl group, 2-thiazolyl group, 5-methylthiazol-2-yl group, 4-ethyl-5-phenylthiazol-2-yl group, 5-carboxymethyl-4-phenylthiazol-2-yl group, 5-methylcarbamoyl-4-phenylthiazol-2-yl group, 5-ethyl carbamoyl-4-phenylthiazol-2-yl group, 5-isopropylcarbamoyl-4-phenyl thiazol-2-yl group, 5-(2-phenethyl)carbamoyl-4-phenylthiazol-2-yl group, 4-(n-butyl)-5-phenylthiazol-2-yl group, 4-methyl-5-[(3-trifluoromethyl)phenyl]thiazol-2-yl group, or 5-(4-fluorophenyl)-4-methylthiazol-2-yl group; and

(38) the medicament having inhibitory action against NF-κB activation which comprises as an active ingredient a substance selected from the group consisting of the compound and a pharmacologically acceptable salt thereof, and a hydrate thereof and a solvate thereof, wherein E is 4-(1,1-dimethyl)ethyl-5-[(2,2-dimethyl)propionyl]thiazol-2-yl group.

The medicament of the present invention may be used as gene expression inhibitor of one or more substances selected from the following substance group δ: [Substance group δ] tumor necrosis factor (TNF), interleukin-1, interleukin-2, interleukin-6, interleukin-δ, granulocyte colony-stimulating factor, interferon β, cell adhension factor ICAM-1, VCAM-1, ELAM-1, nitricoxide synthetase, major histocompatibility antigen family class I, major histocompatibility antigen family class □, 82-microglobulin, immunoglobulin light chain, serum amyloid A, angiotensinogen, complement B, complement C4, c-myc, transcript derived from HIV gene, transcript derived from HTLV gene, transcript derived from simian virus 40 gene, transcript derived from cytomegalovirus gene, and transcript derived from adenovirus gene.

The medicament of the present invention may be used as an inhibitor against production and release of an inflammatory cytokine or as an immunosuppressive agent. The medicament of the present invention may be used for preventive and/or therapeutic treatment of one or more diseases selected from the following disease group ε-1:

[Disease group ε-1] an inflammatory disease, an autoimmune disease, an allergic disease, a cancers such as carcinoma and sarcoma, a metabolic disease, a cardiovascular disease, an angioproliferation disease, a septic disease, a viral disease, or from the following disease group ε-2 which is resulted from NF-κB activation or overproduction of an inflammatory cytokine:

[Disease group ε-2] an autoimmune diseases such as chronic rheumatism, osteoarthritis, systematic lupus erythematosus, systematic scleroderma, polymyositis, Sjoegren's syndrome, vasculitis syndrome, antiphospholipid syndrome, Still's disease, Behcet's disease, periarteritis nodosa, ulcerative colitis, Crohn's disease, active chronic hepatitis, glomerulonephritis, and chronic nephritis, chronic pancreatitis, gout, atherosclerosis, multiple sclerosis, arteriosclerosis, endothelial hypertrophy, psoriasis, psoriatic arthritis, contact dermatitis, atopic dermatitis, allergic disease such as pollinosis, asthma, bronchitis, interstitial pneumonia, lung disease involving granuloma, chronic obstructive pulmonary disease, chronic pulmonary thromboembolism, inflammatory colitis, insulin resistance, obesity, diabetes and its complications (nephropathy, retinopathy, neurosis, hyperinsulinemia, arteriosclerosis, hypertention, peripheral vessel obstruction and the like) a disease with abnormal vascular proliferation such as hyperlipemia, retinopathy, pneumonia, Alzheimer's disease, encephalomyelitis, acute hepatitis, chronic hepatitis, pharmaceutical composition induced toxic hepatopathy, alcoholic hepatitis, viral hepatitis, icterus, cirrhosis, hepatic insufficiency, atrial myxoma, Caslemann's syndrome, mesangial nephritis, kidney cancer, lung cancer, liver cancer, breast cancer, uterine cancer, pancreatic cancer, other solid cancer, sarcoma, osteosarcoma, metastatic invasion of cancer, carceration of inflammatory focus, cancerous cachexia, metastasis of cancer, leukemia such as acute myeloblastic leukemia, multiple myeloma, Lennert's lymphoma, malignant lymphoma, development of carcinostatic resistance of cancer, carciration of foci such as viral hepatitis and cirrhosis, carciration from polyp of colon, brain tumor, nervous tumor, endotoxic shock, sepsis, cytomegaloviral pneumonia, cytomegaloviral retinopathy, adenoviral cold, adenoviral pool fever, adenoviral ophthalmia, conjunctivitis, AIDS, uveitis, diseases or complications provoked by infections of other bacteria, viruses, and mycete, complications after surgery such as generalized inflammatory symptoms, restenosis after percutaneous tubal coronary artery plastic surgery, reperfusion disorders after vascular occulusion opening such as ischemia reperfusion disorders, organ transplantation rejection and reperfusion disorders of heart, liver, or kidney, etc., itch, anorexia, malaise, chronic fatigue syndrome, osteoporosis, metabolic bone disease such as osteocarcinomic pain, deterioration of organ during organ conservation before transplantation.

From another aspect, the present invention provides use of each of the substances for manufacture of the medicament according to the aforementioned (1) to (38).

Furthermore, the present invention provides: a method for inhibiting activation of NF-κB in a mammal including a human, which comprises the step of administering the aforementioned medicament (1) to (38) to a mammal including a human; a method for inhibiting expression of one or more substances selected from the aforementioned substance group δ in a mammal including a human, which comprises the step of administering the aforementioned medicament (1) to (38) to a mammal including a human; a method for inhibiting production and release of an inflammatory cytokine in a mammal including a human, which comprises the step of administering the aforementioned medicament (1) to (38) to a mammal including a human; a method for immune inhibition in a mammal including a human, which comprises the step of administering the aforementioned medicament (1) to (38) to a mammal including a human; a method for preventive and/or therapeutic treatment of one or more diseases selected from aforementioned disease group ε-1, which comprises the step of administering the aforementioned medicament (1) to (38) to a mammal including a human; and a method for preventive and/or therapeutic treatment of one or more diseases selected from aforementioned disease group ε-2 caused by NF-κB activation or inflammatory cytokine overproduction, which comprises the step of administering the aforementioned medicament (1) to (38) to a mammal including a human.

The present invention further provides (1) a compound represented by the general formula (I-1) or a salt thereof, or a hydrate thereof or a solvate thereof:

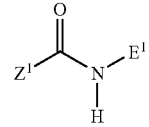

(I-1)

wherein $Z^1$ represents 2-hydroxyphenyl group which may have a substituent in the 5-position or 2-acetoxyphenyl group which may have a substituent in the 5-position, $E^1$ represents a phenyl group substituted with two $C_1$ to $C_6$ halogenated alkyl groups wherein said phenyl group may further have one or more substituents in addition to the two $C_1$ to $C_6$ halogenated alkyl groups, provided that the following compounds are excluded:

N-[3,5-bis(trifluoromethyl)phenyl]-2-hydroxybenzamide,

N-[3,5-bis(trifluoromethyl)phenyl]-5-chloro-2-hydroxybenzamide,

N-[3,5-bis(trifluoromethyl)phenyl]-5-bromo-2-hydroxybenzamide,

N-[3,5-bis(trifluoromethyl)phenyl]-2-hydroxy-5-iodobenzamide,

N-[3,5-bis(trifluoromethyl)phenyl]-2-hydroxy-5-nitrobenzamide, and 2-hydroxy-N-[2,3,5-tris(trifluoromethyl)phenyl]benzamide).

Preferred examples include:

(2) the compound or a pharmacologically acceptable salt thereof, or a hydrate thereof or a solvate thereof wherein $E^1$ is a phenyl group substituted with two $C_1$ to $C_6$ alkyl groups each of which is substituted with one or more fluorine atoms wherein said phenyl group may further have one or more substituents in addition to the two $C_1$ to $C_6$ alkyl groups which are substituted with one or more fluorine atoms;

(3) the compound or a pharmacologically acceptable salt thereof, or a hydrate thereof or a solvate thereof wherein E is a phenyl group substituted with two $C_1$ to $C_6$ alkyl groups each of which is substituted with three or more fluorine atoms wherein said phenyl group may further have one or more substituents in addition to the two $C_1$ to $C_6$ alkyl groups each of which is substituted with three or more fluorine atoms;

(4) the compound or a pharmacologically acceptable salt thereof, or a hydrate thereof or a solvate thereof wherein $E^1$ is a phenyl group substituted with two $C_1$ to $C_6$ alkyl groups each of which is substituted with three or more fluorine atoms;

(5) the compound or a pharmacologically acceptable salt thereof, or a hydrate thereof or a solvate thereof wherein $E^1$ is a group represented by the following formula:

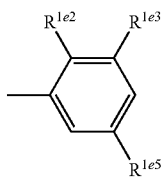

wherein one of $R^{1e2}$ and $R^{1e3}$ represents hydrogen atom and the other represents a $C_1$ to $C_6$ alkyl group substituted with three or more fluorine atoms, and $R^{1e5}$ represents a $C_1$ to $C_6$ alkyl group substituted with three or more fluorine atoms;

(6) the compound or a pharmacologically acceptable salt thereof, or a hydrate thereof or a solvate thereof wherein $E^1$ is 3,5-bis(trifluoromethyl)phenyl group, or 2,5-bis(trifluoromethyl)phenyl group;

(7) the compound or a pharmacologically acceptable salt thereof, or a hydrate thereof or a solvate thereof wherein $E^1$ is 2,5-bis(trifluoromethyl)phenyl group;

(8) the compound or a pharmacologically acceptable salt thereof, or a hydrate thereof or a solvate thereof wherein $Z^1$ is a group represented by the following formula:

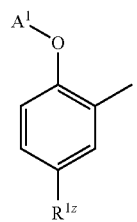

wherein $A^1$ represents hydrogen atom or acetyl group, $R^{1z}$ represents hydrogen atom, a halogen atom, nitro group, cyano group, hydroxy group which may be substituted, amino group which may be substituted, a hydrocarbon group which may be substituted, a heteroring group which may be substituted, an acyl group which may be substituted, an ureido group which may be substituted, a thioureido group which may be substituted, a diazenyl group which may be substituted;

(9) the compound or a pharmacologically acceptable salt thereof, or a hydrate thereof or a solvate thereof wherein $A^1$ is hydrogen atom;

(10) the compound or a pharmacologically acceptable salt thereof, or a hydrate thereof or a solvate thereof wherein $R^{1z}$ is hydrogen atom, a halogen atom, nitro group, cyano group, a $C_1$ to $C_6$ alkoxy group which may be substituted, a di($C_1$ to $C_6$ alkyl)-amino group, a $C_1$ to $C_6$ alkyl group which may be substituted, a $C_1$ to $C_6$ halogenated alkyl group which may be substituted, a $C_2$ to $C_6$ alkenyl group which may be substituted, a $C_2$ to $C_6$ alkynyl group which may be substituted, a $C_6$ to $C_{10}$ aryl group which may be substituted, a $C_7$ to $C_{16}$ aralkyl group which may be substituted, a 5 to 6 membered heteroaryl group which may be substituted, a $C_1$ to $C_6$ alkylcarbonyl group which may be substituted, a $C_1$ to $C_6$ alkoxylcarbonyl group which may be substituted, a 5-membered heteroaryl-sulfonyl group which may be substituted, or diazenyl group which may be substituted;

(11) the compound or a pharmacologically acceptable salt thereof, or a hydrate thereof or a solvate thereof wherein $R^{1z}$ is a halogen atom, a $C_1$ to $C_6$ alkyl groups which may be substituted, a $C_1$ to $C_6$ halogenated alkyl group which may be substituted; and

(12) the compound or a pharmacologically acceptable salt thereof, or a hydrate thereof or a solvate thereof wherein $R^{1z}$ is a halogen atom.

Most preferably, the following compounds or pharmacologically acceptable salts thereof, or hydrates thereof or solvates thereof are provided.

N-[3,5-bis(trifluoromethyl)phenyl]-5-fluoro-2-hydroxybenzamide,

N-[3,5-bis(trifluoromethyl)phenyl]-5-cyano-2-hydroxybenzamide,

N-[3,5-bis(trifluoromethyl)phenyl]-2-hydroxy-5-methylbenzamide,

N-[3,5-bis(trifluoromethyl)phenyl]-5-(1,1-dimethyl)ethyl-2-hydroxybenzamide,

N-[3,5-bis(trifluoromethyl)phenyl]-2-hydroxy-5-(trifluoromethyl)benzamide,

N-[3,5-bis(trifluoromethyl)phenyl]-2-hydroxy-5-(1,1,2,2,2-pentafluoroethyl)benzamide, N-[3,5-bis(trifluoromethyl)phenyl]-2-hydroxy-5-(2-phenylethen-1-yl)benzamide, N-[3,5-bis(trifluoromethyl)phenyl]-5-(2,2-dicyanoethen-1-yl)-2-hydroxybenzamide, 3-({3-[3,5-bis(trifluoromethyl)phenyl]carbamoyl}-4-hydroxyphenyl)-2-cyanoacrylic acid methyl ester, 3-({3-[3,5-bis(trifluoromethyl)phenyl]carbamoyl}-4 hydroxyphenyl)-2-cyanoacrylic acid,
N-[3,5-bis(trifluoromethyl)phenyl]-5-ethynyl-2-hydroxybenzamide,
N-[3,5-bis(trifluoromethyl)phenyl]-2-hydroxy-5-(phenylethynyl)benzamide,
N-[3,5-bis(trifluoromethyl)phenyl]-2-hydroxy-5-[(trimethylsilyl)ethynyl]benzamide,
N-[3,5-bis(trifluoromethyl)phenyl]-4-hydroxybiphenyl-3-carboxamide,
N-[3,5-bis(trifluoromethyl)phenyl]-2-hydroxy-5-(2-phenylethyl)benzamide,
N-[3,5-bis(trifluoromethyl)phenyl]-2-hydroxy-5-(3-thienyl)benzamide,
N-[3,5-bis(trifluoromethyl)phenyl]-2-hydroxy-5-(1-pyrrolyl)benzamide,
N-[3,5-bis(trifluoromethyl)phenyl]-2-hydroxy-5-(2-methylthiazol-4-yl)benzamide,
N-[3,5-bis(trifluoromethyl)phenyl]-2-hydroxy-5-(2-pyridyl)benzamide,
N-[3,5-bis(trifluoromethyl)phenyl]-5-dimethylamino-2-hydroxybenzamide,
5-benzoylamino-N-[3,5-bis(trifluoromethyl)phenyl]-2-hydroxybenzamide,
$N^a$-[3,5-bis(trifluoromethyl)phenyl]-4-hydroxy-$N^1$,$N^1$-dimethyliso phthalamide,
$N^1$,$N^3$-bis[3,5-bis(trifluoromethyl)phenyl]-4-hydroxyisophthalamide,
N-[3,5-bis(trifluoromethyl)phenyl]-2-hydroxy-5-(piperidine-1-carbonyl)benzamide,
N-[3,5-bis(trifluoromethyl)phenyl]-2-hydroxy-5-(4-benzylpiperidine-1-carbonyl)-benzamide,
N-[3,5-bis(trifluoromethyl)phenyl]-5-dimethylsulfamoyl-2-hydroxybenzamide,
N-[3,5-bis(trifluoromethyl)phenyl]-2-hydroxy-5-(pyrrole-1-sulfonyl)benzamide,
5-acetyl-N-[3,5-bis(trifluoromethyl)phenyl]-2-hydroxybenzamide,
N-[3,5-bis(trifluoromethyl)phenyl]-2-hydroxy-5-isobutyrylbenzamide,
N-[3,5-bis(trifluoromethyl)phenyl]-4-hydroxyisophthalamic acid methylester,
N-[3,5-bis(trifluoromethyl)phenyl]-2-hydroxy-5-[(4-nitrophenyl)diazenyl]benzamide,
N-[3,5-bis(trifluoromethyl)phenyl]-2-hydroxy-5-({[(4-pyridin-2-yl)sulfamoyl]phenyl}-diazenyl)benzamide,
N-[3,5-bis(trifluoromethyl)phenyl]-2-hydroxy-5-[(3-phenyl)ureido]benzamide,
N-[3,5-bis(trifluoromethyl)phenyl]-2-hydroxy-5-[(3-phenyl)thioureido]benzamide,
N-[3,5-bis(trifluoromethyl)phenyl]-2-hydroxy-5-(1-hydroxyethyl)benzamide,
N-[3,5-bis(trifluoromethyl)phenyl]-2-hydroxy-5-methoxybenzamide,
N-[3,5-bis(trifluoromethyl)phenyl]-2-hydroxy-5-[1-(methoxyimino)ethyl]benzamide,
5-{1-[(benzyloxy)imino]ethyl}-N-[3,5-bis(trifluoromethyl)phenyl]-2-hydroxybenzamide,
N-[2,5-bis(trifluoromethyl)phenyl]-5-chloro-2-hydroxybenzamide,
N-(2,5-bis(trifluoromethyl)phenyl-5-bromo-2-hydroxybenzamide,
2-acetoxy-N-[3,5-bis(trifluoromethyl)phenyl]benzamide,
2-acetoxy-N-[2,5-bis(trifluoromethyl)phenyl]-5-chlorobenzamide, and
2-acetoxy-N-[3,5-bis(trifluoromethyl)phenyl]-5-chlorobenzamide.

The present invention further provides the compound represented by the following general formula (I-2) or a pharmacologically acceptable salt thereof, or a hydrate thereof or a solvate thereof:

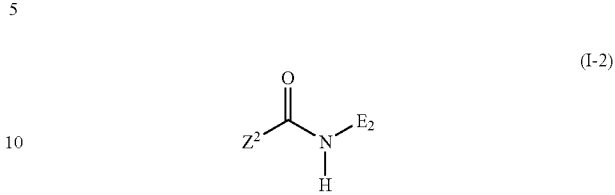

(I-2)

wherein $Z^2$ represents 2-hydroxyphenyl group which may be substituted in the 5-position, or 2-acetoxyphenyl group which may be substituted in the 5-position, $E^2$ represents a phenyl group whose 3-position or 5-position is substituted with a $C_1$ to $C_6$ halogenated alkyl group wherein said phenyl group may further have one or more substituents (except when the substituent is a $C_1$ to $C_6$ halogenated alkyl group) in addition to the $C_1$ to $C_6$ halogenated alkyl group in the 3-position or 5-position, provided that the following compounds are excluded:
5-chloro-2-hydroxy-N-[3-(trifluoromethyl)phenyl]benzamide,
5-bromo-2-hydroxy-N-[3-(trifluoromethyl)phenyl]benzamide,
2-hydroxy-5-iodo-N-[3-(trifluoromethyl)phenyl]benzamide,
5-chloro-N-[4-chloro-3-(trifluoromethyl)phenyl]-2-hydroxybenzamide,
5-chloro-N-[5-chloro-3-(trifluoromethyl)phenyl]-2-hydroxybenzamide,
5-chloro-2-hydroxy-N-[4-nitro-3-(trifluoromethyl)phenyl]benzamide,
5-fluoro-2-hydroxy-N-[2-(2,2,2-trifluoroethoxy)-5-(trifluoromethyl)phenyl]benzamide,
5-fluoro-2-hydroxy-N-[2-(6,6,6-trifluorohexyloxy)-5-(trifluoromethyl)phenyl]-benzamide
5-chloro-2-hydroxy-N-(3-trifluoromethyl-4-{[4-(trifluoromethyl)sulfanyl]phenoxy}-phenyl)benzamide
N-[4-(benzothiazol-2-yl)sulfanyl-3-(trifluoromethyl)phenyl]-5-chloro-2-hydroxybenzamide
5-chloro-N-[2-(4-chlorophenoxy)-5-(trifluoromethyl)phenyl]-2-hydroxybenzamide,
5-chloro-2-hydroxy-N-[2-(4-methylphenoxy)-5-(trifluoromethyl)phenyl]benzamide,
5-chloro-N-[2-(4-chlorophenyl)sulfanyl-5-(trifluoromethyl)phenyl]-2-hydroxybenzamide
5-chloro-2-hydroxy-N-[2-(1-naphthyloxy)-5-(trifluoromethyl)phenyl]benzamide, and
5-chloro-2-hydroxy-N-[2-(2-naphthyloxy)-5-(trifluoromethyl)phenyl]benzamide.
Preferred examples include:
(2) the compound or a pharmacologically acceptable salt thereof, or a hydrate thereof or a solvate thereof wherein $E^2$ is a phenyl group whose 3-position or 5-position is substituted with a $C_1$ to $C_6$ alkyl group which is substituted with one or more fluorine atoms wherein said phenyl group may have one or more substituents (except when the substituent is a $C_1$ to $C_6$ halogenated alkyl group) in addition to the $C_1$ to $C_6$ alkyl group in the 3-position or the 5-position which is substituted with one or more fluorine atoms;
(3) the compound or a pharmacologically acceptable salt thereof, or a hydrate thereof or a solvate thereof wherein $E^2$ is a phenyl group whose 3-position or 5-position is substituted with a $C_1$ to $C_6$ alkyl group which is substituted with three or more fluorine atoms wherein said phenyl group may have one or more substituents (except when the substituent is a $C_1$ to $C_6$ halogenated alkyl group) in addition to the $C_1$ to $C_6$ alkyl group in the 3-position or the 5-position which is substituted with three or more fluorine atoms;

(4) the compound or a pharmacologically acceptable salt thereof, or a hydrate thereof or a solvate thereof wherein $E^2$ is a phenyl group whose 3-position or 5-position is substituted with a $C_1$ to $C_6$ alkyl group which is substituted with three or more fluorine atoms wherein said phenyl group may have one or more substituents selected from the following substituent group γ-7e in addition to the $C_1$ to $C_6$ alkyl group in the 3-position or 5-position which is substituted with three or more fluorine atoms: [substituent group γ-7e] a halogen atom, nitro group, cyano group, a $C_1$ to $C_6$ alkyl group which may be substituted, a 5 to 6 membered nonaromatic heterocyclic group which may be substituted, a $C_1$ to $C_6$ alkoxy group which may be substituted, a $C_1$ to $C_6$ alkyl-sulfanyl group which may be substituted;

(6) the compound or a pharmacologically acceptable salt thereof, or a hydrate thereof or a solvate thereof wherein $E^2$ is 3-(trifluoromethyl)phenyl group, 2-fluoro-3-(trifluoromethyl)phenyl group, 2-fluoro-5-(trifluoromethyl)phenyl group, 2-chloro-5-(trifluoromethyl)phenyl group, 3-fluoro-5-(trifluoromethyl)phenyl group, 3-bromo-5-(trifluoromethyl)phenyl group, 4-fluoro-3-(trifluoromethyl)phenyl group, 4-chloro-3-(trifluoromethyl)phenyl group, 2-nitro-5-(trifluoromethyl)phenyl group, 4-nitro-3-(trifluoromethyl)phenyl group, 4-cyano-3-(trifluoromethyl)phenyl group, 2-methyl-3-(trifluoromethyl)phenyl group, 2-methyl-5-(trifluoromethyl)phenyl group, 4-methyl-3-(trifluoromethyl)phenyl group, 2-methoxy-5-(trifluoromethyl)phenyl group, 3-methoxy-5-(trifluoromethyl)phenyl group, 4-methoxy-3-(trifluoromethyl)phenyl group, 2-(methylsulfanyl)-5-(trifluoromethyl)phenyl group, 2-(1-pyrrolidino)-5-(trifluoromethyl)phenyl group, or 2-morpholino-5-(trifluoromethyl)phenyl group;

(7) the compound or a pharmacologically acceptable salt thereof, or a hydrate thereof or a solvate thereof wherein $Z^2$ is a group represented by the following formula:

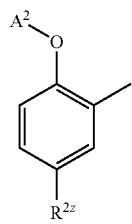

wherein $A^2$ represents hydrogen atom or acetyl group, $R^{3z}$ represents a halogen atom, a $C_1$ to $C_6$ alkyl group or a $C_1$ to $C_6$ halogenated alkyl group;

(8) the compound or a pharmacologically acceptable salt thereof, or a hydrate thereof or a solvate thereof wherein $A^2$ is hydrogen atom; and (9) the compound or a pharmacologically acceptable salt thereof, or a hydrate thereof or a solvate thereof wherein $R^{2z}$ is halogen atom.

Most preferably, the following compounds or pharmacologically acceptable salts thereof, or hydrates thereof or solvates thereof are provided:

5-chloro-N-[2-fluoro-3-(trifluoromethyl)phenyl]-2-hydroxybenzamide,
5-chloro-N-[2-fluoro-5-(trifluoromethyl)phenyl]-2-hydroxybenzamide,
5-chloro-N-[2-chloro-5-(trifluoromethyl)phenyl]-2-hydroxybenzamide,
5-bromo-N-2-chloro-5-(trifluoromethyl)phenyl-2-hydroxybenzamide,
2-acetoxy-5-chloro-N-[2-chloro-5-(trifluoromethyl)phenyl]benzamide,
N-[2-chloro-5-(trifluoromethyl)phenyl]-2-hydroxy-5-methylbenzamide,
5-chloro-N-[3-fluoro-5-(trifluoromethyl)phenyl]-2-hydroxybenzamide,
5-bromo-N-[3-bromo-5-(trifluoromethyl)phenyl]-2-hydroxybenzamide,
5-chloro-N-[3-fluoro-5-(trifluoromethyl)phenyl]-2-hydroxybenzamide,
5-chloro-N-[4-fluoro-3-(trifluoromethyl)phenyl]-2-hydroxybenzamide,
5-bromo-N-[4-chloro-3-(trifluoromethyl)phenyl]-2-hydroxybenzamide,
N-[4-chloro-3-(trifluoromethyl)phenyl]-2-hydroxy-5-methylbenzamide,
5-chloro-2-hydroxy-N-[2-nitro-5-(trifluoromethyl)phenyl]benzamide,
5-bromo-N-[4-cyano-3-(trifluoromethyl)phenyl]-2-hydroxybenzamide,
5-chloro-2-hydroxy-N-[2-methyl-3-(trifluoromethyl)phenyl]benzamide,
5-chloro-2-hydroxy-N-[2-methyl-5-(trifluoromethyl)phenyl]benzamide,
2-hydroxy-5-methyl-N-[2-methyl-5-(trifluoromethyl)phenyl]benzamide,
5-chloro-2-hydroxy-N-[4-methyl-3-(trifluoromethyl)phenyl]benzamide,
2-hydroxy-5-methyl-N-[4-methyl-3-(trifluoromethyl)phenyl]benzamide,
5-bromo-2-hydroxy-N-[2-methoxy-5-(trifluoromethyl)phenyl]benzamide,
5-chloro-2-hydroxy-N-[2-methoxy-5-trifluoromethyl)phenyl]benzamide,
2 hydroxy-N-[2-methoxy-5-(trifluoromethyl)phenyl]-5-methylbenzamide,
5-bromo-2-hydroxy-N-[3-methoxy-5-(trifluoromethyl)phenyl]benzamide,
5-chloro-2-hydroxy-N-[4-methoxy-3-(trifluoromethyl)phenyl]benzamide,
2-hydroxy-N-[4-methoxy-3-(trifluoromethyl)phenyl]-5-methylbenzamide,
5-chloro-2-hydroxy-N-[2-methylsulfanyl-5-(trifluoromethyl)phenyl]benzamide,
5-chloro-2-hydroxy-N-[2-(1-pyrrolidino)-5-(trifluoromethyl)phenyl]benzamide, and
5-chloro-2-hydroxy-N-[2-morpholino-5-(trifluoromethyl)phenyl]benzamide.

Furthermore, the present invention provides (1) the compound represented by the following general formula (I-3) or a pharmacologically acceptable salt thereof, or a hydrate thereof or a solvate thereof:

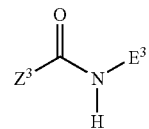

(I-3)

wherein $Z^3$ represents 2-hydroxyphenyl group which may be substituted in the 5-position or 2-acetoxyphenyl group which may be substituted in the 5-position, $E^3$ represents a group represented by the following formula:

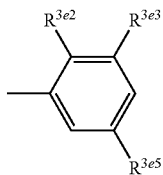

wherein $R^{3e2}$ and $R^{3e3}$ may be the same or different and each represents hydrogen atom, a hydrocarbon group which may be substituted, or hydroxy group which may be substituted, except that where both of $R^{3e2}$ and $R^{3e3}$ are hydrogen atoms is excluded, $R^{3e5}$ represents a $C_2$ to $C_6$ hydrocarbon group which may be substituted.

Preferred examples include:
(2) the compound or a pharmacologically acceptable salt thereof, or a hydrate thereof or a solvate thereof wherein $R^{3e2}$ and $R^{3e3}$ may be the same or different and each represents hydrogen atom, a $C_1$ to $C_6$ alkyl group which may be substituted, or a $C_1$ to $C_6$ alkoxy group which may be substituted, provided that where both of $R^{3e2}$ and $R^{3e3}$ are hydrogen atoms is excluded, $R^{3e5}$ is a $C_2$ to $C_6$ alkyl group which may be substituted;
(3) the compound or a pharmacologically acceptable salt thereof, or a hydrate thereof or a solvate thereof wherein $E^3$ is 2,5-bis[(1,1-dimethyl)ethyl]phenyl group, 3,5-bis[(1,1-dimethyl)ethyl]phenyl group, or 5-(1,1-dimethyl)ethyl-2-methoxyphenyl group;
(4) the compound or a pharmacologically acceptable salt thereof, or a hydrate thereof or a solvate thereof wherein $Z^3$ is a group represented by the following formula:

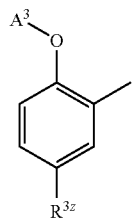

wherein $A^3$ represents hydrogen atom or acetyl group, $R^{3z}$ represents a halogen atom, a $C_1$ to $C_6$ alkyl group, or a $C_1$ to $C_6$ halogenated alkyl group;
(5) the compound or a pharmacologically acceptable salt thereof, or a hydrate thereof or a solvate thereof wherein $A^3$ is hydrogen atom;
(6) the compound or a pharmacologically acceptable salt thereof, or a hydrate thereof or a solvate thereof wherein $R^{3z}$ is halogen atom.

Most preferably, the following compounds or pharmacologically acceptable salts thereof, or hydrates thereof or solvates thereof are provided:
N-{2,5-bis[(1,1-dimethyl)ethyl]phenyl}-5-chloro-2-hydroxybenzamide,
N-{2,5-bis[(1,1-dimethyl)ethyl]phenyl}-2-hydroxy-5-methylbenzamide,
N-{3,5-bis[(1,1-dimethyl)ethyl]phenyl}-5-chloro-2-hydroxybenzamide,
N-{3,5-bis[(1,1-dimethyl)ethyl]phenyl}-5-bromo-2-hydroxybenzamide,
N-{3,5-bis[(1,1-dimethyl)ethyl]phenyl}-2-hydroxy-5-methylbenzamide,
2-acetoxy-N-{3,5-bis[(1,1-dimethyl)ethyl]phenyl}-5-chlorobenzamide,
5-chloro-N-[5-(1,1-dimethyl)ethyl-2-methoxyphenyl]-2-hydroxybenzamide,
N-[5-(1,1-dimethyl)ethyl-2-methoxyphenyl]-2-hydroxy-5-benzamide, and
2-acetoxy-5-chloro-N-[5-(1,1-dimethyl)ethyl-2-methoxyphenyl]benzamide.

The present invention further provides (1) the compound represented by the following general formula (I-4) or a pharmacologically acceptable salt thereof, or a hydrate thereof or a solvate thereof:

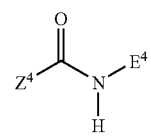

(I-4)

wherein $Z^4$ represents 2-hydroxyphenyl group which may be substituted in the 5-position or 2-acetoxyphenyl group which may be substituted in the 5-position, $E^4$ is a group represented by the following formula:

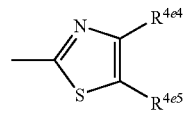

wherein $R^{4e4}$ represents a hydrocarbon group which may be substituted, $R^{4e5}$ represents a halogen atom, cyano group, acyl group which may be substituted, or a heteroring group which may be substituted.

Preferred examples include:
(2) the compound or a pharmacologically acceptable salt thereof, or a hydrate thereof or a solvate thereof wherein $R^{4e4}$ represents a $C_1$ to $C_6$ alkyl group which may be substituted, a $C_1$ to $C_6$ halogenated alkyl group which may be substituted, or a $C_6$ to $C_{10}$ aryl group which may be substituted, $R^{4e5}$ represents a halogen atom, cyano group, a $C_1$ to $C_6$ alkyl-carbonyl group which may be substituted, a $C_6$ to $C_{10}$ aryl-carbonyl group which may be substituted, a $C_1$ to $C_6$ alkoxy-carbonyl group which may be substituted, or a 6-membered nonaromatic heteroring group which may be substituted:
(3) the compound or a pharmacologically acceptable salt thereof, or a hydrate thereof or a solvate thereof wherein $E^4$ is 5-bromo-4-[(1,1-dimethyl)ethyl]thiazol-2-yl group, 5-bromo-4-(trifluoromethyl)thiazol-2-yl group, 5-cyano-4-[(1,1-dimethyl)ethyl]thiazol-2-yl group, 4-(1,1-dimethyl)ethyl-5-[(2,2-dimethyl)propionyl]thiazol-2-yl group, 5-acetyl-4-phenylthiazol-2-yl group, 5-benzoyl-4-phenylthiazol-2-yl group, 4-(1,1-dimethyl)ethyl-5-(ethoxycarbonyl)thiazol-2-yl group, 5-ethoxycarbonyl-4 (trifluoromethyl)thiazol-2-yl group, 5-ethoxycarbonyl-4-phenylthiazol-2-yl group, 5-ethoxycarbonyl-4-(pentafluorophenyl)thiazol-2-yl group, 4-(1,1-dimethyl)ethyl-5-piperidinothiazol-2-yl group, 4-(1,1-dimethyl)ethyl-5-morpholinothiazol-2-yl group, 4-(1,1-dimethyl)ethyl-5-(4-methylpiperidin-1-yl)thiazol-2-yl group, or 4-(1,1-dimethyl)ethyl-5-(4-phenylpiperidin-1-yl)thiazol-2-yl group;

(4) the compound or a pharmacologically acceptable salt thereof, or a hydrate thereof or a solvate thereof wherein E⁴ is 4-(1,1-dimethyl)ethyl-5-[(2,2-dimethyl)propionyl]thiazol-2-yl group;

(5) the compound or a pharmacologically acceptable salt thereof, or a hydrate thereof or a solvate thereof wherein Z⁴ is a group represented by the following formula:

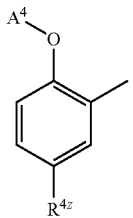

wherein A⁴ represents hydrogen atom or acetyl group, R$^{4z}$ represents a halogen atom, a $C_6$ to $C_{10}$ aryl group which may be substituted, or a 5-membered heteroaryl group;

(6) the compound or a pharmacologically acceptable salt thereof, or a hydrate thereof or a solvate thereof wherein A⁴ is hydrogen atom; and (7) the compound or a pharmacologically acceptable salt thereof, or a hydrate thereof or a solvate thereof wherein R$^{4z}$ is a halogen atoms.

Most preferably, the following compounds or pharmacologically acceptable salts thereof, or hydrates thereof or solvates thereof are provided.

5-bromo-N-{5-bromo-4-[(1,1-dimethyl)ethyl]thiazol-2-yl}-2-hydroxybenzamide,
5-bromo-N-[5-bromo-4-(trifluoromethyl)thiazol-2-yl]-2-hydroxybenzamide,
5-chloro-N-{5-cyano-4-[(1,1-dimethyl)ethyl]thiazol-2-yl}-2-hydroxybenzamide,
5-bromo-N-{5-cyano-4-[(1,1-dimethyl)ethyl]thiazol-2-yl}-2-hydroxybenzamide,
5-chloro-N-{4-(1,1-dimethyl)ethyl-5-[(2,2-dimethyl)propionyl]thiazol-2-yl}-2-hydroxybenzamide,
5-bromo-N-{4-(1,1-dimethyl)ethyl-5-[(2,2-dimethyl)propionyl]thiazol-2-yl}-2-hydroxybenzamide,
N-(5-acetyl-4-phenylthiazol-2-yl)-5-bromo-2-hydroxy benzamide,
N-(5-benzoyl-4-phenylthiazol-2-yl)-5-bromo-2-hydroxybenzamide,
2-(5-bromo-2-hydroxybenzoyl)amino-4-[(1,1-dimethyl)ethyl]thiazol-5-carboxylic acid ethylester,
2-(5-bromo-2-hydroxybenzoyl)amino-4 (trifluoromethyl)thiazol-5-carboxylic acid ethylester,
2-(5-chloro-2-hydroxybenzoyl)amino-4-phenylthiazol-5-carboxylic acid ethylester,
2-(5-bromo-2-hydroxybenzoyl)amino-4-phenylthiazol-5-carboxylic acid ethylester,
2-[(4-hydroxybiphenyl)-3-carbonyl]amino-4-phenylthiazol-5-carboxylic acid ethylester,
2-[(4'-fluoro-4-hydroxybiphenyl)-3-carbonyl]amino-4-phenylthiazol-5-carboxylic acid ethylester,
2-[(2',4'-difluoro-4-hydroxybiphenyl)-3-carbonyl]amino-4-phenylthiazol-5-carboxylic acid ethylester,
2-{([4-hydroxy-4'-(trifluoromethyl)biphenyl]-3-carbonyl}amino-4-phenylthiol-5-carboxylic acid ethylester,
2-[2-hydroxy-5-(1-pyrrolyl)benzoyl]amino 4-phenylthiazol-5-carboxylic acid ethylester,
2-[2-hydroxy-5-(1-thienyl)benzoyl]amino-4-phenylthiazol-5-carboxylic acid ethylester,
2-(5-bromo-2-hydroxybenzoyl)amino-4-(pentafluorophenyl)thiazol-5-carboxylic acid ethylester,
5-bromo-N-[4-(1,1-dimethyl)ethyl-5-piperidinothiazol-2-yl]-2-hydroxybenzamide,
5-bromo-N-[4-(1,1-dimethyl)ethyl-5-morpholinothiazol-2-yl]-2-hydroxybenzamide,
5-bromo-N-[4-(1,1-dimethyl)ethyl-5-(4-methylpiperidin-1-yl)thiazol-2-yl]-2-hydroxybenzamide, and
5-bromo-N-[4-(1,1-dimethyl)ethyl-5-(4-phenylpiperidin-1-yl)thiazol-2-yl]-2-hydroxybenzamide.

BEST MODE FOR CARRYING OUT THE INVENTION

The terms used in the present specification have the following meanings.

As the halogen atom, any of fluorine atom, chlorine atom, bromine atom, or iodine atom may be used unless otherwise specifically referred to.

Examples of the hydrocarbon group include, for example, an aliphatic hydrocarbon group, an aryl group, an arylene group, an aralkyl group, a bridged cyclic hydrocarbon group, a spiro cyclic hydrocarbon group, and a terpene hydrocarbon.

Examples of the aliphatic hydrocarbon group include, for example, alkyl group, alkenyl group, alkynyl group, alkylene group, alkenylene group, alkylidene group and the like which are straight chain or branched chain monovalent or bivalent acyclic hydrocarbon groups; cycloalkyl group, cycloalkenyl group, cycloalkanedienyl group, cycloalkyl-alkyl group, cycloalkylene group, and cycloalkenylene group, which are saturated or unsaturated monovalent or bivalent alicyclic hydrocarbon groups.

Examples of the alkyl group include, for example, methyl, ethyl, n-propyl, isopropyl, n-butyl, isobutyl, sec-butyl, tert-butyl, n-pentyl, isopentyl, 2-methylbutyl, 1-methylbutyl, neopentyl, 1,2-dimethylpropyl, 1-ethylpropyl, n-hexyl, 4-methylpentyl, 3-methylpentyl, 2-methylpentyl, 1-methylpentyl, 3,3-dimethylbutyl, 2,2-dimethylbutyl, 1,1-dimethylbutyl, 1,2-dimethylbutyl, 1,3-dimethylbutyl, 2,3-dimethylbutyl, 2-ethylbutyl, 1-ethylbutyl, 1-ethyl-1-methylpropyl, n-heptyl, n-octyl, n-nonyl, n-decyl, n-undecyl, n-dodecyl, n-tridecyl, n-tetradecyl, and n-pentadecyl group, which are $C_1$ to $C_{15}$ straight chain or branched chain alkyl groups.

Examples of the alkenyl group include, for example, vinyl, prop-1-en-1-yl, allyl, isopropenyl, but-1-en-1-yl, but-2-en-1-yl, but-3-en-1-yl, 2-methylprop-2-en-1-yl, 1-methylprop-2-en-1-yl, pent-1-en-1-yl, pent-2-en-1-yl, pent-3-en-1-yl, pent-4-en-1-yl, 3-methylbut-2-en-1-yl, 3-methylbut-3-en-1-yl, hex-1-en-1-yl, hex-2-en-1-yl, hex-3-en-1-yl, hex-4-en-1-yl, hex-5-en-1-yl, 4-methylpent-3-en-1-yl, 4-methylpent-3-en-1-yl, hept-1-en-1-yl, hept-6-en 1-yl, oct-1-en-1-yl, oct-7-en-1-yl, non-1-en-1-yl, non-8-en-1-yl, dec-1-en-1-yl, dec-9-en-1-yl, undec-1-en-1-yl, undec-10-en-1-yl, dodec-1-en-1-yl, dodec-11-en-1-yl, tridec-1-en-1-yl, tridec-12-en-1-yl, tetradec-1-en-1-yl, tetradec-13-en-1-yl, pentadec-1-en-1-yl, and pentadec-14-en-1-yl group, which are $C_2$ to $C_{15}$ straight chain or branched chain alkenyl groups.

Examples of the alkynyl group include, for example, ethynyl, prop-1-yn-1-yl, prop-2-yn-1-yl, but-1-yn-1-yl, but-3-yn-1-yl, 1-methylprop-2-yn-1-yl, pent-1-yn-1-yl, pent-4-yn-1-yl, hex-1-yn-1-yl, hex-5-yn-1-yl, hept-1-yn-1-yl, hept-6-yn-1-yl, oct-1-yn-1-yl, oct-7-yn-1-yl, non-1-yn-1-yl, non-8-yn-1-yl, dec-1-yn-1-yl, dec-9-yn-1-yl, undec-1-yn-1-yl, undec-10-yn-1-yl, dodec-1-yn-1-yl, dodec-11-yn-1-yl, tridec-1-yn-1-yl, tridec-12-yn-1-yl, tetradec-1-yn-1-yl, tetradec-13-yn-1- yl, pentadec-1-yn-1-yl, and pentadec-14-yn-1-yl group, which are $C_2$ to $C_{15}$ straight chain or branched chain alkynyl groups.

Examples of the alkylene group include, for example, methylene, ethylene, ethane-1,1-diyl, propane-1,3-diyl, propane-1,2-diyl, propane-2,2-diyl, butane-1,4-diyl, pentane-1,5-diyl, hexane-1,6-diyl, and 1,1,4,4-tetramethylbutane-1,4-diyl group, which are $C_1$ to $C_6$ straight chain or branched chain alkylene groups.

Examples of the alkenylene group include, for example, ethene-1,2-diyl, propene-1,3-diyl, but-1-ene-1,4-diyl, but-2-ene-1,4-diyl, 2-methylpropene-1,3-diyl, pent-2-ene-1,5-diyl, and hex-3-ene-1,6-diyl group, which are $C_1$ to $C_6$ straight chain or branched chain alkylene groups.

Examples of the alkylidene group include, for example, methylidene, ethylidene, propylidene, isopropylidene, butylidene, pentylidene, and hexylidene, which are $C_1$ to $C_6$ straight chain or branched chain alkylidene groups.

Examples of the cycloalkyl group include, for example, cyclopropyl, cyclobutyl, cyclopentyl, cyclohexyl, cycloheptyl, and cyclooctyl, which are $C_3$ to $C_8$ cycloalkyl groups.

The aforementioned cycloalkyl group may be fused with benzene ring, naphthalene ring and the like, and examples include, for example, 1-indanyl, 2-indanyl, 1,2,3,4-tetrahydronaphthalen-1-yl, and 1,2,3,4-tetrahydronaphthalen-2-yl group.

Examples of the cycloalkenyl group includes, for example, 2-cyclopropen-1-yl, 2-cyclobuten-1-yl, 2-cyclopenten-1-yl, 3-cyclopenten-1-yl, 2-cyclohexen-1-yl, 3-cyclohexen-1-yl, 1-cyclobuten-1-yl, and 1-cyclopenten-1-yl group, which are $C_3$ to $C_6$ cycloalkenyl groups.

The aforementioned cycloalkenyl group may be fused with benzene ring, naphthalene ring and the like, and examples include, for example, 1-indanyl, 2-indanyl, 1,2,3,4-tetrahydronaphthalen-1-yl, 1,2,3,4,-tetrahydronaphthalen-2-yl, 1-indenyl, and 2-indenyl group.

Examples of the cycloalkanedienyl group include, for example, 2,4-cyclopentadien-1-yl, 2,4-cyclohexanedien-1-yl, and 2,5-cyclohexanedien-1-yl group, which are $C_5$ to $C_6$ cycloalkanedienyl groups.

The aforementioned cycloalkanedienyl group may be fused with benzene ring, naphthalene ring and the like, and examples of the group include, for example, 1-indenyl and 2-indenyl group.

Examples of the cycloalkyl-alkyl group include the group in which one hydrogen atom of alkyl group is substituted with cycloalkyl group, and include, for example, cyclopropylmethyl, 1-cyclopropylethyl, 2-cyclopropylethyl, 3-cyclopropylpropyl, 4-cyclopropylbutyl, 5-cyclopropylpentyl, 6-cyclopropylhexyl, cyclobutylmethyl, cyclopentylmethyl, cyclobutylmethyl, cyclopentylmethyl, cyclohexylmethyl, cyclohexylpropyl, cyclohexylbutyl, cycloheptylmethyl, cyclooctylmethyl, and 6-cyclooctylhexyl group, which are $C_4$ to $C_{14}$ cycloalkyl-alkyl groups.

Examples of the cycloalkylene group include, for example, cyclopropane-1,1-diyl, cyclopropane-1,2-diyl, cyclobutane-1,1-diyl, cyclobutane-1,2-diyl, cyclobutane-1,3-diyl, cyclopentane-1,1-diyl, cyclopentane-1,2-diyl, cyclopentane-1,3-diyl, cyclohexane-1,1-diyl, cyclohexane-1,2-diyl, cyclohexane-1,3-diyl, cyclohexane-1,4-diyl, cycloheptane-1,1-diyl, cycloheptane-1,2-diyl, cyclooctane-1,1,-diyl, and cyclooctane-1,2-diyl group, which are $C_3$ to $C_8$ cycloalkylene groups.

Examples of the cycloalkenylene group include, for example, 2-cyclopropene-1,1-diyl, 2-cyclobutene-1,1-diyl, 2-cyclopentene-1,1-diyl, 3-cyclopentene-3,1-diyl, 2-cyclohexene-1,1-diyl, 2-cyclohexene-1,2-diyl, 2-cyclohexene-1,4-diyl, 3-cyclohexene-1,1-diyl, 1-cyclobutene-1,2-diyl, 1-cyclopentene-1,2-diyl, and 1-cyclohexene-1,2-diyl group, which are $C_3$ to $C_6$ cycloalkenylene groups.

Examples of the aryl group include a monocyclic or a fused polycyclic aromatic hydrocarbon group, and include, for example, phenyl, 1-naphtyl, 2-naphtyl, anthryl, phenanthryl, and acenaphthylenyl group, which are $C_6$ to $C_{14}$ aryl groups.

The aforementioned aryl group may be fused with aforementioned $C_3$ to $C_8$ cycloalkyl group, $C_3$ to $C_6$ cycloalkenyl group, $C_5$ to $C_6$ cycloalkanedienyl group or the like, and the example of the group include, for example, 4-indanyl, 5-indanyl, 1,2,3,4-tetrahydronaphthalen-5-yl, 1,2,3,4-tetrahydronaphthalen-6-yl, 3-acenaphthenyl, 4-acenaphthenyl, inden-4-yl, inden-5-yl, inden-6-yl, inden-7-yl, 4-phenalenyl, 5-phenalenyl, 6-phenalenyl, 7-phenalenyl, 8-phenalenyl, and 9-phenalenyl group.

Examples of the arylene group include, for example, 1,2-phenylene, 1,3-phenylene, 1,4-phenylene, naphthalene-1,2-diyl, naphthalene-1,3-diyl, naphthalene-1,4-diyl, naphthalene-1,5-diyl, naphthalene-1,6-diyl, naphthalene-1,7-diyl, naphthalene-1,8-diyl, naphthalene-2,3-diyl, naphthalene-2,4-diyl, naphthalene-2,5-diyl, naphthalene-2,6-diyl, naphthalene-2,7-diyl, naphthalene-2,8-diyl, and anthracene-1,4-diyl, which are $C_6$ to $C_{14}$ arylene groups.

Examples of the aralkyl group include the group in which one hydrogen atom of alkyl group is substituted with aryl group, and include, for example, benzyl, 1-naphtylmethyl, 2-naphtylmethyl, anthracenylmethyl, phenanthrenyl methyl, acenaphthylenylmethyl, diphenylmethyl, 1-phenethyl, 2-phenethyl, 1-(1-naphthyl)ethyl, 1-(2-naphthyl)ethyl, 2-(1-naphthyl)ethyl, 2-(2-naphthyl)ethyl, 3-phenylpropyl, 3-(1-naphthyl)propyl, 3-(2-naphthyl)propyl, 4-phenylbutyl, 4-(1-naphthyl)butyl, 4-(2-naphthyl)butyl, 5-phenylpentyl, 5-(1-naphthyl)pentyl, 5-(2-naphthyl)pentyl, 6-phenylhexyl, 6-(1-naphthyl)hexyl, and 6-(2-naphthyl)hexyl group, which are $C_7$ to $C_{16}$ aralkyl groups.

Examples of the bridged cyclic hydrocarbon group include, for example, bicyclo[2.1.0]pentyl, bicyclo[2.2.1]heptyl, bicyclo[2.2.1]octyl, and adamanty group.

Examples of the spiro cyclic hydrocarbon group include, for example, spiro[3.4]octyl, and spiro[4.5]decane-1,6-dienyl group.

Examples of the terpene hydrocarbon include, for example, geranyl, neryl, linalyl, phytyl, menthyl, and bornyl group.

Examples of the halogenated alkyl group include the group in which one hydrogen atom of alkyl group is substituted with a halogen atom, and include, for example, fluoromethyl, difluoromethyl, trifluoromethyl, chloromethyl, dichloromethyl, trichloromethyl, bromomethyl, dibromomethyl, tribromomethyl, iodomethyl, diiodomethyl, triiodomethyl, 2,2,2-trifluoroethyl, pentafluoroethyl, 3,3,3-trifluoropropyl, heptafluoropropyl, heptafluoroisopropyl, nonafluorobutyl, and perfluorohexyl group, which are $C_1$ to $C_6$ straight chain or branched chain halogenated alkyl groups substituted with 1 to 13 halogen atoms.

Examples of the heterocyclic group include, for example, a monocyclic or a fused polycyclic hetero aryl group which comprises at least one atom of 1 to 3 kinds of hetero atoms selected from oxygen atom, sulfur atom, nitrogen atom and the like as ring-constituting atoms (ring forming atoms), and a monocyclic or a fused polycyclic nonaromatic heterocyclic group which comprises at least one atom of 1 to 3 kinds of hetero atoms selected from oxygen atom, sulfur atom, nitrogen atom and the like as ring-constituting atoms (ring forming atoms).

Examples of the monocyclic heteroaryl group include, for example, 2-furyl, 3-furyl, 2-thienyl, 3-thienyl, 1-pyrrolyl, 2-pyrrolyl, 3-pyrrolyl, 2-oxazolyl, 4-oxazolyl, 5-oxazolyl, 3-isoxazolyl, 4-isoxazolyl, 5-isoxazolyl, 2-thiazolyl, 4-thiazolyl, 5-thiazolyl, 3-isothiazolyl, 4-isothiazolyl, 5-isothiazolyl, 1-imidazolyl, 2-imidazolyl, 4-imidazolyl, 5-imidazolyl, 1-pyrazolyl, 3-pyrazolyl, 4-pyrazolyl, 5-pyrazolyl, (1,2,3-oxadiazol)-4-yl, (1,2,3-oxadiazol)-5-yl, (1,2,4-oxadiazol)-3-yl, (1,2,4-oxadiazol)-5-yl, (1,2,5-oxadiazol)-3-yl, (1,2,5-oxadiazol)-4-yl, (1,3,4-oxadiazol)-2-yl, (1,3,4-oxadiazol)-5-yl, furazanyl, (1,2,3-thiadiazol)-4-yl, (1,2,3-thiadiazol)-5-yl, (1,2,4-thiadiazol)-3-yl, (1,2,4-thiadiazol)-5-yl, (1,2,5-thiadiazol)-3-yl, (1,2,5-thiadiazol)-4-yl, (1,3,4-thiadiazolyl)-2-yl, (1,3,4-thiadiazolyl)-5-yl, (1H-1,2,3-triazol)-1-yl, (1H-1,2,3-triazol)-4-yl, (1H-1,2,3-triazol)-5-yl, (2H-1,2,3-triazol)-2-yl, (2H-1,2,3-triazol)-4-yl, (1H-1,2,4-triazol)-1-yl, (1H-1,2,4-triazol)-3-yl, (1H-1,2,4-triazol)-5-yl, (4H-1,2,4-triazol)-3-yl, (4H-1,2,4-triazol)-4-yl, (1H-tetrazol)-1-yl, (1H-tetrazol)-5-yl, (2H-tetrazol)-2-yl, (2H-tetrazol)-5-yl, 2-pyridyl, 3-pyridyl, 4-pyridyl, 3-pyridazinyl, 4-pyridazinyl, 2-pyrimidinyl, 4-pyrimidinyl, 5-pyrimidinyl, 2-pyrazinyl, (1,2,3-triazin)-4-yl, (1,2,3-triazin)-5-yl, (1,2,4-triazin)-3-yl, (1,2,4-triazin)-5-yl, (1,2,4-triazin)-6-yl, (1,3,5-triazin)-2-yl, 1-azepinyl, 2-azepinyl, 3-azepinyl, 4-azepinyl, (1,4-oxazepin)-2-yl, (1,4-oxazepin)-3-yl, (1,4-oxazepin)-5-yl, (1,4-oxazepin)-6-yl, (1,4-oxazepin)-7-yl, (1,4-thiazepin)-2-yl, (1,4-thiazepin)-3-yl, (1,4-thiazepin)-5-yl, (1,4-thiazepin)-6-yl, and (1,4-thiazepin)-7-yl group, which are 5- to 7-membered monocyclic heteroaryl groups.

Examples of the fused polycyclic heteroaryl group include, for example, 2-benzofuranyl, 3-benzofuranyl, 4-benzofuranyl, 5-benzofuranyl, 6-benzofuranyl, 7-benzofuranyl, 1-isobenzofuranyl, 4-isobenzofuranyl, 5-isobenzofuranyl, 2-benzo[b]thienyl, 3-benzo[b]thienyl, 4-benzo[b]thienyl, 5-benzo[b]thienyl, 6-benzo[b]thienyl, 7-benzo[b]thienyl, 1-benzo[c]thienyl, 4-benzo[c]thienyl, 5-benzo[c]thienyl, 1-indolyl, 1-indolyl, 2-indolyl, 3-indolyl, 4-indolyl, 5-indolyl, 6-indolyl, 7-indolyl, (2H-isoindol)-1-yl, (2H-isoindol)-2-yl, (2H-isoindol)-4-yl, (2H-isoindol)-5-yl, (1H-indazol)-1-yl, (1H-indazol)-3-yl, (1H-indazol)-4-yl, (1H-indazol)-5-yl, (1H-indazol)-6-yl, (1H-indazol)-7-yl, (2H-indazol)-1-yl, (2H-indazol)-2-yl, (2H-indazol)-4-yl, (2H-indazol)-5-yl, 2-benzoxazolyl, 2-benzoxazolyl, 4-benzoxazolyl, 5-benzoxazolyl, 6-benzoxazolyl, 7-benzoxazolyl, (1,2-benzisoxazol)-3-yl, (1,2-benzisoxazol)-4-yl, (1,2-benzisoxazol)-5-yl, (1,2-benzisoxazol)-6-yl, (1,2-benzisoxazol)-7-yl, (2,1-benzisoxazol)-3-yl, (2,1-benzisoxazol)-4-yl, (2,1-benzisoxazol)-5-yl, (2,1-benzisoxazol)-6-yl, (2,1-benzisoxazol)-7-yl, 2-benzothiazolyl, 4-benzothiazolyl, 5-benzothiazolyl, 6-benzothiazolyl, 7-benzothiazol)-3-yl, (1,2-benzisothiazol)-3-yl (1,2-benzisothiazol)-4-yl, (1,2-benzisothiazol)-5-yl, (1,2-benzisothiazol)-6-yl, (1,2-benzisothiazol)-7-yl, (2,1-benzisothiazol)-3-yl, (2,1-benzisothiazol)-4-yl, (2,1-benzisothiazol)-5-yl, (2,1-benzisothiazol)-6-yl, (2,1-benzisothiazol)-7-yl, (1,2,3-benzoxadiazol)-4-yl, (1,2,3-benzoxadiazol)-5-yl, (1,2,3-benzoxadiazol)-6-yl, (1,2,3-benzoxadiazol)-7-yl, (2,1,3-benzoxadiazol)-4-yl, (2,1,3-benzoxadiazol)-5-yl, (1,2,3-benzothiadiazol)-4-yl, (1,2,3-benzothiadiazol)-5-yl, (1,2,3-benzothiadiazol)-6-yl, (1,2,3-benzothiadiazol)-7-yl, (2,1,3-benzothiadiazol)-4-yl, (2,1,3-benzothiadiazol)-5-yl, (1H-benzotriazol)-1-yl, (1H-benzotriazol)-4-yl, (1H-benzotriazol)-5-yl, (1H-benzotriazol)-6-yl, (1H-benzotriazol)-7-yl, (2H-benzotriazol)-2-yl, (2H-benzotriazol)-4-yl, (2H-benzotriazol)-5-yl, 2-quinolyl, 3-quinolyl, 4-quinolyl, 5-quinolyl, 6-quinolyl, 7-quinolyl, 8-quinolyl, 1-isoquinolyl, 3-isoquinolyl, 4-isoquinolyl, 5-isoquinolyl, 6-isoquinolyl, 7-isoquinolyl, 8-isoquinolyl, 3-cinnolinyl, 4-cinnolinyl, 6-cinnolinyl, 6-cinnolinyl, 7-cinnolinyl, 8-cinnolinyl, 2-quinazolinyl, 4-quinazolinyl, 5-quinazolinyl, 6-quinazolinyl, 7-quinazolinyl, 8-quinazolinyl, 2-quinoxalinyl, 5-quinoxalinyl, 6-quinoxalinyl, 1-phthalazinyl, 5-phthalazinyl, 6-phthalazinyl, 2-naphthyridinyl, 3-naphthyridinyl, 4-naphthyridinyl, 2-purinyl, 6-purinyl, 7-purinyl, 8-purinyl, 2-pteridinyl, 4-pteridinyl, 6-pteridinyl, 7-pteridinyl, 1-carbazolyl, 2-carbazolyl, 3-carbazolyl, 4-carbazolyl, 9-carbazolyl, 2-(α-carbolinyl), 3-(α-carbolinyl), 4-(α-carbolinyl), 5-(α-carbolinyl), 6-(α-carbolinyl), 7-(α-carbolinyl), 8-(α-carbolinyl), 9-(α-carbolinyl), 1-(β-carbolinyl), 3-(β-carbolinyl), 4-(β-carbolinyl), 5-(β-carbolinyl), 6-(β-carbolinyl), 7-(β-carbolinyl), 8-(β-carbolinyl), 9-(β-carbolinyl), 1-(γ-carbolinyl), 2-(γ-carbolinyl), 4-(γ-carbolinyl), 5-(γ-carbolinyl), 6-(γ-carbolinyl), 7-(γ-carbolinyl), 8-(γ-carbolinyl), 9-(γ-carbolinyl), 1-acridinyl, 2-acridinyl, 3-acridinyl, 4-acridinyl, 9-acridinyl, 1-phenoxazinyl, 2-phenoxazinyl, 3-phenoxazinyl, 4-phenoxazinyl, 10-phenoxazinyl, 1-phenothiazinyl, 2-phenothiazinyl, 3-phenothiazinyl, 4-phenothiazinyl, 10-phenothiazinyl, 1-phenazinyl, 2-phenazinyl, 1-phenanthridinyl, 2-phenanthridinyl, 3-phenanthridinyl, 4-phenanthridinyl, 6-phenanthridinyl, 7-phenanthridinyl, 8-phenanthridinyl, 9-phenanthridinyl, 10-phenanthridinyl, 2-phenanthrolinyl, 3-phenanthrolinyl, 4-phenanthrolinyl, 5-phenanthrolinyl, 6-phenanthrolinyl, 7-phenanthrolinyl, 8-phenanthrolinyl, 9-phenanthrolinyl, 10-phenanthrolinyl, 1-thianthrenyl, 2-thianthrenyl, 1-indolizinyl, 2-indolizinyl, 3-indolizinyl, 5-indolizinyl, 6-indolizinyl, 7-indolizinyl, 8-indolizinyl, 1-phenoxathiinyl, 2-phenoxathiinyl, 3-phenoxathiinyl, 4-phenoxathiinyl, thieno[2,3,-b]furyl, pyrrolo[1,2-b]pyridazinyl, pyrazolo[1,5-a]pyridyl, imidazo[11,2-a]pyridyl, imidazo[1,5-a]pyridyl, imidazo[1,2-b]pyridazinyl, imidazo[1,2-a]pyrimidinyl, 1,2,4-triazolo[4,3-a]pyridyl, and 1,2,4-triazolo[4,3-a]pyridazinyl group, which are 8- to 14-membered fused polycyclic heteroaryl groups.

Examples of the monocyclic nonaromatic heterocyclic group include, for example, 1-aziridinyl, 1-azetidinyl, 1-pyrrolidinyl, 2-pyrrolidinyl, 3-pyrrolidinyl, 2-tetrahydrofuryl, 3-tetrahydrofuryl, thiolanyl, 1-imidazolidinyl, 2-imidazolidinyl, 4-imidazolidinyl, 1-pyrazolidinyl, 3-pyrazolidinyl, 4-pyrazolidinyl, 1-(2-pyrrolinyl), 1-(2-imidazolinyl), 2-(2-imidazolinyl), 1-(2-pyrazolinyl), 3-(2-pyrazolinyl), piperidino, 2-piperidinyl, 3-piperidinyl, 4-piperidinyl, 1-homopiperidinyl, 2-tetrahydropyranyl, morpholino, (thiomorpholin)-4-yl, 1-piperazinyl, and 1-homopiperazinyl group, which are 3- to 7-membered saturated or unsaturated monocyclic nonaromatic heterocyclic groups.

Examples of the fused polycyclic nonaromatic heterocyclic group include, for example, 2-quinuclidinyl, 2-chromanyl, 3-chromanyl, 4-chromanyl, 5-chromanyl, 6-chromanyl, 7-chromanyl, 8-chromanyl, 1-isochromanyl, 3-isochromanyl, 4-isochromanyl, 5-isochromanyl, 6-isochromanyl, 7-isochromanyl, 8-isochromanyl, 2-thiochromanyl, 3-thiochromanyl, 4-thiochromanyl, 5-thiochromanyl, 6-thiochromanyl, 7-thiochromanyl, 8-thiochromanyl, 1-isothiochromanyl, 3-isothiochromanyl, 4-isothiochromanyl, 5-isothiochromanyl, 6-isothiochromanyl, 7-isothiochromanyl, 8-isothiochromanyl, 1-indolinyl, 2-indolinyl, 3-indolinyl, 4-indolinyl, 5-indolinyl, 6-indolinyl, 7-indolinyl, 1-isoindolinyl, 2-isoindolinyl, 4-isoindolinyl, 5-isoindolinyl, 2-(4H-chromenyl), 3-(4H-chromenyl), 4-(4H-chromenyl), 5-(4H-chromenyl), 6-(4H-chromenyl), 7-(4H-chromenyl), 8-(4H-chromenyl), 1-isochromenyl, 3-isochromenyl, 4-isochromenyl, 5-isochromenyl, 6-isochromenyl, 7-isochromenyl, 8-isochromenyl, 1-(1H-pyrrolidinyl), 2-(1H-pyrrolidinyl), 3-(1H-pyrrolidinyl), 5-(1H-pyrrolidinyl), 6-(1H-pyrrolidinyl), and 7-(1H-pyrrolidinyl) group, which are 8- to 10-membered saturated or unsaturated fused polycyclic nonaromatic heterocyclic groups.

Among the aforementioned heterocyclic groups, a monocyclic or a fused polycyclic hetero aryl groups which may have 1 to 3 kinds of hetero atoms selected from oxygen atom, sulfur atom, nitrogen atom and the like, in addition to the nitrogen atom that has the bond, as ring-constituting atoms (ring forming atoms), and a monocyclic or a fused polycyclic nonaromatic heterocyclic groups which may have 1 to 3 kinds of hetero atoms selected from oxygen atom, sulfur atom, nitrogen atom and the like, in addition to the nitrogen atom that has the bond, as ring-constituting atoms (ring forming atoms) are referred to as "cyclic amino groups". Examples include, for example, 1-pyrrolidinyl, 1-imidazolidinyl, 1-pyrazolidinyl, 1-oxazolidinyl, 1-thiazolidinyl, piperidino, morpholino, 1-piperazinyl, thiomorpholin-4-yl, 1-homopiperidinyl, 1-homopiperazinyl, 2-pyrrolin-1-yl, 2-imidazolin-1-yl, 2-pyrazolin-1-yl, 1-indolinyl, 2-isoindolinyl, 1,2,3,4-tetrahydroquinolin-1-yl, 1,2,3,4-tetrahydroisoquinolin-2-yl, 1-pyrrolyl, 1-imidazolyl, 1-pyrazolyl, 1-indolyl, 1-indazolyl, and 2-isoindolyl group.

Examples of the hydrocarbon-oxy group include the group in which hydrogen atom of hydroxy group is substituted with hydrocarbon group, and examples of the hydrocarbon include similar groups to the aforementioned hydrocarbon. Examples of the hydrocarbon-oxy group include, for example, alkoxy group (alkyl-oxy group), alkenyl-oxy group, alkynyl-oxy group, cycloalkyl-oxy group, cycloalkyl-alkyl-oxy group and the like which are aliphatic hydrocarbon-oxy groups, aryl-oxy group, aralkyl-oxy group, and alkylene-dioxy group.

Examples of the alkoxy(alkyl-oxy group) include, for example, methoxy, ethoxy, n-propoxy, isopropoxy, n-butoxy, isobutoxy, sec-butoxy, tert-butoxy, n-pentyloxy, isopentyloxy, 2-methylbutoxy, 1-methylbutoxy, neopentyloxy, 1,2-dimethylpropoxy, 1-ethylpropoxy, n-hexyloxy, 4-methylpentyloxy, 3-methylpentyloxy, 2-methylpentyloxy, 1-methylpentyloxy, 3,3-dimethylbutoxy, 2,2-dimethylbutoxy, 1,1-dimethylbutoxy, 1,2-dimethylbutoxy, 1,3-dimethylbutoxy, 2,3-dimethylbutoxy, 2-ethylbutoxy, 1-ethylbutoxy, 1-ethyl-1-methylpropoxy, n-heptyloxy, n-octyloxy, n-nonyloxy, n-decyloxy, n-undecyloxy, n-dodecyloxy, n-tridecyloxy, n-tetradecyloxy, and n-pentadecyloxy group, which are $C_1$ to $C_{15}$ straight chain or branched chain alkoxy groups.

Examples of the alkenyl-oxy group include, for example, vinyloxy, (prop-1-en-1-yl)oxy, allyloxy, isopropenyloxy, (but-1-en-1-yl)oxy, (but-2-en-1-yl)oxy, (but-3-en-1-yl)oxy, (2-methylprop-2-en-yl)oxy, (1-methylprop-2-en-1-yl)oxy, (pent-1-en-1-yl)oxy, (pent-2-en-1-yl)oxy, (pent-3-en-1-yl)oxy, (pent-4-en-1-yl)oxy, (3-methylbut-2-en-1-yl)oxy, (3-methylbut-3-en-1-yl)oxy, (hex-1-en-1-yl)oxy, (hex-2-en-1-yl)oxy, (hex-3-en-1-yl)oxy, (hex-4-en-1-yl)oxy, (hex-5-en-1-yl)oxy, (4-methylpent-3-en-1-yl)oxy, (4-methylpent-3-en-1-yl)oxy, (hept-1-en-1-yl)oxy, (hept-6-en-1-yl)oxy, (oct-1-en-1-yloxy, (oct-7-en-1-yl)oxy, (non-1-en 1-yl)oxy, (non-8-en-1-yl)oxy, (dec-1-en-1-yl)oxy, (dec-9-en-1-yl)oxy, (undec-1-en-1-yl)oxy, (undec-10-en-1-yl)oxy, (dodec-1-en-1-yl)oxy, (dodec-1-en-1-yl)oxy, (tridec-1-en-1-yl)oxy, (tridec-12-en-1-yl)oxy, (tetradec-1-en-1-yl)oxy, (tetradec-13-en-1-yl)oxy, (pentadec-1-en-1-yl)oxy, and (pentadec-14-en-1-yl)oxy group, which are $C_2$ to $C_{15}$ straight chain or branched chain alkenyl-oxy groups.

Examples of the alkynyl-oxy group include, for example, ethynyloxy, (prop-1-yn-1-yl)oxy, (prop-2-yn-1-yl)oxy, (but-1-yn-1-yl)oxy, (but-3-yn-1-yl)oxy, (1-methylprop-2-yn-1-yl)oxy, (pent-1-yn-1-yl)oxy, (pent-4-yn-1-yl)oxy, (hex-1-yn-1-yl)oxy, (hex-5-yn-1-yl)oxy, (hept-1-yn-1-yl)oxy, (hept-6-yn-1-yl)oxy, (oct-1-yn-1-yl)oxy, (oct-7-yn-1-yl)oxy, (non-1-yn-1-yl)oxy, (non-8-yn-1-yl)oxy, (dec-1-yn-1-yl)oxy, (dec-9-yn-1-yl)oxy, (undec-1-yn-1-yl)oxy, (undec-10-yn-1-yl)oxy, (dodec-1-yn-1-yl)oxy, (dodec-11-yn-1-yl)oxy, (tridec-1-yn-1-yl)oxy, (tridec-12-yn-1-yl)oxy, (tetradec-1-yn-1-yl)oxy, (tetradec-13-yn-1-yl)oxy, (pentadec-1-yn-1-yl)oxy, and (pentadec-14-yn-1-yl)oxy group, which are $C_2$ to $C_{15}$ straight chain or branched chain alkynyl-oxy groups.

Examples of the cycloalkyl-oxy group include, for example, cyclopropoxy, cyclobutoxy, cyclopentyloxy, cyclohexyloxy, cycloheptyloxy, and cyclooctyloxy group, which are $C_3$ to $C_8$ cycloalkyl-oxy groups.

Examples of the cycloalkyl-alkyl-oxy group include, for example, cyclopropylmethoxy, 1-cyclopropylethoxy, 2-cyclopropylethoxy, 3-cyclopropylpropoxy, 4-cyclopropylbutoxy, 5-cyclopropylpentyloxy, 6-cyclopropylhexyloxy, cyclobutylmethoxy, cyclopentylmethoxy, cyclobutylmethoxy, cyclopentylmethoxy, cyclohexylmethoxy, 2-cyclohexylethoxy, 3-cyclohexylpropoxy, 4-cyclohexylbutoxy, cycloheptylmethoxy, cyclooctylmethoxy, and 6-cyclooctylhexyloxy group, which are $C_4$ to $C_{14}$ cycloalkyl-alkyl-oxy groups.

Examples of the aryl-oxy group include, for example, phenoxy, 1-naphthyloxy, 2-naphthyloxy, anthryloxy, phenanthryloxy, and acenaphthylenyloxy group, which are $C_6$ to $C_{14}$ aryl-oxy groups.

Examples of the aralkyl-oxy group include, for example, benzyloxy, 1-naphthylmethoxy, 2-naphthylmethoxy, anthracenylmethoxy, phenanthrenylmethoxy, acenaphthylenylmethoxy, diphenylmethoxy, 1-phenethyloxy, 2-phenethyloxy, 1-(1-naphthyl-naphthyl)ethoxy, 1-(2-naphthyl)ethoxy, 2-(1-naphthyl)ethoxy, 2-(2-naphthyl)ethoxy, 3-phenylpropoxy, 3-(1-naphthyl)propoxy, 3-(2-naphthyl)propoxy, 4-phenylbutoxy, 4-(1-naphthyl)butoxy, 4-(2-naphthyl)butoxy, 5-phenylpentyloxy, 5-(1-naphthyl)pentyloxy, 5-(2-naphthyl)pentyloxy, 6-phenylhexyloxy, 6-(1-naphthyl)hexyloxy, and 6-(2-naphthyl)hexyloxy group, which are $C_7$ to $C_{16}$ aralkyl-oxy groups.

Examples of the alkylenedioxy group include, for example, methylenedioxy, ethylenedioxy, 1-methylmethylenedioxy, and 1,1-dimethylmethylenedioxy group.

Examples of the halogenated alkoxy group (halogenated alkyl-oxy group) include the group in which hydrogen atom of hydroxy group is substituted with halogenated alkyl group, and include, for example, fluoromethoxy, difluoromethoxy, chloromethoxy, bromomethoxy, iodomethoxy, trifluoromethoxy, trichloromethoxy, 2,2,2-trifluoroethoxy, pentafluoroethoxy, 3,3,3-trifluoropropoxy, heptafluoropropoxy, heptafluoroisopropoxy, nonafluorobutoxy, and perfluorohexyloxy group, which are $C_1$ to $C_6$ straight chain or branched chain halogenated alkoxy groups substituted with 1 to 13 halogen atoms.

Examples of the heterocyclic-oxy group include the group in which hydrogen atom of hydroxy group is substituted with the heterocyclic group, and examples of the heteroring include similar groups to the aforementioned heterocyclic group. Examples of the heterering-oxy group include, for example, a monocyclic heteroaryl-oxy group, a fused polycyclic heteroaryl-oxy group, a monocyclic nonaromatic heteroring-oxy group, a fused polycyclic nonaromatic heteroring-oxy group and the like.

Examples of the monocyclic heteroaryl-oxy group include, for example, 3-thienyloxy, (isoxazol-3-yl)oxy, (thiazol-4-yl)oxy, 2-pyridyloxy, 3-pyridyloxy, 4-pyridyloxy, and (pyrimidin-4-yl)oxy group.

Examples of the fused polycyclic heteroaryl-oxy group include, 5-indolyloxy, (benzimidazol-2-yl)oxy, 2-quinolyloxy, 3-quinolyloxy, and 4-quinolyloxy group.

Examples of the monocyclic nonaromatic heterocyclic-oxy group include, for example, 3-pyrrolidinyloxy, and 4-piperidinyloxy group.

Examples of the fused polycyclic non-aromatic heteroring-oxy group include, for example, 3-indolynyloxy, and 4-chromanyloxy group.

Examples of the hydrocarbon-sulfanyl group include the group in which hydrogen atom of sulfanyl group is substituted with a hydrocarbon group, and examples of the hydrocarbon include similar groups to the aforementioned hydrocarbon. Examples of the hydrocarbon-sulfanyl group include, for example, alkyl-sulfanyl group, alkenyl-sulfanyl group, alkynyl-sulfanyl group, cycloalkyl-sulfanyl group, cycloalkyl-alkyl-sulfanyl group and the like which are aliphatic hydrocarbon-sulfanyl groups, aryl-sulfanyl group, and aralkyl-sulfanyl group.

Examples of the alkyl-sulfanyl group include, for example, methylsulfanyl, ethylsulfanyl, n-propylsulfanyl, isopropylsulfanyl, n-butylsulfanyl, isobutylsulfanyl, sec-butylsulfanyl, tert-butylsulfanyl, n-pentylsulfanyl, isopentylsulfanyl, (2-methylbutyl)sulfanyl, (1-methylbutyl)sulfanyl, neopentylsulfanyl, (1,2-dimethylpropyl)sulfanyl, (1-ethylpropyl)sulfanyl, n-hexylsulfanyl, (4-methylpentyl)sulfanyl, (3-methylpentyl)sulfanyl, (2-methylpentyl)sulfanyl, (1-methylpentyl)sulfanyl, (3,3-dimethylbutyl)sulfanyl, (2,2-dimethylbutyl)sulfanyl, (1,1-dimethylbutyl)sulfanyl, (1,2-dimethylbutyl)sulfanyl, (1,3-dimethylbutyl)sulfanyl, (2,3-dimethylbutyl)sulfanyl, (2-ethylbutyl)sulfanyl, (1-ethylbutyl)sulfanyl, (1-ethyl-1-methylpropyl)sulfanyl, n-heptylsulfanyl, n-octylsulfanyl, n-nonylsulfanyl, n-decylsulfanyl, n-undecylsulfanyl, n-dodecylsulfanyl, n-tridecylsulfanyl, n-tetradecylsulfanyl, and n-pentadecylsulfanyl group, which are $C_1$ to $C_{15}$ straight chain or branched chain alkyl-sulfanyl groups.

Examples of the alkenyl-sulfanyl group include, for example, vinylsulfanyl, (prop-1-en-1-yl)sulfanyl, allylsulfanyl, isopropenylsulfanyl, (but-1-en-1-yl)sulfanyl, (but-2-en-1-yl)sulfanyl, (but-3-en-1-yl)sulfanyl, (2-methylprop-2-en-1-yl)sulfanyl, (1-methylprop-2-en-1-yl)sulfanyl, (pent-1-en-1-yl)sulfanyl, (pent-2-en-1-yl)sulfanyl, (pent-3-en-1-yl)sulfanyl, (pent-4-en-1-yl)sulfanyl, (3-methylbut-2-en-1-yl)sulfanyl, (3-methylbut-3-en-1-yl)sulfanyl, (hex-1-en-1-yl)sulfanyl, (hex-2-en-1-yl)sulfanyl, (hex-3-en-1-yl)sulfanyl, (hex-4-en-1-yl) sulfanyl, (hex-5-en-1-yl)sulfanyl, (4-methylpent-3-en-1-yl)sulfanyl, (4-methylpent-3-en-1-yl)sulfanyl, (hept-1-en-1-yl)sulfanyl, (hept-6-en-1-yl)sulfanyl, (oct-1-en-1-yl)sulfanyl, (oct-7-en-1-yl)sulfanyl, (non-1-en-1-yl)sulfanyl, (non-8-en-1-yl)sulfanyl, (dec-1-en-1-yl)sulfanyl, (dec-9-en-1-yl)sulfanyl, (undec-1-en-1-yl)sulfanyl, (undec-10-en-1-yl)sulfanyl, (dodec-1-en-1-yl)sulfanyl, (dodec-11-en-1-yl)sulfanyl, (tridec-1-en-1-yl)sulfanyl, (tridec-12-en-1-yl)sulfanyl, (tetradec-1-en-1-yl)sulfanyl, (tetradec-13-en-1-yl)sulfanyl, (pentadec-1-en-1-yl)sulfanyl, and (pentadec-14-en-1-yl)sulfanyl, which are $C_2$ to $C_{15}$ straight chain or branched chain alkenyl-sulfanyl groups.

Examples of the alkynyl-sulfanyl group include, for example, ethynylsulfanyl, (prop-1-yn-1-yl)sulfanyl, (prop-2-yn-1-yl)sulfanyl, (but-1-yn-1-yl)sulfanyl, (but-3-yn-1-yl)sulfanyl, (1-methylprop-2-yn-1-yl)sulfanyl, (pent-1-yn-1-yl)sulfanyl, (pent-4-yn-1-yl)sulfanyl, (hex-1-yn-1-yl)sulfanyl, (hex-5-yn-1-yl)sulfanyl, (hept-1-yn-1-yl)sulfanyl, (hept-6-yn-1-yl)sulfanyl, (oct-1-yn-1-yl)sulfanyl, (oct-7-yn-1-yl)sulfanyl, (non-1-yn-1-yl)sulfanyl, (non-8-yn-1-yl)sulfanyl, (dec-1-yn-1-yl)sulfanyl, (dec-9-yn-1-yl)sulfanyl, (undec-1-yn-1-yl)sulfanyl, (undec-10-yn-1-yl)sulfanyl, (dodec-1-yn-1-yl)sulfanyl, (dodec-11-yn-1-yl)sulfanyl, (tridec-1-yn-1-yl)sulfanyl, (tridec-12-yn-1-yl)sulfanyl, (tetradec-1-yn-1-yl)sulfanyl, (tetradec-13-yn-1-yl)sulfanyl, (pentadec-1-yn-1-yl)sulfanyl, and (pentadec-14-yn-1-yl)sulfanyl, which are $C_2$ to $C_{15}$ straight chain or branched chain alkynyl-sulfanyl groups.

Examples of the cycloalkyl-sulfanyl group include, for example, cyclopropylsulfanyl, cyclobutylsulfanyl, cyclopentylsulfanyl, cyclohexylsulfanyl, cycloheptylsulfanyl, and cyclooctylsulfanyl group, which are $C_3$ to $C_8$ cycloalkyl-sulfanyl groups.

Examples of the cycloalkyl-alkyl-sulfanyl group include, for example, (cyclopropylmethyl)sulfanyl, (1-cyclopropylethyl)sulfanyl, (2-cyclopropyl ethyl)sulfanyl, (3-cyclopropylpropyl)sulfanyl, (4-cyclopropylbutyl)sulfanyl, (5-cyclopropylpentyl)sulfanyl, (6-cyclopropylhexyl)sulfanyl, (cyclobutylmethyl)sulfanyl, (cyclopentylmethyl)sulfanyl, (cyclobutylmethyl)sulfanyl, (cyclopentylmethyl)sulfanyl, (cyclohexylmethyl)sulfanyl, (2-cyclohexylethyl)sulfanyl, (3-cyclohexylpropyl)sulfanyl, (4-cyclohexylbutyl)sulfanyl, (cycloheptylmethyl)sulfanyl, (cyclooctylmethyl)sulfanyl, and (6-cyclooctylhexyl)sulfanyl group, which are $C_4$ to $C_{14}$ cycloalkyl-alkyl-sulfanyl groups.

Examples of the aryl-sulfanyl group include, for example, phenylsulfanyl, 1-naphthylsulfanyl, 2-naphthylsulfanyl, anthrylsulfanyl, fenanthrylsulfanyl, and acenaphthylenylsulfanyl group, which are $C_6$ to $C_{14}$ aryl-sulfanyl groups.

Examples of the aralkyl-sulfanyl group include, for example, benzylsulfanyl, (1-naphthylmethyl)sulfanyl, (2-naphthylmethyl)sulfanyl, (anthracenylmethyl)sulfanyl, (phenanthrenylmethyl)sulfanyl, (acenaphthylenylmethyl)sulfanyl, (diphenylmethyl)sulfanyl, (1-phenethyl)sulfanyl, (2-phenethyl)sulfanyl, (1-(1-naphthyl)ethyl)sulfanyl, (1-(2-naphthyl)ethyl)sulfanyl, (2-(1-naphthyl)ethyl)sulfanyl, (2-(2-naphthyl)ethyl)sulfanyl, (3-phenylpropyl)sulfanyl, (3-(1-naphthyl)propyl)sulfanyl, (3-(2-naphthyl)propyl)sulfanyl, (4-phenylbutyl)sulfanyl, (4-(1-naphthyl)butyl)sulfanyl, (4-(2-naphthyl)butyl)sulfanyl, (5-phenylpentyl)sulfanyl, (5-(1-naphthyl)pentyl)sulfanyl, (5-(2-naphthyl)pentyl)sulfanyl, (6-phenylhexyl)sulfanyl, (6-(1-naphthyl)hexyl)sulfanyl, and (6-(2-naphthyl)hexyl)sulfanyl group, which are $C_7$ to $C_{16}$ aralkyl-sulfanyl groups.

Examples of the halogenated alkyl-sulfanyl group include the group in which hydrogen atom of sulfanyl group is substituted with a halogenated alkyl group, and include, for example, (fluoromethyl)sulfanyl, (chloromethyl)sulfanyl, (bromomethyl)sulfanyl, (iodomethyl)sulfanyl, (difluoromethyl)sulfanyl, (trifluoromethyl)sulfanyl, (trichloromethyl)sulfanyl, (2,2,2-trifluoroethyl)sulfanyl, (pentafluoroethyl)sulfanyl, (3,3,3-trifluoropropyl)sulfanyl, (heptafluoropropyl)sulfanyl, (heptafluoroisopropyl)sulfanyl, (nonafluorobutyl)sulfanyl, and (perfluorohexyl)sulfanyl group, which are $C_1$ to $C_6$ straight chain or branched chain halogenated alkyl-sulfanyl groups substituted with 1 to 13 halogen atoms.

Examples of the heterocyclic-sulfanyl group include the group in which hydrogen atom of sulfanyl group is substituted with the heterocyclic group, and examples of the heteroring include similar groups to the aforementioned heterocyclic group. Examples of the heteroring-sulfanyl group include, for example, monocyclic heteroaryl-sulfanyl group, fused polycyclic heteroaryl-sulfanyl group, monocyclic nonaromatic heteroring-sulfanyl group, and fused polycyclic nonaromatic heteroring-sulfanyl group.

Examples of the monocyclic heteroaryl-sulfanyl group include, for example, (imidazol-2-yl)sulfanyl, (1,2,4-triazol-2-yl)sulfanyl, (pyridin-2-yl)sulfanyl, (pyridin-4-yl)sulfanyl, and (pyrimidin-2-yl)sulfanyl group.

Examples of the fused polycyclic heteroaryl-sulfanyl group include, for example, (benzimidazol-2-yl)sulfanyl, (quinolin-2-yl)sulfanyl, and (quinolin-4-yl)sulfanyl group.

Examples of the monocyclic non-aromatic heteroring-sulfanyl group include, for example, (3-pyrrolidinyl)sulfanyl group and (4-piperidinyl)sulfanyl group.

Examples of the fused polycyclic nonaromatic heteroring-sulfanyl group include, for example, (3-indolinyl)sulfanyl and (4-chromanyl)sulfanyl group.

Examples of the acyl group include, for example, formyl group, glyoxyloyl group, and thioformyl group, and the group represented by the following formulas:

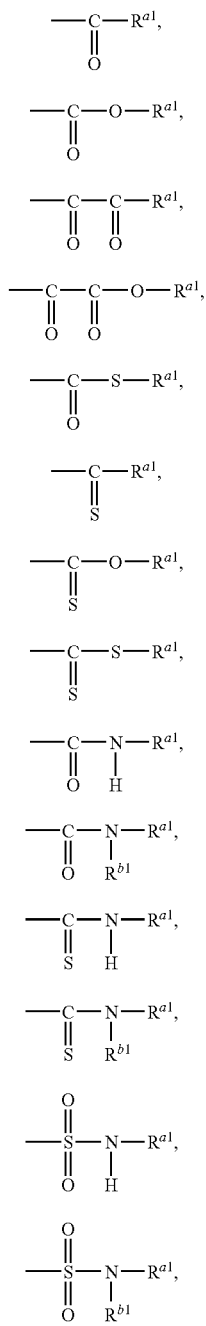

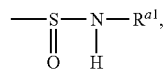

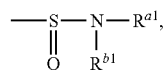

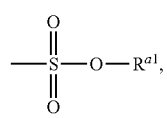

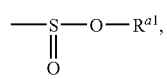

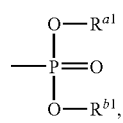

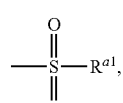

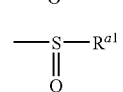

wherein $R^{a1}$ and $R^{b1}$ may be the same or different and each represents a hydrocarbon group or heterocyclic group, or $R^{a1}$ and $R^{b1}$ combine to each other, together with the nitrogen atom to which they bind, to form a cyclic amino group.

In the definition of the aforementioned acyl group, among the groups represented by the formula (ω-1A), those groups in which $R^{a1}$ is a hydrocarbon group are referred to as "hydrocarbon-carbonyl groups" whose examples include, for example, acetyl, propionyl, butyryl, isobutyryl, valeryl, isovaleryl, pivaloyl, lauroyl, myristoyl, palmitoyl, acryloyl, propioloyl, methacryloyl, crotonoyl, isocrotonoyl, cyclohexylcarbonyl, cyclohexylmethylcarbonyl, benzoyl, 1-naphthoyl, 2 naphthoyl, and phenylacetyl group. Those groups in which $R^{a1}$ is a heterocyclic group are referred to as "heteroring-carbonyl" groups whose examples include, for example, 2-thenoyl, 3-furoyl, nicotinoyl, and isonicotinoyl group.

Among the groups represented by the formula (ω-2A), those groups in which $R^{a1}$ is a hydrocarbon group are referred to as "hydrocarbon-oxy-carbonyl groups" whose examples include, for example, methoxycarbonyl, ethoxycarbonyl, phenoxycarbonyl, and benzyloxycarbonyl, and those groups in which $R^{a1}$ is a heterocyclic group are referred to as "heteroring-oxy-carbonyl groups" whose example includes, for example, 3-pyridyloxycarbonyl group.

Among the groups represented by the formula (ω-3A), those groups in which $R^{a1}$ is a hydrocarbon group are referred to as "hydrocarbon-carbonyl-carbonyl groups" whose example includes, for example, pyruvoyl group, and those groups in which $R^{a1}$ is a heterocyclic group are referred to as "heteroring-carbonyl-carbonyl groups".

Among the groups represented by the formula (ω-4A), those groups in which $R^{a1}$ is a hydrocarbon group are referred to as "hydrocarbon-oxy-carbonyl-carbonyl groups" whose examples include, for example, methoxalyl and ethoxalyl groups, and those groups in which $R^{a1}$ is a heterocyclic group are referred to as "heteroring-oxy-carbonyl-carbonyl groups".

Among the groups represented by the formula (ω-5A), those groups in which $R^{a1}$ is a hydrocarbon group are referred to as "hydrocarbon-sulfanyl-carbonyl groups", and those groups in which $R^{a1}$ is a heterocyclic group are referred to as "heteroring-sulfanyl-carbonyl groups".

Among the groups represented by the formula (ω-6A), those groups in which $R^{a1}$ is a hydrocarbon group are referred to as "hydrocarbon-thiocarbonyl groups", and those groups in which $R^{a1}$ is a heterocyclic group are referred to as "heteroring-thiocarbonyl groups".

Among the groups represented by the formula (ω-7A), those groups in which $R^{a1}$ is a hydrocarbon group are referred to as "hydrocarbon-oxy-thiocarbonyl groups", and those groups in which $R^{a1}$ is a heterocyclic group are referred to as "heteroring-oxy-thiocarbonyl groups".

Among the groups represented by the formula (ω-8A), those groups in which $R^{a1}$ is a hydrocarbon group are referred to as "hydrocarbon-sulfanyl-thiocarbonyl groups", and those groups in which $R^{a1}$ is a heterocyclic group are referred to as "heteroring-sulfanyl-thiocarbonyl groups".

Among the groups represented by the formula (ω-9A), those groups in which $R^{a1}$ is a hydrocarbon group are referred to as referred to as "N-hydrocarbon-carbamoyl groups" whose example includes, for example, N-methylcarbamoyl group, and those groups in which $R^{a1}$ is a heterocyclic group are referred to as "N-heteroring-carbamoyl groups".

Among the groups represented by the formula (ω-10A), those groups in which both $R^{a1}$ and $R^{b1}$ are hydrocarbon groups are referred to as "N,N-dihydrocarbon-carbamoyl groups" whose example includes, for example, N,N-dimethylcarbamoyl group, those groups in which both $R^{a1}$ and $R^{b1}$ are heterocyclic groups are referred to as "N,N-di(heteroring)-carbamoyl groups", those groups in which $R^{a1}$ is a hydrocarbon group and $R^{b1}$ is a heterocyclic group are referred to as "N-hydrocarbon-N-heteroring-substituted carbamoyl groups", and those groups in which $R^{a1}$ at and $R^{b1}$ combine to each other, together with the nitrogen atom to which they bind, to form a cyclic amino group are referred to as "cyclic amino-carbonyl groups" whose example includes, for example, morpholino-carbonyl.

Among the groups represented by the formula (ω-11A), those groups in which $R^{a1}$ is a hydrocarbon group are referred to as "N-hydrocarbon-thiocarbamoyl groups", and those groups in which $R^{a1}$ is a heterocyclic group are referred to as "N-heteroring-thiocarbamoyl groups".

Among the groups represented by the formula (ω-12A), those groups in which both $R^{a1}$ and $R^{b1}$ are hydrocarbon groups are referred to as "N,N-di(hydrocarbon)-thiocarbamoyl groups", those groups in which both $R^{1a}$ and $R^{b1}$ are heterocyclic groups are referred to as "N,N-di(heteroring)-thiocarbamoyl groups", those groups in which $R^{a1}$ is a hydrocarbon group and $R^{b1}$ is a heterocyclic group are referred to as "N-hydrocarbon-N-heteroring-thiocarbamoyl groups", and those groups in which $R^{a1}$ and $R^{b1}$ combine to each other, together with the nitrogen atom to which they bind, to form a cyclic amino group are referred to as "cyclic amino-thiocarbonyl groups".

Among the groups represented by the formula (ω-13A), those groups in which $R^{a1}$ is a hydrocarbon group are referred to as "N-hydrocarbon-sulfamoyl groups", and those groups in which $R^{a1}$ is a heterocyclic group are referred to as "N-heteroring-sulfamoyl groups".

Among the groups represented by the formula (ω-14A), those groups in which both $R^{a1}$ and $R^{b1}$ are hydrocarbon groups are referred to as "N,N-di(hydrocarbon)-sulfamoyl groups" whose example includes, for example, N,N-dimethylsulfamoyl group, those groups in which both $R^{a1}$ and $R^{b1}$ are heterocyclic groups are referred to as "N,N-di(heteroring)-sulfamoyl groups", those groups in which $R^{a1}$ is a hydrocarbon group and $R^{b1}$ is a heterocyclic group are referred to as "N-hydrocarbon-N-heteroring-sulfamoyl groups", and those groups in which $R^{a1}$ and $R^{b1}$ combine to each other, together with the nitrogen atom to which they bind, to form a cyclic amino group are referred to as "cyclic amino-sulfonyl groups" which include, for example 1-pyrrolylsulfonyl group.

Among the groups represented by the formula (ω-15A), those groups in which $R^{a1}$ is a hydrocarbon group are referred to as "N-hydrocarbon-sulfinamoyl groups", and those groups in which $R^{a1}$ is a heterocyclic group are referred to as "N-heteroring-sulfinamoyl groups".

Among the groups represented by the formula (ω-16A), those groups in which both $R^{a1}$ and $R^{b1}$ are hydrocarbon groups are referred to as "N,N-di(hydrocarbon)-sulfinamoyl groups", those groups in which both $R^{a1}$ and $R^{b1}$ are heterocyclic groups are referred to as "N,N-di(heteroring)-sulfinamoyl groups", those groups in which $R^{a1}$ is a hydrocarbon group and $R^{b1}$ is a heterocyclic group are referred to as "N-hydrocarbon-N-heteroring-sulfinamoyl groups", and those groups in which $R^{a1}$ and $R^{b1}$ combine to each other, together with the nitrogen atom to which they bind, to form a cyclic amino group are referred to as "cyclic amino-sulfinyl groups".

Among the groups represented by the formula (ω-17A), those groups in which $R^{a1}$ is a hydrocarbon group are referred to as "hydrocarbon-oxy-sulfonyl groups", and those groups in which $R^{a1}$ is a heterocyclic group are referred to as "heteroring-oxy-sulfonyl groups".

Among the groups represented by the formula (ω-18A), those groups in which $R^{a1}$ is a hydrocarbon group are referred to as "hydrocarbon-oxy-sulfinyl groups", and those groups in which $R^{a1}$ is a heterocyclic group are referred to as "heteroring-oxy-sulfinyl groups".

Among the groups represented by the formula (ω-19A), those groups in which both $R^{a1}$ and $R^{b1}$ are hydrocarbon groups are referred to as "O,O'-di(hydrocarbon)-phosphono groups", those groups in which both $R^{a1}$ and $R^{b1}$ are heterocyclic groups are referred to as "O,O'-di(heteroring)-phosphono groups", and those groups in which $R^{a1}$ is a hydrocarbon group and $R^{b1}$ is a heterocyclic group are referred to as "O-hydrocarbon-O'-heteroring-phosphono groups".

Among the groups represented by the formula (ω-20A), those groups in which $R^{a1}$ is a hydrocarbon group are referred to as "hydrocarbon-sulfonyl groups" whose examples include, for example, methanesulfonyl and benzenesulfonyl, and those groups in which $R^{a1}$ is a heterocyclic group are referred to as "heteroring-sulfonyl groups".

Among the groups represented by the formula (ω-21A), those groups in which $R^{a1}$ is a hydrocarbon group are referred to as "hydrocarbon-sulfinyl groups" whose examples include, for example, methylsulfinyl and benzenesulfinyl, and those groups in which $R^{a1}$ is a heterocyclic group are referred to as "heteroring-sulfinyl groups".

Examples of the hydrocarbon in the groups represented by the aforementioned formulas (ω-1A) through (ω-21A) include the similar groups to the aforementioned hydrocarbon group. Examples of the hydrocarbon-carbonyl groups represented by the formula (ω-1A) include, for example, an alkyl-carbonyl group, an alkenyl-carbonyl group, an alkynyl-carbonyl group, a cycloalkyl-carbonyl group, a cycloalkenyl-carbonyl group, a cycloalkanedienyl-carbonyl group, a cycloalkyl-alkyl-carbonyl group which is an aliphatic hydrocarbon-carbonyl group, an aryl-carbonyl group, an aralkyl-carbonyl group, a bridged cyclic hydrocarbon-carbonyl group, a spirocyclic hydrocarbon-carbonyl group, and a terpene family hydrocarbon-carbonyl. In the following, groups represented by the formulas (ω-2A) through (ω-21A) are similar to those explained above.

Examples of the heteroring in the groups represented by the aforementioned formulas (ω-1A) through (ω-21A) include similar groups to the aforementioned heterocyclic group. Examples of the heteroring-carbonyl group represented by the formula (ω-1A) include, for example, a monocyclic heteroaryl-carbonyl group, a fused polycyclic heteroaryl-carbonyl group, a monocyclic nonaromatic heteroring-carbonyl group, and a fused polycyclic nonaromatic heteroring-carbonyl. In the following, groups represented by the formulas (ω-2A) through (ω-21A) are similar to those explained above.

Examples of the cyclic amino in the groups represented by the aforementioned formulas (ω-10A) through (ω-16A) include similar groups to the aforementioned cyclic amino group.

The aforementioned acyl group, carbamoyl group, thiocarbamoyl group, sulfamoyl group, and sulfinamoyl group are generically referred to as "acyl groups" which may be substituted.

In the present specification, when a certain functional group is defined as "which may be substituted", the definition means that the functional group may sometimes have one or more substituents at chemically substitutable positions, unless otherwise specifically mentioned. Kind of substituents, number of substituents, and the position of substituents existing in the functional groups are not particularly limited, and when two or more substituents exist, they may be the same or different. Examples of the substituent existing in the functional-group include, for example, halogen atoms, oxo group, thioxo group, nitro group, nitroso group, cyano group, isocyano group, cyanato group, thiocyanato group, isocyanato group, isothiocyanato group, hydroxy group, sulfanyl group, carboxy group, sulfanylcarbonyl group, oxalo group, methooxalo group, thiocarboxy group, dithiocarboxy group, carbamoyl group, thiocarbamoyl group, sulfo group, sulfamoyl group, sulfino group, sulfinamoyl group, sulfeno group, sulfenamoyl group, phosphono group, hydroxyphosphonyl group, hydrocarbon group, heterocyclic group, hydrocarbon-oxy group, heteroring-oxy group, hydrocarbon-sulfanyl group, heteroring-sulfanyl group, acyl group, amino group, hydrazino group, hydrazono group, diazenyl group, ureido group, thioureido group, guanidino group, carbamoimidoyl group (amidino group), azido group, imino group, hydroxyamino group, hydroxyimino group, aminooxy group, diazo group, semicarbazino group, semicarbazono group, allophanyl group, hydantoyl group, phosphano group, phosphoroso group, phospho group, boryl group, silyl group, stannyl group, selanyl group, oxido group and the like.

When two or more substituents exist according to the abovementioned definition of "which may be substituted", said two or more substituents may combine to each other, together with atom(s) to which they bind, to form a ring. For these cyclic groups, as ring-constituting atoms (ring forming atoms), one to three kinds of one or more hetero atoms selected from oxygen atom, sulfur atom, nitrogen atom and the like may be included, and one or more substituents may exist on the ring. The ring may be monocyclic or fused polycyclic, and aromatic or nonaromatic.

The above substituents according to the abovementioned definition of "which may be substituted" may further be substituted with the aforementioned substituents at the chemically substitutable positions on the substituent. Kind of substituents, number of substituents, and positions of substituents are not particularly limited, and when the substituents are substituted with two or more substituents, they may be the same or different. Examples of the substituent include, for example, a halogenated alkyl-carbonyl group (trifluoroacetyl group as an example), a halogenated alkyl-sulfonyl group (trifluoromethanesulfonyl group as an example), an acyl-oxy group, an acyl-sulfanyl group, an N-hydrocarbon-amino group, an N,N-di(hydrocarbon)-amino group, an N-heteroring-amino group, an N-hydrocarbon-N-heteroring-amino group, an acyl-amino group, and a di(acyl)-amino group. Moreover, substitution on the aforementioned substituents may be repeated multiple orders.

Examples of the acyl-oxy group include the group in which hydrogen atom of hydroxy group is substituted with acyl group, and include, for example, formyloxy group, glyoxyloyloxy group, and thioformyloxy group, and the group represented by the following formulas:

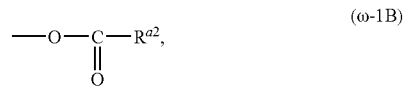
(ω-1B)

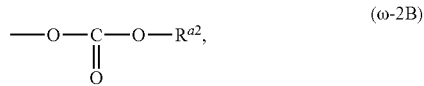
(ω-2B)

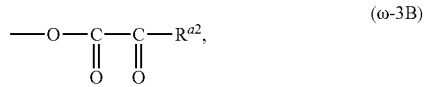
(ω-3B)

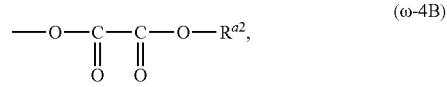
(ω-4B)

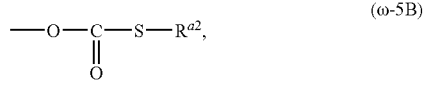
(ω-5B)

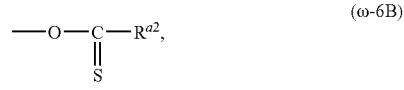
(ω-6B)

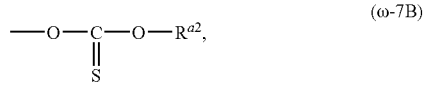
(ω-7B)

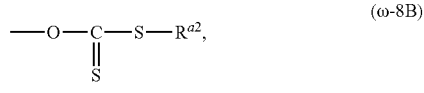
(ω-8B)

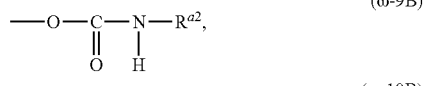
(ω-9B)

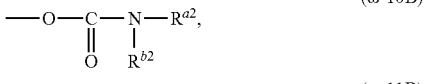
(ω-10B)

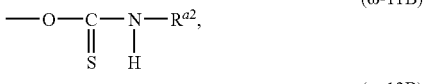
(ω-11B)

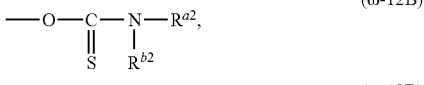
(ω-12B)

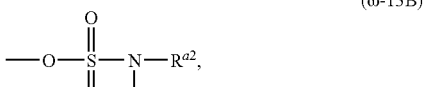
(ω-13B)

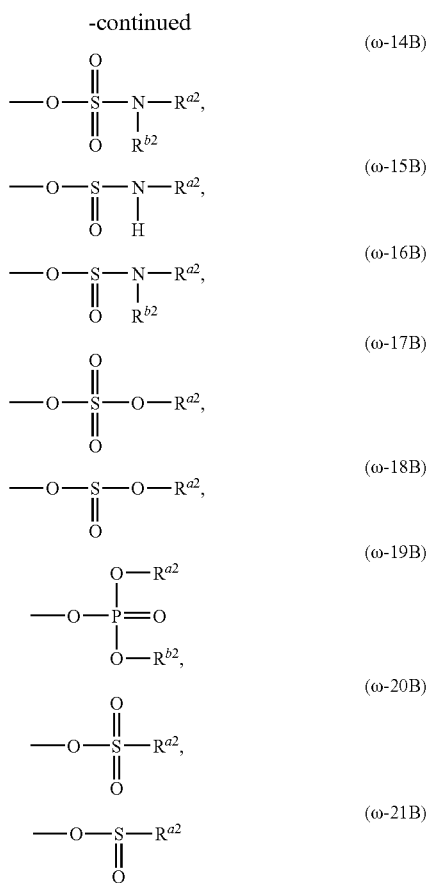

wherein $R^{a2}$ and $R^{b2}$ may be the same or different and represent a hydrocarbon group or a heterocyclic group, or $R^{a2}$ and $R^{b2}$ combine to each other, together with the nitrogen atom to which they bind, to form a cyclic amino group.

In the definition of aforementioned acyl-oxy group, among the groups represented by the formula (ω-1B), those groups in which $R^{a2}$ is a hydrocarbon group are referred to as "hydrocarbon-carbonyl-oxy group" whose examples include, for example, acetoxy and benzoyloxy group, and those groups in which $R^{a2}$ is a heterocyclic group are referred to as "heteroring-carbonyl-oxy group".

Among the groups represented by the formula (ω-2B), those groups in which $R^{a2}$ is a hydrocarbon group are referred to as "hydrocarbon-oxy-carbonyl-oxy group", and those groups in which $R^{a2}$ is a heterocyclic group are referred to as "heteroring-oxy-carbonyl-oxy group".

Among the groups represented by the formula (ω-3B), those groups in which $R^{a2}$ is a hydrocarbon group are referred to as "hydrocarbon-carbonyl-carbonyl-oxy group", and groups in which $R^{a2}$ is a heterocyclic group are referred to as "heteroring-carbonyl-carbonyl-oxy group".

Among the groups represented by the formula (ω-4B), those groups in which $R^{a2}$ is a hydrocarbon group are referred to as "hydrocarbon-oxy-carbonyl-carbonyl-oxy group", and groups in which $R^{a2}$ is a heterocyclic group are referred to as "heteroring-oxy-carbonyl-carbonyl-oxy group".

Among the groups represented by the formula (ω-5B), those groups in which $R^{a2}$ is a hydrocarbon group are referred to as "hydrocarbon-sulfanyl-carbonyl-oxy group", and groups where $R^{a2}$ is a heterocyclic group are referred to as "heteroring-sulfanyl-carbonyl-oxy group".

Among the groups represented by the formula (ω-6B), those groups in which $R^{a2}$ is a hydrocarbon group are referred to as "hydrocarbon-thiocarbonyl-oxy group", and groups where $R^{a2}$ is a heterocyclic group are referred to as "hetero ring-thiocarbonyl-oxy group".

Among the groups represented by the formula (ω-7B), those groups in which $R^{a2}$ is a hydrocarbon group are referred to as "hydrocarbon-oxy-thiocarbonyl-oxy group", and groups in which $R^{a2}$ is a heterocyclic group are referred to as "heteroring-oxy-thiocarbonyl-oxy group".

Among the groups represented by the formula (ω-8B), those groups in which $R^{a2}$ is a hydrocarbon group are referred to as "hydrocarbon-sulfanyl-thiocarbonyl-oxy group", and groups wherein $R^{a2}$ is a heterocyclic group are referred to as "heteroring-sulfanyl-thiocarbonyl-oxy group".

Among the groups represented by the formula (ω-9B), those groups in which $R^{a2}$ is a hydrocarbon group are referred to as "N-hydrocarbon-carbamoyl-oxy group", and groups in which $R^{a2}$ is a heterocyclic group are referred to as "N-heteroring-carbamoyl-oxy group".

Among the groups represented by the formula (ω-10B), those groups in which both $R^{a2}$ and $R^{b2}$ are hydrocarbon groups are referred to as "N,N-di(hydrocarbon)-carbamoyl-oxy group", those groups in which both $R^{a2}$ and $R^{b2}$ are heterocyclic groups are referred to as "N,N-di(heteroring)-carbamoyl-oxy group", those groups in which $R^{a2}$ is a hydrocarbon group and $R^{b2}$ is a heterocyclic group are referred to as "N-hydrocarbon-N-heteroring-carbamoyl-oxy group", and those groups in which $R^{a2}$ and $R^{b2}$ combine each other, together with the nitrogen atom to which they bind, to form a cyclicic amino group are referred to as "cyclicamino-carbonyl-oxy group".

Among the groups represented by the formula (ω-11B), those groups in which $R^{a2}$ is a hydrocarbon group are referred to as "N-hydrocarbon-thiocarbamoyl-oxy group", and those groups in which $R^{a2}$ is a heterocyclic group are referred to as "N-heteroring-thiocarbamoyl-oxy group".

Among the groups represented by the formula (ω-12B), those groups in which both $R^{a2}$ and $R^{b2}$ are hydrocarbon groups are referred to as "N,N-di(hydrocarbon)-thiocarbamoyl-oxy group", those groups in which both $R^{a2}$ and $R^{b2}$ are heterocyclic groups are referred to as "N,N-di(heteroring)-thiocarbamoyl-oxy group", those groups wherein $R^{a2}$ is a hydrocarbon group and $R^{b2}$ is a heterocyclic group are referred to as "N-hydrocarbon-N-heteroring-thiocarbamoyl-oxy group", and those groups in which $R^{a2}$ and $R^{b2}$ combine to each other, together with the nitrogen atom to which they bind, to form a cyclic amino group are referred to as "cyclicamino-thiocarbonyl-oxy group".

Among the groups represented by the formula (ω-13B), those groups in which $R^{a2}$ is a hydrocarbon group are referred to as "N-hydrocarbon-sulfamoyl-oxy groups", and those groups in which $R^{a2}$ is a heterocyclic group are referred to as "N-heteroring-sulfamoyl-oxy groups".

Among the groups represented by the formula (ω-14B), those groups in which both $R^{a2}$ and $R^{b2}$ are hydrocarbon groups are referred to as "N,N-di(hydrocarbon)-sulfamoyl-oxy groups", those groups in which both $R^{a2}$ and $R^{b2}$ are heterocyclic groups are referred to as "N,N-di(heteroring)-sulfamoyl-oxy groups", those groups in which $R^{a2}$ is a hydrocarbon group and $R^{b2}$ is a heterocyclic group are referred to as "N-hydrocarbon-N-heteroring-sulfamoyl-oxy groups", and those groups in which $R^{a2}$ and $R^{b2}$ combine to each other, together with the nitrogen atom to which they bind, to form a cyclic amino group are referred to as "cyclic amino-sulfonyl-oxy groups".

Among the groups represented by the formula (ω-15B), those groups in which $R^{a2}$ is a hydrocarbon group are referred to as "N-hydrocarbon-sulfinamoyl-oxy groups", and those groups where $R^{a2}$ is a heterocyclic group are referred to as "N-heterocyclic-sulfinamoyl-oxy groups".

Among the groups represented by the formula (ω-16B), those groups in which both $R^{a2}$ and $R^{b2}$ are hydrocarbon groups are referred to as "N,N-di(hydrocarbon)-sulfinamoyl-oxy groups", those groups in which both $R^{a2}$ and $R^{b2}$ are heterocyclic groups are referred to as "N,N-di(heteroring)-sulfinamoyl-oxy groups", those groups in which $R^{a2}$ is a hydrocarbon group and $R^{b2}$ is a heterocyclic group are referred to as "N-hydrocarbon-N-heteroring-sulfinamoyl-oxy groups", and those groups in which $R^{a2}$ and $R^{b2}$ combine to each other, together with the nitrogen atom to which they bind, to form a cyclic amino group are referred to as "cyclic amino-sulfinyl-oxy group".

Among the groups represented by the formula (ω-17B), those groups in which $R^{a2}$ is a hydrocarbon group are referred to as "hydrocarbon-oxy-sulfonyl-oxy group", and those groups in which $R^{a2}$ is a heterocyclic group are referred to as "heteroring-oxy-sulfonyl-oxy group".

Among the groups represented by the formula (ω-18B), those groups in which $R^{a2}$ is a hydrocarbon group are referred to as "hydrocarbon-oxy-sulfinyl-oxy groups", those groups in which $R^{a2}$ is a heterocyclic group are referred to as "heteroring-oxy-sulfinyl-oxy groups".

Among the groups represented by the formula (ω-19B), those groups in which both $R^{a2}$ and $R^{b2}$ are hydrocarbon groups are referred to as "O,O'-di(hydrocarbon)-phosphono-oxy group", groups in which both $R^{a2}$ and $R^{b2}$ are heterocyclic groups are referred to as "O,O'-di(heteroring)-phosphono-oxy group", and those groups in which $R^{a2}$ is a hydrocarbon group and $R^{b2}$ is a heterocyclic group are referred to as "O-hydrocarbon substituted-O'-heteroring substituted phosphono-oxy group".

Among the groups represented by the formula (ω-20B), those groups in which $R^{a2}$ is a hydrocarbon group are referred to as "hydrocarbon-sulfonyl-oxy group", and those groups in which $R^{a2}$ is a heterocyclic group referred to as "heteroring-sulfonyl-oxy group".

Among the groups represented by the formula (ω-21B), those groups in which $R^{a2}$ is a hydrocarbon group are referred to as "hydrocarbon-sulfinyl-oxy group", and those groups in which $R^{a2}$ is a heterocyclic group are referred to as "heteroring-sulfinyl-oxy group".

Examples of the hydrocarbon in the groups represented by the aforementioned formulas (ω-1B) through (ω-21B) include the similar groups to the aforementioned hydrocarbon group. Examples of the hydrocarbon-carbonyl-oxy groups represented by the formula (ω-1B) include, for example, an alkyl-carbonyl-oxy group, an alkenyl-carbonyl-oxy group, an alkynyl-carbonyl-oxy group, a cycloalkyl-carbonyl-oxy group, a cycloalkenyl-carbonyl-oxy group, a cycloalkanedienyl-carbonyl-oxy group, and a cycloalkyl-alkyl-carbonyl-oxy group, which are aliphatic hydrocarbon-carbonyl-oxy groups, an aryl-carbonyl-oxy group, an aralkyl-carbonyl-oxy group, a bridged cyclic hydrocarbon-carbonyl-oxy group, a spirocyclic hydrocarbon-carbonyl-oxy group, and a terpene family hydrocarbon-carbonyl-oxy group. In the following, groups represented by the formulas (ω-2B) through (ω-21B) are similar to those explained above.

Examples of the heteroring in the groups represented by the aforementioned formulas (ω-1B) through (ω-21B) include similar groups to the aforementioned heterocyclic group. Examples of the heteroring-carbonyl group represented by the formula (ω-1B) include, for example, a monocyclic heteroaryl-carbonyl group, a fused polycyclic heteroaryl-carbonyl group, a monocyclic nonaromatic heteroring-carbonyl group, and a fused polycyclic nonaromatic heteroring-carbonyl group. In the following, groups represented by the formulas (ω-2B) through (ω-21B) are similar to those groups mentioned above.

Examples of the cyclic amino in the groups represented by the aforementioned formulas (ω-10B) through (ω-16B) include similar groups to the aforementioned cyclic amino group.

The aforementioned acyl-oxy group, hydrocarbon-oxy group, and heterocyclic-oxy group are generically referred to as "substituted oxy group". Moreover, these substituted oxy group and hydroxy group are generically referred to as "hydroxy group" which may be substituted.

Examples of the acyl-sulfanyl include the group in which hydrogen atom of sulfanyl group is substituted with acyl group, and include, for example, formylsulfanyl group, glyoxyloylsulfanyl group, and thioformylsulfanyl group, and groups represented by the following formulas:

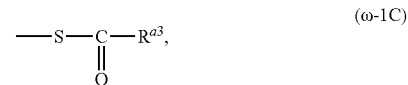

(ω-1C)

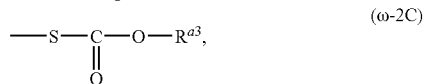

(ω-2C)

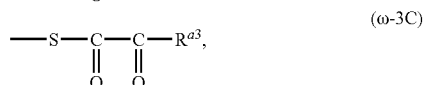

(ω-3C)

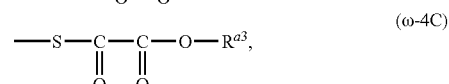

(ω-4C)

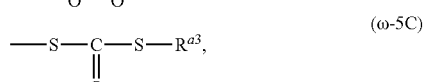

(ω-5C)

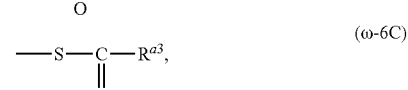

(ω-6C)

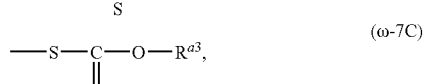

(ω-7C)

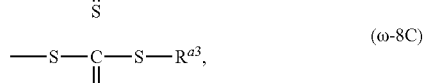

(ω-8C)

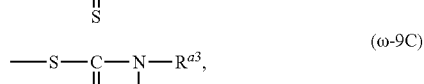

(ω-9C)

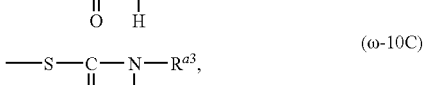

(ω-10C)

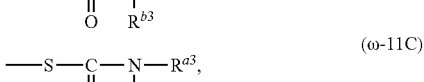

(ω-11C)

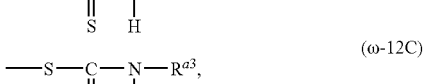

(ω-12C)

(ω-13C)

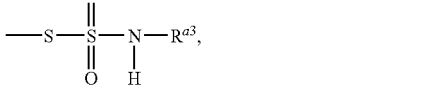

-continued

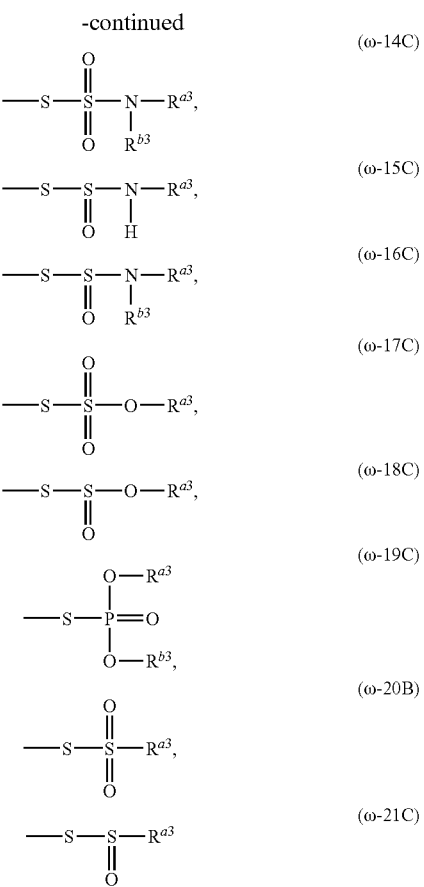

wherein $R^{a3}$ and $R^{b3}$ may be the same or different and represent a hydrocarbon group which may be substituted or a heterocyclic group which may be substituted, or $R^{a3}$ and $R^{b3}$ combine to each other, together with the nitrogen atom to which they bind, to form a cyclic amino group which may be substituted.

In the definition of aforementioned acyl-sulfanyl group, among the groups represented by the formula (ω-1C), those groups in which $R^{a3}$ is a hydrocarbon group are referred to as "hydrocarbon-carbonyl-sulfanyl group", and those groups in which $R^{a3}$ is a heterocyclic group are referred to as "heteroring-carbonyl-sulfanyl group".

Among the groups represented by the formula (ω-2C), those groups in which $R^{a3}$ is a hydrocarbon group are referred to as "hydrocarbon-oxy-carbonyl-sulfanyl group", and those groups in which $R^{a3}$ is a heterocyclic group are referred to as "heteroring-oxy-carbonyl-sulfanyl group".

Among the groups represented by the formula (ω-3C), those groups in which $R^{a3}$ is a hydrocarbon group are referred to as "hydrocarbon-carbonyl-carbonyl-sulfanyl group", and those groups in which $R^{a3}$ is a heterocyclic group are referred to as "heteroring-carbonyl-carbonyl-sulfanyl group".

Among the groups represented by the formula (ω-4C), those groups in which $R^{a3}$ is a hydrocarbon group are referred to as "hydrocarbon-oxy-carbonyl-carbonyl-sulfanyl group", and those groups in which $R^{a3}$ is a heterocyclic group are referred to as "heteroring-oxy-carbonyl-carbonyl-sulfanyl group".

Among the groups represented by the formula (ω-5C), those groups in which $R^{a3}$ is a hydrocarbon group are referred to as "hydrocarbon-sulfanyl-carbonyl-sulfanyl group", and those groups in which $R^{a3}$ is a heterocyclic group are referred to as "heteroring-sulfanyl-carbonyl-sulfanyl group".

Among the groups represented by the formula (ω-6C), those groups in which $R^{a3}$ is a hydrocarbon group are referred to as "hydrocarbon-thiocarbonyl-sulfanyl group", and those groups in which $R^{a3}$ is a heterocyclic group are referred to as "heteroring-thiocarbonyl-sulfanyl group".

Among the groups represented by the formula (ω-7C), those groups in which $R^{a3}$ is a hydrocarbon group are referred to as "hydrocarbon-oxy-thiocarbonyl-sulfanyl group", and those groups in which $R^{a3}$ is a heterocyclic group are referred to as "heteroring-oxy-thiocarbonyl-sulfanyl group".

Among the groups represented by the formula (ω-8C), those groups in which $R^{a3}$ is a hydrocarbon group are referred to as "hydrocarbon-sulfanyl-thiocarbonyl-sulfanyl group", and those groups in which $R^{a3}$ is a heterocyclic group are referred to as "heteroring-sulfanyl-thiocarbonyl-sulfanyl group".

Among the groups represented by the formula (ω-9C), those groups in which $R^{a3}$ is a hydrocarbon group are referred to as "N-hydrocarbon-carbamoyl-sulfanyl group", and those groups in which $R^{a3}$ is a heterocyclic group are referred to as "N-heteroring-carbamoyl-sulfanyl group".

Among the groups represented by the formula (ω-10C), those groups in which both $R^{a3}$ and $R^{b3}$ are a hydrocarbon groups are referred to as "N,N-di(hydrocarbon)-carbamoyl-sulfanyl group", those groups in which both $R^{a3}$ and $R^{b3}$ are heterocyclic groups are referred to as "N,N-di(heteroring)-carbamoyl-sulfanyl group", groups in which $R^{a3}$ is a hydrocarbon group and $R^{b3}$ is a heterocyclic group are referred to as "N-hydrocarbon-N-heteroring-carbomoyl-sulfanyl group", and those groups in which $R^{a3}$ and $R^{b3}$ combine to each other, together with the nitrogen atom to which they bind, to form a cyclic amino group are referred to as "cyclicamino-carbonyl-sulfamoyl group".

Among the groups represented by the formula (ω-11C), those groups in which $R^{a3}$ is a hydrocarbon group are referred to as "N-hydrocarbon-thiocarbamoyl-sulfanyl group", and those groups in which $R^{a3}$ is a heterocyclic group are referred to as "N-heteroring-thiocarbamoyl-sulfanyl group".

Among the groups represented by the formula (ω-12C), those groups in which both $R^{a3}$ and $R^{b3}$ are hydrocarbon groups are referred to as "N,N-di(hydrocarbon)-thiocarbamoyl-sulfanyl group", those groups in which and $R^{a3}$ and $R^{b3}$ are heterocyclic groups are referred to as "N,N-di(heteroring)-thiocarbamoyl-sulfanyl group", those groups in which $R^{a3}$ is a hydrocarbon group and $R^{b3}$ is a heterocyclic group are referred to as "N-hydrocarbon-N-heteroring-thiocarbamoyl-sulfanyl group", and those groups in which $R^{a3}$ and $R^{b3}$ combine to each other, together with the nitrogen atom to which they bind, to form a cyclic amino group are referred to as "cyclicamino-thiocarbonyl-sulfamoyl group".

Among the groups represented by the formula (ω-13C), those groups in which $R^{a3}$ is a hydrocarbon group are referred to as "N-hydrocarbon-sulfamoyl-sulfanyl group", and those groups in which $R^{a3}$ is a heteroring group are referred to as "N-heterocyclic-sulfamoyl-sulfanyl group".

Among the groups represented by the formula (ω-14C), those groups in which both $R^{a3}$ and $R^{b3}$ are hydrocarbon groups are referred to as "N,N-di(hydrocarbon)-sulfamoyl-sulfanyl group", those groups in which both $R^{a3}$ and $R^{b3}$ are heterocyclic groups are referred to as "N,N-di(heteroring)-sulfamoyl-sulfinyl group", those groups in which $R^{a3}$ is a hydrocarbon group and $R^{b3}$ is a heterocyclic group are referred to as "N-hydrocarbon-N-heteroring-sulfamoyl-sulfanyl group", and those groups in which $R^{a3}$ and $R^{b3}$ combine to each other, together with the nitrogen atom to which they bind, to form a cyclic amino group are referred to as "cyclicamino-sulfonyl-sulfanyl group".

Among the groups represented by the formula (ω-15C), those groups in which $R^{a3}$ is a hydrocarbon group are referred to as "N-hydrocarbon-sulfinamoyl-sulfanyl group", and those groups in which $R^{a3}$ is a heteroring group are referred to as "N-heterocyclic-sulfinamoyl-sulfanyl group".

Among the groups represented by the formula (ω-16C), those groups in which both $R^{a3}$ and $R^{b3}$ are hydrocarbon groups are referred to as "N,N-di(hydrocarbon)-sulfinamoyl-sulfanyl group", those groups in which both $R^{a3}$ and $R^{b3}$ are heterocyclic groups are referred to as "N,N-di(heteroring)-sulfinamoyl-sulfanyl group", those groups in which $R^{a3}$ is a hydrocarbon group and $R^{b3}$ is a heterocyclic group are referred to as "N-hydrocarbon-N-heteroring-sulfinamoyl-sulfanyl group", and those groups in which $R^{a3}$ and $R^{b3}$ combine to each other, together with the nitrogen atom to which they bind, to form a cyclic amino group are referred to as "cyclicamino-sulfanyl-sulfanyl group".

Among the groups represented by the formula (ω-17C), those groups in which $R^{a3}$ is a hydrocarbon group are referred to as "hydrocarbon-oxy-sulfonyl-sulfanyl group", and those groups in which $R^{a3}$ is a heteroring group are referred to as "heterocyclic-oxy-sulfonyl-sulfanyl group".

Among the groups represented by the formula (ω-18C), those groups in which $R^{a3}$ is a hydrocarbon group are referred to as "hydrocarbon-oxy-sulfinyl-sulfanyl group", and those groups in which $R^{a3}$ is a heteroring group are referred to as "heterocyclic-oxy-sulfinyl-sulfanyl group".

Among the groups represented by the formula (ω-19C), those groups in which both $R^{a3}$ and $R^{b3}$ are hydrocarbon groups are referred to as "O,O'-di(hydrocarbon)-phosphono-sulfanyl group", those groups in which both $R^{a3}$ and $R^{b3}$ are heterocyclic groups are referred to as "O,O'-di(heteroring)-phosphono-sulfanyl group", and those groups in which $R^{a3}$ is a hydrocarbon group and $R^{b3}$ is a heteroring group are referred to as "O-hydrocarbon-O'-heterocyclic-phosphono-sulfanyl group". Among the groups represented by the formula (ω-20C), those groups in which $R^{a3}$ is a hydrocarbon group are referred to as "hydrocarbon-sulfonyl-sulfanyl group", and those groups in which $R^{a3}$ is a heterocyclic group are referred to as "heteroring-sulfonyl-sulfanyl group".

Among the groups represented by the formula (ω-21C), those groups in which $R^{a3}$ is a hydrocarbon group are referred to as "hydrocarbon-sulfinyl-sulfanyl group", and those groups in which $R^{a3}$ is a heteroring group are referred to as "heterocyclic-sulfinyl-sulfanyl group".

Examples of the hydrocarbon in the groups represented by the aforementioned formulas (ω-1C) through (ω-21C) include similar groups to the aforementioned hydrocarbon group. Examples of the hydrocarbon-carbonyl-sulfanyl groups represented by the formula (ω-1C) include, for example, an alkyl-carbonyl-sulfanyl group, an alkenyl-carbonyl-sulfanyl group, an alkynyl-carbonyl-sulfanyl group, a cycloalkyl-carbonyl-sulfanyl group, a cycloalkenyl-carbonyl-sulfanyl group, a cycloalkanedienyl-carbonyl-sulfanyl group, a cycloalkyl-alkyl-carbonyl-sulfanyl group which is an aliphatic hydrocarbon-carbonyl-sulfanyl groups, an aryl-carbonyl-sulfanyl group, an aralkyl-carbonyl-sulfanyl group, a bridged cyclic hydrocarbon-carbonyl-sulfanyl group, a spiro cyclic hydrocarbon-carbonyl-sulfanyl group, and a terpene family hydrocarbon-carbonyl-sulfanyl group. In the following, groups represented by the formulas (ω-2C) through (ω-21C) are similar to those mentioned above.

Examples of the heteroring in the groups represented by the aforementioned formulas (ω-1C) through (ω-21C) include similar groups to the aforementioned heterocyclic group. Examples of the heteroring-carbonyl-sulfanyl group represented by the formula (ω-1C) include, for example, a monocyclic heteroaryl-carbonyl-sulfanyl group, a fused polycyclic heteroaryl-carbonyl-sulfanyl group, a monocyclic nonaromatic heteroring-carbonyl-sulfanyl group, and a fused polycyclic non-aromatic heteroring-carbonyl-sulfanyl group. In the following, groups represented by the formula (ω-2C) through (ω-21C) are similar to those groups mentioned above.

Examples of the cyclic amino in the groups represented by the aforementioned formulas (ω-10C) through (ω-16C) include similar groups to the aforementioned cyclic amino group.

The aforementioned acyl-sulfanyl group, hydrocarbon-sulfanyl group, and heterocyclic-sulfanyl group are generically referred to as "substituted sulfanyl group". These substituted sulfanyl group and sulfanyl group are generically referred to as "sulfanyl groups" which may be substituted.

Examples of the N-hydrocarbon-amino group include the group in which one hydrogen atom of amino group is substituted with a hydrocarbon group, and include, for example, an N-alkyl-amino group, an N-alkenyl-amino group, an N-alkynyl-amino group, an N-cycloalkyl-amino group, an N-cycloalkyl-alkyl-amino group, an N-aryl-amino group, and an N-aralkyl-amino group.

Examples of the N-alkyl-amino group include, for example, methylamino, ethylamino, n-propylamino, isopropylamino, n-butylamino, isobutylamino, sec-butylamino, tert-butylamino, n-pentylamino, isopentylamino, (2-methylbutyl)amino, (1-methylbutyl)amino, neopentylamino, (1,2-dimethylpropyl)amino, (1-ethylpropyl)amino, n-hexylamino, (4-methylpentyl)amino, (3-methylpentyl)amino, (2-methylpentyl)amino, (1-methylpentyl)amino, (3,3-dimethylbutyl)amino, (2,2-dimethylbutyl)amino, (1,1-dimethylbutyl)amino, (1,2-dimethylbutyl)amino, (1,3-dimethylbutyl)amino, (2,3-dimethylbutyl)amino, (2-ethylbutyl)amino, (1-ethylbutyl)amino, (1-ethyl-1-methylpropyl)amino, n-heptylamino, n-octylamino, n-nonylamino, n-decylamino, n-undecylamino, n-dodecylamino, n-tridecylamino, n-tetradecylamino, and n-pentadecylamino group, which are $C_1$ to $C_{15}$ straight chain or branched chain N-alkyl amino groups.

Examples of the N-alkenyl-amino group include, for example, vinyl amino, (prop-1-en-1-yl)amino, allylamino, isopropenylamino, (but-1-en-1-yl)amino, (but-2-en-1-yl)amino, (but-3-en-1-yl)amino, (2-methylprop-2-en-1-yl)amino, (1-methylprop-2-en-1-yl)amino, (pent-1-en-1-yl)amino, (pent-2-en-1-yl)amino, (pent-3-en-1-yl)amino, (pent-4-en-1-yl)amino, (3-methylbut-2-en-1-yl)amino, (3-methylbut-3-en-1-yl)amino, (hex-1-en-1-yl)amino, (hex-2-en-1-yl)amino, (hex-3-en-1-yl)amino, (hex-4-en-1-yl)amino, (hex-5-en-1-yl)amino, (4-methylpent-3-en-1-yl)amino, (4-methylpent-3-en-1-yl)amino, (hept-1-en-1-yl)amino, (hept-6-en-1-yl)amino, (oct-1-en-1-yl)amino, (oct-7-en-1-yl)amino, (non-1-en-1-yl)amino, (non-8-en-1-yl)amino, (dec-1-en-1-yl)amino, (dec-9-en-1-yl)amino, (undec-1-en-1-yl)amino, (undec-10-en-1-yl)amino, (dodec-1-en-1-yl)amino, (dodec-11-en-1 yl)amino, (tridec-1-en-1-yl)amino, (tridec-12-en-1-yl)amino, (tetradec-1-en-1-yl)amino, (tetradec-13-en-1-yl)amino, (pentadec-1-en-1-yl)amino, and (pentadec-14-en-1-yl)amino group, which are $C_2$ to $C_{15}$ straight chain or branched chain N-alkenyl amino groups.

Examples of the N-alkynl-amino group-include, for example, ethynylamino, (prop-1-yn-1-yl)amino, (prop-2-yn-1-yl)amino, (but-1-yn-1-yl)amino, (but-3-yn-1-yl)amino, (1-methylprop-2-yn-1-yl)amino, (pent-1-yn-1-yl)amino, (pent-4-yn-1-yl)amino, (hex-1-yn-1-yl)amino, (hex-5-yn-1-yl)amino, (hept-1-yn-1-yl)amino, (hept-6-yn-1-yl)amino, (oct-1-yn-1-yl)amino, (oct-7-yn-1-yl)amino, (non-1-yn-1-yl)amino, (non-8-yn-1-yl)amino, (dec-1-yn-1-yl)amino, (dec-9-yn-1-yl)amino, (undec-1-yn-1-yl)amino, (undec-10-yn-1-yl)amino, (dodec-1-yn-1-yl)amino, (dodec-11-yn-1-yl)amino, (tridec-1-yn-1-yl)amino, (tridec-12-yn-1-yl)amino, (tetradec-1-yn-1-yl)amino, (tetradec-13-yn-1-yl)amino, (pentadec-1-yn-1-yl)amino, and (pentadec-14-yn-1-yl)amino group, which are $C_2$ to $C_{15}$ straight chain or branched chain N-alkynyl-amino groups.

Examples of the N-cycloalkyl-amino group include, for example, cyclopropylamino, cyclobutylamino, cyclopentylamino, cyclohexylamino, cycloheptylamino, and cyclooctylamino group, which are $C_3$ to $C_8$ N-cycloalkyl-amino groups.

Examples of the N-cycloalkyl-alkyl-amino group include, for example, (cyclopropylmethyl)amino, (1-cyclopropylethyl)amino, (2-cyclopropylethyl)amino, (3-cyclopropylpropyl)amino, (4-cyclopropylbutyl)amino, (5-cyclopropylpentyl)amino, (6-cyclopropylhexyl)amino, (cyclobutylmethyl)amino, (cyclopentylmethyl)amino, (cyclobutylmethyl)amino, (cyclopentylmethyl)amino, (cyclohexylmethyl)amino, (2-cyclohexylethyl)amino, (3-cyclohexylpropyl)amino, (4-cyclohexylbutyl)amino, (cycloheptylmethyl)amino, (cyclooctylmethyl)amino, and (6-cyclooctylhexyl)amino, which are $C_4$ to $C_{14}$ N-cycloalkyl-alkyl-amino groups.

Examples of the N-aryl-amino group include, for example, phenylamino, 1-naphthylamino, 2-naphtylamino, anthrylamino, phenanthrylamino, and acenaphthylenylamino, which are $C_6$ to $C_{14}$ N-mono-arylamino groups.

Examples of the N-aralkyl-amino group include, for example, benzylamino, (1-naphthylmethyl)amino, (2-naphthylmethyl)amino, (anthracenylmethyl)amino, (phenanthrenylmethyl)amino, (acenaphthylenylmethyl)amino, (diphenylmethyl)amino, (1-phenethyl)amino, (2-phenethyl)amino, (1-(1-naphthyl)ethyl)amino, (1-(2-naphthyl)ethyl)amino, (2-(1-naphthyl)ethyl)amino, (2-(2-naphthyl)ethyl)amino, (3-phenylpropyl)amino, (3-(1-naphthyl)propyl)amino, (3-(2-naphthyl)propyl)amino, (4-phenylbutyl)amino, (4-(1-naphthyl)butyl)amino, (4-(2-naphthyl)butyl)amino, (5-phenylpentyl)amino, (5-(1-naphthyl)pentylamino, (5-(2-naphthyl)pentyl)amino, (6-phenylhexyl)amino, (6-(1-naphthyl)hexyl)amino, and (6-(2-naphthyl)hexyl)amino, which are $C_7$ to $C_{16}$ N-aralkyl-amino groups.

Examples of the N,N-di(hydrocarbon)-amino group include the group in which 2 hydrogen atoms of amino group are substituted with hydrocarbon group, and include, for example, N,N-dimethylamino, N,N-diethylamino, N-ethyl-N-methylamino, N,N-di-n-propylamino, N,N-diisopropylamino, N-allyl-N-methylamino, N-(prop-2-yn-1-yl)-N-methylamino, N,N-dicyclohexylamino, N-cyclohexyl-N-methylamino, N-cyclohexylmethylamino-N-methylamino, N,N-diphenylamino, N-methyl-N-phenylamino, N,N-dibenzylamino, and N-benzyl-N-methylamino group.

Examples of the N-heteroring-amino group include the group in which one hydrogen atom of amino group is substituted with heterocyclic group, and include, for example, (3-pyrrolizinyl)amino, (4-piperidinyl)amino, (2-tetrahydropyranyl)amino, (3-indolinyl)amino, (4-chromanyl)amino, (3-thienyl)amino, (3-pyridyl)amino, (3-quinolyl)amino, and (5-indolyl)amino.

Examples of the N-hydrocarbon-N-heteroring-amino group include the group in which 2 hydrogen atoms of amino group are substituted with hydrocarbon group and heterocyclic group respectively, and include, for example, N-methyl-N-(4-piperidinyl)amino, N-(4-chromanyl)-N-methylamino, N-methyl-N-(3-thienyl)amino, N-methyl-N-(3-pyridyl)amino, N-methyl-N-(3-quinolyl)amino and the like.

Examples of the acyl-amino group include the group in which one hydrogen atom of the amino group is substituted with an acyl group, and include, for example, formylamino group, glyoxyloylamino group, and thioformylamino group, and groups represented by the following formulas:

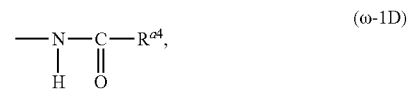
(ω-1D)

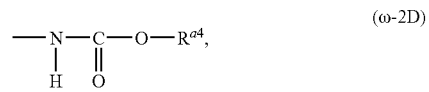
(ω-2D)

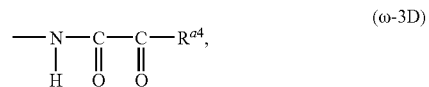
(ω-3D)

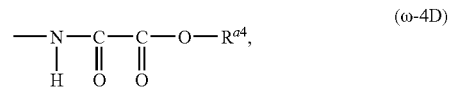
(ω-4D)

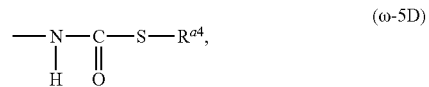
(ω-5D)

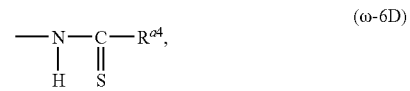
(ω-6D)

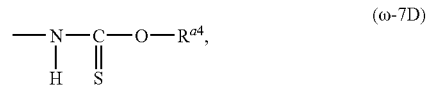
(ω-7D)

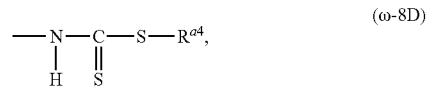
(ω-8D)

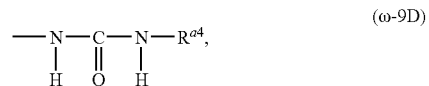
(ω-9D)

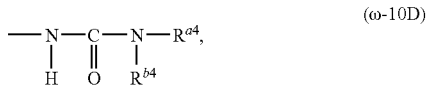
(ω-10D)

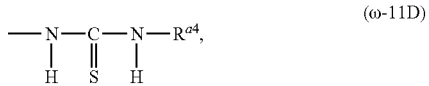
(ω-11D)

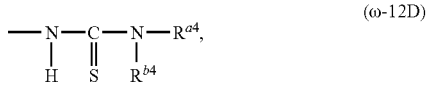
(ω-12D)

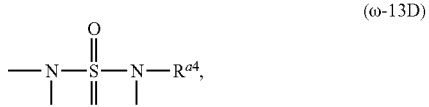
(ω-13D)

(ω-14D)

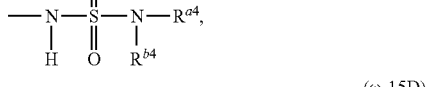
(ω-15D)

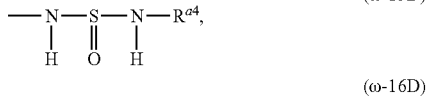
(ω-16D)

(ω-17D)

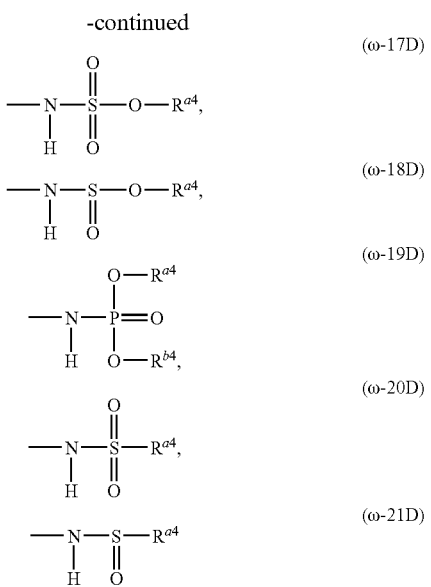

(ω-18D)

(ω-19D)

(ω-20D)

(ω-21D)

wherein $R^{a4}$ and $R^{b4}$ may be the same or different and represent a hydrocarbon group which may be substituted or a heterocyclic group which may be substituted, or $R^{a4}$ and $R^{b4}$ combine to each other, together with the nitrogen atom to which they bind, to form a cyclic amino group which may be substituted.

In the definition of the aforementioned acyl-amino group, among the groups represented by the formula (ω-1D), those groups in which $R^{a4}$ is a hydrocarbon group are referred to as "hydrocarbon-carbonyl-amino group", and those groups in which $R^{a4}$ is a heterocyclic group are referred to as "heteroring-carbonyl-amino group".

Among the groups represented by the formula (ω-2D), those groups in which $R^{a4}$ is a hydrocarbon group are referred to as "hydrocarbon-oxy-carbonyl-amino group", and those groups in which $R^{a4}$ is a heterring group are referred to as "heterocyclic-oxy-carbonyl-amino group".

Among the groups represented by the formula (ω-3D), those groups in which $R^{a4}$ is a hydrocarbon group are referred to as "hydrocarbon-carbonyl-carbonyl-amino group", and those groups in which $R^{a4}$ is a heterocyclic group are referred to as "heteroring-carbonyl-carbonylamino group".

Among the groups represented by the formula (ω-4D), those groups in which $R^{a4}$ is a hydrocarbon group are referred to as "hydrocarbon-oxy-carbonyl-carbonyl-amino group", and those groups in which $R^{a4}$ is a heterocyclic group are referred to as "heteroring-oxy-carbonyl-carbonyl-amino group".

Among the groups represented by the formula (ω-5D), those groups in which $R^{a4}$ is a hydrocarbon group are referred to as "hydrocarbon-sulfanyl-carbonyl-amino group", and those groups in which $R^{a4}$ is a heterocyclic group are referred to as "heteroring-sulfanyl-carbonyl-amino group".

Among the groups represented by the formula (ω-6D), those groups in which $R^{a4}$ is a hydrocarbon group are referred to as "hydrocarbon-thiocarbonyl-amino group", and those groups in which $R^{a4}$ is a heterocyclic group are referred to as "heteroring-thiocarbonyl-amino group".

Among the groups represented by the formula (ω-7D), those groups in which $R^{a4}$ is a hydrocarbon group are referred to as "hydrocarbon-oxy-thiocarbonyl-amino group", and those groups in which $R^{a4}$ is a heterocyclic group are referred to as "heteroring-oxy-thiocarbonyl-amino group".

Among the groups represented by the formula (ω-8D), those groups in which $R^{a4}$ is a hydrocarbon group are referred to as "hydrocarbon-sulfanyl-thiocarbonyl-amino group", and those groups in which $R^{a4}$ is a heterocyclic group are referred to as "heteroring-sulfanyl-thiocarbonyl-amino group".

Among the groups represented by the formula (ω-9D), those groups in which $R^{a4}$ is a hydrocarbon group are referred to as "N-hydrocarbon-carbamoyl group", and those groups in which $R^{a4}$ is a heterocyclic group are referred to as "N-heteroring-carbamoyl-amino group".

Among the groups represented by the formula (ω-10D), those groups in which both $R^{a4}$ and $R^{b4}$ are hydrocarbon groups are referred to as "N,N-di(hydrocarbon)-carbamoyl-amino group", those groups in which both $R^{a4}$ and $R^{b4}$ are heterocyclic groups are referred to as "N,N-di(heteroring)-carbamoyl-amino group", those groups in which $R^{a4}$ is a hydrocarbon group and $R^{b4}$ is a heterocyclic group are referred to as "N-hydrocarbon-N heteroring-carbamoyl-amino group", and those groups in which $R^{a4}$ and $R^{b4}$ combine to each other, together with the nitrogen atom to which they bind, to form a cyclic amino group are referred to as "cyclicamino-carbonyl-amino group".

Among the groups represented by the formula (ω-11D), those groups in which $R^{a4}$ is a hydrocarbon group are referred to as "N-hydrocarbon-thiocarbamoyl-amino group", and those groups in which $R^{a4}$ is a heterring group are referred to as "N-heterocyclic-thiocarbamoyl-amino group".

Among the groups represented by the formula (ω-12D), those groups in which both $R^{a4}$ and $R^{b4}$ are hydrocarbon groups are referred to as "N,N-di(hydrocarbon)-thiocarbamoyl-amino group", those groups in which both $R^{a4}$ and $R^{b4}$ are heterocyclic groups are referred to as "N,N-di(heteroring)-thiocarbamoyl-amino group", those groups in which $R^{a4}$ is a hydrocarbon group and $R^{b4}$ is a heterocyclic group are referred to as "N-hydrocarbon-N-heteroring-thiocarbamoyl-amino group", and those groups in which $R^{a4}$ and $R^{b4}$ combine to each other, together with the nitrogen atom to which they bind, to form a cyclic amino group are referred to as "cyclicamino-thiocarbonyl-amino group".

Among the groups represented by the formula (ω-13D), those groups in which $R^{a4}$ is a hydrocarbon group are referred to as "N-hydrocarbon-sulfamoyl-amino group", and those groups in which $R^{a4}$ is a heterocyclic group are referred to as "N-heteroring-sulfamoyl-amino group".

Among the groups represented by the formula (ω-14D), those groups in which both $R^{a4}$ and $R^{b4}$ are hydrocarbon groups are referred to as "di(hydrocarbon)-sulfamoyl-amino group", those groups in which both $R^{a4}$ and $R^{b4}$ are heterocyclic groups are referred to as "N,N-di(heteroring)-sulfamoyl-amino group", those groups in which $R^{a4}$ is a hydrocarbon group and $R^{b4}$ is a heterocyclic group are referred to as "N-hydrocarbon-N-heteroring-sulfamoyl-amino group", and those groups in which $R^{a4}$ and $R^{b4}$ combine to each other, together with the nitrogen atom to which they bind, to form a cyclic amino group are referred to as "cyclicamino-sulfonyl-amino group".

Among the groups represented by the formula (ω-15D), those groups in which $R^{a4}$ is a hydrocarbon group are referred to as "N-hydrocarbon-sulfinamoyl-amino group", and those groups in which $R^{a4}$ is a heterocyclic group are referred to as "N-heteroring-sulfinamoyl-amino group".

Among the groups represented by the formula (ω-16D), those groups in which both $R^{a4}$ and $R^{b4}$ are hydrocarbon groups are referred to as "N,N-di(hydrocarbon)-sulfinamoyl-amino group", those groups in which both $R^{a4}$ and $R^{b4}$ are heterocyclic groups are referred to as "N,N-di(heteroring)-sulfinamoyl-amino group", groups in which $R^{a4}$ is a hydrocarbon group and $R^{b4}$ is a heterocyclic group are referred to as "N-hydrocarbon-N-heterring-sulfinamoyl-amino group", and those groups in which $R^{a4}$ and $R^{b4}$ combine to each other, together with the nitrogen atom to which they bind, to form a cyclic amino group are referred to as "cyclicamino-sulfinyl-amino group".

Among the groups represented by the formula (ω-17D), those groups in which $R^{a4}$ is a hydrocarbon group are referred to as "hydrocarbon-oxy-sulfonyl-amino group", and those groups in which $R^{a4}$ is a heterocyclic group are referred to as "heterring-oxy-sulfonyl-amino group".

Among the groups represented by the formula (ω-18D), those groups in which $R^{a4}$ is a hydrocarbon group are referred to as "hydrocarbon-oxy-sulfinyl-amino group", and those groups in which $R^{a4}$ is a heterocyclic group are referred to as "heterring-oxy-sulfinyl-amino group".

Among the groups represented by the formula (ω-19D), those groups in which both $R^{a4}$ and $R^{b4}$ are hydrocarbon groups are referred to as "O,O'-di(hydrocarbon)-phosphono-amino group", those groups in which both $R^{a4}$ and $R^{b4}$ are heterocyclic groups are referred to as "O,O'-di(heterring)-phosphono-amino group", and those groups in which $R^{a4}$ is a hydrocarbon group and $R^{b4}$ is a heterocyclic group are referred to as "O-hydrocarbon-O'-heterring-phosphono-amino group".

Among the groups represented by the formula (ω-20D), those groups in which $R^{a4}$ is a hydrocarbon group are referred to as "hydrocarbon-sulfonyl-amino group", and those groups in which $R^{a4}$ is a heterocyclic group are referred to as "heterring-sulfonyl-amino group".

Among the groups represented by the formula (ω-21D), those groups in which $R^{a4}$ is a hydrocarbon group are referred to as "hydrocarbon-sulfinyl-amino group", and those groups in which $R^{a4}$ is a heterocyclic group are referred to as "heterring-sulfinyl-amino group".

Examples of the hydrocarbon in the groups represented by the aforementioned formulas (ω-1D) through (ω-21D), similar groups to the aforementioned hydrocarbon group. Examples of the hydrocarbon-carbonyl-amino groups represented by the formula (ω-1D) include, for example, an alkyl-carbonyl-amino group, an alkenyl-carbonyl-amino group, an alkynyl-carbonyl-amino group, a cycloalkyl-carbonyl-amino group, a cycloalkenyl-carbonyl-amino group, a cycloalkanedienyl-carbonyl-amino group, a cycloalkyl-alkyl-carbonyl-amino group which is an aliphatic hydrocarbon-carbonyl-amino groups, an aryl-carbonyl-amino group, an aralkyl-carbonyl-amino group, a bridged cyclic hydrocarbon-carbonyl-amino group, a spiro cyclic hydrocarbon-carbonyl-amino group, and a terpene family hydrocarbon-carbonyl-amino group. In the following, groups represented by the formulas (ω-2D) through (ω-21D) are similar to those explained above.

Examples of the heterring in the groups represented by the aforementioned formulas (ω-1D) through (ω-21D) include similar groups to the aforementioned heterocyclic group. Examples of the heterring-carbonyl-amino group represented by the formula (ω-1D) include, for example, a monocyclic heteroaryl-carbonyl-amino group, a fused polycyclic heteroaryl-carbonyl-amino group, a monocyclic non-aromatic heterocyclic-carbonyl-amino group, and a fused polycyclic nonaromatic heterocyclic-carbonyl-amino group. In the following, groups represented by the formulas (ω-2D) through (ω-21D) are similar to those groups mentioned above.

Examples of the cyclic amino in the groups represented by the aforementioned formulas (ω-10D) through (ω-16D) include similar groups to the aforementioned cyclic amino group.

The aforementioned di(acyl)-amino group include the group in which 2 hydrogen atoms of amino group are substituted with acyl groups in the definitions of the aforementioned substituents according to "which may be substituted". Examples include, for example, di(formyl)-amino group, di(glyoxyloyl)-amino group, and di(thioformyl)-amino group, and groups represented by the following formulas:

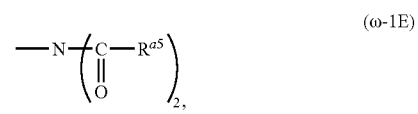
(ω-1E)

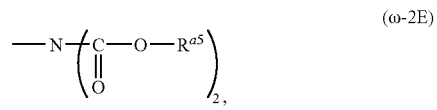
(ω-2E)

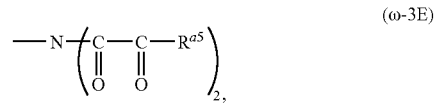
(ω-3E)

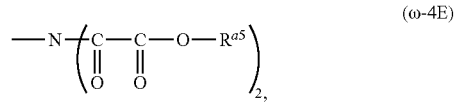
(ω-4E)

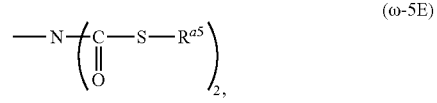
(ω-5E)

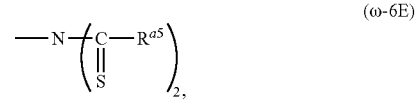
(ω-6E)

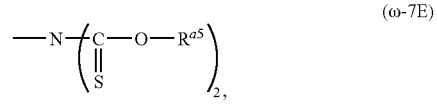
(ω-7E)

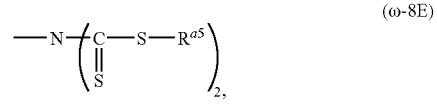
(ω-8E)

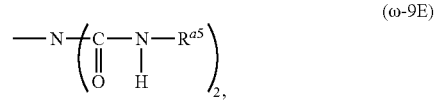
(ω-9E)

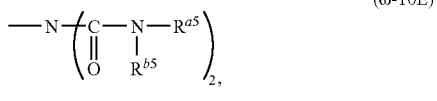
(ω-10E)

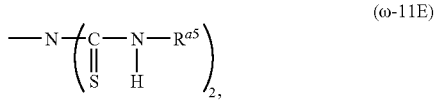
(ω-11E)

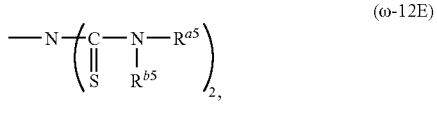
(ω-12E)

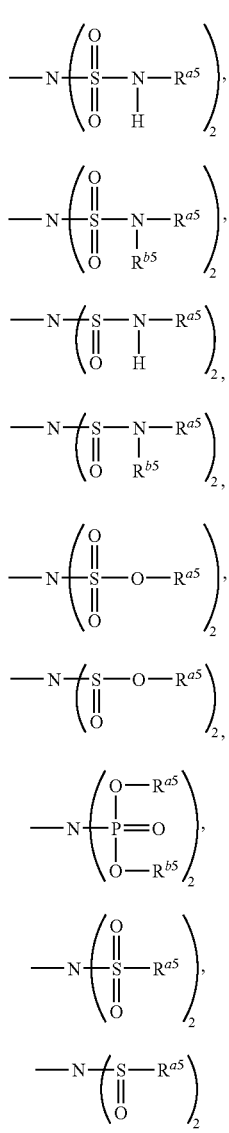

wherein $R^{a5}$ and $R^{b5}$ may be the same or different and represent hydrogen atom, a hydrocarbon group which may be substituted, or a heterocyclic group which may be substituted, or $R^{a5}$ and $R^{b5}$ combine to each other, together with the nitrogen atom to which they bind, to form a cyclic amino group which may be substituted.

In the definition of aforementioned di(acyl)-amino group, among the groups represented by the formula (ω-1E), those groups in which $R^{a5}$ is a hydrocarbon group are referred to as "bis(hydrocarbon-carbonyl)-amino group", and those groups in which $R^{a5}$ is a heteroring group are referred to as "bis(heterocyclic-carbonyl)-amino group".

Among the groups represented by the formula (ω-2E), those groups in which $R^{a5}$ is a hydrocarbon group are referred to as "bis(hydrocarbon-oxy-carbonyl)-amino group", and those groups in which $R^{a5}$ is a heterocyclic group are referred to as "bis(heteroring-oxy-carbonyl)-amino group".

Among the groups represented by the formula (ω-3E), those groups in which $R^{a5}$ is a hydrocarbon group are referred to as "bis(hydrocarbon-carbonyl-carbonyl)-amino group", and those groups in which $R^{a5}$ is a heterocyclic group are referred to as "bis(heteroring-carbonyl-carbonyl)-amino group". Among the groups represented by the formula (ω-4E), those groups in which $R^{a5}$ is a hydrocarbon group are referred to as "bis(hydrocarbon oxy-carbonyl-carbonyl)-amino group", and those groups in which $R^{a5}$ is a heterocyclic group are referred to as "bis(heteroring-oxy-carbonyl-carbonyl)-amino group".

Among the groups represented by the formula (ω-5E), those groups in which $R^{a5}$ is a hydrocarbon group are referred to as "bis(hydrocarbon-sulfanyl-carbonyl)-amino group", and those groups in which $R^{a5}$ is a heterocyclic group are referred to as "bis(heteroring-sulfanyl-carbonyl)-amino group".

Among the groups represented by the formula (ω-6E), those groups in which $R^{a5}$ is a hydrocarbon group are referred to as "bis(hydrocarbon-thiocarbonyl)-amino group", and those groups in which $R^{a5}$ is a heterocyclic group are referred to as "bis(heteroring-thiocarbonyl)-amino group".

Among the groups represented by the formula (ω-7E), those groups in which $R^{a5}$ is a hydrocarbon group are referred to as "bis(hydrocarbon-oxy-thiocarbonyl)-amino group", and those groups in which $R^{a5}$ is a heterocyclic group are referred to as "bis(ringoxy-thiocarbonyl)-amino group".

Among the groups represented by the formula (ω-8E), those groups in which $R^{a5}$ is a hydrocarbon group are referred to as "bis(hydrocarbon-sulfanyl-thiocarbonyl)-amino group", and those groups in which $R^{a5}$ is a heterocyclic group are referred to as "bis(heteroring-sulfanyl-thiocarbonyl)-amino group".

Among the groups represented by the formula (ω-9E), those groups in which $R^{a5}$ is a hydrocarbon group are referred to as "bis(N-hydrocarbon-carbamoyl)-amino group", and those groups in which $R^{a5}$ is a heterocyclic group are referred to as "bis(N-heteroring-carbamoyl)-amino group".

Among the groups represented by the formula (ω-10E), those groups in which both $R^{a5}$ and $R^{b5}$ are hydrocarbon groups are referred to as "bis[N,N-di(hydrocarbon)-carbamoyl]-amino group", those groups in which both $R^{a5}$ and $R^{b5}$ are heterocyclic groups are referred to as "bis[N,N-di(heteroring)-carbamoyl]-amino group", groups in which $R^{a5}$ is a hydrocarbon group and $R^{b5}$ is a heterocyclic group are referred to as "bis(N-hydrocarbon-N-heteroring-carbamoyl)-amino group", and those groups in which $R^{a5}$ and $R^{b5}$ combine to each other, together with the nitrogen atom to which they bind, to form a cyclic amino groups are referred to as "bis(cyclicamino-carbonyl)amino group".

Among the groups represented by the formula (ω-11E), those groups in which $R^{a5}$ is a hydrocarbon group are referred to as "bis(N-hydrocarbon-thiocarbamoyl)-amino group", and those groups in which $R^{a5}$ is a heterocyclic group are referred to as "bis(N-heteroring-thiocarbamoyl)-amino group".

Among the groups represented by the formula (ω-12E), those groups in which both $R^{a5}$ and $R^{b5}$ are hydrocarbon groups are referred to as "bis[N,N-di(hydrocarbon)-thiocarbamoyl]-amino group", those groups in which both $R^{a5}$ and $R^{b5}$ are heterocyclic groups are referred to as "bis[N,N-di(heteroring)-thiocarbamoyl]-amino group", those groups in which $R^{a5}$ is a hydrocarbon group and $R^{b5}$ is a heterocyclic group are referred to as "bis(N-hydrocarbon-N-heteroring-thiocarbamoyl)-amino group", and those groups in which $R^{a5}$ and $R^{b5}$ combine to each other, together with the nitrogen atom to which they bind, to form a cyclic amino group are referred to as "bis(cyclicamino-thiocarbonyl)-amino group".

Among the groups represented by the formula (ω-13E), those groups in which $R^{a5}$ is a hydrocarbon group are referred to as "bis(N-hydrocarbon-sulfamoyl)-amino group", and those groups in which $R^{a5}$ is a heterocyclic group are referred to as "bis(N-heteroring-sulfamoyl)-amino group".

Among the groups represented by the formula (ω-14E), those groups in which both $R^{a5}$ and $R^{b5}$ are hydrocarbon groups are referred to as "bis[N,N-di(hydrocarbon)-sulfamoyl]-amino group", those groups in which both $R^{a5}$ and $R^{b5}$ are heterocyclic groups are referred to as "bis[N,N-di(heteroring)-sulfamoyl]-amino group", those groups in which $R^{a5}$ is a hydrocarbon group and $R^{b5}$ is a heterocyclic group are referred to as "bis(N-hydrocarbon-N-heteroring-sulfamoyl)-amino group", and those groups in which $R^{a5}$ and $R^{b5}$ combine to each other, together with the nitrogen atom to which they bind, to form a cyclic amino group are referred to as "bis(cyclicamino-sulfonyl)amino group".

Among the groups represented by the formula (ω-15E), those groups in which $R^{a5}$ is a hydrocarbon group are referred to as "bis(N-hydrocarbon-sulfinamoyl)-amino group", and those groups in which $R^{a5}$ is a heterocyclic group are referred to as "bis(N-heteroring-sulfinamoyl)-amino group".

Among the groups represented by the formula (ω-16E), those groups in which $R^{a5}$ and $R^{b5}$ are hydrocarbon groups are referred to as "bis[N,N-di(hydrocarbon)-sulfinamoyl]-amino group", those groups in which $R^{a5}$ and $R^{b5}$ are heterocyclic groups are referred to as "bis[N,N-di(heteroring)-sulfinamoyl]-amino group", those groups in which $R^{a5}$ is a hydrocarbon group and $R^{b5}$ is a heterocyclic group are referred to as "bis(N-hydrocarbon-N-heteroring-sulfinamoyl)-amino group", and those groups in which $R^{a5}$ and $R^{b5}$ combine to each other, together with the nitrogen atom to which they bind, to form a cyclic amino group are referred to as "bis(cyclicamino-sulfinyl)amino group".

Among the groups represented by the formula (ω-17E), those groups in which $R^{a5}$ is a hydrocarbon group are referred to as "bis(hydrocarbon-oxy-sulfonyl)-amino group", and those groups in which $R^{a5}$ is a heterocyclic group are referred to as "bis(heteroring-oxy-sulfonyl)-amino group".

Among the groups represented by the formula (ω-18E), those groups in which $R^{a5}$ is a hydrocarbon group are referred to as "bis(hydrocarbon-oxy-sulfinyl)-amino group", and those groups in which $R^{a5}$ is a heterocyclic group are referred to as "bis(heteroring-oxy-sulfinyl)-amino group".

Among the groups represented by the formula (ω-19E), those groups in which both $R^{a5}$ and $R^{b5}$ are hydrocarbon groups are referred to as "bis[O,O'-di(hydrocarbon)-phosphono]-amino group", those groups in which both $R^{a5}$ and $R^{b5}$ are heterocyclic groups are referred to as "bis[O,O'-di(heteroring)-phosphono]-amino group", and those groups in which $R^{a5}$ is a hydrocarbon group and $R^{b5}$ is a heterocyclic group are referred to as "bis(O-hydrocarbon-O'heteroring-phosphono)-amino group".

Among the groups represented by the formula (ω-20E), those groups in which $R^{a5}$ is a hydrocarbon group are referred to as "bis(hydrocarbon-sulfonyl)-amino group", and those groups in which $R^{a5}$ is a heterocyclic group are referred to as "bis(heteroring-sulfonyl)-amino group".

Among the groups represented by the formula (ω-21E), those groups in which $R^{a5}$ is a hydrocarbon group are referred to as "bis(hydrocarbon-sulfinyl)-amino group", and those groups in which $R^{a5}$ is a heterocyclic group are referred to as "bis(heteroring-sulfinyl)-amino group".

Examples of the hydrocarbon in the groups represented by the aforementioned formulas (ω-1E) through (ω-21E) include similar groups to the aforementioned hydrocarbon group. Examples of the bis(hydrocarbon-carbonyl)-amino groups represented by the formula (ω-1E) include, a bis (alkyl-carbonyl)-amino group, a bis(alkenyl-carbonyl)-amino group, a bis(alkynyl-carbonyl)-amino group, a bis(cycloalkyl-carbonyl)-amino group, a bis(cycloalkenyl-carbonyl)-amino group, a bis(cycloalkanedienyl-carbonyl)-amino group, a bis(cycloalkyl-alkyl-carbonyl)-amino group which is a bis(aliphatic hydrocarbon-carbonyl)-amino group, a bis(aryl-carbonyl)-amino group, a bis(aralkyl-carbonyl)-amino group, a bis(bridged cyclic hydrocarbon-carbonyl)-amino group, a bis(spiro cyclic hydrocarbon-carbonyl)-amino group, and a bis(terpene family hydrocarbon-carbonyl)-amino group. In the following, groups represented by the formulas (ω-2E) through (ω-21E) are similar to those explained above.

Examples of the heteroring in the groups represented by the aforementioned formulas (ω-1E) through (ω-21E) include similar groups to the aforementioned heterocyclic group. Examples of the bis(heteroring-carbonyl)-amino group represented by the formula (ω-1E) include, for example, bis(monocyclic heteroaryl-carbonyl)-amino group, bis(fused polycyclic heteroaryl-carbonyl)-amino group, bis (monocyclic nonaromatic heterocyclic-carbonyl)-amino group, and bis(fused polycyclic nonaromatic heterocyclic-carbonyl)-amino group. In the following, groups represented by the formulas (ω-2E) through (ω-21E) are similar to those groups mentioned above.

Examples of the cyclic amino in the groups represented by the aforementioned formulas (ω-10E) through (ω-16E) include similar groups to the aforementioned cyclic amino group.

The aforementioned acyl-amino group and di(acyl)-amino group are generically referred to as "acyl substituted amino group". Furthermore, the aforementioned N-hydrocarbon-amino group, N,N-di(hydrocarbon)-amino group, N-heterocyclic-amino group, N-hydrocarbon-N-heterocyclic-amino group, cyclic amino group, acyl-amino group, and di(acyl)-amino group are generically referred to as "substituted amino group". These substituted amino group and amino group are generically referred to as "amino groups which may be substituted".

In the following, compounds represented by the aforementioned general formulas (I), (I-1), (I-2), (I-3), (I-4) are explained in details.

"Connecting group whose number of atoms of main chain is 2 to 4" in the definition of X means connecting groups wherein 2 to 4 atoms in a main chain link together between rings Z and E. The aforementioned "number of atoms of the main chain" is counted so as to minimize the number of connecting atoms existing between the rings Z and E, regardless of the presence or absence of hetero atom(s). For example, the number of atoms of 1,2-cyclopentylene is counted as 2, the number of atoms of 1,3-cyclopentylene is counted as 3, the number of atoms of 1,4-phenylene is counted as 4, the number of atoms of 2,6-pyridine-diyl is counted as 3.

The aforementioned "connecting group whose number of atoms of main chain is 2 to 4" is formed by one functional group selected from the following group of divalent group ξ-1, or formed by combining 2 to 4 functional groups of 1 to 4 kinds selected from the following divalent group ξ-2.

[Divalent group ξ-1] the groups of the following formulas:

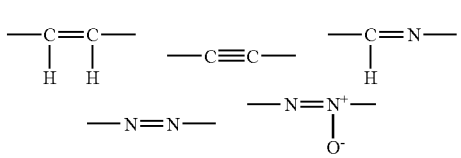

[Divalent group ξ-2] the groups of the following formulas:

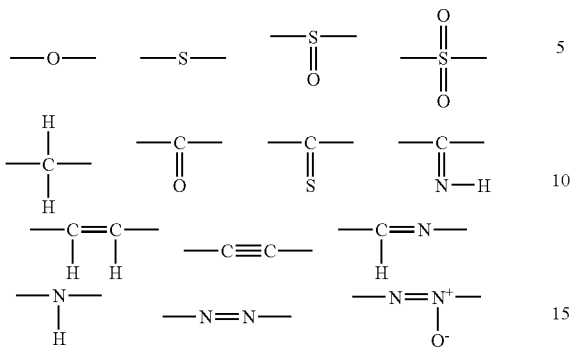

When 2 or more divalent groups combine, each group may be the same or different.

The aforementioned "connecting group whose number of atoms of a main chain is 2 to 4" is preferably a group selected from the following "connecting group α".

[Connecting group α] the following formulas:

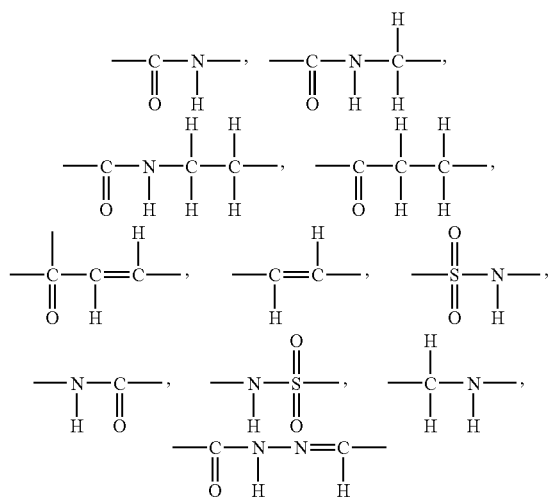

wherein the bond at the left end binds to ring Z and the bond at the right end binds to to E.

The group represented by the following formula is most preferred:

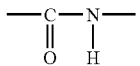

wherein, the bond at the left end binds to ring Z and the bond at the right end binds to E.

Examples of the substituent, according to "connecting group which may be substituted" in the definition of "a connecting group whose number of atoms of the main chain is 2 to 4", include similar groups to the substituents in the definition of the aforementioned "which may be substituted". A $C_1$ to $C_5$ alkyl group is preferred, and a methyl group is more preferred. The substituent may combine with a substituent of the ring E or Z, together with atoms to which they bind, to form a cyclic group which may be substituted. Examples include the compounds represented by the general formula (I) being those represented by the following formulas:

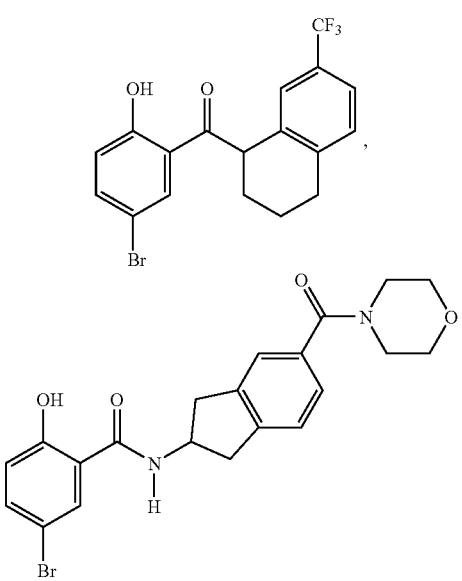

In the aforementioned general formula (I), examples of A include hydrogen atom and an acetyl group, and hydrogen atom is preferred.

Examples of the "arene" in "an arene which may be substituted" in the definition of ring Z include a monocyclic or fused heterocyclic aromatic hydrocarbon, and include, for example, benzene ring, naphthalene ring, anthracene ring, phenanthrene ring, and acenaphylene ring. $C_6$ to $C_{10}$ arenes such as benzene ring, naphthalene ring and the like are preferred, benzene ring and naphthalene ring are more preferred, and benzene ring is most preferred.

When ring Z is a benzene ring, substituents according to the definition of "which may be substituted in addition to the group represented by formula —O—A wherein A has the same meaning as that defined in the general formula (I) and the group represented by formula —X—E wherein each of X and E has the same meaning as that defined in the general formula (I)" are preferred to locate on the position of $R^z$ when the following partial formula (Iz-1) in the general formula containing ring Z

is a group represented by the following formula (Iz-2).

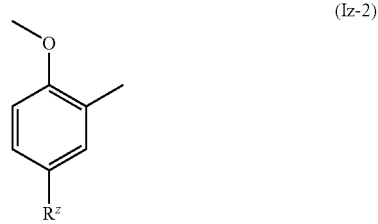

Examples of the "hetero arene" in "a hetero arene which may be substituted" in the definition of ring Z include a monocyclic or a fused polycyclic aromatic heterocyclic rings containing at least one of 1 to 3 kinds of heteroatoms selected from oxygen atom, sulfur atom and nitrogen atom and the like as ring-constituting atoms (ring forming atoms), and include, for example, furan ring, thiphene ring, pyrrole ring, oxazole ring, isoxazole ring, thiazole ring, isothiazole ring, imidazole ring, pyrazole ring, 1,2,3-oxadiazole ring, 1,2,3-thiadiazole ring, 1,2,3-triazole ring, pyridine ring, pyridazine ring, pyrimidine ring, pyrazine ring, 1,2,3-triazine ring, 1,2,4-triazine ring, 1H-azepine ring, 1,4-oxepine ring, 1,4-thiazepine ring, benzofuran ring, isobenzofuran ring, benzo[b]thiophene ring, benzo[c]thiophene ring, indole ring, 2H-isoindole ring, 1H-indazole ring, 2H-indazole ring, benzooxazole ring, 1,2-benzoisooxazole ring, 2,1-benzoisooxazole ring, benzothiazole ring, 1,2-benzoisothiazole ring, 2,1-benzoisothiazole ring, 1,2,3-benzooxadiazole ring, 2,1,3-benzooxadiazole ring, 1,2,3-benzothiadiazole ring, 2,1,3-benzothiadiazole ring, 1H-benzotriazole ring, 2H-benzotriazole ring, quinoline ring, isoquinoline ring, cinnoline ring, quinazoline ring, quinoxaline ring, phthalazine ring, naphthyridine ring, 1H-1,5-benzodiazepine ring, carbazole ring, α-carboline ring, β-carboline ring, γ-carboline ring, acridine ring, phenoxazine ring, phenothiazine ring, phenazine ring, phenanthridine ring, phenanthroline ring, thianthrene ring, indolizine ring, and phenoxathiine ring, which are 5 to 14 membered monocyclic or fused polycyclic aromatic heterocyclic rings. 6 to 13 membered monocyclic or fused polycyclic aromatic heterocyclic rings are preferred, and pyridine ring, indole ring, quinoxaline ring, and carbazole ring are more preferred.

Examples of the substituent in the definition of "which may be substituted in addition to the group represented by formula —O—A wherein A has the same meaning as that defined in the general formula (I) and the group represented by formula —X—E wherein each of X and E has the same meaning as that defined in the general formula (I)" in the definition of ring Z include similar groups to the substituent explained for the definition "which may be substituted". When ring Z is "a benzene ring which may be substituted in addition to the group represented by formula —O—A wherein A has the same meaning as that defined in the general formula (I) and the group represented by formula —X—E wherein each of X and E has the same meaning as that defined in the general formula (I)", preferred examples of the substituents include halogen atoms, nitro group, cyano group, hydroxy group which may be substituted, amino group which may be substituted, hydrocarbon group which may be substituted, heterocyclic group which may be substituted, acyl group which may be substituted, ureido group which may be substituted, thiureido group which may be substituted, and diazenyl group which may be substituted, which are defined as those of substituent group γ-1z.

Examples of the "hydroxy group which may be substituted" in the definition of the substituent group γ-1z, and the "hydroxy group which may be substituted" in the definition of $R^z$ include similar groups to the "hydroxy group which may be substituted" according to the definition of the aforementioned "which may be substituted", and examples of the substituent include similar groups to the substituents in the definition of the aforementioned "which may be substituted". Hydrocarbon-oxy group which may be substituted is preferred as the "hydroxy group which may be substituted", a $C_1$ to $C_6$ alkoxy group which may be substituted is more preferred, and methoxy group is further preferred.

Examples of the "amino group which may be substituted" in the definition of the substituent group γ-1z, and the "amino group which may be substituted" in the definition of $R^z$ include similar group to the "amino group which may be substituted" according to the definition of the aforementioned "which may be substituted", and examples of the substituent include similar groups to the substituent according to the definition of the aforementioned "which may be substituted". Di(hydrocarbon)-amino group and hydrocarbon-carbonyl-amino group are preferred as the "amino group which may be substituted", di($C_1$ to $C_6$ alkyl)-amino group and $C_6$ to $C_{10}$ aryl-carbonyl-amino group are more preferred, and dimethylamino group and benzoylamino group are further preferred.

Examples of the substituent in the definition of "hydrocarbon group which may be substituted" in the definition of the substituent group γ-1z, and the substituent in the definition of "hydrocarbon group which may be substituted" in the definition of $R^z$ include similar groups to the substituents according to the definition of the aforementioned "which may be substituted". A $C_1$ to $C_6$ alkyl group which may be substituted, a $C_1$ to $C_6$ halogenated alkyl group which may be substituted, a $C_2$ to $C_6$ alkenyl group which may be substituted, a $C_2$ to $C_6$ alkynyl group which may be substituted, a $C_6$ to $C_{10}$ aryl group which may be substituted, and a $C_7$ to $C_{16}$ is aralkyl group which may be substituted are preferred as the "hydrocarbon group which may be substituted", and methyl group, tert-butyl group, 1-hydroxyethyl group, 1-(methoxyimino) ethyl group, 1-[(benzyloxy)imino]ethyl group, trifluoromethyl group, pentafluoroethyl group, phenyl group, 4-(trifluoromethyl)phenyl group, 4-fluorophenyl group, 2,4-difluorophenyl group, 2-phenylethen-1-yl group, 2,2-dicyanoethen-1-yl group, 2-cyano-2-(methoxycarbonyl) ethen-1-yl group, 2-carboxy-2-cyanoethen-1-yl group, ethynyl group, phenylethynyl group, (trimethylsilyl)ethynyl group, phenyl group, and 2-phenethyl group are more preferred.

Examples of the substituent in the definition of "heterocyclic group which may be substituted" in the definition of the substituent group γ-1z, and the substituent in the definition of "heterocyclic group which may be substituted" in the definition of $R^z$ include similar groups to the substituents according to the definition of the aforementioned "which may be substituted". A heteroaryl group which may be substituted is preferred as the "heterocyclic group which may be substituted", a 5 to 6-membered heteroaryl group which may be substituted is more preferred, and 2-thienyl group, 3-thienyl group, 1-pyrrolyl group, 2-methylthiazol-4-yl group, and 2-pyridyl group are further preferred.

Examples of the "acyl group which may be substituted" in the definition of the substituent group γ-1z, and the "acyl group which may be substituted" in the definition of $R^z$ include similar groups exemplified in the aforementioned definition of "acyl group which may be substituted", and examples of the substituent include similar groups to the substituent explained for the definition "which may be substituted". Carbamoyl group which may be substituted, sulfamoyl group which may be substituted, a hydrocarbon-carbonyl group which may be substituted, a hydrocarbon-oxycarbonyl group which may be substituted, a heteroring-carbonyl group which may be substituted, and a heteroring-sulfonyl group which may be substituted are preferred as the "acyl group which may be substituted", carbamoyl group which may be substituted, sulfamoyl group which may be substituted, a $C_1$ to $C_6$ alkyl-carbonyl group which may be substituted, a $C_1$ to $C_6$ alkoxy-carbonyl group which may be substituted, a 5-membered heteroaryl-sulfonyl group which may be substituted, and a 6-membered nonaromatic heterocyclic-sulfonyl group which may be substituted are more preferred, and [3,5-bis(trifluoromethyl)phenyl]carbamoyl group, dimethylcarbamoyl group, dimethylsulfamoyl group, acetyl group, isobutyryl group, methoxycarbonyl group, piperidinocarbonyl group, 4-benzylpiperidinocarbonyl group, and (pyrrol-1-yl)sulfonyl group are further preferred.

Examples of the substituent in the definition of "ureido group which may be substituted" in the definition of the substituent group γ-1z, and the substituent in the definition of "ureido group which may be substituted" in the definition of $R^z$ include similar groups to the substituent explained for the definition "which may be substituted". 3-Phenylureido group is preferred as the "ureido group which may be substituted".

Examples of the substituent in the definition of "thioureido group which may be substituted" in the definition of the substituent group γ-1z, and the substituent in the definition of "thioureido group which may be substituted" in the definition of $R^z$ include similar groups to the substituent explained for the definition "which may be substituted". (3-Phenylthio)ureido group is preferred as the "thioureido group which may be substituted".

Examples of the substituent in the definition of "diazenyl group which may be substituted" in the definition of the substituent group γ-1z, and the substituent in the definition of "diazenyl group which may be substituted" in the definition of $R^z$ include similar groups to the substituent explained for the definition "which may be substituted". (4-Nitrophenyl)diazenyl group and {[(4-pyridin-2-yl)sulfamoyl]phenyl}diazenyl group are preferred as the "diazenyl group which may be substituted".

Examples of $R^z$ include halogen atom, nitro group, cyano group, hydroxy group which may be substituted, amino group which may be substituted, hydrocarbon group which may be substituted, heterocyclic group which may be substituted, acyl group which may be substituted, ureido group which may be substituted, thioureido group which may be substituted, and diazenyl group which may be substituted, and halogen atom is most preferred.

Examples of the aryl group of "an aryl group which may be substituted" in the definition of E include similar groups to the aryl group in the definition of the aforementioned "hydrocarbon group", and $C_6$ to $C_{10}$ aryl groups such as phenyl group, 1-naphthyl group, 2-naphthyl group and the like are preferred, and phenyl group is most preferred.

Examples of the substituent in the definition of "an aryl group which may be substituted" in the definition of E include similar groups to the substituent explained for the definition "which may be substituted".

Preferred embodiments of the phenyl group according to "an aryl group which may be substituted" in the definition of E are:
(1) phenyl group substituted with two $C_1$ to $C_6$ halogenated alkyl groups wherein said phenyl group may be substituted in addition to the two $C_1$ to $C_6$ halogenated alkyl groups:
(2) phenyl group substituted with one $C_1$ to $C_6$ halogenated alkyl group wherein said phenyl group may be substituted (except with a $C_1$ to $C_6$ halogenated alkyl group) in addition to the $C_1$ to $C_6$ halogenated alkyl group; and
(3) phenyl group which may be substituted (except with a $C_1$ to $C_6$ halogenated alkyl group).

Examples of the "$C_1$ to $C_6$ halogenated alkyl group" in "phenyl group substituted with two $C_1$ to $C_6$ halogenated alkyl groups wherein said phenyl group may be substituted in addition to the two $C_1$ to $C_6$ halogenated alkyl groups" in the definition of E include similar groups to those exemplified in the aforementioned definition of "$C_1$ to $C_6$ halogenated alkyl group", and examples of the substituent in the definition of "said phenyl group may be substituted in addition to the two $C_1$ to $C_6$ halogenated alkyl groups" include similar groups to the substituent explained for the definition "which may be substituted".

"Phenyl group substituted with two $C_1$ to $C_6$ halogenated alkyl groups" is preferred as the "phenyl group substituted with two $C_1$ to $C_6$ halogenated alkyl groups wherein said phenyl group may be substituted in addition to the two $C_1$ to $C_6$ halogenated alkyl groups". 3,5-Bis(trifluoromethyl)phenyl group and 2,5-bis(trifluoromethyl)phenyl group are preferred, and 3,5-bis(trifluoromethyl)phenyl group is most preferred.

Examples of the substituent in the definition of "phenyl group substituted with one $C_1$ to $C_6$ halogenated alkyl group wherein said phenyl group may be substituted (except with a $C_1$ to $C_6$ halogenated alkyl group) in addition to one $C_1$ to $C_6$ halogenated alkyl group" in the definition of E include similar groups to the substituent explained for the definition "which may be substituted" (a $C_1$ to $C_6$ halogenated alkyl group is excluded). Halogen atoms, nitro group, cyano group, hydroxy group which may be substituted, hydrocarbon group which may be substituted, heterocyclic group which may be substituted, sulfanyl group which may be substituted which are defined in substituent group γ-1e are preferred.

Examples of the "hydroxy group which may be substituted" in the definition of the substituent group γ-1e include similar groups to the "hydroxy group which may be substituted" in the definition of the aforementioned "which may be substituted", and examples of the substituent include similar groups to the substituent explained for the definition "which may be substituted". Hydrocarbon-oxy group which may be substituted is preferred as the "hydroxy group which may be substituted", $C_1$ to $C_6$ alkoxy group which may be substituted which is defined as substituent group γ-2e is more preferred, and methoxy group is further preferred.

Examples of the substituent in the definition of "hydrocarbon group which may be substituted" in the definition of the substituent group, γ-1e, and the substituent in the definition of "hydrocarbon group which may be substituted" in the definition of $R^z$ include similar groups to the substituent explained for the definition "which may be substituted". A $C_1$ to $C_6$ alkyl group which may be substituted which is defined in substituent group γ-2e is preferred as the "hydrocarbon group which may be substituted", and methyl group is more preferred.

Examples of the substituent in the definition of "heterocyclic group which may be substituted" in the definition of the substituent group γ-1e include similar groups to the substituents explained for the definition "which may be substituted". A 5 to 6-membered non-aromatic heterocyclic group which may be substituted which is defined in substituent group γ-2e is preferred as the "heterocyclic group which may be substituted", and 1-pyrrolidinyl group and morpholino group are more preferred.

Examples of the "sulfanyl group which may be substituted" in the definition of the substituent group γ-1e include similar groups to the "sulfanyl group which may be substituted" according to the definition of the aforementioned "which may be substituted", and examples of the substituent include similar groups to the substituent explained for the definition "which may be substituted". A hydrocarbon-sulfanyl group which may be substituted is preferred as the "sulfanyl group which may be substituted", and a $C_1$ to $C_6$ alkylsulfanyl group which may be substituted, which is defined in substituent group γ-2e, is more preferred, and methylsulfanyl group is further preferred.

Examples of the "$C_1$ to $C_6$ halogenated alkyl group" in "phenyl group substituted with one $C_1$ to $C_6$ halogenated alkyl group wherein said phenyl group may be substituted (except with a $C_1$ to $C_6$ halogenated alkyl group) in addition to the $C_1$ to $C_6$ halogenated alkyl group" in the definition of E include similar groups to the aforementioned "$C_1$ to $C_6$ halogenated alkyl group". $C_1$ to $C_6$ alkyl groups substituted with one or more fluorine atoms are preferred, $C_1$ to $C_6$ alkyl groups substituted with three or more fluorine atoms are more preferred, and trifluoromethyl group is most preferred.

Examples of the "phenyl group substituted with one $C_1$ to $C_6$ halogenated alkyl group wherein said phenyl group may be substituted (except with a $C_1$ to $C_6$ halogenated alkyl group) in addition to the $C_1$ to $C_6$ halogenated alkyl group" in the definition of E include 2-(trifluoromethyl)phenyl group, 3-(trifluoromethyl)phenyl group, 4-(trifluoromethyl)phenyl group, 2-fluoro-3-(trifluoromethyl)phenyl group, 2-chloro-4-(trifluoromethyl)phenyl group, 2-fluoro-5-(trifluoromethyl)phenyl group, 2-chloro-5-(trifluoromethyl)phenyl group, 3-fluoro-5-(trifluoromethyl)phenyl group, 3-bromo-5-(trifluoromethyl)phenyl group, 4-chloro-2-(trifluoromethyl)phenyl group, 4-fluoro-3-(trifluoromethyl)phenyl group, 4-chloro-3-(trifluoromethyl)phenyl group, 2-nitro-5-(trifluoromethyl)phenyl group, 4-nitro-3-(trifluoromethyl)phenyl group, 4-cyano-3-(trifluoromethyl)phenyl group, 2-methyl-3-(trifluoromethyl)phenyl group, 2-methyl-5-(trifluoromethyl)phenyl group, 4-methyl-3-(trifluoromethyl)phenyl group, 2-methoxy-5-(trifluoromethyl)phenyl group, 3-methoxy-5-(trifluoromethyl)phenyl group, 4-methoxy-3-(trifluoromethyl)phenyl group, 2-(methylsulfanyl)-5-(trifluoromethyl)phenyl group, 2-(1-pyrrolidino)-5-(trifluoromethyl)phenyl group, and 2-morpholino-5-(trifluoromethyl)phenyl group. 2-Chloro-5-(trifluoromethyl)phenyl group, 4-chloro-3-(trifluoromethyl)phenyl group, 2-methoxy-5-trifluoromethyl)phenyl group, and 3-methoxy-5-(trifluoromethyl)phenyl group are more preferred, and 2-chloro-5-(trifluoromethyl)phenyl group is most preferred.

Examples of the substituent in the definition of "phenyl group which may be substituted (except with a $C_1$ to $C_6$ halogenated alkyl group)" in the definition of E include similar groups to the substituent explained for the definition "which may be substituted". Halogen atoms, nitro group, hydroxy group which may be substituted, hydrocarbon group which may be substituted, and acyl group which may be substituted which are defined in substituent group γ-3e are preferred.

Examples of the "hydroxy group which may be substituted" in the definition of the substituent group γ-3e include similar groups to the "hydroxy group which may be substituted" according to the definition of the aforementioned "which may be substituted", and examples of the substituent include similar groups to the substituent explained for the definition "which may be substituted". Unsubstituted hydroxy group and a hydrocarbon-oxy group which may be substituted are preferred as the "hydroxy group which may be substituted", and unsubstituted hydroxy group and $C_1$ to $C_6$ alkoxy group which may be substituted which are defined in substituent group γ-4e are more preferred, and unsubstituted hydroxy group and methoxy group are further preferred.

Examples of the substituent in the definition of "hydrocarbon group which may be substituted" in the definition of the substituent group γ-3e include similar groups to the substituent explained for the definition "which may be substituted". A $C_1$ to $C_6$ alkyl group which may be substituted, a $C_6$ to $C_{10}$ aryl group which may be substituted, and a $C_1$ to $C_6$ alkylene group which may be substituted which are defined in substituent group γ-4e are preferred as the "hydrocarbon group which may be substituted", and methyl group, tert-butyl group and 1,1,4,4-tetramethylbutane-1,4-diyl group are more preferred.

Examples of the "acyl group which may be substituted" in the definition of the substituent group γ-3e include the similar group to those exemplified in the aforementioned definition of "acyl group which may be substituted", and examples of the substituent include similar groups to the substituents explained for the definition "which may be substituted". A hydrocarbon-carbonyl group which may be substituted and a hydrocarbon-oxy-carbonyl group which may be substituted are preferred as the "acyl group which may be substituted". A $C_1$ to $C_6$ alkyl-carbonyl group which may be substituted, a $C_1$ to $C_6$ alkoxy-carbonyl group which may be substituted which are defined in substituent group γ-4e are more preferred, and acetyl group and methoxycarbonyl group are further preferred.

Phenyl group, 3-chlorophenyl group, 4-chlorophenyl group, 2,5-dichlorophenyl group, 3,4-dichlorophenyl group, 3,5-difluorophenyl group, 3,5-dichlorophenyl group, 3,4,5-trichlorophenyl group, pentafluorophenyl group, 3,5-dinitrophenyl group, 3,5-dichloro-4-hydroxyphenyl group, 2,5-dimethoxyphenyl group, 3,5-dimethoxyphenyl group, 3,5-dimethylphenyl group, 2,5-bis[(1,1-dimethyl)ethyl]phenyl group, 3,5-bis[(1,1-dimethyl)ethyl]phenyl group, 5-(1,1-dimethyl)ethyl-2-methoxyphenyl group, 3,5,5,8,8-pentamethyl-5,6,7,8-tetrahydronaphthalen-2-yl group, biphenyl-3-yl group, 4-methoxybiphenyl-3-yl group, 8-acetylphenyl group, and 3,5-bis(methoxycarbonyl)phenyl group are preferred as "phenyl group which may be substituted (except with a $C_1$ to $C_6$ halogenated alkyl group)" in the definition of E. 2,5-Bis[(1,1-dimethyl)ethyl]phenyl group, 3,5-bis[(1,1-dimethyl)ethyl]phenyl group, and 5-(1,1-dimethyl)ethyl-2-methoxyphenyl group are more preferred, and 2-chloro-5-(trifluoromethyl)phenyl group is most preferred.

Examples of the "heteroaryl group" in "heteroaryl group which may be substituted" in the definition of E include similar groups to the "monocyclic heteroaryl group" and "fused polycyclic heteroaryl group" in the definition of the aforementioned "heteroaryl group". A 5 to 13-membered heteroaryl group is preferred, and thienyl group, pyrazolyl group, oxazolyl group, thiazolyl group, thiadiazolyl group, pyridyl group, pyrimidinyl group, indolyl group, and carbazolyl group are more preferred, and thiazolyl group is most preferred.

Examples of the substituent in the definition of "heteroaryl group which may be substituted" in the above definition of E include similar groups to the substituent explained for the definition "which may be substituted".

Examples of the substituent in the definition of "thiazolyl group which may be substituted" in the above definition of E include similar groups to the substituent explained for the definition "which may be substituted". Halogen atoms, cyano group, hydrocarbon group which may be substituted, heterocyclic group which may be substituted, and acyl group which may be substituted which are defined as substituent group γ-5e are preferred.

Examples of the substituent in the definition of "hydrocarbon group which may be substituted" in the definition of the substituent group γ-5e include similar groups to the substituents explained for the definition "which may be substituted". A $C_1$ to $C_6$ alkyl group which may be substituted, a $C_1$ to $C_6$ halogenated alkyl group which may be substituted, a $C_6$ to $C_{10}$ aryl group which may be substituted, and a $C_7$ to $C_{16}$ aralkyl group which may be substituted which are defined in substituent group γ-6e are preferred as the "hydrocarbon group which may be substituted". Methyl group, ethyl group, isopropyl group, n-butyl group, tert-butyl group, carboxymethyl group, trifluoromethyl group, phenyl group, 4-fluorophenyl group, 3-(trifluoromethyl)phenyl group, pentafluorophenyl group, and benzyl group are preferred.

Examples of the substituent in the definition of "heterocyclic group which may be substituted" in the definition of the substituent group γ-5e include similar groups to the substituent explained for the definition "which may be substituted". A 6-membered non-aromatic heterocyclic group which may be substituted, which is defined in substituent group γ-6e, is preferred as the "heterocyclic group which may be substituted", and piperidino group, morpholino group, 4-methylpiperidin-1-yl group, and 4-phenylpiperidin-1-yl group are more preferred.

Examples of the "acyl group which may be substituted" in the definition of the substituent group γ-5e include similar groups to those exemplified in the aforementioned definition of "acyl group which may be substituted", and examples of the substituent include similar groups to the substituents explained for the definition "which may be substituted". A hydrocarbon-carbonyl group which may be substituted, a carbamoyl group which may be substituted, and a hydrocarbon-oxy-carbonyl group which may be substituted are preferred as the "acyl group which may be substituted". Carbamoyl group which may be substituted, a $C_1$ to $C_6$ alkyl-carbonyl group which may be substituted, a $C_6$ to $C_{10}$ aryl-carbonyl group which may be substituted, a $C_1$ to $C_6$ alkoxy-carbonyl group which may be substituted which are defined in substituent group γ-6e are more preferred, and N-methylcarbamoyl group, N-ethylcarbamoyl group, N-isopropylcarbamoyl group, N-(2-phenethyl)carbamoyl group, acetyl group, pivaloyl group, benzoyl group, and ethoxycarbonyl group are further preferred.

5-Bromo-4-[(1,1-dimethyl)ethyl]thiazol-2-yl group, 5-bromo-4-(trifluoromethyl)thiazol-2-yl group, 5-cyano-4-[(1,1-dimethyl)ethyl]-thiazol-2-yl group, 4-[(1,1-dimethyl)ethyl]thiazol-2-yl group, 5-phenyl-4-(trifluoromethyl)thiazol-2-yl group, 4-(1,1-dimethyl)ethyl-5-ethylthiazol-2-yl group, 5-methyl-4-phenylthiazol-2-yl group, 4-isopropyl-5-phenylthiazol-2-yl group, 4 benzyl-5-phenylthiazol-2-yl group, 4-(1,1-dimethyl)ethyl-5-[(2,2-dimethyl)propionyl]thiazol-2-yl group, 5-acetyl-4-phenylthiazol-2-yl group, 5-benzoyl-4-phenylthiazol-2-yl group, 4-(1,1-dimethyl)ethyl)-5-(ethoxycarbonyl)thiazol-2-yl group, 5-ethoxycarbonyl-4-(trifluoromethyl)thiazol-2-yl group, 5-ethoxycarbonyl-4-phenylthiazol-2-yl group, 4-(1,1-dimethyl)ethyl-5-piperidinothiazol-2-yl group, 4-(1,1-dimethyl)ethyl-5-morpholinothiazol-2-yl group, 4-(1,1-dimethyl)ethyl)-5-(4-phenylpiperidin-1-yl)thiazol-2-yl group, 4-(1,1-dimethyl)ethyl-5-(4-methylpiperidin-1-yl)thiazol-2-yl group, 4,5-diphenylthiazol-2-yl group, 4-phenylthiazol-2-yl group, 4,5-dimethylthiazol-2-yl group, 2-thiazolyl group, 5-methylthiazol-2-yl group, 4-ethyl-5-phenylthiazol-2-yl group, 5-carboxymethyl-4-phenylthiazol-2-yl group, 5-methylcarbamoyl-4-phenylthiazol-2-yl group, 6-ethylcarbamoyl-4-phenylthiazol-2-yl group, 5-isopropylcarbamoyl-4-phenylthiazol-2-yl group, 5-(2-phenetyl)carbamoyl-4-phenylthiazol-2-yl group, 4-(n-butyl)-5-phenylthiazol-2-yl group, 4-methyl-5-[(3-trifluoromethyl)phenyl]thiazol-2-yl group, and 5-(4-fluorophenyl)-4-methylthiazol-2-yl group are preferred as "thiazolyl group which may be substituted" in the definition of E, and 4-(1,1-dimethyl)ethyl-5-[(2,2-dimethyl)propionyl]thiazol-2-yl group is more preferred.

In the aforementioned general formula (I-1), $Z^1$ is 2-hydroxyphenyl group which may be substituted in the 5-position or 2-acetoxyphenyl group which may be substituted in the 5-position.

Examples of the "halogenated alkyl group" in the "phenyl group substituted with two $C_1$ to $C_6$ halogenated alkyl groups wherein said phenyl group may be substituted in addition to the two $C_1$ to $C_6$ halogenated alkyl groups" in the definition of $E^1$ include similar group to those exemplified in the aforementioned definition of "halogenated alkyl group". Examples of substituents according to the definition of "said phenyl group may be substituted in addition to the two $C_1$ to $C_6$ halogenated alkyl groups" include similar groups to the substituents explained for the definition "which may be substituted". As the "phenyl group substituted with two $C_1$ to $C_6$ halogenated alkyl groups wherein said phenyl group may be substituted in addition to the two $C_1$ to $C_6$ halogenated alkyl groups", an example is a phenyl group substituted with two $C_1$ to $C_6$ alkyl groups which is substituted with one or more fluorine atoms in which said phenyl group may further have substituents in addition to the two $C_1$ to $C_6$ alkyl groups substituted with one or more fluorine atoms. More preferred example is a phenyl group substituted with two $C_1$ to $C_6$ alkyl groups which is substituted with three or more fluorine atoms in which said phenyl group may further have substituents in addition to the two $C_1$ to $C_6$ halogenated alkyl groups which are substituted with one or more fluorine atoms, and a phenyl group substituted with the two $C_1$ to $C_6$ alkyl groups which are substituted with three or more fluorine atoms is further preferred. It is preferred that these two substituents are substituted in the 2-position and 5-position, or 3-position and 5-position on the phenyl group.

Trifluoromethyl group is most preferred as "$C_1$ to $C_6$ alkyl group which is substituted with three or more fluorine atoms" in the definition of $R^{1e2}$, $R^{1e3}$, and $R^{1e5}$.

As $E^1$, 3,5-bis(trifluoromethyl)phenyl group or 2,5-bis(trifluoromethyl)phenyl group is preferred, and 2,5-bis(trifluoromethyl)phenyl group is most preferred.

$A^1$ is hydrogen atom and an acetyl group, and hydrogen atom is preferred.

Examples of the "hydroxy group which may be substituted" in the definition of $R^{1z}$ include similar groups to the "hydroxy group which may be substituted" in the definition of the aforementioned "which may be substituted", and examples of the substituent include similar groups to the substituent explained for the definition "which may be substituted". A hydrocarbon-oxy group which may be substituted is preferred as the "hydroxy group which may be substituted". A $C_1$ to $C_6$ alkoxy group which may be substituted is more preferred, and methoxy group is further preferred.

Examples of the "amino group which may be substituted" in the definition of $R^{1z}$ include similar groups to the "amino group which may be substituted" in the definition of the aforementioned "which may be substituted", and examples of the substituent include similar groups to the substituent explained for the definition "which may be substituted". Di(hydrocarbon)-amino group and hydrocarbon-carbonyl-amino group are preferred as the "amino group which may be substituted", and di($C_1$ to $C_6$ alkyl)-amino group and $C_6$ to $C_{10}$ aryl-amino group are more preferred, and dimethylamino group and benzoylamino group are further preferred.

Examples of the substituent in the definition of "hydrocarbon group which may be substituted" in the definition of $R^{1z}$ include similar groups to the substituent explained for the definition "which may be substituted". A $C_1$ to $C_6$ alkyl group which may be substituted, a $C_1$ to $C_6$ halogenated alkyl group which may be substituted, a $C_2$ to $C_6$ alkenyl group which may be substituted, a $C_2$ to $C_6$ alkynyl group which may be substituted, a $C_6$ to $C_{10}$ aryl group which may be substituted, and a $C_7$ to $C_{16}$ aralkyl group which may be substituted are preferred as the "hydrocarbon group which may be substituted", and methyl group, tert-butyl group, 1-hydroxyethyl group, 1-(methoxyimino)ethyl group, 1-[(benzyloxy)imino]

ethyl group, trifluoromethyl group, pentafluoroethyl group, phenyl group, 4-(trifluoromethyl)phenyl group, 4-fluorophenyl group, 2,4-difluorophenyl group, 2-phenylethen-1-yl group, 2,2-dicyanoethen-1-yl group, 2-cyano-2-(methoxycarbonyl)ethen-1-yl group, 2-carboxy-2-cyanoethen-1-yl group, ethynyl group, phenylethynyl group, (trimethylsilyl)ethynyl group, and 2-phenethyl group are more preferred.

Examples of the substituent in the definition of "heterocyclic group which may be substituted" in the definition of $R^{1z}$ include similar groups to the substituent explained for the definition "which may be substituted". A heteroaryl group which may be substituted is preferred as the "heterocyclic group which may be substituted", and a 5 to 6-membered heteroaryl group which may be substituted is more preferred, and 2-thienyl group, 3-thienyl group, 1-pyrrolyl group, 2-methylthiazol-4-yl group, and 2-pyridyl group are further preferred.

Examples of the "acyl group which may be substituted" in the definition of $R^{1z}$ include similar groups to those exemplified in the aforementioned definition of "acyl group which may be substituted", and examples of the substituent include similar groups to the substituents explained for the definition "which may be substituted". Carbamoyl group which may be substituted, sulfamoyl group which may be substituted, a hydrocarbon-carbonyl group which may be substituted, a hydrocarbon oxy-carbonyl group which may be substituted, a heterocyclic-carbonyl group which may be substituted, and a heterocyclic-sulfonyl group which may be substituted are preferred as the "acyl group which may be substituted", and carbamoyl group which may be substituted, sulfamoyl group which may be substituted, a $C_1$ to $C_6$ alkyl-carbonyl group which may be substituted, a $C_1$ to $C_6$ alkoxy-carbonyl group which may be substituted, a 5-member heteroaryl-sulfonyl group which may be substituted, and a 6-membered nonaromatic heterocyclic-sulfonyl group which may be substituted are more preferred. 3,5-Bis(trifluoromethyl)phenyl]carbamoyl group, dimethylcarbamoyl group, dimethylsulfamoyl group, acetyl group, isobutyryl group, methoxycarbonyl group, piperidinocarbonyl group, 4-benzylpiperidinocarbonyl group, and (pyrrol-1-yl)sulfonyl group are further preferred.

Examples of the substituent in the definition of "ureido group which may be substituted" in the definition $R^{1z}$ include similar groups to the substituents explained for the definition "which may be substituted". 3-Phenylureido group is preferred as the "ureido group which may be substituted".

Examples of the substituent in the definition of "thioureido group which may be substituted" in the definition of $R^{1z}$ include similar groups to the substituents explained for the definition "which may be substituted". (3-Phenylthio)ureido group is preferred as the "thioureido group which may be substituted".

Examples of the substituent in the definition of "diazenyl group which may be substituted" in the definition of $R^{1z}$ include similar groups to the substituents explained for the definition "which may be substituted". (4-Nitrophenyl)diazenyl group and {[(4-pyridin-2-yl)sulfamoyl]phenyl}diazenyl group are preferred as the "diazenyl group which may be substituted".

Examples of $R^{1z}$ include a halogen atom, nitro group cyano group, hydroxy group which may be substituted, amino group which may be substituted, a hydrocarbon group which may be substituted, a heterocyclic group which may be substituted, an acyl group which may be substituted, an ureido group which may be substituted, a thioureido group which may be substituted, a diazenyl group which may be substituted, a halogen atom, a $C_1$ to $C_6$ alkyl group which may be substituted, and a $C_1$ to $C_6$ halogenated alkyl group which may be substituted are preferred, and a halogen atom is most preferred.

Each compound defined by the aforementioned general formula (I-1) or a pharmacologically acceptable salt thereof, and a hydrate thereof and a solvate thereof, except the following 6 compounds, is novel compound, and uses of the compounds according to the present invention relating to the chemical substances are not limited.

N-[3,5-bis(trifluoromethyl)phenyl]-2-hydroxybenzamide
N-[3,5-bis(trifluoromethyl)phenyl]-5-chloro-2-hydroxybenzamide
N-[3,5-bis(trifluoromethyl)phenyl]-5-bromo-2-hydroxybenzamide
N-[3,5-bis(trifluoromethyl)phenyl]-2-hydroxy-5-iodobenzamide
N-[3,5-bis(trifluoromethyl)phenyl]-2-hydroxy-5-nitrobenzamide
2-Hydroxy-N-[2,3,5-tris(trifluoromethyl)phenyl]benzamide In the aforementioned general formula (I-2), $Z^2$ is 2-hydroxyphenyl group which may be substituted in the 5-position or 2-acetoxyphenyl group which may be substituted at the 5-position.

Examples of the "halogenated alkyl group" in "phenyl group wherein a $C_1$ to $C_6$ halogenated alkyl group is substituted in the 3-position or 5-position" in the definition of $E^2$ (wherein said phenyl group may further have one or more substituents (except when the substituent is $C_1$ to $C_6$ halogenated alkyl group) in addition to the $C_1$ to $C_6$ halogenated alkyl group in the 3-position or 5-position) include similar groups to those exemplified in the aforementioned definition of "halogenated alkyl group". A $C_1$ to $C_6$ alkyl group substituted with one or more fluorine atoms is preferred, and a $C_1$ to $C_6$ alkyl group substituted with three or more fluorine atoms is more preferred, and trifluoromethyl group is most preferred. Examples of the substituent in the definition of "phenyl group wherein a $C_1$ to $C_6$ halogenated alkyl group is substituted in the 3-position or 5-position" (wherein said phenyl group may further have one or more substituents (except when the substituent is $C_1$ to $C_6$ halogenated alkyl group) in addition to the $C_1$ to $C_6$ halogenated alkyl group in the 3-position or 5-position) include similar groups to the substituents explained for the definition "which may be substituted". A halogen atom, nitro group, cyano group, a $C_1$ to $C_6$alkyl group which may be substituted, a 5 to 6 membered nonaromatic heterocyclic group which may be substituted, a $C_1$ to $C_6$ alkoxy group which may be substituted, a $C_1$ to $C_6$ alkyl-sulfanyl group which may be substituted, which are defined in substituent group γ-7e, are preferred, and a halogen atom, nitro group, cyano group, methoxy group, methyl group, 1-pyrrolidinyl group, morpholino group, and methyl sulfanyl group are more preferred.

Preferred examples of the "phenyl group wherein a $C_1$ to $C_6$ halogenated alkyl groups is substituted in the 3-position or 5-position (wherein said phenyl group may further have one or more substituents (except when the substituent is a $C_1$ to $C_6$ halogenated alkyl) in addition to the $C_1$ to $C_6$ halogenated alkyl group in the 3-position or 5-position))" in the definition of $E^2$ include 3-(Trifluoromethyl)phenyl group, 2-fluoro-3-(trifluoromethyl)phenyl group, 2-fluoro-5-(trifluoromethyl)phenyl group, 2-chloro-5-(trifluoromethyl)phenyl group, 3-fluoro-5-(trifluoromethyl)phenyl group, 3-bromo-5-(trifluoromethyl)phenyl group, 4 chloro-2-(trifluoromethyl)phenyl group, 4-fluoro-3-(trifluoromethyl)phenyl group, 4-chloro-3-(trifluoromethyl)phenyl group, 2-nitro-5-(trifluoromethyl)phenyl group, 4-nitro-3-(trifluoromethyl)phenyl group, 4-cyano-3-(trifluoromethyl)phenyl group, 2-methyl- 3-(trifluoromethyl)phenyl group, 2-methyl-5-(trifluoromethyl)phenyl group, 4-methyl-3-(trifluoromethyl)phenyl group, 2-methoxy-5-(trifluoromethyl)phenyl group, 3-methoxy-5-(trifluoromethyl)phenyl group, 4-methoxy-3-(trifluoromethyl)phenyl group, 2-(methylsulfanyl)-5-(trifluoromethyl)phenyl group, 2-(1-pyrrolidino)-5-(trifluoromethyl)phenyl group, and 2-morpholino-5-(trifluoro-methyl)phenyl group $A^2$ is hydrogen atom and an acetyl group, and hydrogen atom is preferred.

Examples of $R^{2z}$ include a halogen atom, a $C_1$ to $C_6$ alkyl group which may be substituted, and a $C_1$ to $C_6$ halogenated alkyl group which may be substituted, and preferred examples include a halogen atom, methyl group, tert-butyl group, trifluoromethyl group, and pentafluoromethyl group.

Each compound defined by the aforementioned general formula (I-2) or a pharmacologically acceptable salt thereof, or a hydrate thereof or a solvate thereof, except the following 15 compounds, is novel, and uses of the compounds according to the present invention relating to chemical substances are not limited.

5-chloro-2-hydroxy-N-[3-(trifluoromethyl)phenyl]benzamide
5-bromo-2-hydroxy-N-[3-(trifluoromethyl)phenyl]benzamide
2-hydroxy-5-iodo-N [3-(trifluoromethyl)phenyl]benzamide
5-chloro-N-[4-chloro-3-(trifluoromethyl)phenyl]-2-hydroxybenzamide
5-chloro-N-[5-chloro-3-(trifluoromethyl)phenyl]-2-hydroxybenzamide
5-chloro-2-hydroxy-N-[4-nitro-3-(trifluoromethyl)phenyl]benzamide
5-fluoro-2-hydroxy-N-[2-(2,2,2-trifluoroethoxy)-5-(trifluoromethyl)phenyl]benzamide
5-fluoro-2-hydroxy-N-[2-(6,6,6-trifluorohexyloxy)-5-(trifluoromethy)phenyl]-benzamide
5-chloro-2-hydroxy-N-(3-trifluoromethyl)-4-{[4-(trifluoromethyl)sulfanyl]phenoxy}phenyl)benzamide
N-[4-(benzothiazol-2-yl)sulfanyl-3-(trifluoromethyl)phenyl]-5-chloro-2-hydroxybenzamide
5-chloro-N-[2-(4-chlorophenoxy)-5-(trifluoromethyl)phenyl]-2-hydroxybenzamide
5-chloro-2-hydroxy-N-[2-(4-methylphenoxy)-5-(trifluoromethyl)phenyl]benzamide
5-chloro-N-[2-(4-chlorophenyl)sulfanyl-5-(trifluoromethyl)phenyl]-2-hydroxybenzamide
5-chloro-2-hydroxy-N-[2-(1-naphthyloxy)-5-(trifluoromethyl)phenyl]benzamide
5-chloro-2-hydroxy-N-[2-(2-naphthyloxy)-5-(trifluoromethyl)phenyl]benzamide In the aforementioned general formula (I-3), $Z^3$ is 2-hydroxyphenyl group which may be substituted in the 5-position and 2-acetoxyphenyl group which may be substituted in the 5-position.

Examples of the substituent in the definition of "hydrocarbon group which may be substituted" in the definition of $R^{3e2}$ and $R^{3e3}$ include similar groups to the substituents explained for the definition "which may be substituted". A $C_1$ to $C_6$ alkyl group is preferred as the "hydrocarbon group which may be substituted", and tert-butyl group is most preferred.

Examples of the substituent in the definition of "hydroxy group which may be substituted" in the definition of $R^{3e2}$ and $R^{3e3}$ include similar groups to the substituents explained for the definition "which may be substituted". A $C_1$ to $C_6$ alkoxy group is preferred as the "hydroxy group which may be substituted", and methoxy group is most preferred.

Examples of the substituent in the definition of "$C_2$ to $C_6$ hydrocarbon group which may be substituted" in the definition of $R^{3e5}$ include similar groups to the substituents explained for the definition "which may be substituted". A $C_2$ to $C_6$ alkyl group is preferred as the "$C_2$ to $C_6$ alkyl group which may be substituted", and tert-butyl group is most preferred.

As $E^3$, 2,5-bis[(1,1-dimethyl)ethyl]phenyl group, 3,5-bis[(1,1-dimethyl)ethyl]-phenyl group and 5-(1,1-dimethyl)ethyl-2-methoxyphenyl group are preferred.

$A^3$ is hydrogen atom and an acetyl group, and hydrogen atom is preferred.

Examples of $R^{3z}$ include halogen atom, $C_1$ to $C_6$ alkyl group and $C_1$ to $C_6$ halogenated alkyl group, and halogen atom, methyl group, tert-butyl group, trifluoromethyl group, and pentafluoroethyl group are preferred.

Each compound defined by the aforementioned general formula (I-3) or a pharmacologically acceptable salt thereof, or a hydrate thereof and a solvate thereof is novel, and uses of the compounds according to the present invention relating to chemical substances are not limited.

In the aforementioned general formula (I-4), $Z^4$ includes 2-hydroxyphenyl group which may be substituted in the 5-position and 2-acetoxyphenyl group which may be substituted in the 5-position.

Examples of the substituent in the definition of "hydrocarbon group which may be substituted" in the definition of $R^{4e4}$ include similar groups to the substituent explained for the definition "which may be substituted". A $C_1$ to $C_6$ alkyl group which may be substituted, a $C_1$ to $C_6$ halogenated alkyl group which may be substituted, and a $C_6$ to $C_{10}$ aryl group which may be substituted are preferred as the "hydrocarbon group which may be substituted", and methyl group, isopropyl group, tert-butyl group, phenyl group, and pentafluorophenyl are more preferred.

Examples of the substituent in the definition of "acyl group which may be substituted" in the definition of $R^{4e5}$ include similar groups to the substituents explained for the definition "which may be substituted". A $C_1$ to $C_6$ alkyl-carbonyl group which may be substituted, a $C_6$ to $C_{10}$ aryl-carbonyl group which may be substituted, and a $C_1$ to $C_6$ alkoxy-carbonyl group which may be substituted are preferred as the "acyl group which may be substituted", and acetyl group, pivaloyl group and benzoyl group are more preferred.

Examples of the substituent in the definition of "heterocyclic group which may be substituted" in the definition of $R^{4e5}$ include similar groups to the substituents explained for the definition "which may be substituted". A 6-membered non-aromatic heterocyclic group which may be substituted is preferred as the "heterocyclic group which may be substituted", and piperidino group, morpholino group, 4-methylpiperazin-1-yl group, 4-phenylpiperazin-1-yl group are more preferred.

As $E^4$, 5-bromo-4-[(1,1-dimethyl)ethyl]thiazol-2-yl group, 5-bromo-4-(trifluoromethyl)thiazol-2-yl group, 5-cyano-4-[(1,1-dimethyl)ethyl]thiazol-2-yl group, 4-(1,1-dimethyl)ethyl-5-[(2,2-dimethyl)propionyl]thiazol-2-yl group, 5-acetyl-4-phenylthiazol-2-yl group, 5-benzoyl-4-phenylthiazol-2-yl group, 4-(1,1-dimethyl)ethyl-5-(ethoxycarbonyl)thiazol-2-yl group, 5-ethoxycarbonyl-4-(trifluoromethyl)thiazol-2-yl group, 5-ethoxycarbonyl-4-phenylthiazol-2-yl group, 5-ethoxycarbonyl-4-(pentafluorophenyl)thiazol-2-yl group, 4-(1,1-dimethyl)ethyl-5-piperidinothiazol-2-yl group, 4-(1,1-dimethyl)ethyl-5-morpholinothiazol-2-yl group, 4-(1,1-dimethyl)ethyl-5-(4-methylpiperidin-1-yl)thiazol-2-yl group, and 4-(1,1-dimethyl)ethyl-5-(4-phenylpiperidin-1-yl)thiazol-2-yl group are preferred, and 4-(1,1-dimethyl)ethyl-5-[(2,2-dimethyl)propionyl]thiazol-2-yl group is most preferred.

$A^4$ includes hydrogen atom and an acetyl group, and hydrogen atom is preferred.

Examples of $R^{4z}$ include a halogen atom, a $C_6$ to $C_{10}$ aryl group, and a 5-membered heteroaryl group, and a halogen atom, phenyl group, 4-fluorophenyl group, 2,4-difluorophenyl group, 4-(trifluoromethyl)phenyl group, 1-pyrrolyl group, and 2-thienyl group are preferred.

Each compound defined by the aforementioned general formula (I-4) or a pharmacologically acceptable salt thereof, and a hydrate thereof and a solvate thereof is novel, and uses of the compounds according to the present invention relating to chemical substances are not limited.

The compounds represented by the aforementioned general formulas (I), (I-1), (I-2), (I-3), and (I-4) may form salts. Examples of pharmacologically acceptable salts include, when acidic groups exist, metal salts such as lithium salt, sodium salt, potassium salt, magnesium salt, calsium salts, or ammonium salts such as ammonium salt, methylammonium salt, dimethylammonium salt, trimethylammonium salt, dicyclohexylammonium salt, and when basic groups exist, mineral acid salts such as hydrochloride, oxalate, hydrosulfate, nitrate, phosphate, or organic acid salts such as methane sulfonate, benzene sulfonate, para-toluene sulfonate, acetate, propionate, tartrate, fumarate, maleate, malate, oxalate, succinate, citrate, benzoate, mandelate, cinnamate, lactate. Salts may sometimes be formed with amino acids such as glycine. As active ingredients of the medicament of the present invention, pharmacologically acceptable salts may also be suitably used.

The compounds or salts thereof represented by the aforementioned general formulas (I), (I-1), (I-2), (I-3), and (I-4) may exist as hydrates or solvates. As active ingredients of the medicament of the present invention, any of the aforementioned substances may be used. Furthermore, the compounds represented by the aforementioned general formulas (I), (I-1), (I-2), (I-3), and (I-4) may sometimes have one or more asymmetric carbons, and may exist as steric isomers such as optically active substance and diastereomer. As active ingredients of the medicament of the present invention, pure forms of stereoisomers, arbitrary mixture of enantiomers or diastereomers, and racemates may be used. When the compounds represented by the general formulas (I), (I-1), (I-2), (I-3), and (I-4) have olefinic double bonds, the configuration may be in either E or Z, and as active ingredients of the medicament of the present invention, geometrical isomer in either of the configurations or a mixture thereof may be used.

Examples of the compounds as preferred active ingredients of the medicaments of the present invention are shown below. However, the active ingredients of the medicaments of the present invention are not limited to the compound set out below. In the table, Me represents methyl group, and Et represents ethyl group.

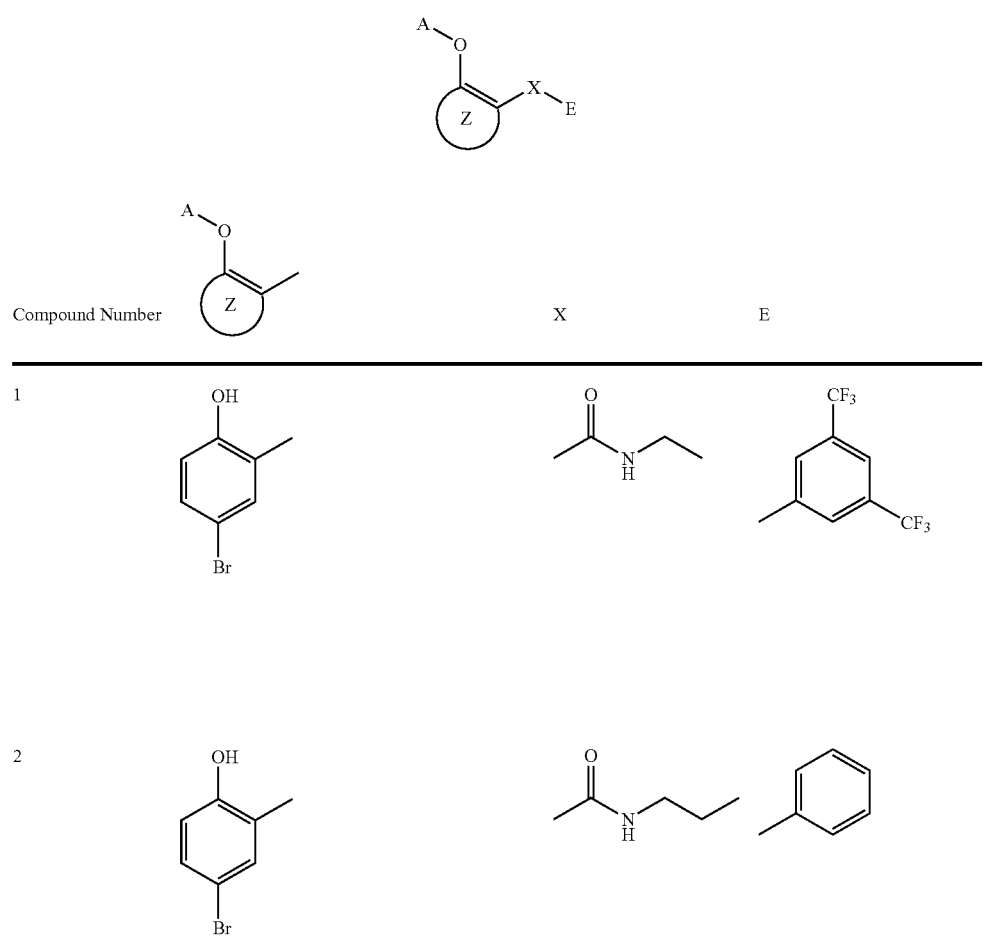

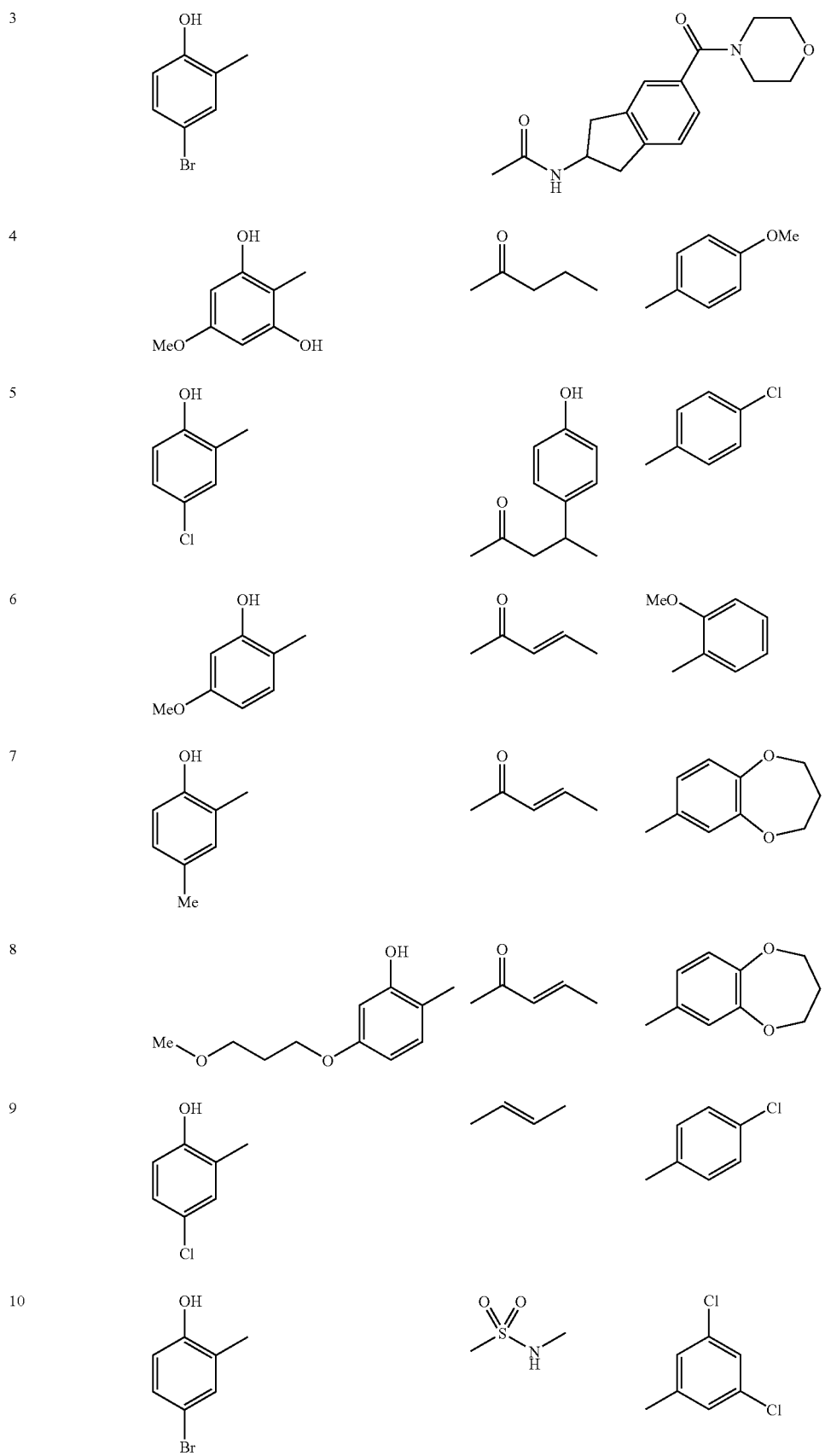

-continued
| 11 | 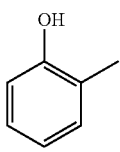 | 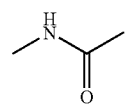 | 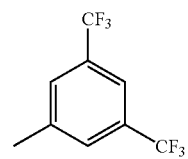 |
| 12 | 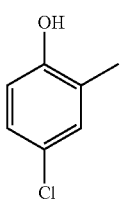 | 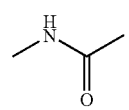 | 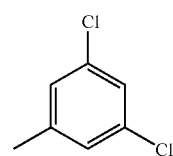 |
| 13 | 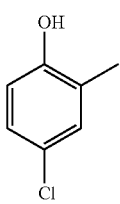 | 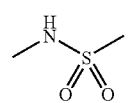 | 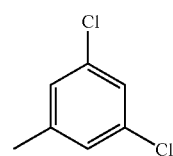 |
| 14 | 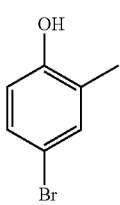 | 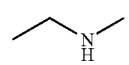 | 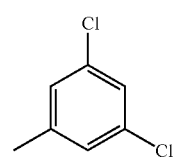 |
| 15 | 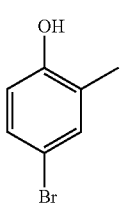 | 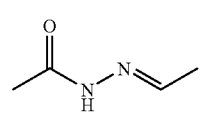 | 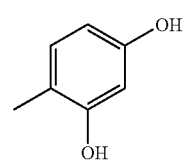 |
| 16 | 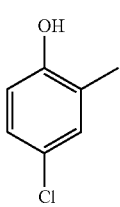 | 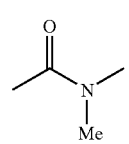 | 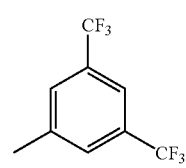 |
| 17 | 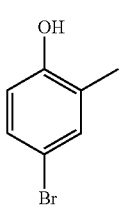 | | 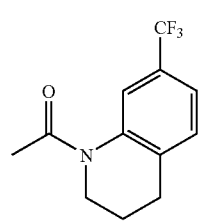 |

-continued
| Compound Number | 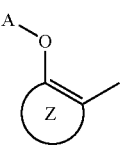 | E |
|---|---|---|
| 18 | 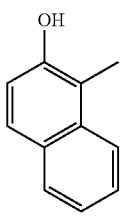 | 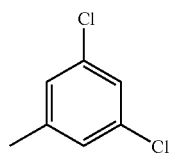 |
| 19 | 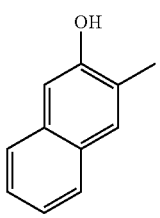 | 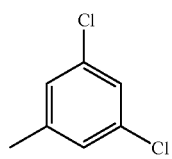 |
| 20 | 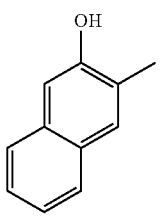 | 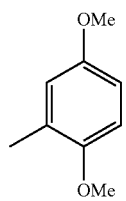 |
| 21 | 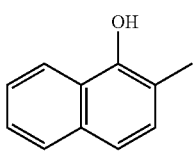 | 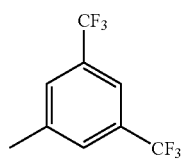 |
| 22 | 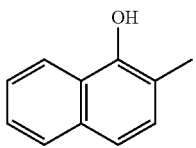 | 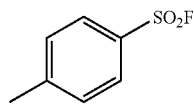 |
| 23 | 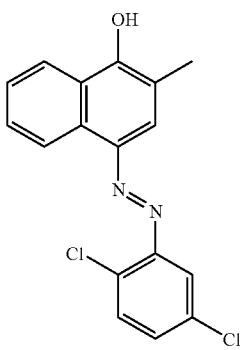 | 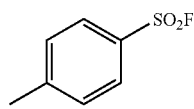 |

| | | |
|---|---|---|
| 24 | 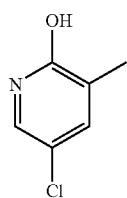 | 
(reproducing structures as images)
| # | Structure A | Structure B |
|---|---|---|
| 24 | 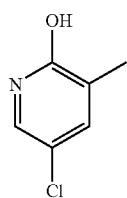 | 3,5-bis(trifluoromethyl)toluene |
| 25 | 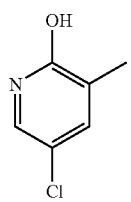 | 4-chloro-2-(trifluoromethyl)toluene |
| 26 | 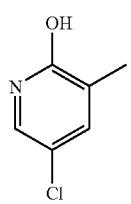 | 3,5-di-tert-butyltoluene |
| 27 | 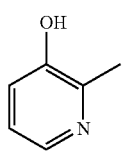 | 3,5-bis(trifluoromethyl)toluene |
| 28 | 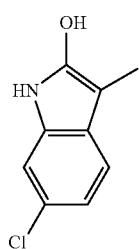 | 3,5-bis(trifluoromethyl)toluene |
| 29 | 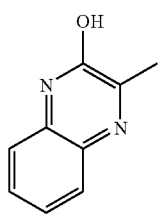 | 3,5-bis(trifluoromethyl)toluene |
| 30 | 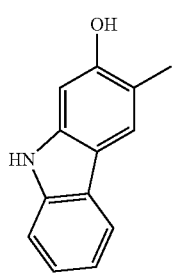 | 4-chlorotoluene |

| | | |
|---|---|---|
| 31 | 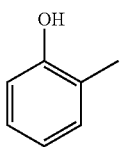 | 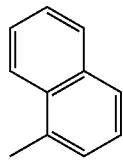 |
| 32 | 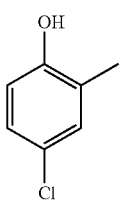 | 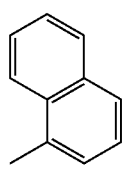 |
| 33 | 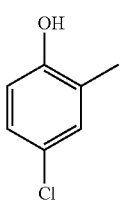 | 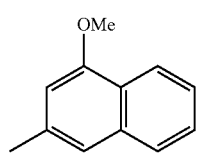 |
| 34 | 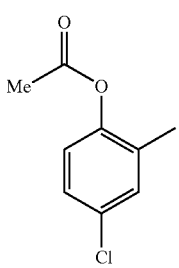 | 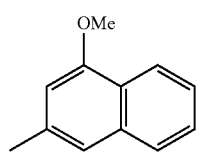 |
| 35 | 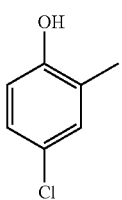 | 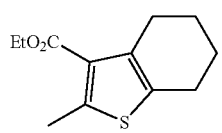 |
| 36 | 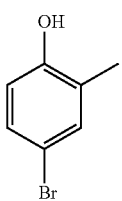 | 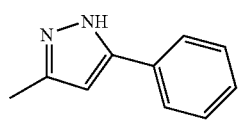 |
| 37 | 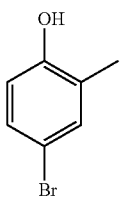 | 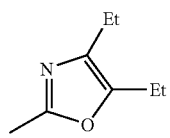 |

-continued
| | | |
|---|---|---|
| 38 | 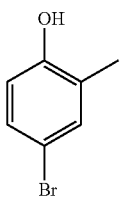 | 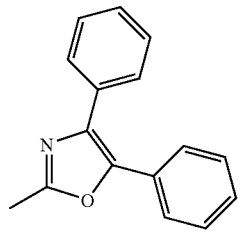 |
| 39 | 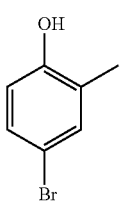 | 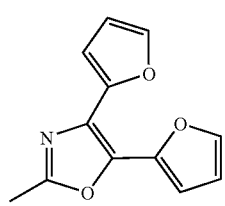 |
| 40 | 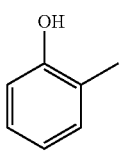 | 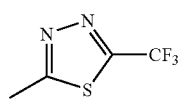 |
| 41 | 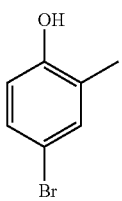 | 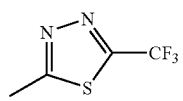 |
| 42 | 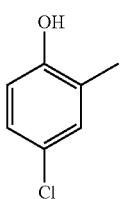 | 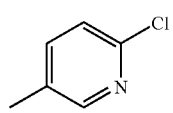 |
| 43 | 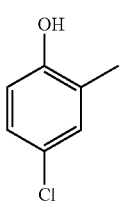 | 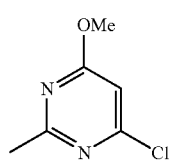 |
| 44 | 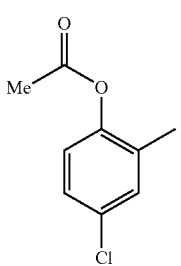 | 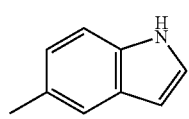 |

-continued
| | | |
|---|---|---|
| 45 | 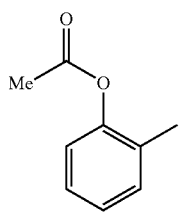 | 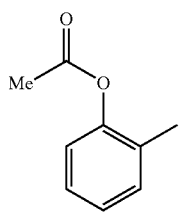 |
| 46 | 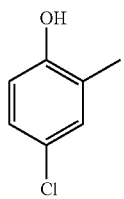 | |
| 47 | 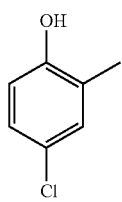 | |
| 48 | 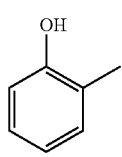 | |
| 49 | 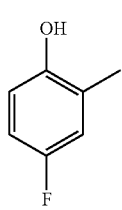 | |
| 50 | 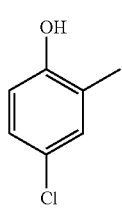 | |
| 51 | 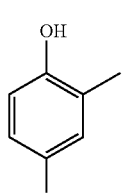 | |
| 52 | 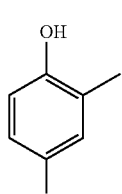 | |

-continued
| 53 | 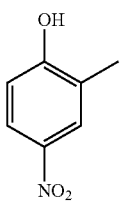 | 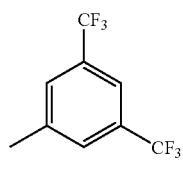 |
| --- | --- | --- |
| 54 | 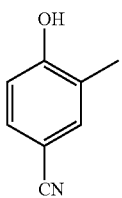 | 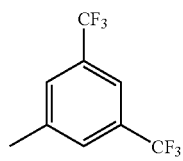 |
| 55 | 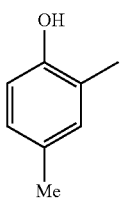 | 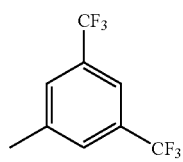 |
| 56 | 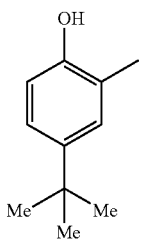 | 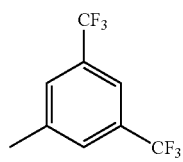 |
| 57 | 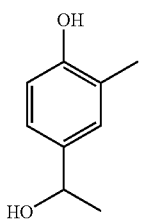 | 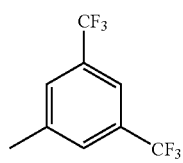 |
| 58 | 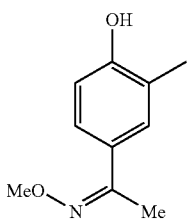 | 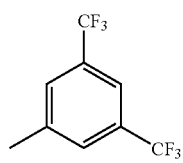 |
| 59 | 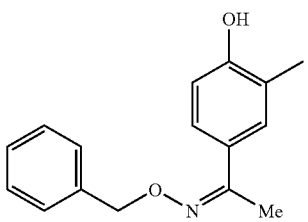 | 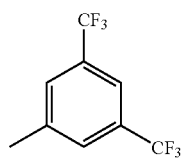 |

| | | |
|---|---|---|
| 60 | 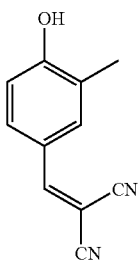 | 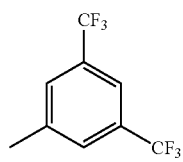 |
| 61 | 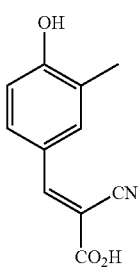 | 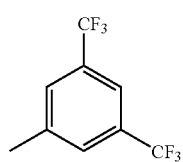 |
| 62 | 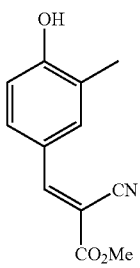 | 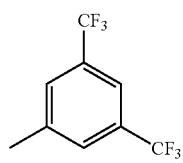 |
| 63 | 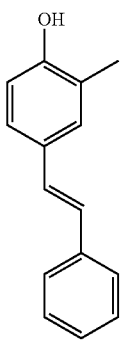 | 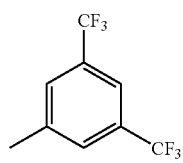 |
| 64 | 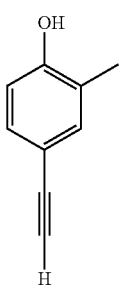 | 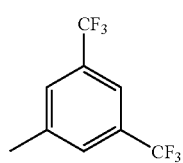 |

| | | |
|---|---|---|
| 65 | 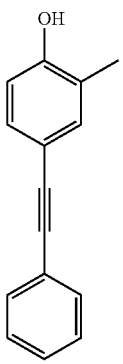 | 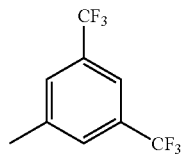 |
| 66 | 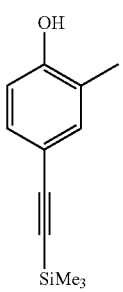 | 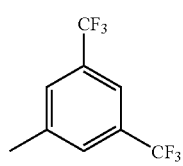 |
| 67 | 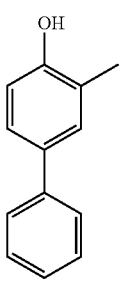 | 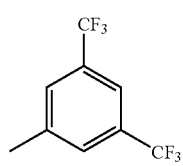 |
| 68 | 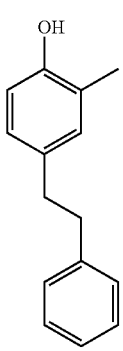 | 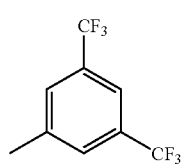 |
| 69 | 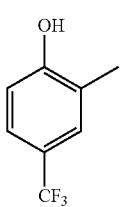 | 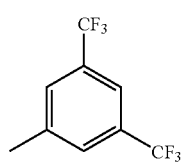 |

-continued
| | | |
|---|---|---|
| 70 | 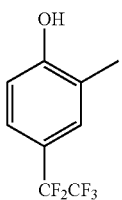 | 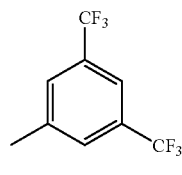 |
| 71 | 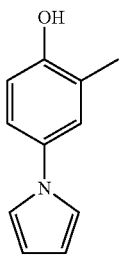 | 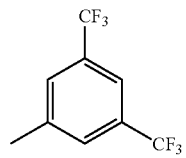 |
| 72 | 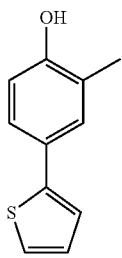 | 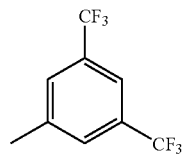 |
| 73 | 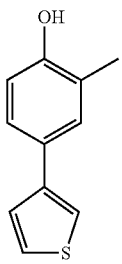 | 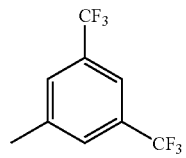 |
| 74 | 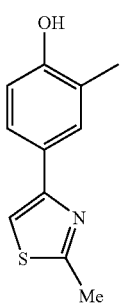 | 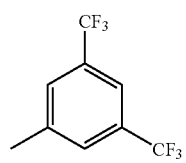 |
| 75 | 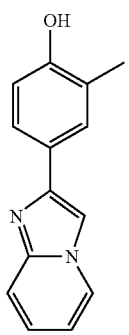 | 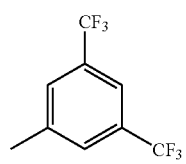 |

-continued
| | | |
|---|---|---|
| 76 | 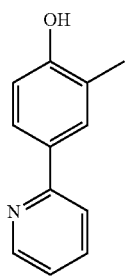 | 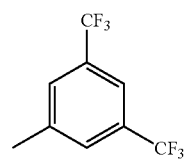 |
| 77 | 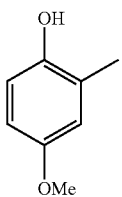 | 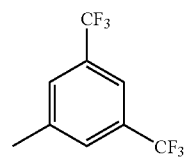 |
| 78 | 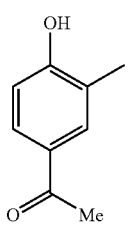 | 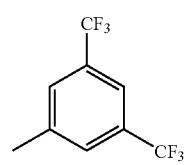 |
| 79 | 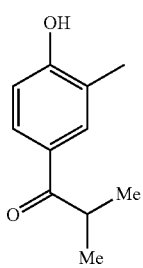 | 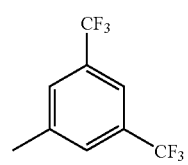 |
| 80 | 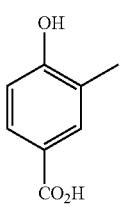 | 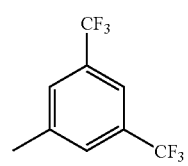 |
| 81 | 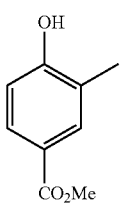 | 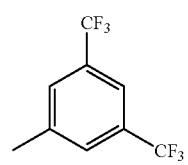 |
| 82 | 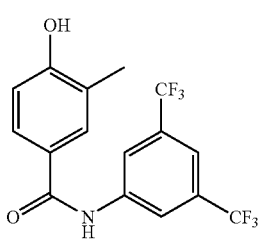 | 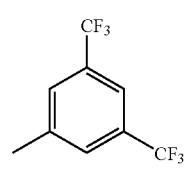 |

| | | |
|---|---|---|
| 83 | 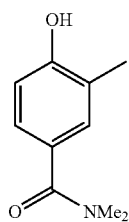 | 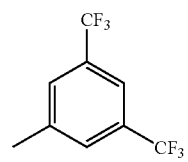 |
| 84 | 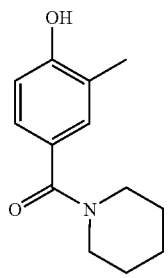 | 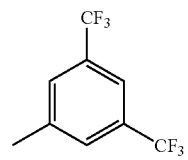 |
| 85 | 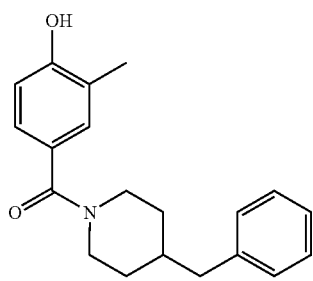 | 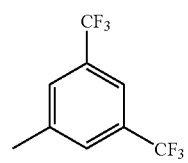 |
| 86 | 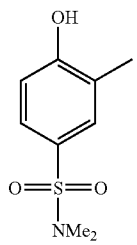 | 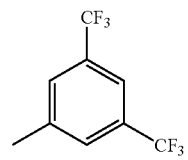 |
| 87 | 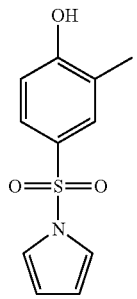 | 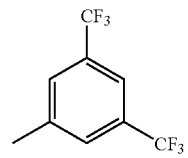 |
| 88 | 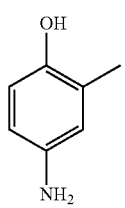 | 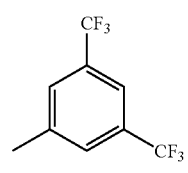 |

| | | |
|---|---|---|
| 89 | 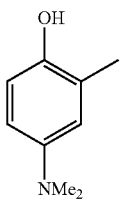 | 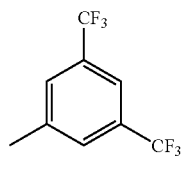 |
| 90 | 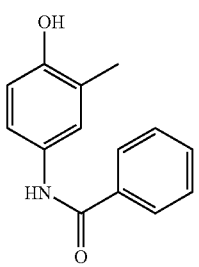 | 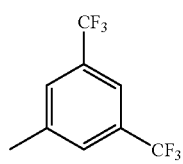 |
| 91 | 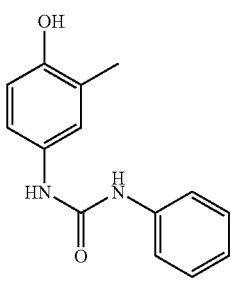 | 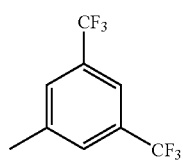 |
| 92 | 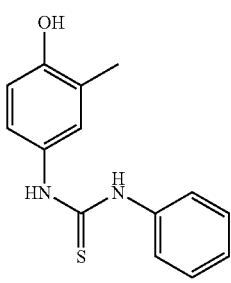 | 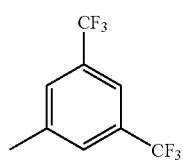 |
| 93 | 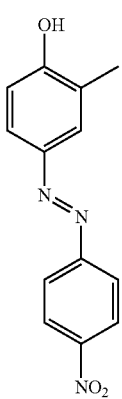 | 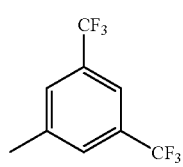 |

-continued
| | | |
|---|---|---|
| 94 | 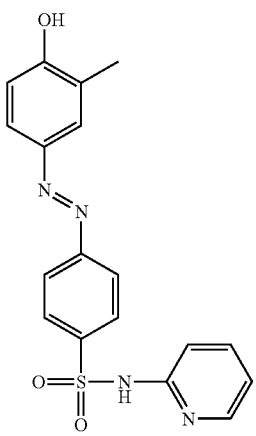 | 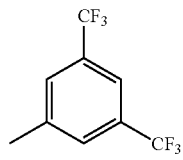 |
| 95 | 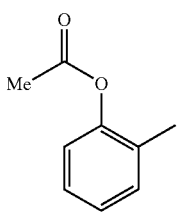 | 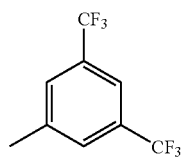 |
| 96 | 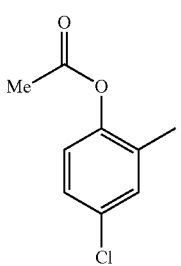 | 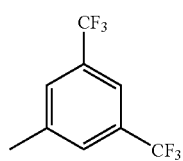 |
| 97 | 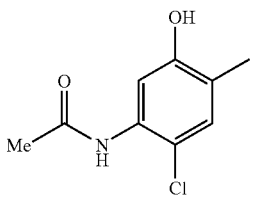 | 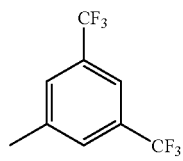 |
| 98 | 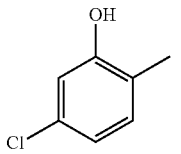 | 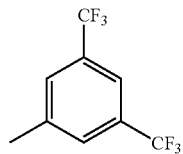 |
| 99 | 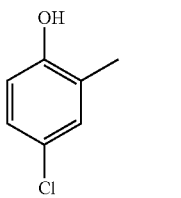 | 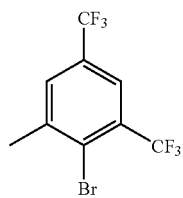 |

-continued
| | | |
|---|---|---|
| 100 | 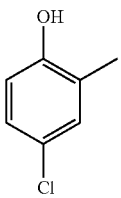 | 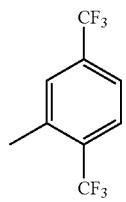 |
| 101 | 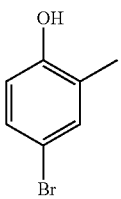 | 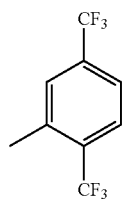 |
| 102 | 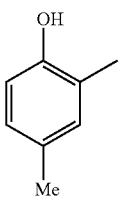 | 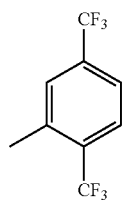 |
| 103 | 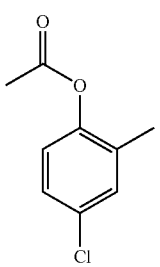 | 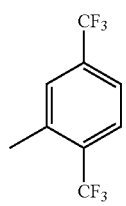 |
| 104 | 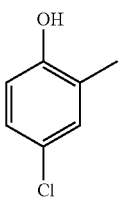 | 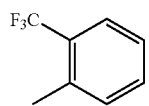 |
| 105 | 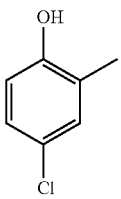 | 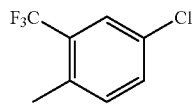 |
| 106 | 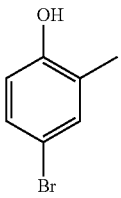 | 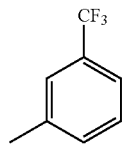 |

-continued
| | | |
|---|---|---|
| 107 | 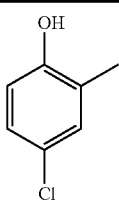 |  |
| 108 | 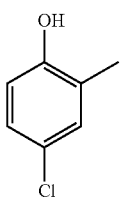 | 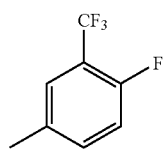 |
| 109 | 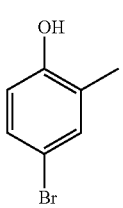 |  |
| 110 | 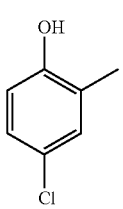 | 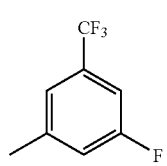 |
| 111 | 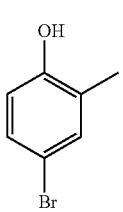 | 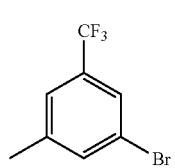 |
| 112 | 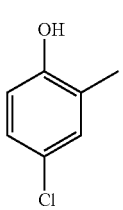 | 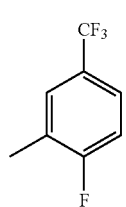 |
| 113 | 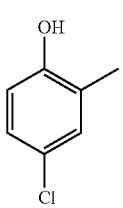 | 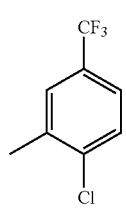 |
| 114 | 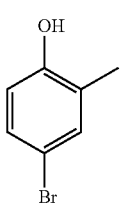 | 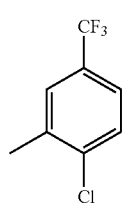 |

-continued
| | | |
|---|---|---|
| 115 | 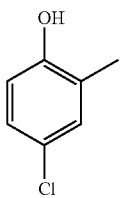 | 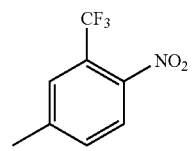 |
| 116 | 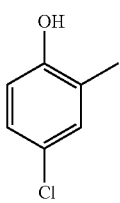 | 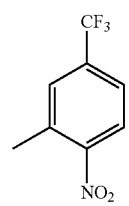 |
| 117 | 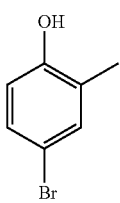 | 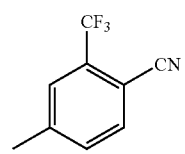 |
| 118 | 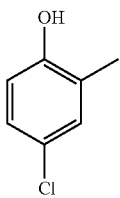 | 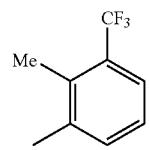 |
| 119 | 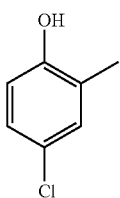 | 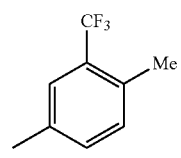 |
| 120 | 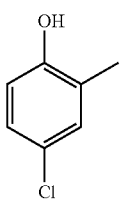 | 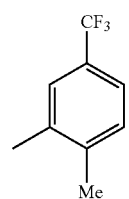 |
| 121 | 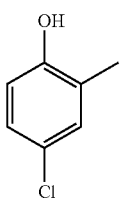 | 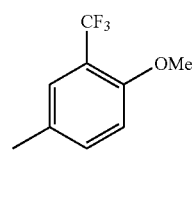 |

-continued
| | | |
|---|---|---|
| 122 | 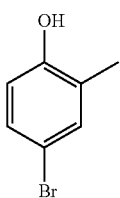 | 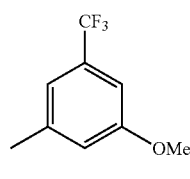 |
| 123 | 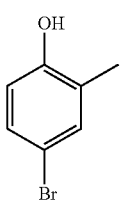 | 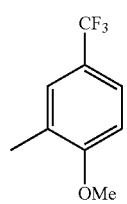 |
| 124 | 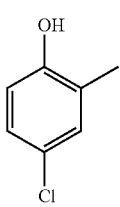 | 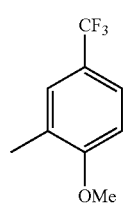 |
| 125 | 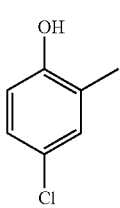 | 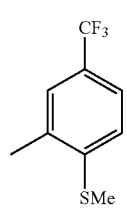 |
| 126 | 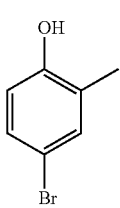 | 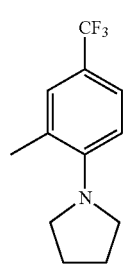 |
| 127 | 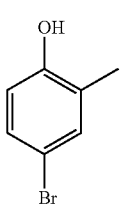 | 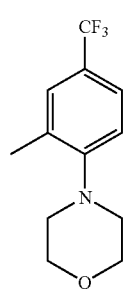 |
| 128 | 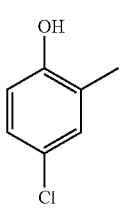 | 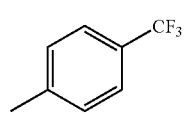 |

| | | |
|---|---|---|
| 129 | 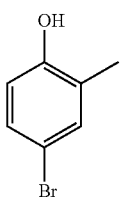 | 2-chloro-4-(trifluoromethyl)toluene structure |
| 130 | 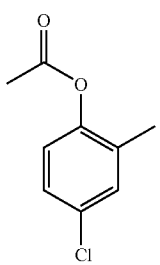 | |
| 131 | 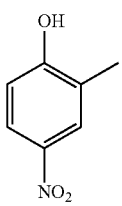 | |
| 132 | 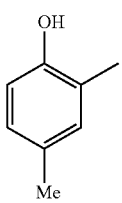 | |
| 133 | 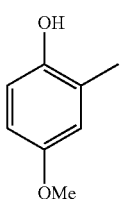 | |
| 134 | 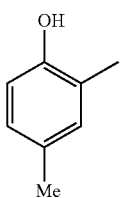 | |
| 135 | 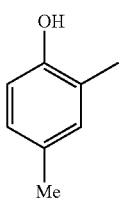 | |

-continued
| | | |
|---|---|---|
| 136 | 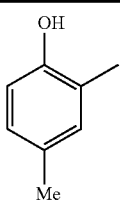 | 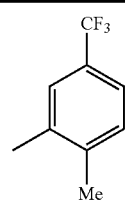 |
| 137 | 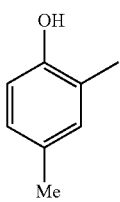 | 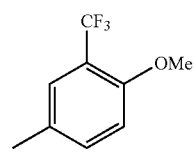 |
| 138 | 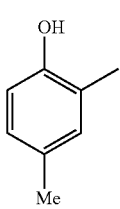 | 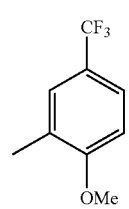 |
| 139 | 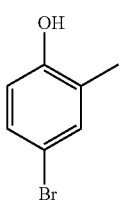 | 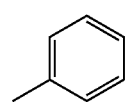 |
| 140 | 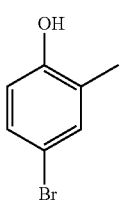 | 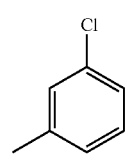 |
| 141 | 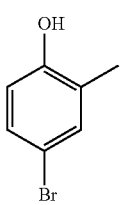 | 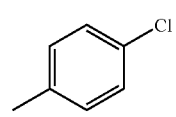 |
| 142 | 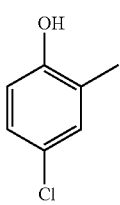 | 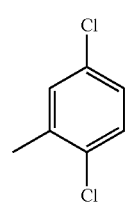 |
| 143 | 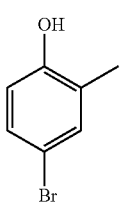 | 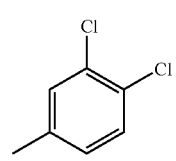 |

| | | |
|---|---|---|
| 144 | 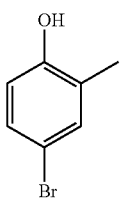 | 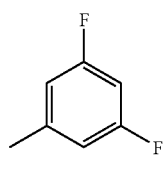 |
| 145 | 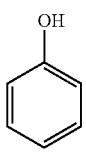 | 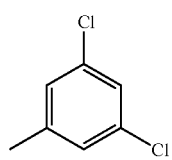 |
| 146 | 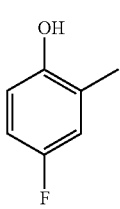 | 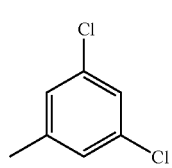 |
| 147 | 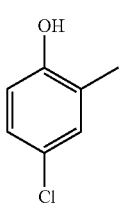 | 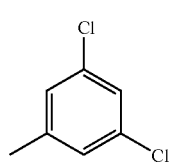 |
| 148 | 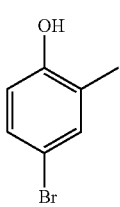 | 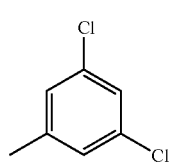 |
| 149 | 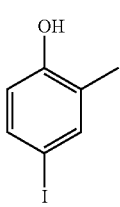 | 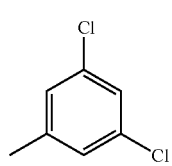 |
| 150 | 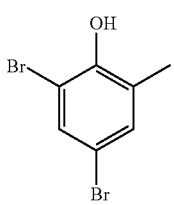 | 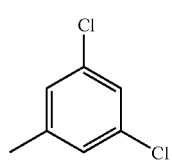 |
| 151 | 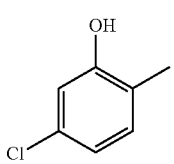 | 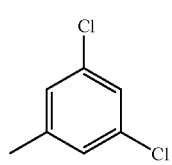 |

-continued
| | | |
|---|---|---|
| 152 | 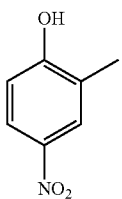 | 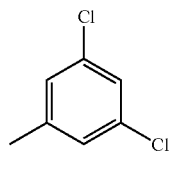 |
| 153 | 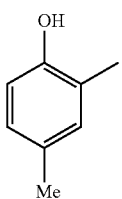 | 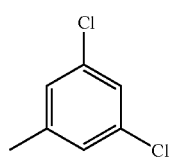 |
| 154 | 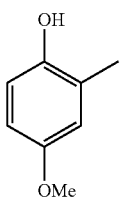 | 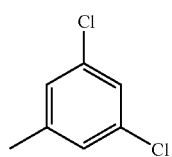 |
| 155 | 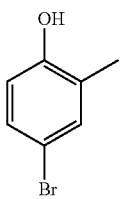 | 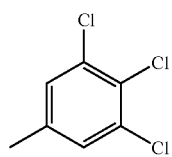 |
| 156 | 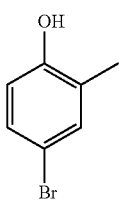 | 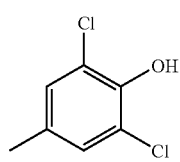 |
| 157 | 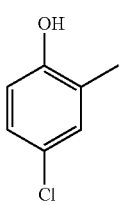 | 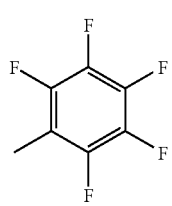 |
| 158 | 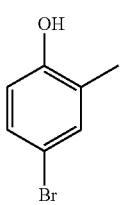 | 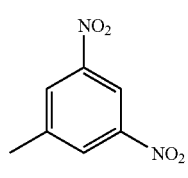 |

-continued
| | | |
|---|---|---|
| 159 | 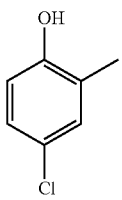 | 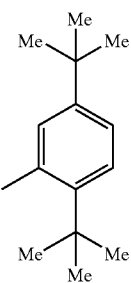 |
| 160 | 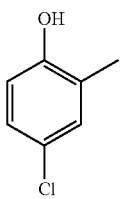 | 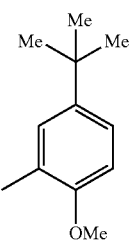 |
| 161 | 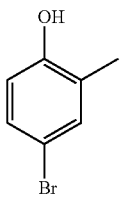 | 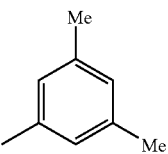 |
| 162 | 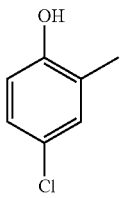 | 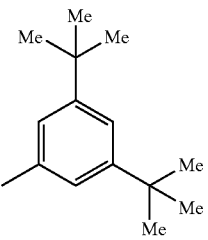 |
| 163 | 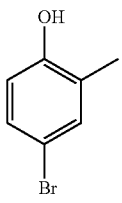 | 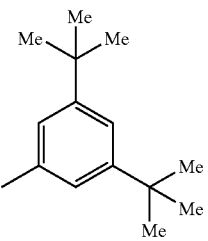 |
| 164 | 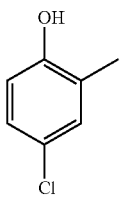 | 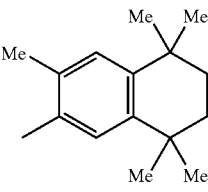 |

-continued
| | | |
|---|---|---|
| 165 | 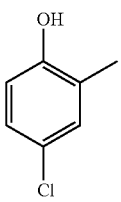 | 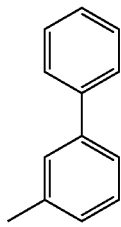 |
| 166 | 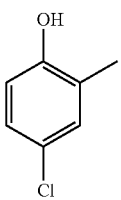 | 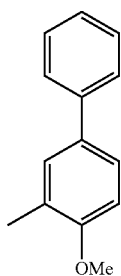 |
| 167 | 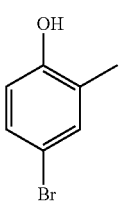 | 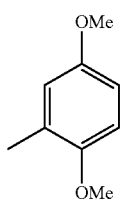 |
| 168 | 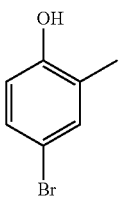 | 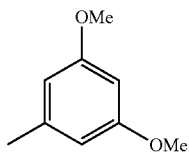 |
| 169 | 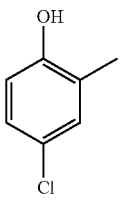 | 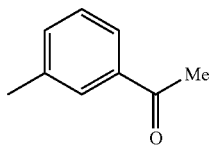 |
| 170 | 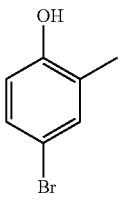 | 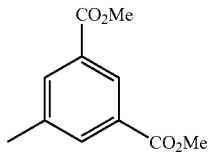 |
| 171 | 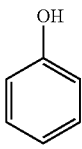 | 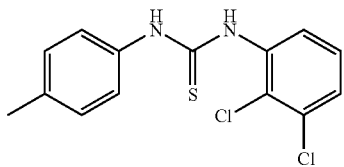 |

-continued
| | | |
|---|---|---|
| 172 | 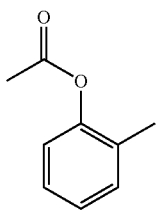 | 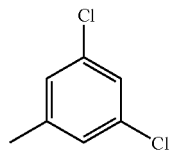 |
| 173 | 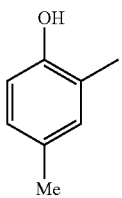 | 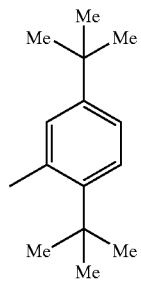 |
| 174 | 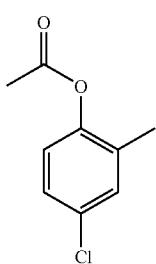 | 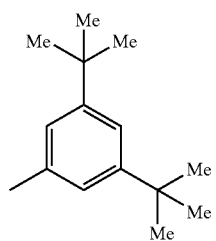 |
| 175 | 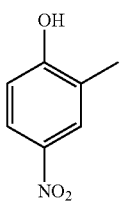 | 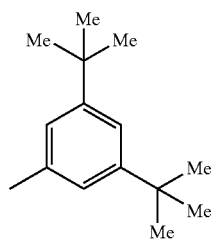 |
| 176 | 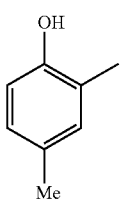 | 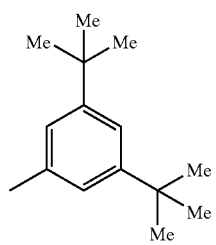 |
| 177 | 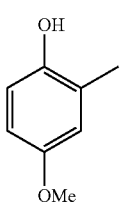 | 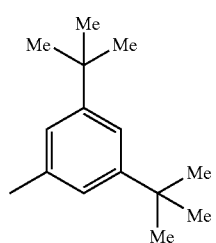 |

-continued
| | | |
|---|---|---|
| 178 | 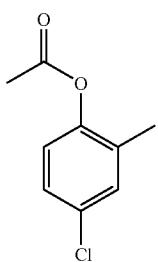 | 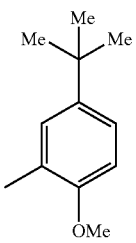 |
| 179 | 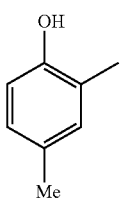 | 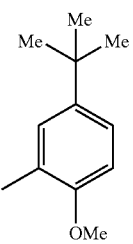 |
| 180 | 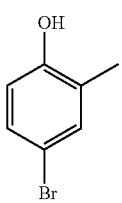 | 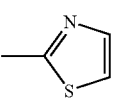 |
| 181 | 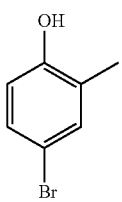 | 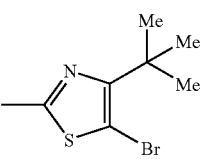 |
| 182 | 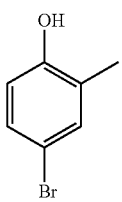 | 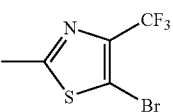 |
| 183 | 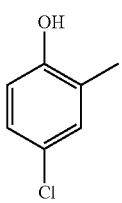 | 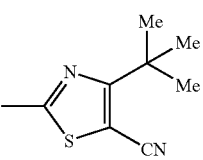 |
| 184 | 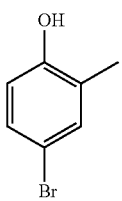 | 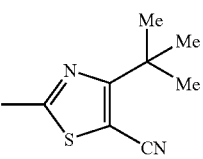 |

-continued
| | | |
|---|---|---|
| 185 | 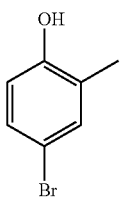 | 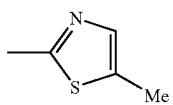 |
| 186 | 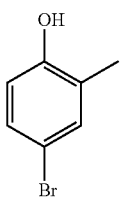 | 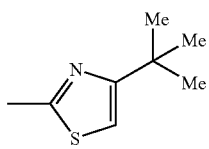 |
| 187 | 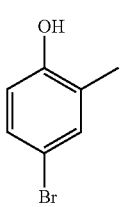 | 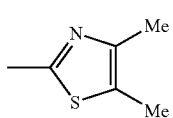 |
| 188 | 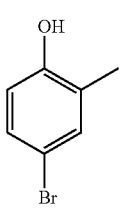 | 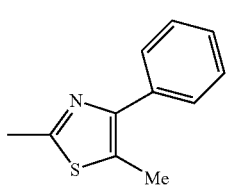 |
| 189 | 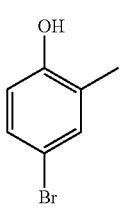 | 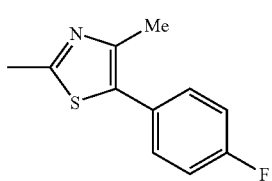 |
| 190 | 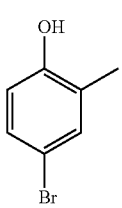 | 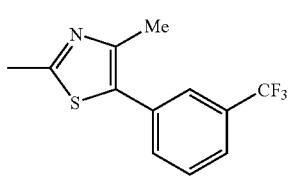 |
| 191 | 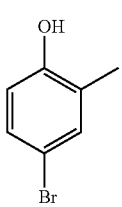 | 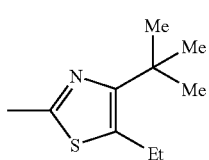 |
| 192 | 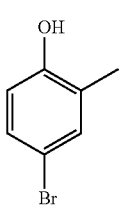 | 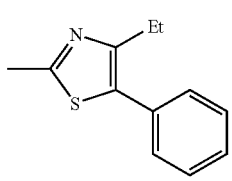 |

-continued
| | | |
|---|---|---|
| 193 | 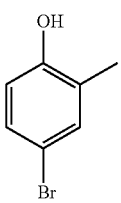 | 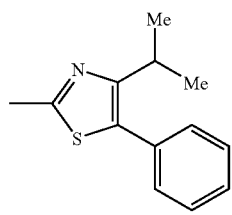 |
| 194 | 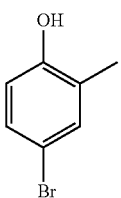 | 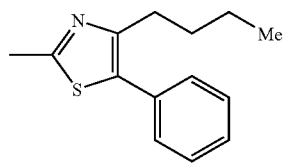 |
| 195 | 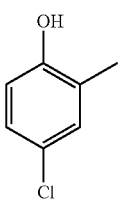 | 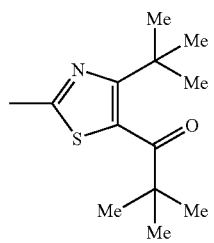 |
| 196 | 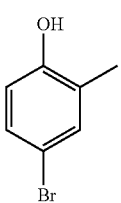 | 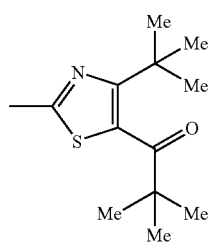 |
| 197 | 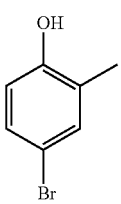 | 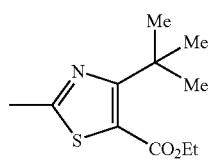 |
| 198 | 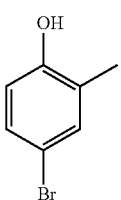 | 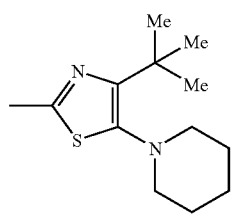 |
| 199 | 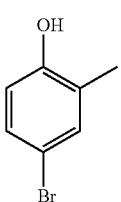 | 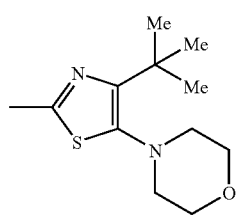 |

| | | |
|---|---|---|
| 200 | 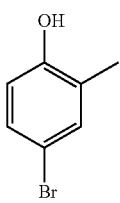 | 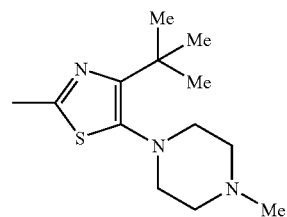 |
| 201 | 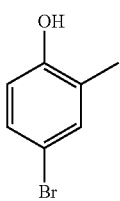 | 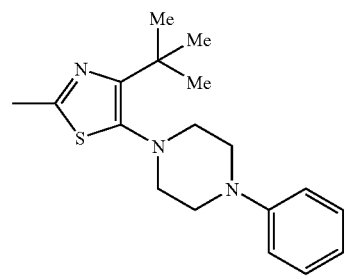 |
| 202 | 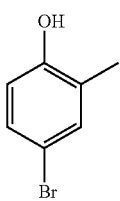 | 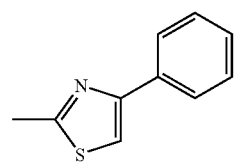 |
| 203 | 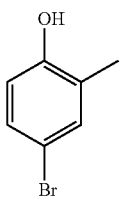 | 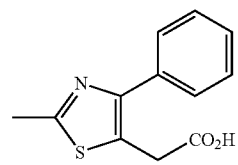 |
| 204 | 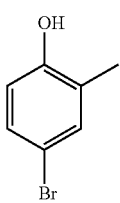 | 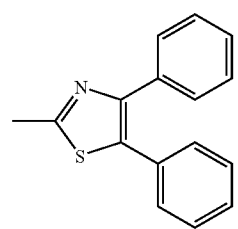 |
| 205 | 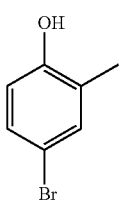 | 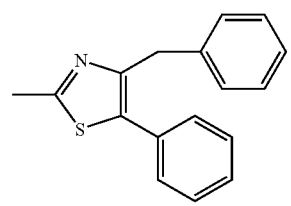 |
| 206 | 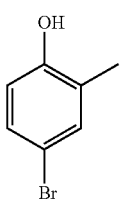 | 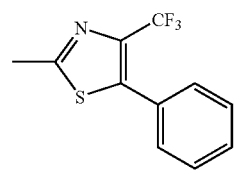 |

-continued
| | | |
|---|---|---|
| 207 | 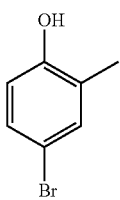 | 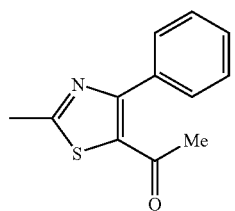 |
| 208 | 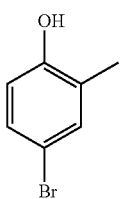 | 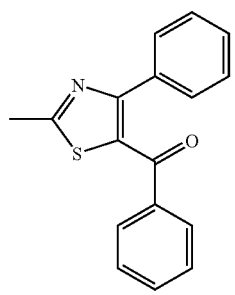 |
| 209 | 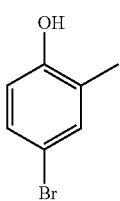 | 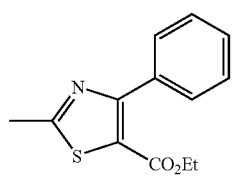 |
| 210 | 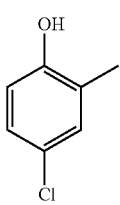 | 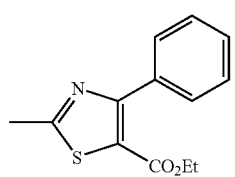 |
| 211 | 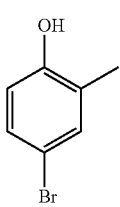 | 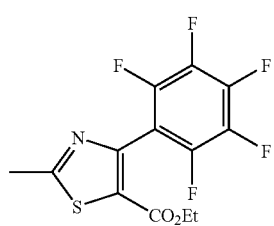 |
| 212 | 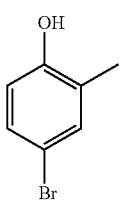 | 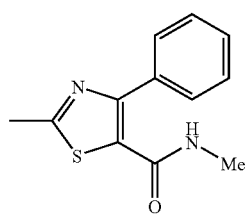 |
| 213 | 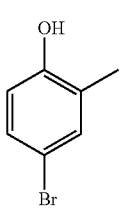 | 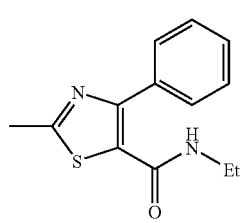 |

-continued
| | | |
|---|---|---|
| 214 | 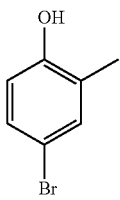 | 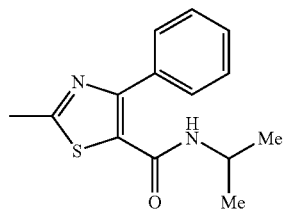 |
| 215 | 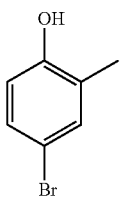 | 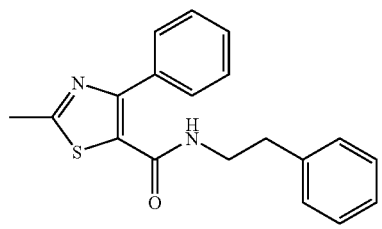 |
| 216 | 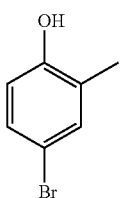 | 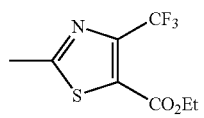 |
| 217 | 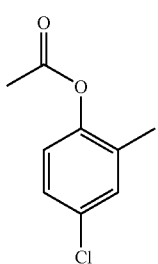 | 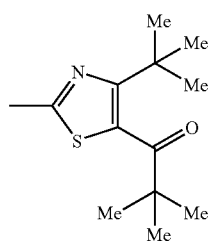 |
| 218 | 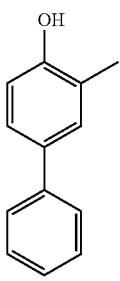 | 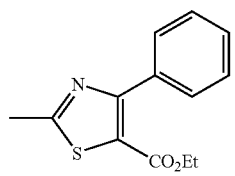 |
| 219 | 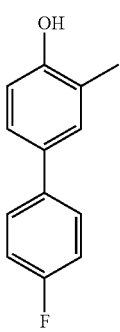 | 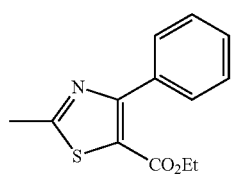 |

-continued
| 220 | 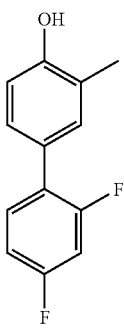 | 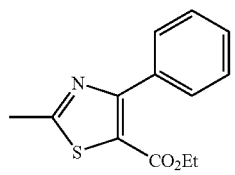 |
| --- | --- | --- |
| 221 | 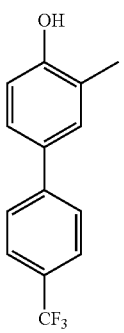 | 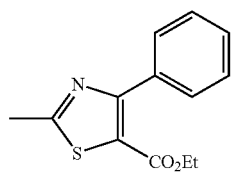 |
| 222 | 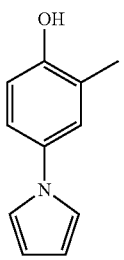 | 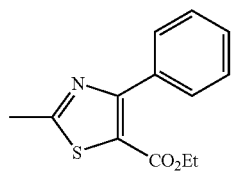 |
| 223 | 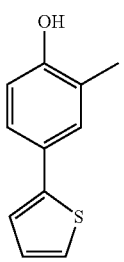 | 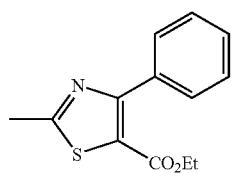 |

The compounds represented by the general formula (I) can be prepared, for example, by methods shown below.

<Method 1>

The compounds represented by the general formula (I), wherein X is —CONH— (the hydrogen atom on the nitrogen may be substituted) can be prepared, for example, by a method described in the reaction scheme 1.

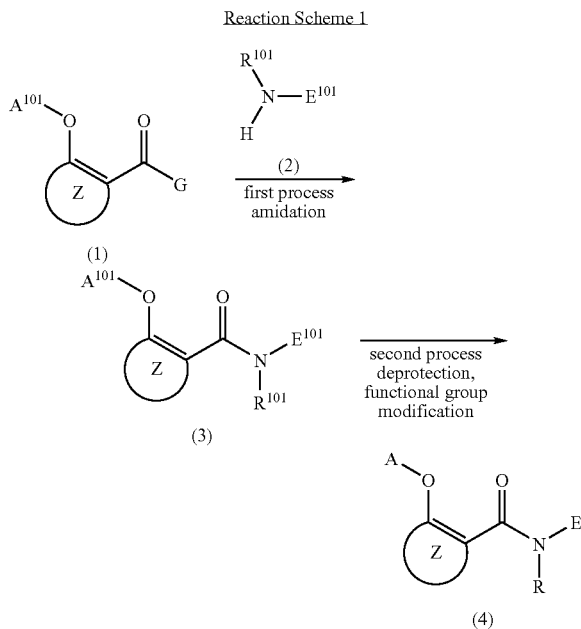

wherein $A^{101}$ represents a hydrogen atom or protecting groups of hydroxy group (preferably, an alkyl group such as methyl group and the like; an aralkyl group such as benzyl group and the like; an acetyl group, an alkoxyalkyl group such as methoxymethyl group and the like; a substituted silyl group such as trimethylsilyl group or the like), $R^{101}$ represents a hydrogen atom, a $C_1$ to $C_6$ alkyl group or the like, $E^{101}$ represents E or precursor of E in the definition of the general formula (I), G represents a hydroxy group, halogen atoms (preferably, a chlorine atom), a hydrocarbon-oxy group (preferably, an aryl-oxy group which may be substituted by halogen atom), an acyl-oxy group, an imido-oxy group or the like.

(First Step)

The amide (3) can be prepared by dehydrocondensation of the carboxylic acid derivative (1) and the amine (2). This reaction is carried out at a reaction temperature of from 0° C. to 180° C. without solvent or in an aprotic solvent, in the existence of an acid halogenating agent or a dehydrocondensating agent, and in the existence of or nonexistence of a base.

As the halogenating agent reagent, examples include, for example, thionyl chloride, thionyl bromide, sulfuryl chloride, phosphorus oxychloride, phosphorus trichloride, phosphorus pentachloride or the like, when $A^{101}$ is hydrogen atom, phosphorus trichloride is preferable, and when $A^{101}$ is acetyl group or the like, phosphorus oxychloride is preferable. As the dehydrocondensating agent, examples include, for example, N,N'-dicyclohexylcarbodiimide, 1-ethyl-3-(3-dimethylaminopropyl)carbodiimide hydrochloride, diphenylphosphorylazide or the like. As the base, examples include inorganic bases such as sodium carbonate, potassium carbonate, sodium hydrocarbonate or the like, or organic bases such as pyridine, triethylamine, N,N'-diethylaniline or the like. As the aprotic solvent, examples include dichloromethane, dichloroethane, chloroform, tetrahydrofuran, 1,4-dioxane, benzene, toluene, monochlorobenzene. o-dichlorobenzene, N,N'-dimethylformamide, N-methylpyrrolidone or the like, when the reaction is carried out in the presence of the acid halogenating agent, particularly, toluene, monochlorobenzene, o-dichlorobenzene are preferable.

Furthermore, a target compound can be prepared, for example, by a method or similar method described in J. Med. Chem., 1998, 41, 2939, that the acid chloride is prepared and isolated from carboxylic acid in advance, then it is made to react with an amine having $E^{101}$.

(Second Process)

When the amide (3) has a protecting group and/or has a favorable substituent for functional group modification, for example, an amino group and its protector or precursor; a carboxy group and its protector or precursor; a hydroxy group and its protector or precursor, the final target compound (4) can be prepared by a reaction for deprotection and/or functional group modification in this step. Various well-known methods can be used for the reaction. For the reaction of deprotection and functional group modification, for example, methods described in "Protective Groups in Organic Syntheses" P. G. M. Wuts, T. Green, Eds., Third version, 1999, Wiley, John & Sons, "Handbook of Reagents for Organic Synthesis" L. A. Paquette, Ed., 4 Volumes, 1999, Wiley, John & Sons can be used, and for reaction of functional group modification, for example, methods described in "Palladium Reagents in Organic Syntheses" R. F. Heck, 1985, Academic Press, "Palladium Reagents and Catalysts:Innovations in Organic Synthesis" J. Tsuji, 1999, Wiley, John & Sons, or the like can be used.

Aforementioned methods are applicable by combining raw materials properly even in the case where X is other connecting group, for example, —$SO_2NH$—, —NHCO—, —$NHSO_2$—, —$CONHCH_2$—, —$CONHCH_2CH_2$—; wherein the hydrogen atom on the said connecting group may be substituted.

<Method 2>

The compounds represented by the general formula (I), wherein X is —$CH_2NH$—, for example, can be prepared by a method described in the reaction scheme 2.

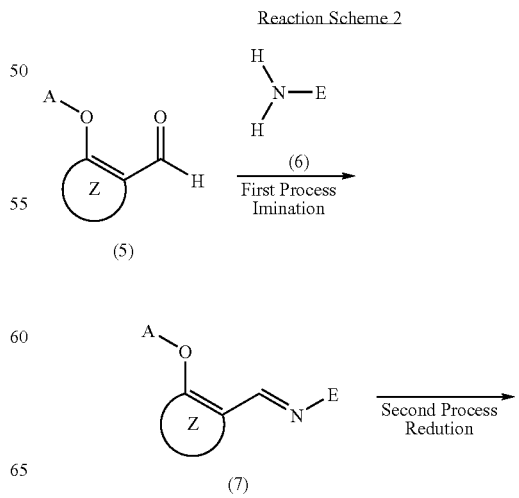

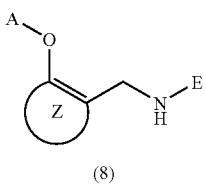

(8)

(wherein each of A and E has the same meaning as that defined in the general formula (I))

First, the imine derivative of the formula (7) (wherein the definition of $R^1$-$R^4$ and B the same as those in the general formula (I)) can be prepared by dehydrocondensation of the aldehyde (5) and the amine (6). This reaction is carried out at a reaction temperature of from 0° C. to 100° C. in a solvent, in the existence of or nonexistence of a dehydrating agent. As the dehydrating agent, examples include anhydrous magnesium sulfate, molecular sieves or the like. As the solvent, examples include nonreactive solvent, and tetrahydrofuran, 1,4-dioxane, methanol, ethanol or the like are preferable.

Aforementioned methods are applicable by combining raw materials properly even in the case where X is other connecting group, for example, —CONHN═CH—; the hydrogen atom on the said connecting group may be substituted.

Next, the target compound (8) can be prepared by reduction of the imine derivative (7). This reaction is carried out at the reaction temperature of from 0° C. to 100° C. in a solvent, in the existence of a reducing agent. As the reducing agent, examples include sodium borohydride, lithium borohydride or the like. As the solvent, examples include nonreactive solvent, and tetrahydrofuran, 1,4-dioxane, methanol, ethanol or the like are preferable. Moreover, this reaction can be carried out by a method of catalytic hydrogenation also. As the catalyst, examples include palladium carbon, platinum carbon, palladium hydroxide, palladium black or the like. As solvent, examples include nonreactive solvent, and tetrahydrofuran, 1,4-dioxane, methanol, ethanol or the like are preferable. The reaction is carried out at the reaction temperature of from 0° C. to 200° C., and the hydrogen pressure is at normal pressure or applied pressure.

<Method 3>

The compounds represented by the general formula (I), wherein X is —CH═CH— (the hydrogen atom on the said connecting group may be substituted), can be prepared by a method described in the reaction scheme 3.

Reaction Scheme 3

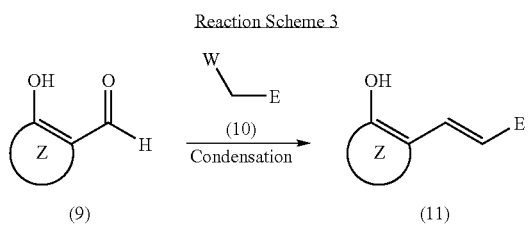

(9)        (11)

wherein each of A and E has the same meaning as that defined in the general formula (I), W represents O,O'-di-hydrocarbon-phosphono group or triarylphosphonium group.

The target compound (11) can be prepared by dehydrocondensation of the aldehyde (9) and the phosphorus compound (10). This reaction is carried out in a solvent at a reaction temperature of from 0° C. to the boiling point of the solvent, in the existence of a base. As the base, examples include inorganic base such as sodium carbonate, potassium carbonate, sodium hydrogencarbonate or the like, or organic base such as pyridine, triethylamine, N,N'-diethylaniline or the like. Examples include nonreactive solvent, and tetrahydrofuran, 1,4-dioxan, methanol, ethanol, water or the like are preferable.

<Method 4>

The compounds represented by the general formula (I), wherein X is —COCH═CH— and —COCH$_2$CH$_2$— (the hydrogen atom on the said connecting group may be substituted), can be prepared by the method, for example, described in the reaction scheme 4.

Reaction Scheme 4

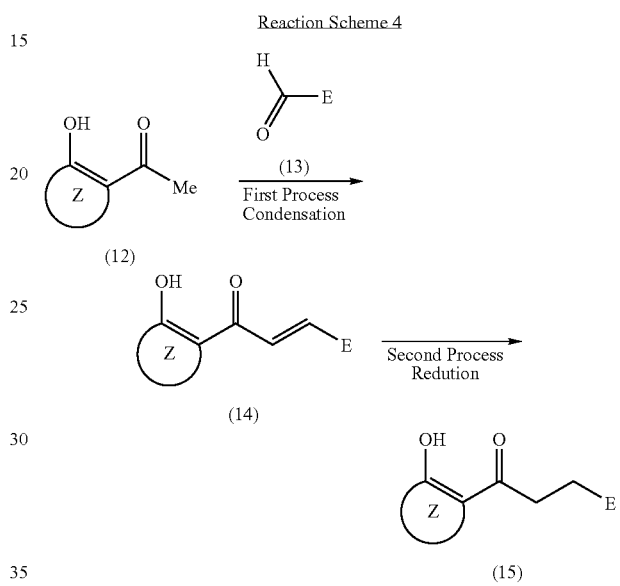

First, the target compound enone (14) can be prepared by dehydrocondensation of the ketone (12) and the aldehyde (13). This reaction is carried out in a solvent at the a reaction temperature of from 0° C. to the boiling point of the solvent in the existence of a base. As the base, examples include inorganic base such as sodium hydroxide, potassium hydroxide, sodium carbonate, potassium carbonate, sodium hydrogencarbonate or the like, or organic base such as pyridine, triethylamine, N,N'-diethylaniline or the like. Examples include nonreactive solvent, and tetrahydrofuran, 1,4-dioxan, methanol, ethanol, water or the like are preferable.

Next, the target compound (15) can be prepared by reduction of the enone (14). This reaction is carried out at the reaction temperature of from 0° C. to 100° C. in solvent, in the existence of a reducing agent. As the reducing agent, examples include sodium borohydride, lithium borohydride or the like. As the solvent, examples include nonreactive solvent, and tetrahydrofuran, 1,4-dioxane, methanol, ethanol or the like are preferable. Moreover, this reaction is carried out by a method of catalytic hydrogenation also. As the catalyst, examples include palladium carbon, platinum carbon, palladium hydroxide, palladium black or the like. As solvent, examples include nonreactive solvent, and tetrahydrofuran, 1,4-dioxane, methanol, ethanol or the like are preferable. The reaction is carried out at the reaction temperature of from 0° C. to 200° C., and the hydrogen pressure is at normal pressure or applied pressure In the examples of the specification, preparation methods of typical compounds included in the general formula (I) are explained in details. Therefore, those skilled in the art can prepare any compound included in the general formula (I) by referring to the explanations of the aforementioned general preparation methods and of specific preparation methods of the examples, selecting appropriate reaction raw materials, reaction reagents, and reaction conditions, and by adding appropriate modification and alteration of these methods, if necessary.

The compounds represented by the general formula (I) have inhibitory action against NF-κB activation and inhibitory action against the production and release of inflammatory cytokines, and are useful as active ingredients of pharmaceutical compositions such as NF-κB inhibitor and inflammatory cytokine release inhibitor. The aforementioned medicament can be suitably used as an expression inhibitor of genes of one or more substances selected from a group comprising tumor necrosis factor (TNF), interleukin-1, interleukin-2, interleukin-6, interleukin-8, granulocyte colony-stimulating factor, interferon β, cell adhesion factor ICAM-1, VCAM-1, and ELAM-1, nitricoxide synthetase, major histocompatibility antigen family class I, major histocompatibility antigen family class II, β2-microglobulin, immunoglobulin light chain, serum amyloid A, angiotensinogen, complement B, complement C4, c-myc, transcript derived from HIV gene, transcript derived from HTLV gene, transcript derived from simian virus 40 gene, transcript derived from cytomegalovirus gene, and transcript derived from adenovirus gene. Moreover, the medicament of the present invention is useful for preventive and/or therapeutic treatment of diseases caused by NF-κB activation and inflammatory cytokine overproduction.

More specifically, the medicament of the present invention may be used for preventive and/or therapeutic treatment of the following diseases wherein NF-κB activation and/or inflammatory cytokine is believed to be involved, for example, autoimmune diseases such as chronic rheumatism, osteoarthritis, systematic lupus erythematosus, systematic scleroderma, polymyositis, Sjoegren's syndrome, vasculitis syndrome, antiphospholipid syndrome, Still's disease, Behcet's disease, periarteritis nodosa, ulcerative colitis, Crohn's disease, active chronic hepatitis, glomerulonephritis, and chronic nephritis, chronic pancreatitis, gout, atherosclerosis, multiple sclerosis, arteriosclerosis, endothelial hypertrophy, psoriasis, psoriatic arthritis, contact dermatitis, atopic dermatitis, allergic disease such as pollinosis, asthma, bronchitis, interstitial pneumonia, lung disease involving granuloma, chronic obstructive lung disease, chronic pulmonary thromboembolism, inflammatory colitis, insulin resistance, obesity, diabetes and its complications (nephropathy, retinopathy, neurosis, hyperinsulinemia, arteriosclerosis, hypercentiona, peripheral vessel obstruction, etc.) diseases involving abnormal vascular proliferation such as hyperlipemia, retinopathy, and pneumonia, Alzheimer's disease, encephalomyelitis, acute hepatitis, chronic hepatitis, drug induced toxic hepatopathy, alcoholic hepatitis, viral hepatitis, icterus, cirrhosis, hepatic insufficiency, atrial myxoma, Caslemann's syndrome, mesangial nephritis, kidney cancer, lung cancer, liver cancer, breast cancer, uterine cancer, pancreatic cancer, other solid cancer, sarcoma, osteosarcoma, metastatic invasion of cancer, carceration of inflammatory focus, cancerous cachexia, metastasis of cancer, leukemia such as acute myeloblastic leukemia, multiple myeloma, Lennert's lymphoma, malignant lymphoma, development of carcinostatic resistance of cancer, carciration of foci such as viral hepatitis and cirrhosis, carciration from polyp of colon, brain tumor, nervous tumor, endotoxic shock, sepsis, cytomegaloviral pneumonia, cytomegaloviral retinopathy, adenoviral cold, adenoviral pool fever, adenoviral ophthalmia, conjunctivitis, AIDS, uveitis, diseases or complications provoked by infections of other bacteria, viruses, and mycetes, complications after surgery such as generalized inflammatory symptoms, restenosis after percutaneous tubal coronary artery plastic surgery, reperfusion disorders after vascular occulusion opening such as ischemia reperfusion disorders, organ transplantation rejection and reperfusion disorders of heart, liver, kidney or the like, itch, anorexia, malaise, chronic fatigue syndrome or the like. Furthermore, inflammatory cytokine and NF-κB are involved in differentiation and activation of osteoclast, and consequently, the medicament of the present invention is also useful for preventive and/or therapeutic treatment of metabolic bone diseases or the like such as osteoporosis and osteocarcinomic pain or the like. The medicament may also be used for prevention of deterioration of an organ during organ conservation before transplantation.

As the active ingredient of the medicament on the present invention, 1 or more kinds of substances selected from the group consisting of the compound represented by the general formula (I) and a pharmacologically acceptable salt thereof, and a hydrate thereof and a solvate thereof may be used. The aforementioned substance, per se, may be administered as the medicament of the present invention, however, preferably, the medicament of the present invention is provided in the form of a pharmaceutical composition comprising the aforementioned substance which is an active ingredient together with one or more pharmacologically acceptable pharmaceutical additives. In the aforementioned pharmaceutical compositions, a ratio of the active ingredient to the pharmaceutical additives is 1 weight % to 90 weight %.

The pharmaceutical compositions of the present invention may be administered as pharmaceutical compositions for oral administration, for example, granules, subtilized granules, powders, hard capsules, soft capsules, syrup, emulsion, suspension, or solution, or may be administered as pharmaceutical compositions for parenteral administration, for example, injections for intravenous administration, intramuscular administration, or subcutaneous administration, drops, suppositories, percutaneous absorbent, transmucosal absorption preparations, nasal drops, ear drops, instillation, and inhalants. Preparations made as pharmaceutical compositions in a form of powder may be dissolved when necessary and used as injections or drip infusions.

For preparation of pharmaceutical compositions, solid or liquid pharmaceutical additives may be used. Pharmaceutical additives may either be organic or inorganic. When an oral solid preparation is prepared, an excipient is added to the active ingredient, and further binders, disintegrator, lubricant, colorant, corrigent are added, if necessary, preparations in the forms of tablets, coating tablets, granules, powders, capsules and the like may be manufactured by common procedures. Examples of the excipient include lactose, sucrose, saccharose, glucose, corn starch, starch, talc, sorbit, crystal cellulose, dextrin, kaolin, calcium carbonate, and silicon dioxide. Examples of the binder include, for example, polyvinyl alcohol, polyvinyl ether, ethyl cellulose, methyl cellulose, gum Arabic, tragacanth, gelatine, shellac, hydroxypropyl cellulose, hydroxypropyl methyl cellulose, calcium citrate, dextrin, and pectin. Examples of the lubricant include, for example, magnesium stearate, talc, polyethylene glycol, silica, and hydrogenated vegetable oil. As the coloring agent, any material can be used which are approved to be added to ordinary pharmaceuticals. As the corrigent, cocoa powder, menthol, aromatic acid, peppermint oil, d-borneol, cinnamon powder and the like can be used. These tables and granules may be applied with sugarcoating, gelatine coating, or an appropriate coating, if necessary. Preservatives, antioxidant and the like may be added, if required.

For liquid preparations for oral administration such as emulsions, syrups, suspensions, and solutions, ordinary used inactive diluents, for example, water or vegetable oil may be used. For these preparations, besides inactive diluents, adjuvants such as wetting agents, suspending aids, sweating agents, flavoring agents, coloring agents or preservatives may be blended. After a liquid preparation is manufactured, the preparation may be filled in capsules made of a absorbable substance such as gelatin. Examples of solvents or suspending agents used for the preparations of parenteral administration such as injections or suppositories include, for example, water, propylene glycol, polyethylene glycol, benzyl alcohol, ethyl oleate, and lecithin. Examples of base materials used for preparation of suppositories include, for example, cacao butter, emulsified cacao butter, lauric fat, and witepsol. Methods for preparation of the aforementioned preparations are not limited, and any method ordinarily used in the art may be used.

When the composition are prepared in the form of injections, carriers such as, for example, diluents including water, ethanol, macrogol, propyleneglycol, citric acid, acetic acid, phosphoric acid, lactic acid, sodium lactate, sulfuric acid and sodium hydroxide, pH modifiers and buffer solutions including sodium citrate, sodium acetate and sodium phosphate, stabilizers such as sodium pyrosulfite, ethylenediaminetetraacetic acid, thioglycolic acid and thiolactate may be used. For the preparation, a sufficient amount of a salt; glucose, mannitol or glycerin may be blended in the preparation to manufacture an isotonic solution, and an ordinary solubilizer, a soothing agent, or a topical anesthetic may be used.

When the preparation in the form of an ointment such as a paste, a cream, and a gel is manufactured, an ordinarily used base material, a stabilizer, a wetting agent, and a preservative may be blended, if necessary, and may be prepared by mixing the components by a common method. As the base material, for example, white petrolatum, polyethylene, paraffin, glycerin, cellulose derivatives, polyethylene glycol, silicon, and bentonite may be used. As the preservative, paraoxy methyl benzoate, paraoxy ethyl benzoate, paraoxy propyl benzoate and the like may be used. When the preparation in the form of a patch is manufactured, the aforementioned ointment, cream gel, or paste and the like may be applied by a common method to an ordinary support. As the support, fabric made of cotton, span rayon, and synthetic fibersor or nonwoven fabric, and a film or a foam sheet such as made of soft vinyl chloride, polyethylene, and polyurethane and the like may be preferably used.

A dose of the medicament of the present invention is not particularly limited. For oral administration, a dose may generally be 0.01 to 5,000 mg per day for an adult as the weight of the compound of the present invention. It is preferred to increase or decrease the above dose appropriately depending on the age, pathological conditions, and symptoms of a patient. The above dose may be administered once a day or 2 to 3 times a day as divided portions with proper intervals, or intermittent administration for every several days may be acceptable. When the medicament is used as an injection, the dose may be 0.001 to 100 mg per day for an adult as the weight of the compound of the present invention.

EXAMPLES

The present invention will be explained more specifically with reference to the following examples. However the scope of the present invention is not limited to the following examples. And the commercially available compounds, which were purchased and used for the examinations, are contained in these examples. As for such compounds, the suppliers of the reagents and the catalog code numbers are shown.

Example 1

Preparation of N-{[3,5-bis(trifluoromethyl)phenyl]methyl}-5-bromo-2-hydroxybenzamide (Compound No. 1).

Under argon atmosphere, 1-(3-dimethylaminopropyl)-3-ethylcarbodiimide hydrochloride (it is abbreviated as WSC•HCl hereafter; 192 mg, 1 mmol) was added to a mixture of 5-bromosalicylic acid (217 mg, 1 mmol), 3,5-bis(trifluoromethyl)benzylamine (243 mg, 1 mmol), 4-dimethylaminopyridine (12 mg, 0.1 mmol) and tetrahydrofuran (10 mL), and the mixture was stirred at room temperature for 1 hour. The reaction mixture was poured into diluted hydrochloric acid and extracted with ethyl acetate. After the organic layer was washed with water and brine, dried over anhydrous magnesium sulfate, the residue obtained by evaporation under reduced pressure was purified by chromatography on silica gel (n-hexane:ethyl acetate=4:1) to give the title compound (244.8 mg, 55.4%) as a white solid.

$^1$H-NMR (DMSO-$d_6$): δ 4.69 (2H, d, J=5.7 Hz), 6.93 (1H, d, J=8.7 Hz), 7.56 (1H, dd, J=8.7, 2.4 Hz), 8.02 (1H, d, J=2.4 Hz), 8.06 (3H, s), 9.41 (1H, t, J=5.7 Hz), 12.13 (1H, s).

Example 2

5-Bromo-2-hydroxy-N-(2-phenethyl)benzamide (Compound No. 2)

(1) 2-Acetoxy-N-(2-phenethyl)benzamide o-Acetylsalicyloyl chloride (0.20 g, 1.00 mmol) was dissolved in benzene (8 mL). Phenethylamine (0.12 g, 1.00 mmol) and pyridine (0.3 mL) were added, and the mixture was stirred at room temperature for 2 hours. The reaction mixture was poured into diluted hydrochloric acid and extracted with ethyl acetate. After the organic layer was washed with water and brine, dried over anhydrous sodium sulfate, the residue obtained by evaporation under reduced pressure was purified by chromatography on silica gel (n-hexane:ethyl acetate=2:1→1:1) to give the title compound (155.5 mg, 54.9%) as a white crystal.

$^1$H-NMR (CDCl$_3$): δ 2.09 (3H, s), 2.92 (2H, t, J=6.8 Hz), 3.71 (2H, q, J=6.8 Hz), 6.32 (1H, brs), 7.07 (1H, dd, J=8.4, 1.2 Hz), 7.23-7.35 (6H, m), 7.44 (1H, ddd, J=8.0, 7.6, 1.6 Hz), 7.73 (1H, dd, J=7.6, 1.6 Hz).

(2) 2-Hydroxy-N-(2-phenethyl)benzamide

Methanol (5 mL) and 2 N sodium hydroxide (0.1 mL) were added to 2-acetoxy-N-(2-phenethyl)benzamide (155.5 mg), and the mixture was stirred at room temperature for 30 minutes. The reaction mixture was poured into diluted hydrochloric acid and extracted with ethyl acetate. After the organic layer was washed with water and brine, dried over anhydrous sodium sulfate, the residue obtained by evaporation under reduced pressure was crystallized (dichloromethane/hexane) to give the title compound (106.9 mg, 80.7%) as a white solid.

$^1$H-NMR (DMSO-$d_6$): δ 2.86 (2H, t, J=7.6 Hz), 3.52 (1H, q, J=7.6 Hz), 6.84-6.88 (2H, m), 7.18-7.31 (5H, m), 7.37 (1H, ddd, J=8.4, 7.2, 1.6 Hz), 7.80 (1H, dd, J=8.4, 1.6 Hz), 8.84 (1H, s), 12.51 (1H, s).

(3) 5-Bromo-2-hydroxy-N-(2-phenethyl)benzamide

Carbon tetrachloride (5 mL), iron powder (0.03 g) and bromine (25 μl, 0.48 mmol) were added to 2-hydroxy-N-(2-phenethyl)benzamide (79.6 mg, 0.33 mmol), and the mixture was stirred at room temperature for 1 hour. The reaction mixture was poured into aqueous sodium hydrogen sulfite and extracted with ethyl acetate. After the organic layer was washed with brine, dried over anhydrous sodium sulfate, the residue obtained by evaporation under reduced pressure was purified by chromatography on silica gel (n-hexane:ethyl acetate=5:1) to give the title compound (62 mg, 58.7%) as white powder.

$^1$H-NMR (DMSO-$d_6$): δ 2.85 (2H, t, J=7.6 Hz), 3.52 (1H, q, J=7.6 Hz), 6.87 (1H, d, J=8.8 Hz), 7.18-7.31 (5H, m), 7.52 (1H, dd, J=8.8, 2.4 Hz), 8.01 (1H, d, J=2.4 Hz), 8.90 (1H, s), 12.51 (1H, s).

Example 3

5-Bromo-2-hydroxy-N-[5-(morpholinocarbonyl)indan-2-yl]benzamide (Compound No. 3)

WSC•HCl (96 mg, 0.5 mmol) was added to a solution of 5-bromosalicylic acid (109 mg, 0.5 mmol), 2-amino-5-(morpholino)carbonylindan (refer to Chem. Pharm. Bull., 2000, 48, 131; 141 mg, 0.5 mmol) and triethylamine (70 μL, 0.5 mmol) in dichloromethane (5 mL), and the mixture was stirred at 40° C. for 1.5 hours. After cooling, the reaction mixture was diluted with ethyl acetate, washed with 2 N hydrochloric acid, water and brine one after another, dried over anhydrous magnesium sulfate, concentrated, and the residue was purified by column chromatography on silica gel (dichloromethane:methanol=19:1) to give the title compound (26 mg, 11.9%) as a white crystal.

$^1$H-NMR (CDCl$_3$): δ 2.66 (1H, dd, J=16.2, 7.2 Hz), 2.82 (1H, dd, J=16.2, 7.2 Hz), 3.16-3.25 (2H, m), 3.43-3.86 (8H, m), 4.79-4.92 (1H, m), 6.88 (1H, d, J=8.7 Hz), 7.14-7.15 (3H, m), 7.46 (1H, dd, J=8.7, 2.4 Hz), 7.74 (1H, d, J=7.8 Hz), 7.84 (1H, d, J=2.4 Hz).

Example 4

3-(4-Chlorophenyl)-1-(2,6-dihydroxyphenyl)-3-(4-hydroxyphenyl)propan-1-one (Compound No. 4)

This compound is a commercially available compound.
Supplier: Apin Chemicals.
Catalog code number: N 0100D.

Example 5

1-(5-Chloro-2-hydroxyphenyl)-3-(4-methoxyphenyl)propan-1-one (Compound No. 5)

This compound is a commercially available compound.
Supplier: Specs.
Catalog code number: AI-233/31581024.

Example 6

1-(2-Hydroxy-4-methoxyphenyl)-3-(2-methoxyphenyl)propen-1-one (Compound No. 6)

This compound is a commercially available compound.
Supplier: Maybridge.
Catalog code number: RJC 00106.

Example 7

3-(3,4-Dihydro-2H-benzo[b][1,4]dioxepin-7-yl)-1-(2-hydroxy-5-methylphenyl)propen-1-one (Compound No. 7)

This compound is a commercially available compound.
Supplier: Maybridge.
Catalog code number: BTB 13230.

Example 8

3-(3,4-Dihydro-2H benzo[b][1,4]dioxepin-7-yl)-1-[2-hydroxy-4-(methoxylmethyl)phenyl]propen-1-one (Compound No. 8)

This compound is a commercially available compound.
Supplier: Maybridge.
Catalog code number: BTB 114482.

Example 9

4-Chloro-2-[(4-chlorophenyl)ethen-2-yl]phenol (Compound No. 9)

5-Chlorosalicylaldehyde (313 mg, 2 mmol) and 4-chlorobenzyltriphenyl-phosphonium chloride (847 mg, 2 mmol) were dissolved in N,N-dimethylfomamide (20 mL). Potassium carbonate (1.382 g, 10 mmol) dissolved in water (10 mL) was added, and the mixture was refluxed for 5 hours. After cooling, the reaction mixture was poured into 2 N hydrochloric acid and extracted with ethyl acetate. After the organic layer was washed with water and brine, dried over anhydrous magnesium sulfate, the residue obtained by evaporation under reduced pressure was purified by chromatography on silica gel (n-hexane:ethyl acetate=3:1) to give the title compound (44.6 mg, 8.4%) as a light gray solid.

$^1$H-NMR (CDCl$_3$): δ 5.04 (1H, s), 6.74 (1H, d, J=9.0 Hz), 7.05 (1H, d, J=16.5 Hz), 7.10 (1H, dd, J=8.4, 2.4 Hz), 7.26 (1H, d, J=16.5 Hz), 7.33 (2H, d, J=8.4 Hz), 7.45 (2H, d, J=8.4 Hz), 7.49 (1H, d, J=2.4 Hz).

Example 10

5-Bromo-N-(3,5-dichloro)phenyl-2-hydroxybenzenesulfonamide (Compound No. 10)

(1) 5-Bromo-N-(3,5-dichloro)phenyl-2-methoxybenzenesulfonamide.

5-Bromo-2-methoxybenzenesulfonyl chloride (857 mg, 3 mmol) was dissolved in dichloromethane (6 mL). A solution of 3,5-dichloroaniline (510 mg, 3.15 mmol) and pyridine (261 mg, 3.3 mmol) in dichloromethane (2 mL) was added dropwise under ice cooling and argon atmosphere, and the mixture was stirred at room temperature for 6 hours. After the reaction mixture was diluted with dichloromethane, washed with 2 N hydrochloric acid, water and brine one after another, dried over anhydrous magnesium sulfate, the solvent was evaporated under reduced pressure. The obtained residue was crystallized from n-hexane-ethyl acetate to give 5-bromo-2-methoxy-N-(3,5-dichloro)benzenesulfonamide (900 mg, 73.0%) as a white crystal.

$^1$H-NMR (DMSO-$d_6$): δ 4.03 (3H, s), 6.92 (1H, d, J=9.0 Hz), 7.01 (2H, d, J=1.8 Hz), 7.07-7.08 (1H, m), 7.24 (1H, brs), 7.63 (1H, dd, J=8.7, 2.4 Hz), 7.99 (1H, d, J=2.4 Hz).

(2) 5-Bromo-N-(3,5-dichloro)phenyl-2-hydroxybenzenesulfonamide

A mixture of the white crystal of 5Bromo-N-(3,5-dichloro)phenyl-2-methoxybenzenesulfonamide (206 mg, 0.5 mmol), lithium iodide (134 mg, 1 mmol) and 2,4,6-collidine (5 mL) was refluxed for 30 minutes under argon atmosphere. After cooling to room temperature, the reaction mixture was poured into 2 N hydrochloric acid and extracted with ethyl acetate. After the ethyl acetate layer was washed with water and brine one after another, dried over anhydrous magnesium sulfate, the solvent was evaporated under reduced pressure. The obtained residue was crystallized from n-hexane-ethyl acetate to give the title compound (90 mg, 45.3%) as a white crystal.

mp 158-159° C. $^1$H-NMR (DMSO-$d_6$, δ): 6.92 (1H, d, J=8.7 Hz), 7.11 (2H, d, J=2.1 Hz), 7.21-7.22 (1H, m), 7.62 (1H, dd, J=8.7, 2.7 Hz), 7.80 (1H, d, J=2.4 Hz), 10.70 (1H, br), 11.37 (1H, br).

Example 11

3,5-Bis(trifluoromethyl)-N-(2-hydroxyphenyl)benzamide (Compound No. 11)

2-Aminophenol (120 mg, 1.1 mmol) was dissolved in dichloromethane (5 mL). A solution of 3,5-bis(trifluoromethyl)benzoyl chloride (300 mg, 1.1 mmol) in dichloromethane (3 mL) and pyridine (0.5 mL) was added dropwise under ice cooling and argon atmosphere, and the mixture was stirred at room temperature for 1 hour. The reaction mixture was poured into 2 N hydrochloric acid and extracted with ethyl acetate. After the ethyl acetate layer was washed with water and brine one after another, dried over anhydrous magnesium sulfate, the solvent was evaporated under reduced pressure. The obtained residue was dissolved in ethanol (5 mL), added dropwise 2 N sodium hydroxide (0.1 mL, 0.2 mmol), and stirred at room temperature for 30 minutes. The reaction mixture was poured into 2 N hydrochloric acid and extracted with ethyl acetate. After the ethyl acetate layer was washed with water and brine one after another, dried over anhydrous sodium sulfate, the solvent was evaporated under reduced pressure. The obtained residue was purified by column chromatography on silica gel (n-hexane:ethyl acetate=4:1) to give the title compound (288 mg, 73.6%) as a light pink crystal.

mp 183° C. (dec.). $^1$H-NMR (DMSO-$d_6$, δ): 6.83 (1H, td, J=8.0, 1.2 Hz), 6.93 (1H, dd, J=8.0, 1.2 Hz), 7.08 (1H, td, J=8.0, 1.6 Hz), 7.50 (1H, d, J=8.0 Hz), 8.35 (2H, s), 9.61 (1H, s), 10.16 (1H, s).

Example 12

N-(5-Chloro-2-hydroxyphenyl)-3,5-dichlorobenzamide (Compound No. 12)

2-Amino-4-chlorophenol (316 mg, 2.2 mmol) and triethylamine (243 mg, 2.4 mmol) were dissolved in dichloromethane (5 mL). A solution of 3,5-dichlorobenzoyl chloride (419 mg, 2 mmol) in dichloromethane (2 mL) was added dropwise under ice cooling and argon atmosphere, and the mixture was stirred at room temperature for 15 hours. After the reaction mixture was diluted with ethyl acetate, washed with water and brine one after another, dried over anhydrous magnesium sulfate, the solvent was evaporated under reduced pressure. The obtained residue was purified by column chromatography on silica gel (n-hexane-ethyl acetate=3:1) to give a light brown solid. The solid was suspended and washed with n-hexane-ethyl acetate under heating at reflux to give the title compound (205 mg, 32.4%) as a white crystal.

mp 251-252° C. $^1$H-NMR (DMSO-$d_6$): δ 6.93 (1H, d, J=9.0 Hz), 7.11 (1H, dd, J=8.7, 2.7 Hz), 7.67 (2H, d, J=2.7 Hz), 7.86-7.87 (1H, m), 7.97 (1H, d, J=1.8 Hz), 9.85 (1H, s), 10.03 (1H, s).

Example 13

N-(5-Chloro-2-hydroxyphenyl)-3,5-dichlorobenesulfonamide (Compound No. 13)

2-Amino-4-chlorophenol (287 mg, 2 mmol) and 3,5-dichlorobenzenesulfonyl chloride (540 mg, 2.2 mmol) were dissolved in dichloromethane (4 mL). Pyridine (1 mL) was added dropwise under ice cooling and argon atmosphere, and the mixture was stirred at room temperature for 1 hour. The reaction mixture was poured into 2 N hydrochloric acid and extracted with ethyl acetate. After the ethyl acetate layer was washed with water and brine one after another, dried over anhydrous magnesium sulfate, the solvent was evaporated under reduced pressure. The obtained residue was purified by column chromatography on silica gel (n-hexane:ethyl acetate=3:1→1:1) to give a reddish brown solid. The solid was crystallized from n-hexane-ethyl acetate to give the title compound (445 mg, 63.1%) as a slight dark brown crystal.

mp 190-191° C. $^1$H-NMR (DMSO-$d_6$): δ 7.68 (1H, d, J=9.0 Hz), 7.08 (1H, dd, J=8.7, 2.7 Hz), 7.17 (1H, d, J=2.4 Hz), 7.70 (2H, d, J=1.8 Hz), 7.95-7.96 (1H, m), 10.00 (1H, s), 10.06 (1H, s),

Example 14

N-[(5-Bromo-2-hydroxyphenyl)methyl]-3,5-dichloroaniline (Compound No. 14)

(1) 4-Bromo-2-[(3,5-diphenylimino)methyl]phenol

A mixture of 5-bromosalicylaldehyde (1.01 g, 5 mmol), 3,5-dichloroaniline (810 mg, 5 mmol) and ethanol (25 mL) was refluxed for 1 hour under argon atmosphere. After the reaction mixture was cooled to room temperature, the separated crystal was filtered to give 3,5-dichloro-N-(5-bromo-2-hydroxybenzylidene)aniline (1.52 g, 88.2%) as an orange crystal.

mp 161-163° C. $^1$H-NMR (CDCl$_3$, δ): 6.94 (1H, d, J=9.0 Hz), 7.16 (2H, d, J=1.8 Hz), 7.30-7.31 (1H, m), 7.47-7.53 (2H, m), 8.51 (1H, s).

(2) N-[(5 Bromo-2-hydroxyphenyl)methyl]-3,5-dichloroaniline 3,5-Dichloro-N-(5-bromo-2-hydroxybenzylidene)aniline (1.04 g, 3 mmol) was dissolved in tetrahydrofuran (12 mL) and ethanol (6 mL). Sodium borohydride (113 mg, 3 mmol) was added under ice cooling and argon atmosphere, and the mixture was stirred at room temperature for 12 hours. Acetone (10 mL) was added to the reaction mixture, and the residue obtained by concentration under reduced pressure was added water and extracted with dichloromethane. After the dichloromethane layer was washed with water and brine one after another, dried over anhydrous magnesium sulfate, the solvent was evaporated under reduced pressure. The obtained residue was purified by column chromatography on silica gel (n-hexane:ethyl acetate=4:1) to give a light yellow viscous material. This was crystallized by n-hexane to give the title compound (971 mg, 93.3%) as a white crystal.

mp 125-126° C. $^1$H-NMR (CDCl$_3$, δ): δ 4.31 (2H, s), 6.64 (2H, d, J=1.8 Hz), 6.74-6.77 (1H, m), 6.84-6.85 (1H, m), 7.30-7.34 (2H, m).

Example 15

5-Chloro-2-hydroxybenzoic acid (2,4-dihydroxybenzylidene)hydrazide (Compound No. 15)

This compound is a commercially available compound.
Supplier: Sigma-Aldrich.
Catalog code number: S3203-5.

Example 16

N-[3,5-Bis(trifluoromethyl)phenyl]-5-chloro-2-hydroxy-N-methylbenzamide (Compound No. 16)

A mixture of 5-chlorosalicylic acid (173 mg, 1 mmol), 3,5-bis(trifluoromethyl)-N-methylaniline (243 mg, 1 mmol). phosphorus trichloride (44 μl, 0.5 mmol) and monochlorobenzene (5 mL) was refluxed for 3 hours under argon atmosphere. After the reaction mixture was cooled to room temperature, n-hexane (50 mL) was added, and the separated crude crystal was filtered and dissolved in ethyl acetate (50 mL). After the ethyl acetate solution was washed with water and brine one after another, dried over anhydrous sodium sulfate, the solvent was evaporated under reduced pressure. The obtained residue was purified by column chromatography on silica gel (n-hexane:ethyl acetate=2:1) to give the title compound (75 mg, 13.9%) as a white crystal.
$^1$H-NMR (CDCl$_3$): δ 6.59 (1H, d, J=2.4 Hz), 6.94 (1H, d, J=9.0 Hz), 7.21 (1H, dd, J=9.0, 2.7 Hz), 7.58 (2H, s), 7.80 (1H, s), 10.00 (1H, brs).

Example 17

1-(5-Bromo-2-hydroxy)benzoyl-7-(trifluoromethyl)-1,2,3,4-tetrahydroquinoline (Compound No. 17)

Using 5-bromosalicylic acid and 7-(trifluoromethyl)-1,2,3,4-tetrahydroquinoline as the raw materials, the same operation as the example 16 gave the title compound.
Yield: 42.0%. $^1$H-NMR (CDCl$_3$): δ 2.08 (2H, m), 2.92 (2H, t, J=6.6 Hz), 3.95 (2H, t, J=6.6 Hz), 6.91-6.94 (2H, m), 7.14 (1H, s), 7.32-7.35 (2H, m), 7.40 (1H, dd, J=8.7, 2.4 Hz), 10.06 (1H, s).

Example 18

N-(3,5-Dichlorophenyl)-2-hydroxy-1-naphthamide (Compound No. 18)

Using 2-hydroxynaphthalene-1-carboxylic acid and 3,5-dichloroaniline as the raw materials, the same operation as the example 16 gave the title compound.
Yield: 51.2%. mp 246-243° C. $^1$H-NMR (DMSO-d$_6$): δ 7.26 (1H, d, J=9.3 Hz), 7.31-7.37 (2H, m), 7.44-7.50 (1H, m), 7.62-0.68 (1H, m), 7.85-7.90 (4H, m), 10.23 (1H, s), 10.74 (1H, s)

Example 19

N-(3,5-Dichlorophenyl)-3-hydroxy-2-naphthamide (Compound No. 19)

Using 3-hydroxynaphthalene-2-carboxylic acid and 3,5-dichloroaniline as the raw materials, the same operation as the example 16 gave the title compound.
mp 254-255° C. $^1$H-NMR (DMSO-d$_6$): 7.34-7.39 (3H, m), 7.49-7.54 (1H, m), 7.76-7.79 (1H, m), 7.89 (2H, d, J=1.8 Hz), 7.92 (1H, m), 8.39 (1H, s), 10.75 (1H, s), 11.01 (1H, s).

Example 20

N-(3,5-Dimethoxyphenyl)-3-hydroxy-2-naphthamide (Compound No. 20)

This compound is a commercially available compound.
Supplier: Sigma-Aldrich.
Catalog code number: S01361-8.

Example 21

N-[3,5-Bis(trifluoromethyl)phenyl]-1-hydroxy-2-naphthamide (Compound No. 21)

Using 1-hydroxynaphthalene-2-carboxylic acid and 3,5-bis(trifluoromethyl)aniline as the raw materials, the same operation as the example 16 gave the title compound.
Yield: 65.5%. $^1$H-NMR (DMSO-d$_6$): δ 7.51 (1H, d, J=9.0 Hz), 7.60 (1H, td, J=7.8, 0.9 Hz), 7.70 (1H, td, J=7.8, 0.9 Hz), 7.89 (1H, s), 7.93 (1H, d, J=8.4 Hz), 8.09 (1H, d, J=9.0 Hz), 8.33 (1H, d, J=8.7 Hz), 8.51 (2H, s), 10.92 (1H, s), 13.36 (1H, s).

Example 22

{[(1-Hydroxynaphthalen-2-yl)carbonyl]amino}benzenesulfonyl fluoride (Compound No. 22)

This compound is a commercially available compound.
Supplier: Sigma-Aldrich.
Catalog code number: S58026-0.

Example 23

4-({[4-(2,5-Dichlorophenyl)azo-1-hydroxynaphthalen-2-yl]-carbonyl}amino)benzenesulfonyl fluoride (Compound No. 23)

This compound is a commercially available compound.
Supplier: Sigma-Aldrich.
Catalog code number: S63263-5.

Example 24

N-[3,5-Bis(trifluoromethyl)phenyl]-5-chloro-2-hydroxypyridine-3-carboxamide (Compound No. 24)

5-Chloro-2-hydroxynicotinic acid (174 mg, 1 mmol), 3,5-bis(trifluoromethyl)aniline (275 mg, 1.2 mmol) and pyridine (316 mg, 4 mmol) were dissolved in tetrahydrofuran (20 mL) and dichloromethane (10 mL). Phosphorus oxychloride (0.112 ml, 1.2 mmol) was added, and the mixture was stirred at room temperature for 2 hours. The reaction mixture was poured into ethyl acetate (100 mL) and 0.2 N hydrochloric acid (100 mL), filtered through celite after stirring for 30 minutes, and the water layer of the filtrate was extracted with ethyl acetate. After the combined ethyl acetate layer was washed with water and brine one after another, dried over anhydrous magnesium sulfate, the solvent was evaporated under reduced pressure. The residue was purified by column chromatography on silica gel (n-hexane:ethyl acetate=2:1→1:1) to give a light yellow solid. This was suspended and washed with ethanol under heating at reflux to give the title compound (183 mg, 47.6%) as a white crystal.

mp>270° C. $^1$H-NMR (DMSO-d$_6$): δ 7.83 (1H, s), 8.15 (1H, d, J=3.3 Hz), 8.36 (1H, d, J=3.0 Hz), 8.40 (2H, s), 12.43 (1H, s).

Example 25

N-[2-Chloro-5-(trifluoromethyl)phenyl]-5-chloro-2-hydroxynicotinamide (Compound No. 25)

Using 5-chloro-2-hydroxynicotinic acid and 2-chloro-5-(trifluoromethyl)aniline as the raw materials, the same operation as the example 24 gave the title compound.

Yield: 42.9%. $^1$H-NMR (DMSO-d$_6$): δ 7.52 (1H, dd, J=8.4, 2.1 Hz), 7.81 (1H, d, J=8.4 Hz), 8.16 (1H, s), 8.39 (1H, d, J=2.7 Hz), 8.96 (1H, d, J=2.1 Hz), 12.76 (1H, s), 13.23 (1H, s).

Example 26

N-{3,5-Bis[(1,1-dimethyl)ethyl]phenyl}-5-chloro-2-hydroxynicotinamide (Compound No. 26)

Using 5-chloro-2-hydroxynicotinic acid and 3,5-bis[(1,1-dimethyl)ethyl]aniline as the raw materials, the same operation as the example 24 gave the title compound.

Yield: 59.1%. $^1$H-NMR (DMSO-d$_6$): δ 1.29 (18H, s), 7.18 (1H, t, J=1.8 Hz), 7.52 (2H, d, J=1.8 Hz), 8.07 (1H, d, J=2.4 Hz), 8.35 (1H, d, J=3.3 Hz), 11.92 (1H, s), 13.10 (1H, s).

Example 27

N-[3,5-Bis(trifluoromethyl)phenyl]-3-hydroxypyridine-2-carboxamide (Compound No. 27)

Using 3-hydroxypyridine-2-carboxylic acid and 3,5-bis(trifluoromethyl)aniline as the raw materials, the same operation as the example 24 gave the title compound.

Yield: 45.0%. $^1$H-NMR (CDCl$_3$): δ 7.40 (1H, dd, J=8.4, 1.8 Hz), 7.46 (1H, dd, J=8.4, 4.2 Hz), 7.68 (1H, s), 8.16 (1H, dd, J=4.2, 1.2 Hz), 8.25 (2H, s), 10.24 (1H, s), 11.42 (1H, s).

Example 28

N-[3,5-Bis(trifluoromethyl)phenyl]-6-chloro-2-hydroxyindole-3-carboxamide (Compound No. 28)

Under argon atmosphere, 3,5-bis(trifluoromethyl)isocyanate (255 mg, 1.0 mmol) was dissolved in tetrahydrofuran (5 mL). A solution of 6-chloro-oxindole (184 mg, 1.1 mmol) in tetrahydrofuran (5 ml) and triethylamine (0.3 mL) were added, and the mixture was stirred at room temperature for 4 hours. The reaction mixture was poured into diluted hydrochloric acid and extracted with ethyl acetate. After the organic layer was washed with water and brine, dried over anhydrous magnesium sulfate, the residue obtained by evaporation under reduced pressure was purified by chromatography on silica gel (n-hexane:ethyl acetate=4:1) to give the title compound (172.2 mg, 40.7%) as a pink solid.

$^1$H-NMR (DMSO-d$_6$): δ 3.97 (2H, s), 7.29 (1H, dd, J=8.1, 2.1 Hz), 7.41 (1H, d, J=8.1 Hz), 7.88 (1H, s), 8.04 (1H, d, J=2.1 Hz), 8.38 (2H, s), 10.93 (1H, s).

Example 29

N-[3,5-Bis(trifluoromethyl)phenyl]-3-hydroxyquinoxaline-2-carboxamide (Compound No. 29)

Using 3-hydroxyquinoxaline-2-carboxylic acid and 3,5-bis(trifluoromethyl)aniline as the raw materials, the same operation as the example 16 gave the title compound.

Yield: 2.7%. $^1$H-NMR (DMSO-d$_6$): δ 7.40-7.45 (2H, m), 7.69 (1H, td, J=8.4, 1.5 Hz), 7.90-7.93 (2H, m), 8.41 (2H, s), 11.64 (1H, s), 13.02 (1H, s).

Example 30

N-(4-Chlorophenyl)-2-hydroxy-9H-carbazole-3-carboxamide (Compound No. 30)

This compound is a commercially available compound.
Supplier: Sigma-Aldrich.
Catalog code number: S83846-2.

Example 31

2-Hydroxy-N-(1-naphthyl)benzamide (Compound No. 31)

This compound is a commercially available compound.
Supplier: Maybridge.
Catalog code number: RDR 01818.

Example 32

5-Chloro-2-hydroxy-N-(1-naphthyl)benzamide (Compound No. 32)

Using 5-chlorosalicylic acid and 1-naphthylamine as the raw materials, the same operation as the example 16 gave the title compound.

Yield: 66.0%. $^1$H-NMR (DMSO-d$_6$): δ 7.09 (1H, d, J=8.7 Hz), 7.51-7.61 (4H, m), 7.85 (1H, d, J=8.4 Hz), 7.96 (1H, d, J=7.5 Hz), 7.99-8.05 (2H, m), 8.13 (1H, d, J=2.7H), 10.88 (1H, s), 12.31 (1H, s).

Example 33

5-Chloro-2-hydroxy-N-(4-methoxynaphthalen-2-yl)benzamide (Compound No. 33)

Using 5-chlorosalicylic acid and 4-methoxy-1-naphthylamine as the raw materials, the same operation as the example 16 gave the title compound.

Yield: 84.3%. $^1$H-NMR (DMSO-d$_6$): δ 3.99 (3H, s), 7.05 (1H, d, J=9.0 Hz), 7.30 (1H, d, J=1.5 Hz), 7.39-7.45 (1H, m), 7.48-7.54 (2H, m), 7.83 (1H, d, J=7.8 Hz), 8.00 (1H, s), 8.02 (1H, d, J=2.4 Hz), 8.09 (1H, d, J=7.8 Hz), 10.54 (1H, s), 11.88 (1H, s).

Example 34

2-Acetoxy-5-Chloro-N-(4-methoxynaphthalen-2-yl)benzamide (Compound No. 34)

Using 2-acetoxy-5-chlorobenzoic acid and 4-methoxy-1-naphthylamine as the raw materials, the same operation as the example 24 gave the title compound. (2-Acetoxy-5-chlorobenzoic acid: refer to Eur. J. Med. Chem., 1996, 31, 861.)

Yield: 39.9% red solid. $^1$H-NMR (DMSO-d$_6$): δ 2.23 (3H, s), 3.96 (3H, s), 7.23 (1H, d, J=1.2 Hz), 7.34 (1H, d, J=8.7 Hz), 7.40 (1H, dt, J=8.1, 1.2 Hz), 7.50 (1H, dt, J=8.1, 1.5 Hz), 7.67 (1H, dd, J=8.7, 2.7 Hz), 7.81 (1H, d, J=8.7 Hz), 8.72 (1H, d, J=3.0 Hz), 8.02 (1H, s), 8.08 (1H, d, J=8.7 Hz), 10.58 (1H, s).

Example 35

2-(5-Chloro-2-hydroxybenzoyl)amino-4,5,6,7-tetrahydrobenzo[b]-thiophene-3-carboxylic acid ethyl ester (Compound No. 35)

Using 5-chlorosalicylic acid and 2-amino-4,5,6,7-tetrahydrobenzo[b]thiophene-3-carboxylic acid ethyl ester as the raw materials, the same operation as the example 16 gave the title compound.

Yield: 49.6%. $^1$H-NMR (DMSO-d$_6$): δ 1.32 (3H, t, J=7.2 Hz), 1.74 (4H, br), 2.63 (2H, br), 2.75 (2H, br), 4.30 (2H, q, J=7.2 Hz), 7.06 (1H, d, J=9.0 Hz), 7.80 (1H, dd, J=8.7, 3.0 Hz), 7.92 (1H, d, J=3.0 Hz), 12.23 (1H, s), 13.07 (1H, s).

Example 36

5-Bromo-2-hydroxy-N-(5-phenylpyrazol-3-yl)benzamide (Compound No. 36)

Using 5-bromosalicylic acid and 3-amino-5-phenylpyrazole as the raw materials, the same operation as the example 16 gave the title compound.

Yield: 9.2%. $^1$H-NMR (DMSO-d$_6$): δ 6.98 (1H, d, J=8.8 Hz), 7.01 (1H, s), 7.35 (1H, t, J=7.6 Hz), 7.46 (2H, t, J=7.6 Hz), 7.58 (1H, dd, J=8.8, 2.8 Hz), 7.74-7.76 (2H, m), 8.19 (1H, s), 10.86 (1H, s), 12.09 (1H, s), 13.00 (1H, brs).

Example 37

5-Bromo-N-(4,5-diethyloxazol-2-yl)-2-hydroxybenzamide (Compound No. 37)

(1) 2-Amino-4,5-diethyloxazole

Propioin (1.03 g, 8.37 mmol) was dissolved in ethanol (15 mL). Cyanamide (0.75 g, 17.7 mmol) and sodium ethoxide (1.21 g, 17.7 mmol) were added, and the mixture was stirred at room temperature for 3.5 hours. The reaction mixture was poured into water and extracted with ethyl acetate. After the organic layer was washed with water and brine, dried over anhydrous sodium sulfate, the residue obtained by evaporation under reduced pressure was purified by chromatography on silica gel (dichloromethane:methanol=9:1) to give the title compound (369.2 mg, 29.7%) as a yellow amorphous.

$^1$H-NMR (DMSO-d$_6$): δ 1.04 (3H, t, J=7.5 Hz), 1.06 (3H, t, J=7.5 Hz), 2.20 (2H, q, J=7.5 Hz), 2.43 (2H, q, J=7.5 Hz), 6.15 (2H, s).

(2) 2-Acetoxy-5-bromo-N-(4,5-diethyloxazol-2-yl)benzamide

Using 2-acetoxy-5-bromobenzoic acid and 2-amino-4,5-diethyloxazole as the raw materials, the same operation as the example 24 gave the title compound. (2-Acetoxy-5-bromobeazoic acid: refer to Eur. J. Med. Chem., 1996, 31, 861.)

Yield: 22.0%. $^1$H-NMR (CDCl$_3$): δ 1.22 (3H, t, J=7.5 Hz), 1.23 (3H, t, J=7.5 Hz), 2.48 (2H, q, J=7.5 Hz), 2.57 (2H, q, J=7.5 Hz), 6.96 (1H, d, J=8.7 Hz), 7.58 (1H, dd, J=8.7, 2.7 Hz), 8.32 (1H, s), 11.40 (1H, br).

(3) 5-Bromo-N-(4,5-diethyloxazol-2-yl)-2-hydroxybenzamide

Using 2-acetoxy-5-bromo-N-(4,5-diethyloxazol-2-yl)benzamide as the raw material, the same operation as the example 2 (2) gave the title compound.

Yield: 70.2%. $^1$H-NMR (CDCl$_3$): δ 1.25 (3H, t, J=7.5 Hz), 1.26 (3H, t, J=7.5 Hz), 2.52 (2H, q, J=7.5 Hz), 2.60 (2H, q, J=7.5 Hz), 6.84 (1H, d, J=8.7 Hz), 7.43 (1H, dd, J=8.7, 3.0 Hz), 8.17 (1H, d, J=3.0 Hz), 11.35 (1H, br), 12.83 (1H, br).

Example 38

5-Bromo-N-(4,5-diphenyloxazol-2-yl)-2-hydroxybenzamide (Compound No. 38)

Using 5-bromosalicylic acid and 2-amino-4,5-diphenyloxazole as the raw materials, the same operation as the example 16 gave the title compound. (2-Amino-4,5-diphenyloxazole: refer to Zh. Org. Khim., 1980, 16, 2185.)

Yield: 32.6%. mp 188-189° C. $^1$H-NMR (DMSO-d$_6$, δ): 6.98 (1H, d, J=8.7 Hz), 7.40-7.49 (6H, m), 7.53-7.56 (2H, m), 7.59-7.63 (3H, m), 8.01 (1H, d, J=2.4 Hz), 11.80 (2H, brs).

Example 39

5-Bromo-N-[4,5-bis(furan-2-yl)oxazol-2-yl]-2-hydroxybenzamide (Compound No. 39)

(1) 2-Amino-4,5-bis(furan-2-yl)oxazole

Furoin (0.50 g, 2.60 mmol) was dissolved in ethanol (15 mL). Cyanamide (218.8 mg, 5.20 mmol) and sodium ethoxide (530.8 mg, 7.80 mmol) were added, and the mixture was stirred at room temperature for 2 hours. The reaction mixture was poured into water and extracted with ethyl acetate. After the organic layer was washed with water and brine, dried over anhydrous sodium sulfate, the residue obtained by evaporation under reduced pressure was purified by chromatography on silica gel (hexane:ethyl acetate=1:1→1:2) to give the title compound (175.0 mg, 31.1%) as a dark brown crystal.

$^1$H-NMR (DMSO-d$_6$): δ 6.59 (1H, dd, J=3.3, 2.1 Hz), 6.62 (1H, dd, J=3.3, 2.1 Hz), 6.73 (1H, dd, J=3.3, 0.6 Hz), 6.80 (1H, dd, J=3.3, 0.9 Hz), 7.05 (2H, s), 7.75-7.76 (2H, m).

(2) 5-Bromo-N-[4,5-bis(furan 2-yl)oxazol-2-yl]-2-hydroxybenzamide

Using 5-bromosalicylic acid and 2-amino-4,5-bis(furan-2-yl)oxazole as the raw materials, the same operation as the example 16 gave the title compound.

Yield: 12.9%. $^1$H-NMR (DMSO-d$_6$): δ 6.65 (1H, dd, J=3.6, 10.5 Hz), 6.68 (1H, dd, J=3.6, 1.8 Hz), 6.75 (1H, d, J=8.7 Hz), 6.92 (1H, dd, J=3.6, 0.9 Hz), 6.93 (1H, d, J=3.3 Hz), 7.37 (1H, dd, J=8.7, 2.7 Hz), 7.80 (1H, dd, J=1.8, 0.9 Hz), 7.84 (1H, dd, J=1.8, 0.9 Hz), 7.92 (1H, d, J=3.0 Hz), 14.88 (2H, br).

Example 40

2-Hydroxy-N-5-[(trifluoromethyl)-1,3,4-thiadiazol-2-yl]benzamide (Compound No. 40)

(1) 2-Acetoxy-N-5-[(trifluoromethyl)-1,3,4-thiadizol-2-yl]benzamide

Using o-acetylsalicyloyl chloride and 2-amino-5-(trifluoromethyl)-1,3,4-thiadiazole as the raw materials, the same operation as the example 2(1) gave the title compound.

Yield: 51.1%. $^1$H-NMR (DMSO-d$_6$, δ): 2.23 (3H, s), 7.32 (1H, dd, J=8.0, 1.2 Hz), 7.45 (1H, td, J=7.6, 1.2 Hz), 7.69 (1H, td, J=8.0, 2.0 Hz), 7.87 (1H, dd, J=8.0, 2.0 Hz), 13.75 (1H, brs).

(2) 2-Hydroxy-N-5-[(trifluoromethyl)-1,3,4-thiadiazol-2-yl]benzamide

Using 2-acetoxy-N-5-[(trifluoromethyl)-1,3,4-thiadiazol-2-yl]benzamide as the raw material, the same operation as the example 2(2) gave the title compound.

Yield: 92.9%. $^1$H-NMR (DMSO-d$_6$): δ 7.00 (1H, td, J=8.0, 0.8 Hz), 7.06 (1H, d, J=8.4 Hz). 7.51 (1H, ddd, J=8.4, 7.6, 2.0 Hz), 7.92 (1H, dd, J=8.0, 1.6 Hz), 12.16 (1H, br).

Example 41

5-Bromo-2-hydroxy-N-[5-trifluoromethyl)-1,3,4-thiadiazol-2-yl]benzamide (Compound No. 41)

Using 5-bromosalicylic acid and 2-amino-5-(trifluoromethyl)-1,3,4-thiadiazole as the raw materials, the same operation as the example 16 gave the title compound.

Yield: 80.2%. $^1$H-NMR (DMSO-d$_6$): δ 7.01 (1H, d, J=9.0 Hz), 7.63 (1H, dd, J=8.7, 2.7 Hz), 7.97 (1H, d, J=2.4 Hz).

Example 42

5-Chloro-N-(2-chloropyridin-4-yl)-2-hydroxybenzamide (Compound No. 42)

Using 5-chlorosalicylic acid and 4-amino-2-chloropyridine as the raw materials, the same operation as the example 16 gave the title compound.

Yield: 12.2%. $^1$H-NMR (DMSO-d$_6$): δ 7.04 (1H, d, J=9.0 Hz), 7.49 (1H, dd, J=9.0, 3.0 Hz), 7.54 (1H, d, J=8.4 Hz), 7.88 (1H, d, J=2.7 Hz), 8.21 (1H, dd, J=8.7, 2.7 Hz), 8.74 (1H, d, J=2.7 Hz), 10.62 (1H, s), 11.57 (1H, s).

Example 43

5-Chloro-N-(6-chloro-4-methoxypyrimidin-2-yl)-2-hydroxybenzamide (Compound No. 43)

Using 5-chlorosalicylic acid and 2-amino-6-chloro-4-methoxypyrimidine as the raw materials, the same operation as the example 16 gave the title compound.

Yield: 2.2%, white solid. $^1$H-NMR (DMSO-d$_6$): δ 3.86 (3H, s), 6.85 (1H, s), 7.01 (1H, d, J=9.0 Hz), 7.47 (1H, dd, J=9.0, 3.0 Hz), 7.81 (1H, d, J=3.0 Hz), 11.08 (1H, s), 11.65 (1H, s).

Example 44

2-Aceoxy-5-chloro-N-(indol-2-yl)benzamide (Compound No. 44)

Using 2-acetoxy-5-chlorosalicylic acid and 2-aminoindole as the raw materials, the same operation as the example 24 gave the title compound.

Yield: 13.3%. $^1$H-NMR (DMSO-d$_6$): δ 2.20 (3H, s), 6.41 (1H, t, J=2.1 Hz), 7.27-7.36 (4H, m), 7.63 (1H, dd, J=8.7, 2.7 Hz), 7.74 (1H, d, J=2.7 Hz), 7.93 (1H, s), 10.21 (1H, s), 11.04 (1H, s).

Example 45

7-[(2-Acetoxybenzoyl)amino]indole-3-carboxylic acid ethyl ester (Compound No. 45)

This compound is a commercially available compound.
Supplier: Peakdale.
Catalog code number: PFC-0448.

Example 46

5-Chloro-2-hydroxy-N-(quinolin-3-yl)benzamide (Compound No. 46)

Using 5-chlorosalicylic acid and 2-aminoquinoline as the raw materials, the same operation as the example 16 gave the title compound.

Yield: 4.3%. $^1$H-NMR (DMSO-d$_6$): δ 7.07 (1H, d, J=8.7 Hz), 7.51 (1H, dd, J=9.0, 3.0 Hz), 7.61 (1H, dt, J=7.8, 1.2 Hz), 7.70 (1H, dt, J=7.8, 1.5 Hz), 7.98 (2H, d, J=3.0 Hz), 8.01 (1H, s), 8.82 (1H, d, J=2.4 Hz), 10.80 (1H, s), 11.74 (1H, s).

Example 47

N-(9-Ethylcarbazol-3-yl)-5-chloro-2-hydroxybenzamide (Compound No. 47)

Using 5-chlorosalicylic acid and 3-amino-9-ethylcarbazole as the raw materials, the same operation as the example 16 gave the title compound.

Yield: 64.6%. $^1$H-NMR (DMSO-d$_6$): δ 1.33 (3H, t, J=7.0 Hz), 4.46 (2H, q, J=7.0 Hz), 7.04 (1H, d, J=9.0 Hz), 7.21 (1H, t, J=7.3 Hz), 7.45-7.52 (2H, m), 7.64-7.65 (2H, m), 7.70 (1H, d, J=8.4, 1.9 Hz), 8.11-8.15 (2H, m), 8.49 (1H, d, J=1.9 Hz), 10.55 (1H, s), 12.22 (1H, s).

Example 48

2-Acetoxy-[3,5-bis(trifluoromethyl)phenyl]benzamide (Compound No. 95)

Using o-acetylsalicyloyl chloride and 3,5-bis(trifluoromethyl)aniline as the raw materials, the same operation as the example 2(1) gave the title compound.

Yield: 84.2%. $^1$H-NMR (DMSO-d$_6$): δ 2.36 (3H, s), 7.19 (1H, dd, J=8.0, 1.2 Hz), 7.39 (1H, td, J=7.6, 1.2 Hz), 7.57 (1H, ddd, J=8.0, 7.6, 1.6 Hz), 7.65 (1H, s), 7.83 (1H, dd, J=8.0, 1.6 Hz), 8.11 (2H, s), 8.31 (1H, s).

Example 49

N-[3,5-Bis(trifluoromethyl)phenyl]-2-hydroxybenzamide (Compound No. 48)

Using 2-acetoxy-[3,5-bis(trifluoromethyl)phenyl]benzamide as the raw material, the same operation as the example 2(2) gave the title compound.

Yield: 45.1%. $^1$H-NMR (DMSO-d$_6$): δ 6.96-7.02 (2H, m), 7.45 (1H, ddd, J=9.0, 7.2, 1.6 Hz), 7.81 (1H, s), 7.87 (1H, dd, J=8.0, 1.6 Hz), 8.46 (2H, s), 10.80 (1H, s), 11.26 (1H, s).

Example 50

N-[3,5-Bis(trifluoromethyl)phenyl]-5-fluoro-2-hydroxybenzamide (Compound No. 49)

Using 5-fluorosalicylic acid and 3,5-bis(trifluoromethyl)aniline as the raw materials, the same operation as the example 16 gave the title compound.

Yield: 58.7%. $^1$H-NMR (DMSO-d$_6$): δ 7.04 (1H, ddd, J=9.0, 4.5, 1.2 Hz), 7.30-7.37 (1H, m), 7.66 (1H, ddd, J=9.0, 3.3, 1.2 Hz), 7.84 (1H, s), 8.46 (2H, s), 10.85 (1H, s), 11.21 (1H, brs).

Example 51

N-[3,5-Bis(trifluoromethyl)phenyl]-5-chloro-2-hydroxybenzamide (Compound No. 50)

Using 5-chlorosalicylic acid and 3,5-bis(trifluoromethyl)aniline as the raw materials, the same operation as the example 16 gave the title compound.

Yield: 85.5%. $^1$H-NMR (DMSO-$d_6$): δ 7.05 (1H, d, J=8.7 Hz), 7.49 (1H, dd, J=8.7, 2.7 Hz), 7.85 (1H, s), 7.87 (1H, d, J=2.7 Hz), 8.45 (2H, s), 10.85 (1H, s), 11.39 (1H, s).

Example 52

N-[3,5-Bis(trifluoromethyl)phenyl]-5-bromo-2-hydroxybenzamide (Compound No. 51)

Using 5-bromosalicylic acid and 3,5-bis(trifluoromethyl)aniline as the raw materials, the same operation as the example 16 gave the title compound.

Yield: 88.5%. $^1$H-NMR (DMSO-$d_6$): δ 6.98 (1H, d, J=8.8 Hz), 7.59 (1H, dd, J=8.8, 2.8 Hz), 7.83 (1H, s), 7.98 (1H, d, J=2.8 Hz), 8.43 (2H, s), 10.82 (1H, s), 11.37 (1H, s).

Example 53

N-[3,5-Bis(trifluoromethyl)phenyl]-2-hydroxy-5-iodobenzamide (Compound No. 52)

Using 5-iodosalicylic acid and 3,5-bis(trifluoromethyl)aniline as the raw materials, the same operation as the example 16 gave the title compound.

Yield: 62.2%. $^1$H-NMR (DMSO-$d_6$): δ 6.86 (1H, d, J=8.4 Hz), 7.74 (1H, dd, J=8.7, 2.4 Hz), 7.84 (1H, s), 8.13 (1H, d, J=2.1 Hz), 8.84 (2H, s), 10.82 (1H, s), 11.41 (1H, s).

Example 54

N-[3,5-Bis(trifluoromethyl)phenyl]-2-hydroxy-5-nitrobenzamide (Compound No. 53)

Using 5-nitrosalicylic acid and 3,5-bis(trifluoromethyl)aniline as the raw materials, the same operation as the example 16 gave the title compound.

Yield: 57.2%. $^1$H-NMR (DMSO-$d_6$): δ 7.18 (1H, d, J=9.0 Hz), 7.86 (1H, s), 8.31 (1H, dd, J=9.0, 3.0 Hz), 8.45 (2H, s), 8.70 (1H, d, J=3.0 Hz), 11.12 (1H, s).

Example 55

N-[3,5-Bis(trifluoromethyl)phenyl]-5-cyano-2-hydroxybenzamide (Compound No. 54)

Using 5-cyanosalicylic acid and 3,5-bis(trifluoromethyl)aniline as the raw materials, the same operation as the example 16 gave the title compound.

Yield: 16.6%. $^1$H-NMR (DMSO-$d_6$): δ 7.15 (1H, d, J=8.1 Hz), 7.85 (1H, s), 7.86 (1H, dd, J=8.7, 2.1 Hz), 8.22 (1H, d, J=2.4 Hz), 8.43 (2H, s), 10.93 (1H, s), 12.00 (1H, brs).

Example 56

N-[3,5-Bis(trifluoromethyl)phenyl]-2-hydroxy-5-methylbenzamide (Compound No. 55)

Using 5-methylsalicylic acid and 3,5-bis(trifluoromethyl)aniline as the raw materials, the same operation as the example 16 gave the title compound.

Yield: 54.9%. $^1$H-NMR (DMSO-$d_6$): δ 6.92 (1H, d, J=8.7 Hz), 7.28 (1H, dd, J=8.7, 1.8 Hz), 7.7 (1H, d, J=1.8 Hz), 7.82 (1H, s), 8.47 (2H, s), 10.80 (1H, s), 11.14 (1H, s).

Example 57

N-[3,5-Bis(trifluoromethyl)phenyl]5-(1,1-dimethyl)ethyl-2-hydroxybenzamide (Compound No. 56)

Using 5-[(1,1-dimethyl)ethyl]salicylic acid and 3,5-bis(trifluoromethyl)aniline as the raw materials, the same operation as the example 16 gave the title compound.

Yield: 53.8%. $^1$H-NMR (DMSO-$d_6$): δ 1.30 (9H, s), 6.96 (1H, d, J=8.7 Hz), 7.50 (1H, dd, J=8.7, 2.4 Hz), 7.82 (1H, d, J=2.4 Hz), 7.83 (1H, s), 8.46 (2H, s), 10.80 (1H, s), 11.12 (1H, s).

Example 58

5-Acetyl-N-[3,5-bis(trifluoromethyl)phenyl]-2-hydroxybenzamide (Compound No. 78)

(1) 5-Acetyl-2-benzyloxybenzoic acid methyl ester

A mixture of 5-acetylsalicylic acid methyl ester (13.59 g, 70 mmol), benzyl bromide (17.96 g, 105 mmol), potassium carbonate (19.35 g, 140 mmol) and methylethylketone (350 mL) was refluxed far 8 hours. After cooling, the solvent was evaporated under reduced pressure. 2 N hydrochloric acid was added to the residue, and it was extracted with ethyl acetate. After the ethyl acetate layer was washed with water and brine, dried over anhydrous magnesium sulfate and concentrated, the residue was recrystallized from isopropyl ether to give the title compound (14.20 g, 71.4%) as a white solid.

$^1$H-NMR (CDCl$_3$): δ 2.58 (3H, s), 3.93 (3H, s), 5.27 (2H, s), 7.07 (1H, d, J=8.7 Hz), 7.26-7.43 (3H, m), 7.47-7.50 (2H, m), 8.07 (1H, dd, J=8.7, 2.4 Hz), 8.44 (1H, d, J=2.4 Hz).

(2) 5-Acetyl-2-benzyloxybenzoic acid

5-Acetyl-2-benzyloxybenzoic acid methyl ester (5.69 g, 20 mmol) was dissolved in a mixed solvent of methanol (20 mL) and tetrahydrofuran (20 mL). 2 N sodium hydroxide (11 mL) was added dropwise, and the mixture was stirred for 8 hours. The solvent was evaporated under reduced pressure. 2 N hydrochloric acid was added to the residue, and it was extracted with dichloromethane. After the dichloromethane layer was washed with water and brine, dried over anhydrous magnesium sulfate and concentrated, the residue was washed with isopropyl ether to give the title compound (4.92 g, 91.0%) as a white solid.

$^1$H-NMR (DMSO-$d_6$): δ 2.55 (3H, s), 5.32 (2H, s), 7.30-7.43 (4H, m), 7.49-7.52 (2H, m), 8.09 (1H, dd, J=9.0, 2.7 Hz), 8.22 (1H, d, J=2.4 Hz).

(3) 5-Acetyl-2-benzyloxy-N-[3,5-bis(trifluoromethyl)phenyl]benzamide

Using 5-acetyl-2-benzyloxybenzoic acid and 3,5-bis(trifluoromethyl)aniline as the raw materials, the same operation as the example 24 gave the title compound (5.47 g, 63.1%) as a slight yellowish green solid.

$^1$H-NMR (DMSO-$d_6$): δ 2.57 (3H, s), 7.11 (1H, d, J=8.7 Hz), 7.86 (1H, s), 8.05 (1H, dd, J=8.4, 2.1 Hz), 8.44 (1H, d, J=2.1 Hz), 8.47 (2H, s), 10.96 (1H, s), 11.97 (1H, brs).

(4) Preparation of 5-acetyl-N-[3,5-bis(trifluoromethyl)phenyl]-2-hydroxybenzamide Ethanol (6 mL) and tetrahydrofuran (72 mL) were added to 5-acetyl-2-benzyloxy-N-[3,5-bis(trifluoromethyl)phenyl]benzamide (602 mg, 1.25 mmol) and 5% palladium-carbon (60 mg), and the mixture was hydrogenated at room temperature for 30 minutes. After the insoluble matter was filtered off, the solvent was evaporated under reduced pressure and the residue was recrystallized from n-hexane-ethyl acetate to give the title compound (230 mg, 47.0%) as a white solid.

$^1$H-NMR (DMSO-d$_6$): δ 2.59 (3H, s), 5.35 (2H, s), 7.32-7.36 (3H, m), 7.43 (1H, d, J=8.7 Hz), 7.52-7.55 (2H, m), 7.82 (1H, s), 8.16 (1H, dd, J=8.7, 2.4 Hz), 8.25 (1H, d, J=2.4 Hz), 8.31 (2H, s), 10.89 (1H, s).

Example 59

N-[3,5-Bis(trifluoromethyl)phenyl]-2-hydroxy-5-(1-hydroxyethyl)benzamide (Compound No. 57)

5-Acetyl-N-[3,5-bis(trifluoromethyl)phenyl]-2-hydroxybenzamide (50.5 mg, 0.13 mmol) was suspended in ethanol (2 mL). Sodium borohydride (23.6 mg, 0.62 mmol) was added, and the mixture was stirred at room temperature for 12 hours. The reaction mixture was poured into diluted hydrochloric acid and extracted with ethyl acetate. After the organic layer was washed with water and brine, dried over anhydrous sodium sulfate, the residue obtained by evaporation under reduced pressure was washed with isopropyl ether/n-hexane under suspension to give the title compound (39.7 mg, 78.3%) as white powder.

$^1$H-NMR (DMSO-d$_6$): δ 1.34 (3H, d, J=6.3 Hz), 4.71 (1H, q, J=6.3 Hz), 5.18 (1H, brs), 6.97 (1H, d, J=8.4 Hz), 7.44 (1H, dd, J=8.4, 2.1 Hz), 7.84 (1H, s), 7.86 (1H, d, J=2.1 Hz), 8.48 (2H, s), 10.85 (1H, s), 11.32 (1H, s).

Example 60

N-[3,5-Bis(trifluoromethyl)phenyl]-2-hydroxy-5-[(1-methoxyimino)ethyl]benzamide (Compound No. 58)

5-Acetyl-N-[3,5-bis(trifluoromethyl)phenyl]-2-hydroxybenzamide (100.0 mg, 0.26 mmol) was dissolved in ethanol (3 mL). Pyridine (45 μl, 0.56 mmol) and O-methylhydroxylamine hydrochloride (25.8 mg, 0.31 mmol) were added, and the mixture was refluxed for 1 hour. After cooling, the reaction mixture was poured into diluted hydrochloric acid and extracted with ethyl acetate. After the organic layer was washed with water and brine, dried over anhydrous sodium sulfate, the residue obtained by evaporation under reduced pressure was purified by chromatography on silica gel (hexane:ethyl acetate=4:1) to give the title compound (102.1 mg, 95.3%) as a white crystal.

$^1$H-NMR (DMSO-d$_6$): δ 2.19 (3H, s), 3.91 (3H, s), 7.05 (1H, d, J=8.7 Hz), 7.77 (1H, dd, J=8.7, 2.4 Hz), 7.85 (1H, s), 8.09 (1H, d, J=2.4 Hz), 8.47 (2H, s), 10.87 (1H, s), 11.48 (1H, s).

Example 61

5-[(1-Benzyloxyimino)ethyl]-N-[3,5-bis(trifluoromethy)phenyl]-2-hydroxybenzamide (Compound No. 59)

Using 5-acetyl-N-[3,5-bis(trifluoromethyl)phenyl]-2-hydroxybenzamide and O-benzylhydroxylamine hydrochloride as the raw materials, the same operation as the example 60 gave the title compound.

Yield: 79.9%. $^1$H-NMR (DMSO-d$_6$): δ 2.24 (3H, s), 5.20 (2H, s), 7.04 (1H, d, J=8.7 Hz), 7.29-7.47 (5H, m), 7.76 (1H, dd, J=8.7, 2.4 Hz), 7.85 (1H, s), 8.07 (1H, d, J=2.1 Hz), 8.46 (2H, s), 10.87 (1H, s), 11.47 (1H, s).

Example 62

N-[3,5-Bis(trifluoromethyl)phenyl]-5-(2,2-dicyanoethen-1-yl)-2-hydroxybenzamide (Compound No. 60)

(1) 5-(2,2-Dicyanoethen-1-yl)-2-hydroxybenzoic acid

Malononitrile (132 mg, 2 mmol) was dissolved in ethanol (6 mL), and 5-formylsalicylic acid (332 mg, 2 mmol) was added. After cooling with ice bath, benzylamine (0.1 mL) was added and the mixture was stirred at room temperature for 2 hours. The separated yellow crystal was filtered and recrystallized (ethanol) to give the title compound (139.9 mg, 32.7%) as a light yellow solid.

$^1$H-NMR (DMSO-d$_6$): δ 7.12 (1H, d, J=8.7 Hz), 8.09 (1H, dd, J=8.7, 2.4 Hz), 8.41 (1H, s), 8.50 (1H, d, J=2.4 Hz).

(2) N-[3,5-Bis(trifluoromethyl)phenyl]-5-(2,2-dicyanoethen-1-yl)-2-hydroxybenzamide Using 5-(2,2-dicyanoethen-1-yl)-2-hydroxybenzoic acid and 3,5-bis(trifluoromethyl)aniline as the raw materials, the same operation as the example 16 gave the title compound.

Yield: 9.1%. $^1$H-NMR (DMSO-d$_6$): δ 7.13 (1H, d, J=9.0 Hz), 7.83 (1H, s), 8.04 (1H, dd, J=9.0, 2.4 Hz), 8.36 (1H, s), 8.38 (1H, d, J=2.4 Hz), 8.43 (2H, s), 11.43 (1H, s).

Example 63

3-({N-[3,5-Bis(trifluoromethyl)phenyl]carbamoyl}-4-hydroxyphenyl)-2-cyanoacrylic acid methyl ester (Compound No. 62)

(1) 5-[(2-Cyano-2-methoxycarbonyl)ethen-1-yl]-2-hydroxybenzoic acid

Triethylamine (0.2 mL) was added to a mixture of 5-formylsalicylic acid (332 mg, 2 mmol). Cyanoacetic acid methyl ester (198 mg, 2 mmol) and acetic acid (6 mL), and the mixture was refluxed for 5 hours. After cooling, the reaction mixture was poured into water, and the separated crystal was filtered and recrystallized (n-hexane) to give the title compound (327.7 mg, 66.3%) as a light yellow solid.

$^1$H-NMR (DMSO-d$_6$): δ 3.85 (3H, s), 7.15 (1H, d, J=8.7 Hz), 8.20 (1H, dd, J=8.7, 2.4 Hz), 8.37 (1H, s), 8.66 (1H, d, J=2.4 Hz).

(2) 3-({N-[3,5-Bis(trifluoromethyl)phenyl]carbamoyl}-4-hydroxyphenyl)-2-cyanoacrylic acid methyl ester Using 5-[(2-cyano-2-methoxycarbonyl)ethen-1-yl]-2-hydroxybenzoic acid and 3,5-bis(trifluoromethyl)aniline as the raw materials, the same operation as the example 16 gave the title compound.

Yield: 66.3%. $^1$H-NMR (DMSO-d$_6$): δ 3.85 (3H, s), 7.15 (1H, d, J=8.7 Hz), 8.20 (1H, dd, J=8.7, 2.4 Hz), 8.37 (1H, s), 8.66 (1H, d, 2.4 Hz).

Example 64

3-({N-[3,5-Bis(trifluoromethyl)phenyl]carbamoyl}-4-hydroxyphenyl)-2-cyanoacrylic acid (Compound No. 61)

3-({N-[3,5-Bis(trifluoromethyl)phenyl]carbamoyl}-4 hydroxyphenyl)-2-cyanoacrylic acid methyl ester (50 mg, 0.11 mmol) was dissolved in ethanol (5 mL). 2 N sodium hydroxide (0.11 ml, 0.22 mmol) was added, and the mixture was stirred at room temperature for 3 hours. The reaction mixture was poured into diluted hydrochloric acid and extracted with ethyl acetate. After the organic layer was washed with brine, dried over anhydrous magnesium sulfate, the residue obtained by evaporation under reduced pressure was recrystallized (ethyl acetate) to give the title compound (13.5 mg, 30.4%) as a light yellow solid.

$^1$H-NMR (DMSO-d$_6$): δ 7.12 (1H, d, J=8.4 Hz), 7.84 (1H, s), 7.94 (1H, dd, J=8.4, 2.1 Hz), 8.38 (1H, d, J=2.1 Hz), 8.45 (2H, s), 9.87 (1H, s), 11.41 (1H, s).

Example 65

N-[3,5-Bis(trifluoromethyl)phenyl]-2-hydroxy-5-(2-phenylethen-1-yl)benzamide (Compound No. 63)

A mixture of N-[3,5-bis(trifluoromethyl)phenyl]-2-hydroxy-5-iodo-benzamide (475 mg, 1 mmol), styrene (130 mg, 1.25 mmol), palladium acetate (4.5 mg, 0.02 mmol), tris(ortho-tolyl)phosphine (12.2 mg, 0.04 mmol), diisopropylamine (388 mg, 3 mmol) and N,N-dimethylformamide (2 mL) was refluxed for 8 hours. After cooling, water was added to the reaction mixture, and it was extracted with ethyl acetate. After the ethyl acetate layer was washed with water and brine, dried over anhydrous magnesium sulfate and concentrated, the residue was purified by column chromatography on silica gel (hexane-isopropyl ether: 2/1→1/1) to give the title compound (173 mg, 38.3%) as a pale yellow solid.

$^1$H-NMR (DMSO-d$_6$): δ 7.04 (1H, d, J=8.4 Hz), 7.20-7.29 (3H, m), 7.38 (2H, t, J=7.5 Hz), 7.59 (2H, d, J=7.5 Hz), 7.72 (1H, dd, J=8.4, 2.1 Hz), 7.86 (1H, s), 8.07 (1H, d, J=2.1 Hz), 8.49 (2H, s), 10.89 (1H, s), 11.33 (1H, brs).

Example 66

N-[3,5-Bis(trifluoromethyl)phenyl]-2-hydroxy-5-[(trimethylsilyl)-ethynyl]benzamide (Compound No. 66)

N-[3,5-Bis(trifluoromethyl)phenyl]-2-hydroxy-5-iodo-benzamide (950 mg, 2 mmol) and trimethylsilylacetylene (246 mg, 2.5 mmol) were dissolved in triethylamine (2 mL) and N,N-dimethylformamide (4 mL). Tetrakis(triphenylphosphine)palladium (23 mg, 0.02 mmol) and cuprous iodide (4 mg, 0.02 mmol) were added under argon atmosphere, and the mixture was stirred at 40° C. for 2 hours. After cooling to room temperature, the reaction mixture was poured into ethyl acetate (100 mL) and 1 N citric acid (100 mL), stirred, and filtered through celite. After the ethyl acetate layer was washed with water and brine one after another, dried over anhydrous magnesium sulfate, the solvent was evaporated under reduced pressure. The obtained residue was purified by column chromatography on silica gel (n-hexane:ethyl acetate=19:1) to give a light orange solid. This was crystallized by n-hexane to give the title compound (286 mg, 32.1%) as a white crystal.

$^1$H-NMR (DMSO-d$_6$): δ 0.23 (9H, s), 7.00 (1H, d, J=8.7 Hz), 7.54 (1H, dd, J=8.7, 2.4 Hz), 7.85 (1H, s), 7.98 (1H, d, J=2.1 Hz), 8.46 (2H, s), 10.86 (1H, s), 11.69 (1H, s).

Example 67

N-[3,5-Bis(trifluoromethyl)phenyl]-5-ethynyl-2-hydroxybenzamide (Compound No. 64)

N-[3,5-Bis(trifluoromethyl)phenyl]-2-hydroxy-5-[(trimethylsilyl)ethynyl]benzamide (233 mg, 0.5 mmol) was dissolved in methanol (1 mL). 2 N sodium hydroxide (1 mL) was added, and the mixture was stirred at room temperature for 1 hour. The reaction mixture was poured into 2 N hydrochloric acid and extracted with ethyl acetate. After the ethyl acetate layer was washed with water and brine one after another, dried over anhydrous magnesium sulfate, the solvent was evaporated under reduced pressure. The obtained residue was crystallized from ethanol-water to give the title compound (67 mg, 35.9%) as a light gray crystal.

$^1$H-NMR (DMSO-d$_6$): δ 4.11 (1H, s), 7.02 (1H, d, J=8.4 Hz), 7.55 (1H, dd, J=8.4, 2.1 Hz), 7.85 (1H, s), 7.98 (1J, d, J=2.1 Hz), 8.46 (2H, s), 8.46 (2H, s), 10.86 (1H, s), 11.62 (1H, s).

Example 68

N-[3,5-Bis(trifluoromethyl)phenyl]-2-hydroxy-5-(phenylethynyl)-benzamide (Compound No. 65)

Using N-[3,5-bis(trifluoromethyl)phenyl]-2-hydroxy-5-iodobenzamide and phenylacetylene as the raw materials, the same operation as the example 66 gave the title compound.

$^1$H-NMR (DMSO-d$_6$): δ 7.06 (1H, d, J=8.4 Hz), 7.42-7.46 (3H, m), 7.53-7.57 (2H, m), 7.64 (1H, dd, J=8.7, 2.1 Hz), 7.86 (1H, s), 8.06 (1H, d, J=2.1 Hz), 8.48 (2H, s), 10.94 (1H, s), 11.64 (1H, brs).

Example 69

N-[3,5-Bis(trifluoromethyl)phenyl]-4-hydroxybiphenyl-3-carboxamide (Compound No. 67)

N-[3,5-Bis(trifluoromethyl)phenyl]-2-hydroxy-5-iodo-benzamide (200 mg, 0.42 mmol) was dissolved in 1,2-dimethoxyethane (3 mL). Tetrakis(triphenylphosphine)palladium (16 mg, 0.0014 mmol) was added under argon atmosphere, and the mixture was stirred at room temperature for 5 minutes. Then dihydroxyphenylborane (57 mg, 0.47 mmol) and 1M sodium carbonate (1.3 mL) were added and refluxed for 2 hours. After cooling to room temperature, the reaction mixture was poured into diluted hydrochloric acid and extracted with ethyl acetate. After the ethyl acetate layer was washed with water and brine one after another, dried over anhydrous sodium sulfate, the solvent was evaporated under reduced pressure. The obtained residue was purified by column chromatography on silica gel (n-hexane:ethyl acetate=6:1→3:1) to give the title compound (109 mg, 61.1%) as a white crystal.

$^1$H-NMR (DMSO-d$_6$): δ 7.12 (1H, d, J=8.7 Hz), 7.33-7.38 (1H, m), 7.48 (2H, t, J=7.5 Hz), 7.67-7.70 (2H, m), 7.79 (1H, dd, J=8.4, 2.4 Hz), 7.87 (1H, s), 8.17 (1H, d, J=2.4 Hz), 8.49 (2H, s), 10.92 (1H, s), 11.41 (1H, s).

Example 70

N-[3,5-Bis(trifluoromethyl)phenyl]-2-hydroxy-5-(2-phenethyl)benzamide (Compound No. 63)

Using N-[3,5-bis(trifluoromethyl)phenyl]-2-hydroxy-5-(phenylethynyl)benzamide as the raw material, the same operation as the example 58(4) gave the title compound.

Yield: 86.2%. $^1$H-NMR (DMSO-d$_6$): δ 2.88 (4H, s), 6.93 (1H, d, J=8.1 Hz), 7.15-7.34 (6H, m), 7.76 (1H, d, J=2.4 Hz), 7.84 (1H, s), 8.47 (2H, s), 10.79 (1H, s), 11.15 (1H, s).

Example 71

N-[3,5-Bis(trifluoromethyl)phenyl]-2-hydroxy-5-(trifluoromethyl)-benzamide (Compound No. 69)

Using 2-hydroxy-5-(trifluoromethyl)benzoic acid and 3,5-bis(trifluoromethyl)aniline as the raw materials, the same operation as the example 16 gave the title compound. (2-Hydroxy-5-(trifluoromethyl)benzoic acid: refer to Chem. Pharm. Bull., 1996, 44, 734.)

Yield: 44.7%. $^1$H-NMR (CDCl$_3$, δ): 7.17 (1H, d, J=9.0 Hz), 7.72-7.75 (2H, m), 7.86 (1H, s), 8.17 (2H, s), 8.35 (1H, s), 11.88 (1H, s).

Example 72

N-[3,5-Bis(trifluoromethyl)phenyl]-2-hydroxy-5-(pentafluoroethyl)-benzamide (Compound No. 70)

Using 2-hydroxy-5-(pentafluoroethyl)benzoic acid and 3,5-bis(trifluoromethyl)aniline as the raw materials, the same operation as the example 16 gave the title compound. (2-Hydroxy-5-(pentafluoroethyl)benzoic acid: refer to Chem. Pharm. Bull., 1996, 44, 734.)

Yield: 65.7%. $^1$H-NMR (CDCl$_3$, δ): 7.19 (1H, d, J=9.0 Hz), 7.70 (1H, dd, J=8.7, 2.1 Hz), 7.81 (1H, d, J=2.1 Hz), 8.17 (2H, s), 8.37 (1H, s), 11.92 (1H, s).

Example 73

N-[3,5-Bis(trifluoromethyl)phenyl]2-hydroxy-5-(pyrrol-1-yl)benzamide (Compound No. 71)

Using 2-hydroxy-5-(pyrrol-1-yl)benzoic acid and 3,5-bis(trifluoromethyl)-aniline as the raw materials, the same operation as the example 16 gave the title compound.

Yield: 57.8%. $^1$H-NMR (DMSO-d$_6$): δ 6.27 (2H, dd, J=2.4, 1.8 Hz), 7.10 (1H, d, J=9.0 Hz), 7.29 (2H, dd, J=2.4, 1.8 Hz), 7.66 (1H, dd, J=9.0, 2.7 Hz), 7.86 (1H, s), 7.98 (1H, d, J=2.4 Hz), 8.47 (2H, s), 10.89 (1H, s), 11.24 (1H, s).

Example 74

N-[3,5-Bis(trifluoromethyl)phenyl]-2-hydroxy-5-(thiophen-2-yl)-benzamide (Compound No. 72)

Using N-[3,5-bis(trifluoromethyl)phenyl]-2-hydroxy-5-iodobenzamide and 2-thipheneboronic acid as the raw materials, the same operation as the example 69 gave the title compound.

$^1$H-NMR (DMSO-d$_6$): δ 7.08 (1H, d, J=8.4 Hz), 7.14 (1H, dd, J=5.4, 3.6 Hz), 7.45 (1H, dd, J=3.6, 1.2 Hz), 7.51 (1H, dd, J=5.1, 0.9 Hz), 7.75 (1H, dd, J=8.4, 2.4 Hz), 7.59 (1H, s), 8.08 (1H, d, J=2.4 Hz), 8.48 (2H, s), 10.91 (1H, s), 11.38 (1H, s).

Example 75

N-[3,5-Bis(trifluoromethyl)phenyl]-2-hydroxy-5-(thiophen-3-yl)-benzamide (Compound No. 73)

Using N-[3,5-bis(trifluoromethyl)phenyl] 2-hydroxy-5-iodobenzamide and 3-thipheneboronic acid as the raw materials, the same operation as the example 69 gave the title compound.

Yield: 38.7%. $^1$H-NMR (DMSO-d$_6$): δ 7.06 (1H, d, J=8.7 Hz), 7.57 (1H, dd, J=4.8, 1.5 Hz), 7.66 (1H, dd, J=4.8, 3.0 Hz), 7.81-7.84 (2H, m), 7.86 (1H, s), 8.18 (1H, d, J=2.1 Hz), 8.49 (2H, s), 10.90 (1H, s), 11.33 (1H, s).

Example 76

N-[3,5-Bis(trifluoromethyl)phenyl]-2-hydroxy-5-(2-methylthiazol-4-yl)benzamide (Compound No. 75)

(1) 2-Benzyloxy-5-(2-bromoacetyl)-N-[3,5-bis(trifluoromethyl)phenyl]benzamide

5-Acetyl-2-benzyloxy-N-[3,5-bis(trifluoromethyl)phenyl]benzamide (4.81 g, 10 mmol) was dissolved in THF (30 ml). Phenyltrimethylammonium bromide (3.75 g, 10 mmol) was added, and the mixture was stirred at room temperature for 12 hours. The reaction mixture was poured into water and extracted with ethyl acetate. After the organic layer was washed with aqueous sodium hydrogen sulfite, water, and brine, dried over anhydrous magnesium sulfate, the residue obtained by evaporation under reduced pressure was purified by chromatography on silica gel (hexane:ethyl acetate=4:1), and recrystallized (ethyl acetate/hexane) to give the title compound (2.39 g, 42.7%) as a white solid.

$^1$H-NMR (DMSO-d$_6$): δ 4.91 (2H, s), 5.36 (2H, s), 7.32-7.35 (3H, m), 7.47 (1H, d, J=9.0 Hz), 7.52-7.56 (2H, m), 7.82 (1H, s), 8.21 (1H, dd, J=8.7, 2.4 Hz), 8.29 (1H, d, J=2.4 Hz), 8.31 (2H, s), 10.91 (1H, s).

(2) 2-Benzyloxy-N-[3,5-bis(trifluoromethyl)phenyl]-5-(2-methylthiazol-4-yl)benzamide A mixture of 2-benzyloxy-5-(2-bromoacetyl)-N-[3,5-bis(trifluoromethyl)-phenyl]benzamide (280 mg, 0.5 mmol), thioacetamide (41 mg, 0.55 mmol), sodium hydrogen carbonate (50 mg, 0.6 mmol) and ethanol (15 mL) was refluxed for 1 hour. The reaction mixture was poured into water, neutralized by sodium hydrogen carbonate, and extracted with ethyl acetate. After the organic layer was washed with water and saturated brin, dried over anhydrous magnesium sulfate, the residue obtained by evaporation under reduced pressure was purified by chromatography on silica gel (hexane:ethyl acetate=4:1) to give the title compound (181 mg, 67.5%) as a white solid.

$^1$H-NMR (DMSO-d$_6$): δ 2.72 (3H, s), 5.29 (2H, s), 7.33-7.36 (3H, m), 7.40 (1H, d, J=9.0 Hz), 7.54-7.57 (2H, m), 7.81 (1H, s), 7.94 (1H, s), 8.12 (1H, dd, J=8.7, 2.1 Hz), 8.27 (1H, d, J=2.1 Hz), 8.31 (2H, s), 10.86 (1H, s).

(3) N-[3,5Bis(trifluoromethyl)phenyl]-2-hydroxy-5-(2-methylthiazol-4-yl)benzamide 2-Benzyloxy-N-[3,5-bis(trifluoromethyl)phenyl]-5-(2-methylthiazol-4-yl)benzamide (160 mg, 0.3 mmol) and 10% Pd—C (240 mg) were dissolved in ethanol (10 ml) and stirred for 3.5 hours under hydrogen atmosphere. The reaction mixture was filtered and the filtrate was evaporated under reduced pressure to give the title compound (103.4 mg, 79.2%) as a white solid.

$^1$H-NMR (DMSO-d$_6$): δ 2.72 (3H, s), 7.08 (1H, d, J=8.7 Hz), 7.83 (1H, s), 7.85 (1H, s), 8.01 (1H, dd, J=8.7, 2.4 Hz), 8.42 (1H, d, J=2.1 Hz), 8.50 (2H, s), 10.96 (1H, s), 11.40 (1H, s).

Example 77

N-[3,5-Bis(trifluoromethyl)phenyl]-2-hydroxy-5-(imidazo[1,2-a]-pyridin-2-yl)benzamide (Compound No. 75)

A mixture of 2-benzyloxy-5-(2-bromoacetyl)-N-[3,5-bis(trifluoromethyl)-phenyl]benzamide (280 mg, 0.5 mmol), 2-aminopyridine (51.8 mg, 0.55 mmol), sodium hydrogen carbonate (50 mg, 0.6 mmol) and ethanol (10 mL) was refluxed for 2 hours. After cooling, the reaction mixture was poured into aqueous sodium hydrogen carbonate and extracted with ethyl acetate. After the organic layer was washed with water and brine, dried over anhydrous magnesium sulfate, the residue obtained by evaporation under reduced pressure was purified by chromatography on silica gel (n-hexane:ethyl acetate=1:2) to give the title compound (130.3 mg, 45.9%) as a white solid. Then, a mixture of this solid (108 mg, 0.19 mmol), 10% Pd—C (11 mg), ethanol (8 mL) and ethyl acetate (8 mL) was stirred for 7 hours under hydrogen atmosphere. The reaction mixture was filtered and the residue obtained by evaporation of the filtrate under reduced pressure was purified by chromatography on silica gel (n-hexane:ethyl acetate=1:3) to give the title compound (18.3 mg, 20.2%) as a white solid.

$^1$H-NMR (DMSO-d$_6$): δ 6.90 (1H, dt, J=6.6, 0.9 Hz), 7.10 (1H, d, J=8.7 Hz), 7.25 (1H, m), 7.57 (1H, d, J=9.0 Hz), 7.86 (1H, s), 8.04 (1H, dd, J=8.7, 2.1 Hz), 8.35 (1H, s), 8.48-8.56 (4H, m), 11.00 (1H, s), 11.41 (1H, s).

Example 78

N-[3,5-Bis(trifluoromethyl)phenyl]-2-hydroxy-5-(pyridin-2-yl)benzamide (Compound No. 76)

(1) N-[3,5-Bis(trifluoromethyl)phenyl]-5-iodo-2-methoxymethoxybenzamide

A mixture of N-[3,5-bis(trifluoromethyl)phenyl]-2-hydroxy-5-iodobenzamide (4.75 g, 10 mmol), chloromethyl methyl ether (1.14 ml, 15 ml), potassium carbonate (2.76 g, 20 mmol) and acetone (50 mL) was refluxed for 8 hours. The reaction mixture was poured into diluted hydrochloric acid and extracted with ethyl acetate. After the organic layer was washed with water and brine, dried over anhydrous magnesium sulfate, the residue obtained by evaporation under reduced pressure was purified by chromatography on silica gel (hexane:ethyl acetate=3:1), and recrystallized (n-hexane/ethyl acetate) to give the title compound (3.96 g, 76.3%) as a white solid.

$^1$H-NMR (DMSO-d$_6$): δ 3.38 (3H, s), 5.28 (2H, s), 7.12 (1H, d, J=9.0 Hz), 7.81 (1H, s), 7.82 (1H, dd, J=8.7, 2.4 Hz), 7.88 (1H, d, J=2.4 Hz), 8.40 (2H, s), 10.87 (1H, s).

(2) N-[3,5-Bis(trifluoromethyl)phenyl]-2-methoxymethoxy-5-(pyridin-2-yl)benzamide N-[3,5-Bis(trifluoromethyl)phenyl]-5-iodo-2-methoxymethoxybenzamide (0.20 g, 0.39 mmol) was dissolved in N,N-dimethylformamide (8 ml). Tri-n-butyl(2-pyridyl)tin (0.13 ml, 0.41 mmol) and dichlorobis(triphenylphosphine) palladium (32.1 mg, 0.05 mmol) were added, and the mixture was stirred at 100° C. for 1.5 hours. After cooling, the reaction mixture was poured into water and extracted with ethyl acetate. After the organic layer was washed with water and brine, dried over anhydrous sodium sulfate, the residue obtained by evaporation under reduced pressure was purified by chromatography on silica gel (n-hexane:ethyl acetate=2:1→1:1) to give the title compound (37.9 mg, 20.8%) as a white powder.

$^1$H-NMR (CDCl$_3$): δ 3.64 (3H, s), 5.53 (2H, s), 7.23-7.28 (1H, m), 7.36 (1H, d, J=8.7 Hz), 7.65 (1H, s), 7.77-7.84 (2H, m), 8.20 (2H, s), 8.31 (1H, dd, J=8.7, 2.4 Hz), 8.68-8.70 (1H, m), 8.83 (1H, d, J=2.4 Hz), 10.12 (1H, s).

(3) N-[3,5-Bis(trifluoromethyl)phenyl]-2-hydroxy-5-(pyridin-2-yl)benzamide

Methanol (3 ml) and concentrated hydrochloric acid (0.5 ml) were added to N-[3,5-bis(trifluoromethyl)phenyl]-2-methoxymethoxy-5-(pyridin-2-yl)benzamide (37.9 mg, 0.08 mmol), and the mixture was refluxed for 2 hours. After cooling, the reaction mixture was poured into saturated aqueous sodium hydrogen carbonate and extracted with ethyl acetate. After the organic layer was washed with water and brine, dried over anhydrous sodium sulfate, the residue obtained by evaporation under reduced pressure was purified by chromatography on silica gel (n-hexane:ethyl acetate=2:1) to give the title compound (16.2 mg, 47.2%) as a white powder.

$^1$H-NMR (DMSO-d$_6$): δ 7.13 (1H, d, J=8.4 Hz), 7.73 (1H, ddd, J=7.5, 6.3, 1.2 Hz), 7.86-7.91 (2H, m), 7.97 (1H, d, J=7.8 Hz), 8.20 (1H, dd, J=8.7, 2.1 Hz), 8.50 (2H, s), 8.59 (1H, d, J=2.4 Hz), 8.64-8.66 (1H, m), 10.97 (1H, s), 11.53 (1H, s).

Example 79

N-[3,5-Bis(trifluoromethyl)phenyl]-2-hydroxy-5-methoxybenzamide (Compound No. 77)

Using 5-methoxysalicylic acid and 3,5-bis(trifluoromethyl)aniline as the raw materials, the same operation as the example 16 gave the title compound.

Yield: 56.8%. $^1$H-NMR (DMSO-d$_6$): δ 3.77 (3H, s), 6.97 (1H, d, J=9.0 Hz), 7.10 (1H, dd, J=9.0, 3.0 Hz), 7.43 (1H, d, J=3.0 Hz), 7.84 (1H, s), 8.47 (2H, s), 10.84 (1H, s), 10.91 (1H, s).

Example 80

N-[3,5-Bis(trifluoromethyl)phenyl]-2-hydroxy-5-isobutyrylbenzamide (Compound No. 79)

(1) 5-Acetyl-2-methoxybenzoic acid methyl ester

A mixture of 5-acetylsalicylic acid methyl ester (5.00 g, 25.7 mmol), sodium carbonate (7.10 g, 51.4 mmol) and N,N-dimethylformamide (25 mL) was cooled with ice bath. Methyl iodide (2.5 mL, 40.1 mmol) was added, and the mixture was stirred at room temperature for 3 hours. The reaction mixture was poured into water, neutralized by hydrochloric acid, and extracted with ethyl acetate. After the organic layer was washed with water and brine, dried over anhydrous sodium sulfate, the residue obtained by evaporation under reduced pressure was washed under suspension (isopropyl ether/n-hexane) to give the title compound (5.17 g, 96.5%) as a white crystal.

$^1$H-NMR (CDCl$_3$): δ 2.59 (3H, s), 3.92 (3H, s), 3.99 (3H, s), 7.04 (1H, d, J=8.7 Hz), 8.12 (1H, dd, J=8.7, 2.4 Hz), 8.41 (1H, d, J=2.4 Hz).

(2) 5-Isobutyryl-2-methoxybenzoic acid methyl ester

A mixture of 5-acetyl-2-methoxybenzoic acid methyl ester (0.50 g, 2.40 mmol), potassium tert-butoxide (0.81 g, 7.22 mmol) and tetrahydrofuran (10 mL) was cooled with ice bath. Methyl iodide (0.5 mL, 8.03 mmol) was added, and the mixture was stirred at room temperature for 1 hour. The reaction mixture was poured into water, neutralized by hydrochloric acid, and extracted with ethyl acetate. After the organic layer was washed with water and brine, dried over anhydrous sodium sulfate, the residue obtained by evaporation under reduced pressure was purified by chromatography on silica gel (n-hexane:ethyl acetate=3:1→2:1) to give the title compound (143.1 mg, 25.2%) as a light yellow oil.

$^1$H-NMR (CDCl$_3$): δ 1.22 (6H, d, J=6.9 Hz), 3.52 (1H, m), 3.92 (3H, s), 3.98 (3H, s), 7.05 (1H, d, J=8.7 Hz), 8.13 (1H, dd, J=8.7, 2.4 Hz), 8.42 (1H, d, J=2.4 Hz).

(3) 5-Isobutyryl-2-methoxybenzoic acid

5-Isobutyryl-2-methoxybenzoic acid methyl ester (143.1 mg, 0.60 mmol) was dissolved in methanol (5 mL). 2 N aqueous sodium hydroxide (1 ml) was added, and the mixture was refluxed for 1 hour. After cooling, the reaction mixture was poured into 2 N hydrochloric acid and extracted with ethyl acetate. The organic layer was washed with water and brine, dried over anhydrous sodium sulfate, and evaporated under reduced pressure to give the title compound (134 mg, yield:quantitative) as a white crystal.

$^1$H-NMR (CDCl$_3$): δ 1.22 (6H, d, J=6.9 Hz), 3.59 (1H, m), 4.15 (3H, s), 7.16 (1H, d, J=8.7 Hz), 8.24 (1H, dd, J=8.7, 2.4 Hz), 8.73 (1H, d, J=2.1 Hz).

(4) 5-Butyryl-N-[3,5-bis(trifluoromethyl)phenyl]-2-methoxybenzamide

Using 5-isobutyryl-2-methoxybenzoic acid and 3,5-bis(trifluoromethyl)aniline as the raw materials, the same operation as the example 16 gave the title compound.

$^1$H-NMR (CDCl$_3$): δ 1.23 (6H, d, J=6.9 Hz), 3.64 (1H, m), 4.20 (3H, s), 7.18 (1H, d, J=8.7 Hz), 7.65 (1H, s), 8.19 (2H, s), 8.22 (1H, dd, J=8.7, 2.1 Hz), 8.88 (1H, d, J=2.1 Hz), 9.98 (1H, s).

(5) N-[3,5-Bis(trifluoromethyl)phenyl]-2-hydroxy-5-isobutyrylbenzamide

A mixture of 5-butyryl-N-(3,5-bis(trifluoromethyl)phenyl-2-methoxy-benzamide (143.4 mg, 0.33 mmol), 2,4,6-collidine (3 ml) and lithium iodide (53.1 mg, 0.40 mmol) was refluxed for 1 hour. After cooling, the reaction mixture was poured into 2N hydrochloric acid and extracted with ethyl acetate. After the organic layer was washed with brine, dried over anhydrous sodium sulfate, the residue obtained by evaporation under reduced pressure was purified by chromatography on silica gel (n-hexane:ethyl acetate=3:1) and crystallized (ethyl acetate/isopropyl ether) to give the title compound (90.3 mg, 65.3%) as a white crystal.

$^1$H-NMR (DMSO-d$_6$): δ 1.12 (6H, d, J=6.9 Hz), 3.66 (1H, m), 7.12 (1H, d, J=8.4 Hz), 7.85 (1H, s), 8.07 (1H, dd, J=8.4, 2.4 Hz), 8.45 (1H, d, J=2.4 Hz), 8.47 (2H, s), 10.93 (1H, s), 11.95 (1H, brs).

Example 81

N-[3,5-Bis(trifluoromethyl)phenyl]-4-hydroxyisophthalamic acid methyl ester (Compound No. 81)

Using 4-hydroxyisophthalic acid 1-methyl ester and 3,5-bis(trifluoromethyl)-aniline as the raw materials, the same operation as the example 16 gave the title compound.

Yield: 91.5%. $^1$H-NMR (DMSO-d$_6$): δ 3.85 (3H, s), 7.12 (1H, d, J=8.4 Hz), 7.86 (1H, s), 8.02 (1H, dd, J=8.7, 2.4 Hz), 8.46-8.47 (3H, m), 10.96 (1H, s), 12.03 (1H, brs).

Example 82

N-[3,5-Bis(trifluoromethyl)phenyl]-4-hydroxyisophthalamic acid (Compound No. 80)

N-[3,5-Bis(trifluoromethyl)phenyl]-4-hydroxyisophthalamic acid methyl ester (2.85 g, 7 mmol) was suspended in a mixed solvent of methanol (14 mL) and tetrahydrofuran (14 mL). 2 N aqueous sodium hydroxide (14 mL) was added, and the mixture was refluxed for 2 hours. After cooling, the reaction mixture was added 2 N hydrochloric acid (20 ml) and the separated solid was filtered, washed with water, dried to give the title compound (2.68 g, 97.4%) as a white crystal.

$^1$H-NMR (DMSO-d$_6$): δ 7.10 (1H, d, J=8.7 Hz), 7.82 (1H, s), 7.86 (1H, s), 8.01 (1H, dd, J=8.7, 2.4 Hz), 8.47 (2H, s), 8.48 (1H, d, J=2.4 Hz), 10.97 (1H, s), 11.98 (1H, brs).

Example 83

N$^1$,N$^3$-Bis[3,5-bis(trifluoromethyl)phenyl]-4-hydroxyisophthalamide (Compound No. 82)

Using 4-hydroxyisophthalic acid (182 mg, 1 mmol), 3,5-bis(trifluoromethyl)-aniline (687 mg, 3 mmol), phosphorus trichloride (87 μl; 1 mmol) and toluene (10 mL), the same operation as the example 16 gave the title compound (151 mg, 25.0%) as a white crystal.

$^1$H-NMR (DMSO-d$_6$): δ 7.18 (1H, d, J=8.7 Hz), 7.82 (1H, s), 7.86 (1H, s), 8.11 (1H, dd, J=8.7, 2.4 Hz), 8.50 (2H, s), 8.54 (2H, s), 8.56 (1H, d, J=2.4 Hz), 10.79 (1H, s), 10.99 (1H, s), 11.84 (1H, brs).

Example 84

N$^3$-[3,5-Bis(trifluoromethyl)phenyl]-4-hydroxy-N$^1$,N$^1$-dimethylisophthal-amide (Compound No. 83)

(1) 4-Benzyloxy-N-[3,5-bis(trifluoromethyl)phenyl]isophthalamic acid methyl ester Sodium hydride (60%; 1.04 g, 26 mmol) was washed with n-hexane, suspended in N,N-dimethylformamide (100 mL). A solution of N-[3,5-bis(trifluoromethyl)-phenyl]-4-hydroxyisophthalamic acid methyl ester (8.15 g, 20 mmol) in N,N-dimethylformamide (100 mL) was added dropwise under cooling with ice bath. After the addition was finished, the mixture was stirred at room temperature for 1 hour. A solution of benzyl bromide (4.45 g, 26 mmol) in N,N-dimethylformamide (10 mL) was added, and the mixture was stirred at 60° C. for 3 hours. After cooling, the reaction mixture was poured into ice and water, and extracted with ethyl acetate. After the organic layer was washed with water and brine, dried over anhydrous magnesium sulfate, the residue obtained by evaporation under reduced pressure was recrystallized (ethyl acetate/n-hexane) to give the title compound (5.38 g, 54.1%) as a white solid.

$^1$H-NMR (DMSO-d$_6$): δ 3.87 (3H, s), 5.33 (2H, s), 7.33-7.36 (3H, m), 7.46 (1H, d, J=8.7 Hz), 7.53-7.56 (2H, m), 7.82 (1H, s), 8.15 (1H, dd, J=8.7, 2.1 Hz), 8.25 (1H, d, J=2.1 Hz), 8.28 (2H, s), 10.87 (1H, s).

(2) 4-Benzyloxy-N-[3,5-bis(trifluoromethyl)phenyl]isophthalamic acid

Using 4-benzyloxy-N-[3,5-bis(trifluoromethyl)phenyl]isophthalamic acid methyl ester as the raw material, the same operation as the example 82 gave the title compound.

Yield: 79.7%. $^1$H-NMR (DMSO-d$_6$): δ 5.32 (2H, s), 7.32-7.34 (3H, m), 7.43 (1H, d, J=8.7 Hz), 7.52-7.56 (2H, m), 7.81 (1H, s), 8.12 (1H, dd, J=8.7, 2.1 Hz), 8.22 (1H, d, J=2.1 Hz), 8.28 (2H, s), 10.85 (1H, s), 13.81 (1H, brs).

(3) 4-Benzyloxy-N$^3$-[3,5-bis(trifluoromethyl)phenyl]-N$^1$,N$^1$-dimethylisophthalamide WSC.HCl (95 mg, 0.50 mmol) was added to a solution of 4-benzyl-N-[3,5-bis(trifluoromethyl)phenyl]isophthalamic acid (242 mg, 0.50 mmol), dimethylamine hydrochloride (41 mg, 0.05 mmol) and triethylamine (51 mg, 0.50 mmol) in tetrahydrofuran (5 mL) under ice cooling, and the mixture was stirred at room temperature for 3 hours. The reaction mixture was poured into water and extracted with ethyl acetate. After the organic layer was washed with diluted hydrochloric acid, water and brine, dried over anhydrous magnesium sulfate, the residue obtained by evaporating the solvent under reduced pressure was purified by chromatography on silica gel (hexane:ethyl acetate=1:4) to give the title compound (165 mg, 64.9%) as a white solid.

$^1$H-NMR (DMSO-d$_6$): δ 2.99 (6H, s), 5.29 (2H, s), 7.32-7.38 (4H, m), 7.52-7.56 (2H, m), 7.64 (1H, dd, J=8.7, 2.1 Hz), 7.73 (1H, d, J=2.1 Hz), 7.80 (1H, s), 8.28 (2H, s), 10.83 (1H, s).

(4) N$^3$-[3,5-bis(trifluoromethyl)phenyl]-4-hydroxy-N$^1$,N$^1$-dimethylisophthalamide A solution of 4-benzyloxy-N$^3$-[3,5-bis(trifluoromethyl)phenyl]-N$^1$,N$^1$-dimethyl-isophthalamide (141 mg, 0.28 mmol) and 5% Pd—C (14 mg) in the mixture of ethanol (5 ml) and ethyl acetate (5 ml) was stirred at room temperature for 1 hour under hydrogen atmosphere. The reaction mixture was filtered and the filtrate was evaporated under reduced pressure to give the title compound (106 mg, 91.2%) as a white solid.

¹H-NMR (DMSO-d₆): δ 2.98 (6H, s), 7.02 (1H, d, J=8.7 Hz), 7.52 (1H, dd, J=8.7, 2.1 Hz), 7.84 (1H, s), 7.95 (1H, d, J=2.1 Hz), 8.46 (2H, s), 11.10 (1H, brs), 11.63 (1H, brs).

Example 85

N-[3,5-Bis(trifluoromethyl)phenyl]-2-hydroxy-5-(piperidine-1-carbonyl)benzamide (1) 2-Benzyloxy-N-[3,5-bis(trifluoromethyl)phenyl]-5-(piperidine-1-carbonyl)benzamide Using 4-benzyl-N-[3,5-bis(trifluoromethyl)phenyl]isophthalamic acid and piperidine as the raw materials, the same operation as the example 84(3) gave the title compound.

Yield: 56.4%. ¹H-NMR (CDCl₃): δ 1.53-1.70 (6H, m), 3.44 (2H, brs), 3.70 (2H, brs), 5.26 (2H, s), 7.24 (1H, d, J=8.7 Hz), 7.26 (1H, s), 7.52-7.58 (5H, m), 7.66 (2H, s). 7.74 (1H, dd, J=8.7, 2.4 Hz), 8.37 (1H, d, J=2.1 Hz), 10.27 (1H, s).

(2) N-[3,5-Bis(trifluoromethyl)phenyl]-2-hydroxy-5-(piperidine-1-carbonyl)benzamide Using 2-benzyloxy N-[3,5-bis(trifluoromethyl)phenyl]-5-(piperidine-1-carbonyl)benzamide as the raw material, the same operation as the example 84(4) gave the title compound.

Yield: 96.3%, white solid. ¹H-NMR (DMSO-d₆): δ 1.51 (4H, brs), 1.60-1.65 (2H, m), 3.47 (4H, brs), 7.04 (1H, d, J=8.4 Hz), 7.48 (1H, dd, J=8.4, 2.1 Hz), 7.85 (1H, s), 7.92 (1H, d, J=2.1 Hz). 8.46 (2H, s), 10.99 (1H, s), 11.64 (1H, brs).

Example 86

5-(4-Benzylpiperidine-1-carbonyl)-N-[3,5-bis(trifluoromethy)phenyl]-2-hydroxybenzamide (1) 2-Benzyl-5-(4-benzylpiperidine-1-carbonyl)-N-[3,5-bis(trifluoromethyl)-phenyl]benzamide Using 4-benzyl-N-[3,5-bis(trifluoromethyl)phenyl]isophthalamic acid and 4-benzylpiperidine as the raw materials, the same operation as the example 84(3) gave the title compound.

Yield: 76.7%. ¹H-NMR (CD₃OD): δ 1.18-1.38 (2H, m), 1.67 (1H, brs), 1.74 (1H, brs), 1.84-1.93 (1H, m), 2.60 (2H, d, J=7.2 Hz), 2.83 (1H, brs), 3.10 (1H, brs), 3.78 (1H, brs), 4.59 (1H, brs), 5.34 (2H, s), 7.15-7.18 (3H, m), 7.24-7.28 (2H, m), 7.40-7.46 (4H, m), 7.57-7.63 (3H, m), 7.65 (1H, dd, J=8.7, 2.4 Hz), 7.96 (2H, s), 8.05 (1H, d, J=2.1 Hz).

(2) N-[3,5-Bis(trifluoromethyl)phenyl]-2-hydroxy-5-(4-benzylpiperidine-1-carbonyl)benzamide Using 2-benzyl-5-(4-benzylpiperidine-1-carbonyl)-N-[3,5-bis(trifluoromethyl)-phenyl]benzamide as the raw material, the same operation as the example 84(4) gave the title compound.

Yield: 54.3%, white solid. ¹H-NMR (DMSO-d₆): δ 1.08-1.22 (2H, m), 1.59-1.62 (2H, m), 1.77-1.80 (1H, m), 2.50-2.55 (2H, m), 2.87 (2H, brs), 3.75 (1H, br), 4.39 (1H, br), 7.06 (1H, d, J=8.4 Hz), 7.17-7.20 (3H, m), 7.28 (2H, t, J=7.2 Hz), 7.49 (1H, dd, J=8.4, 2.1 Hz), 7.84 (1H, s), 7.93 (1H, d, J=2.1 Hz), 8.47 (2H, s), 10.89 (1H, s), 11.65 (1H, s).

Example 87

N-[3,5-Bis(trifluoromethyl)phenyl]-5-dimethylsulfamoyl-2-hydroxybenzamide (1) 2-Methoxy-5-sulfamoylbenzoic acid Methyl 2-methoxy-5-sulfamoylbenzoate (4.91 g, 20 mmol) was dissolved in methanol (30 mL). 2 N aqueous sodium hydroxide (30 mL, 60 mmol) was added, and the mixture was stirred at room temperature for 1 hour. The reaction mixture was poured into 2 N hydrochloric acid, and the separated solid was filtered to give the title compound (4.55 g, 98.3%) as a white solid.

¹H-NMR (DMSO-d₆): δ 3.89 (3H, s), 7.30 (1H, d, J=8.7 Hz), 7.32 (2H, s), 7.92 (1H, dd, J=8.7, 2.7 Hz), 8.09 (1H, d, J=2.7 Hz), 13.03 (1H, br).

(2) N-[3,5-Bis(trifluoromethyl)phenyl]-2-methoxy-5-sulfamoylbenzamide

Using 2-methoxy-5-sulfamoylbenzoic acid and 3,5-bis(trifluoromethyl)aniline as the raw materials, the same operation as the example 24 gave the title compound.

Yield: 24.2%. ¹H-NMR (DMSO-d₆): δ 3.97 (3H, s), 7.38 (2H, s), 7.39 (1H, d, J=8.7 Hz), 7.85 (1H, s), 7.96 (1H, dd, J=8.7, 2.4 Hz), 8.06 (1H, d, J=2.4 Hz), 8.43 (2H, s), 10.87 (1H, s).

(3) N-[3,5-Bis(trifluoromethyl)phenyl]-5-dimethylsulfamoyl-2-methoxybenzamide

A suspension of N-[3,5-bis(trifluoromethyl)phenyl]-2-methoxy-5-sulfamoylbenzamide (442 mg, 1.0 mmol), methyl iodide (710 mg, 5.0 mmol) and sodium carbonate (415 mg, 3.0 mmol) in acetonitrile (10 mL) was refluxed for 3 hours. After cooling to room temperature, the reaction mixture was poured into water and extracted with ethyl acetate. After the organic layer was washed with water and brine, dried over anhydrous magnesium sulfate, the residue obtained by evaporating the solvent under reduced pressure was recrystallized from a mixed solvent of n-hexane and ethyl acetate (2:1) to give the title compound (207 mg, 44.1%) as a white solid.

¹H-NMR (DMSO-d₆): δ 2.62 (6H, s), 3.99 (3H, s), 7.45 (1H, d, J=9.0 Hz), 7.85 (1H, s), 7.91 (1H, dd, J=8.7, 2.4 Hz), 7.95 (1H, d, J=2.4 Hz), 8.43 (2H, s), 10.90 (1H, s).

(4) N-[3,5-Bis(trifluoromethyl)phenyl]-5-dimethylsulfamoyl-2-hydroxybenzamide

Using N-[3,5-bis(trifluoromethyl)phenyl]-5-dimethylsulfamoyl-2-methoxybenzamide as the raw material, the same operation as the example 80(5) gave the title compound.

¹H-NMR (DMSO-d₆): δ 2.77 (3H, d, J=4.5 Hz), 4.37 (1H, brs), 6.70 (1H, d, J=3.6 Hz), 7.04 (2H, s).

Example 88

N-[3,5-Bis(trifluoromethyl)phenyl]-2-hydroxy-5-(pyrrole-1-sulfonyl)benzamide (Compound No. 87)

(1) N-[3,5-Bis(trifluoromethyl)phenyl]-2-methoxy-5-(pyrrole-1-sulfonyl)benzamide A mixture of N-[3,5-bis(trifluoromethyl)phenyl)phenyl]-2-methoxy-5-sulfamoyl-benzamide (442 mg, 1 mmol), 2,5-dimethoxytetrahydrofuran (159 mg, 1.2 mmol) and acetic acid (5 mL) was refluxed for 2 hours. After cooling, the reaction mixture was poured into water and extracted with ethyl acetate. After the organic layer was washed with water, saturated aqueous sodium hydrogen carbonate and brine, dried over anhydrous magnesium sulfate, the residue obtained by evaporating the solvent under reduced pressure was purified by chromatography on silica gel (n-hexane:ethyl acetate=3:2) to give the title compound (436.5 mg, 88.6%) as a white solid.

¹H-NMR (DMSO-d₆): δ 3.96 (3H, s), 6.36 (2H, d, J=2.4, 2.1 Hz), 7.37 (2H, dd, J=2.4, 2.1 Hz), 7.42 (1H, d, J=9.0 Hz), 7.85 (1H, s), 8.80 (1H, dd, J=9.0, 2.4 Hz), 8.18 (1H, d, J=2.7 Hz), 8.38 (2H, s), 10.92 (1H, s).

(2) N-[3,5-Bis(trifluoromethyl)phenyl]-2-hydroxy-5-(pyrrole-1-sulfonyl)benzamide Using N-[3,5-bis(trifluoromethyl)phenyl]-2-methoxy-5-(pyrrole-1-sulfonyl)-benzamide as the raw material, the same operation as the example 80(5) gave the title compound.

Yield: 79.4%. $^1$H-NMR (DMSO-$d_6$, δ): 6.36 (2H, dd, J=2.4, 2.1 Hz), 7.18 (1H, d, J=9.0 Hz), 7.34 (2H, d, J=2.4, 2.1 Hz), 7.86 (1H, s), 7.99 (1H, dd, J=9.0, 2.7 Hz), 8.31 (1H, d, J=2.7 Hz), 8.42 (2H, s), 10.98 (1H, s).

Example 89

5-Amino-N-[3,5-bis(trifluoromethyl)phenyl]-2-hydroxybenzamide (Compound No. 88)

Using N-[3,5-bis(trifluoromethyl)phenyl]-2-hydroxy-5-nitrobenzamide as the raw material, the same operation as the example 84(4) gave the title compound.

Yield: 98.0%. $^1$H-NMR (DMSO-$d_6$): δ 4.79 (2H, brs), 6.76 (1H, d, J=2.1 Hz), 6.76 (1H, s), 7.09 (1H, dd, J=2.1, 1.2 Hz), 7.80 (1H, s), 8.45 (2H, s), 10.30 (1H, br), 10.84 (1H, s).

Example 90

N-[3,5-Bis(trifluoromethyl)phenyl]-5-dimethylamino-2-hydroxybenzamide

Using 5-dimethylaminosalicylic acid and 3,5-bis(trifluoromethyl)aniline as the raw materials, the same operation as the example 16 gave the title compound.

Yield: 28.8%. $^1$H-NMR (DMSO-$d_6$): δ 2.85 (6H, s), 6.92 (1H, d, J=9.0 Hz), 7.01 (1H, dd, J=8.7, 3.0 Hz), 7.22 (1H, d, J=3.0 Hz), 7.84 (1H, s), 8.47 (2H, s), 10.62 (1H, s), 10.83 (1H, s).

Example 91

5-Benzoylamino-N-[3,5-bis(trifluoromethyl)phenyl]-2-hydroxybenzamide (Compound No. 90)

Under argon atmosphere, a mixture of 5-amino-N-[3,5-bis(trifluoromethyl)-phenyl]-2-hydroxybenzamide (364 mg, 1 mmol), pyridine (95 mg, 1.2 mmol) and tetrahydrofuran (10 mL) was cooled on ice. Benzoyl chloride (155 mg, 1.1 mmol) was added, and the mixture was stirred for 1 hour. The reaction mixture was poured into water and extracted with ethyl acetate. After the organic layer was washed with water and brine, dried over anhydrous magnesium sulfate, the residue obtained by evaporation under reduced pressure was purified by chromatography on silica gel (n-hexane:ethyl acetate=4:1) to give the title compound (121 mg, 25.7%) as a white solid.

$^1$H-NMR (DMSO-$d_6$): δ 7.04 (1H, d, J=8.7 Hz), 7.51-7.62 (3H, m), 7.81 (1H, dd, J=8.7, 2.4 Hz), 7.83 (1H, s), 7.98 (2H, d, J=7.2 Hz), 8.22 (1H, d, J=2.4 Hz), 8.49 (2H, s), 10.27 (1H, s), 10.89 (1H, s), 11.07 (1H, s).

Example 92

N-[3,5-Bis(trifluoromethyl)phenyl]-2-hydroxy-5-[(3-phenyl)ureido]benzamide (Compound No. 91)

5-Amino-N-[3,5-bis(trifluoromethyl)phenyl]-2-hydroxybenzamide (100.2 mg, 0.28 mmol) was dissolved in acetonitrile (4 ml). 4-Dimethylaminopyridine (3 mg) and phenylisocyanate (30 μl, 0.28 mmol) were added, and the mixture was stirred at 60° C. for 5 minutes. The reaction mixture was concentrated and the residue was purified by chromatography on silica gel (hexane:ethyl acetate=1:1) to give the title compound (54.8 mg, 41.2%) as a light brown solid.

$^1$H-NMR (DMSO-$d_6$): δ 6.93-6.98 (1H, m), 6.97 (1H, d, J=9.3 Hz), 7.27 (2H, t, J=7.8 Hz), 7.34-7.46 (2H, m), 7.50 (1H, dd, J=9.0, 2.4 Hz), 7.83 (1H, s), 7.88 (1H, s), 8.47 (2H, s), 8.56 (1H, s), 8.63 (1H, s), 10.87 (1H, s), 10.89 (1H, s).

Example 93

N-[3,5-Bis(trifluoromethyl)phenyl]-2-hydroxy-5-[(3-phenyl)-thioureido]benzamide (Compound No. 92)

Using 5-amino-N-[3,5-bis(trifluoromethyl)phenyl]-2-hydroxybenzamide and phenylisothiocyanate as the raw materials, the same operation as the example 92 gave the title compound.

Yield: 66.3%. $^1$H-NMR (DMSO-$d_6$): δ 7.00 (1H, d, J=8.4 Hz), 7.13 (1H, tt, J=7.5, 1.2 Hz), 7.34 (2H, t, J=7.8 Hz), 7.45-7.51 (3H, m), 7.84 (1H, s), 7.87 (1H, d, J=2.7 Hz), 8.47 (2H, s), 9.65 (1H, s), 9.74 (1H, s), 10.84 (1H, s), 11.32 (1H, s).

Example 94

N-[3,5-Bis(trifluoromethyl)phenyl]-2-hydroxy-5-[(4-nitrophenyl)-diazenyl]benzamide (Compound No. 93)

Using 5-[(4-nitrophenyl)diazenyl]salicylic acid and 3,5-bis(trifluoromethyl)aniline as the raw materials, the same operation as the example 16 gave the title compound.

Yield: 11.3%. $^1$H-NMR (DMSO-$d_6$): δ 7.23 (1H, d, J=9.0 Hz), 7.87 (1H, s), 8.06 (2H, d, J=9.0 Hz), 8.10 (1H, d, J=9.0, 2.4 Hz), 8.44 (2H, d, J=9.00 Hz), 8.50 (2H, s), 8.53 (1H, d, J=2.4 Hz), 11.13 (1H, s), 12.14 (1H, br).

Example 95

N-[3,5-Bis(trifluoromethyl)phenyl]-2-hydroxy-5-({[(4-pyridin-2-yl)sulfamoyl]phenyl}diazenyl)benzamide (Compound No. 94)

Using 5-({[(4-pyridin-2-yl)sulfamoyl]phenyl}diazenyl) salicylic acid and 3,5-bis(trifluoromethyl)aniline as the raw materials, the same operation as the example 16 gave the title compound.

Yield: 7.9%. $^1$H-NMR (DMSO-$d_6$): δ 6.87 (1H, t, J=6.0 Hz), 7.22 (1H, d, J=8.7 Hz), 7.21-7.23 (1H, m), 7.77 (1H, t, J=8.4 Hz), 7.87 (1H, s), 7.95-7.98 (3H, m), 8.03-8.07 (4H, m), 8.47 (1H, d, J=2.4 Hz), 8.49 (2H, s), 11.14 (1H, s), 12.03 (1H, br).

Example 96

2-Acetoxy-N-[3,5-bis(trifluoromethyl)phenyl]-5-chlorobenzamide (Compound No. 96)

N-[3,5-Bis(trifluoromethyl)phenyl]-5-chloro-2-hydroxybenzamide (1.51 g, 3 mmol) and pyridine (285 mg, 3.6 mmol) were dissolved in tetrahydrofuran (6 mL). Acetyl chloride (234 mg, 3.3 mmol) was added dropwise under ice cooling, and the mixture was stirred at room temperature for 1 hour. The solvent was evaporated under reduced pressure. 2 N hydrochloric acid was added to the residue, and it was extracted with ethyl acetate. After the ethyl acetate layer was washed with water and brine, dried over anhydrous magnesium sulfate and concentrated, the residue was recrystallized from n-hexane-ethyl acetate to give the title compound (1.06 g, 83.0%) as a white solid.

$^1$H-NMR (DMSO-$d_6$): δ 2.22 (3H, s), 7.35 (1H, d, J=9.0 Hz), 7.71 (1H, dd, J=8.7, 2.7 Hz), 7.85 (1H, s), 7.88 (1H, d, J=2.7 Hz), 8.37 (2H, s), 11.05 (1H, brs).

Example 97

4-Acetylamino-N-[3,5-bis(trifluoromethyl)phenyl]-5-chloro-2-hydroxybenzamide (Compound No. 97)

(1) 4-Acetylamino-5-chloro-2-methoxybenzoic acid

Using 4-acetylamino-5-chloro-2-methoxybenzoic acid methyl ester as the raw material, the same operation as the example 82 gave the title compound.

Yield: 38.0%. $^1$H-NMR (DMSO-$d_6$): δ 2.16 (3H, s), 3.78 (3H, s), 7.72 (1H, s), 7.77 (1H, s), 9.57 (1H, s), 12.74 (1H, s).

(2) 4-Acetylamino-N-[3,5-bis(trifluoromethyl)phenyl]-5-chloro-2-methoxybenzamide Using 4-acetylamino-5-chloro-2-methoxybenzoic acid and 3,5-bis(trifluoromethyl)aniline as the raw materials, the same operation as the example 24 gave the title compound.

Yield: 23.8%. $^1$H-NMR (DMSO-$d_6$): δ 2.17 (3H, s), 3.89 (3H, s), 7.77-7.82 (3H, m), 8.45-8.49 (2H, m), 9.66 (1H, s), 10.68 (1H, s).

(3) 4-Acetylamino-N-[3,5-bis(trifluoromethyl)phenyl]-5-chloro-2-hydroxybenzamide Using 4-acetylamino-N-[3,5-bis(trifluoromethyl)phenyl]-5-chloro-2-methoxybenzamide as the raw material, the same operation as the example 80 gave the title compound.

Yield: 72.8%. $^1$H-NMR (DMSO-$d_6$): δ 2.17 (3H, s), 7.75 (1H, s), 7.82 (1H, s), 7.95 (1H, s), 8.44 (2H, s), 9.45 (1H, s), 11.16 (1H, brs), 11.63 (1H, brs).

Example 98

N-[3,5-Bis(trifluoromethyl)phenyl]-4-chloro-2-hydroxybenzamide (Compound No. 98)

Using 4-chlorosalicylic acid and 3,5-bis(trifluoromethyl)aniline as the raw materials, the same operation as the example 16 gave the title compound.

Yield: 55.8%. $^1$H-NMR (DMSO-$d_6$): δ 7.05-7.08 (2H, m), 7.84-7.87 (2H, m), 8.45 (2H, s), 10.84 (1H, s), 11.64 (1H, brs).

Example 99

N-[3,5-Bis(trifluoromethyl)-2-bromophenyl]-5-chloro-2-hydroxybenzamide (Compound No. 99)

Using 5-chlorosalicylic acid and 3,5-bis(trifluoromethyl)-2-bromoaniline as the raw materials, the same operation as the example 16 gave the title compound.

Yield: 14.5%. $^1$H-NMR (DMSO-$d_6$): δ 7.11 (1H, d, J=9.0 Hz), 7.53 (1H, dd, J=9.0, 2.7 Hz), 7.91 (1H, d, J=1.8 Hz), 7.98 (1H, d, J=2.7 Hz), 9.03 (1H, d, J=1.8 Hz), 11.26 (1H, brs).

Example 100

N-[2,5-Bis(trifluoromethyl)phenyl]-5-chloro-2-hydroxybenzamide (Compound No. 100)

Using 5-chlorosalicylic acid and 2,5-bis(trifluoromethyl)aniline as the raw materials, the same operation as the example 16 gave the title compound.

Yield: 3.6%. $^1$H-NMR (CDCl$_3$): δ 7.03 (1H, d, J=8.7 Hz), 7.43-7.48 (2H, m), 6.61 (1H, d, J=8.1 Hz), 7.85 (1H, d, J=8.4 Hz), 8.36 (1H, brs), 8.60 (1H, s), 11.31 (1H, s).

Example 101

N-[2,5-Bis(trifluoromethyl)phenyl]-5-bromo-2-hydroxybenzamide (Compound No. 101)

Using 5-bromosalicylic acid and 2,5-bis(trifluoromethyl)aniline as the raw materials, the same operation as the example 16 gave the title compound.

Yield: 24.0%. $^1$H-NMR (DMSO-$d_6$): δ 7.03 (1H, d, J=8.7 Hz), 7.65 (1H, dd, J=8.7, 2.7 Hz), 7.76 (1H, d, J=8.4 Hz), 8.03 (1H, d, J=8.1 Hz), 8.11 (1H, d, J=2.7 Hz), 8.74 (1H, s), 11.02 (1H, s), 12.34 (1H, s).

Example 102

N-[2,5-Bis(trifluoromethyl)phenyl]-2-hydroxy-5-methylbenazamide (Compound No. 102)

Using 5-methylsalicylic acid and 2,5-bis(trifluoromethyl)aniline as the raw materials, the same operation as the example 16 gave the title compound.

Yield: 1.5%. $^1$H-NMR (CDCl$_3$): 2.36 (3H, m) 6.97 (1H, d, J=8.4 Hz), 7.23 (1H, s), 7.32 (1H, dd, J=8.4, 1.5 Hz), 7.57 (1H, d, J=8.4 Hz), 7.83 (1H, d, J=8.4 Hz), 8.46 (1H, s), 8.69 (1H, s), 11.19 (1H, s).

Example 103

2-Acetoxy-N-[2,5-bis(trifluoromethyl)phenyl]-5-chlorobenzamide (Compound No. 103)

Using N-[2,5-bis(trifluoromethyl)phenyl] 5-chloro-2-hydroxybenzamide and acetyl chloride as the raw materials, the same operation as the example 96 gave the title compound.

Yield: 6.6%. $^1$H-NMR (CDCl$_3$): δ 2.35 (3H, s), 7.17 (1H, d, J=8.7 Hz), 7.54 (1H, dd, J=8.7, 2.4 Hz), 7.55 (1H, d, J=8.1 Hz), 7.80 (1H, d, J=8.1 Hz), 7.95 (1H, d, J=2.4 Hz), 8.60 (1H, s), 8.73 (1H, s).

Example 104

5-Chloro-2-hydroxy-N-[2-(trifluoromethyl)phenyl]benzamide (Compound No. 104)

Using 5-chlorosalicylic acid and 2-(trifluoromethyl)aniline as the raw materials, the same operation as the example 16 gave the title compound.

Yield: 58.0%. $^1$H-NMR (DMSO-$d_6$): δ 7.07 (1H, d, J=8.7 Hz). 7.42 (1H, t, J=7.5 Hz), 7.52 (1H, d, J=8.7, 2.7 Hz), 7.74 (1H, t, J=8.1 Hz), 7.77 (1H, t, J=8.1 Hz), 7.99 (1H, d, J=2.7 Hz), 8.18 (1H, d, J=8.1 Hz), 10.76 (1H, s), 12.22 (1H, s).

Example 105

5-Chloro-N-[4-chloro-2-trifluoromethyl)phenyl]-2-hydroxybenzamide (Compound No. 105)

Using 5-chlorosalicylic acid and 4-chloro-2-(trifluoromethyl)aniline as the raw materials, the same operation as the example 16 gave the title compound.

Yield: 21.5%. $^1$H-NMR (DMSO-$d_6$): δ 7.07 (1H, d, J=8.7 Hz), 7.52 (1H, dd, J=8.7, 2.7 Hz), 7.80-7.85 (2H, m), 7.97 (1H, d, J=2.7 Hz), 8.26 (1H, d, J=8.4 Hz), 10.80 (1H, s), 12.26 (1H, s),

Example 106

5-Bromo-2-hydroxy-N-[3-(trifluoromethyl)phenyl]benzamide (Compound No. 106)

Using 5-bromosalicylic acid and 3-(trifluoromethyl)aniline as the raw materials, the same operation as the example 16 gave the title compound.

Yield: 50.3%. $^1$H-NMR (DMSO-$d_6$, δ): 6.98 (1H, d, J=8.7 Hz), 7.48-7.52 (1H, m), 7.59 (1H, dd, J=8.7, 2.7 Hz), 7.62 (1H, t, J=8.1 Hz), 7.92-7.96 (1H, m), 8.02 (1H, d, J=2.4 Hz), 8.20 (1H, s), 10.64 (1H, s), 11.60 (1H, s).

Example 107

5-Chloro-N-[2-fluoro-3-(trifluoromethyl)phenyl]-2-hydroxybenzamide (Compound No. 107)

Using 5-chlorosalicylic acid and 2-fluoro-3-(trifluoromethyl)aniline as the raw materials, the same operation as the example 16 gave the title compound.

Yield: 71.7%, white solid. $^1$H-NMR (DMSO-$d_6$): δ 7.07 (1H, d, J=9.0 Hz), 7.46 (1H, t, J=7.8 Hz), 7.52 (1H, dd, J=9.0, 2.7 Hz), 7.58 (1H, t, J=7.2 Hz), 7.96 (1H, d, J=2.7 Hz), 8.49 (1H, t, J=7.2 Hz), 10.82 (1H, s), 12.13 (1H, brs).

Example 108

5-Chloro-N-[4-fluoro-3-(trifluoromethyl)phenyl]-2-hydroxybenzamide (Compound No. 108)

Using 5-chlorosalicylic acid and 4-fluoro-3-(trifluoromethyl)aniline as the raw materials, the same operation as the example 16 gave the title compound.

Yield: 72.1%, white solid. $^1$H-NMR (DMSO-$d_6$): δ 7.03 (1H, d, J=9.0 Hz), 7.48 (1H, dd, J=8.7, 2.7 Hz), 7.56 (1H, d, J=9.9 Hz), 7.90 (1H, d, J=2.7 Hz), 7.99-8.03 (1H, m), 8.21 (1H, dd, J=6.6, 2.4 Hz), 10.63 (1H, s), 11.58 (1H, s).

Example 109

5-Bromo-N-[4-chloro-3-(trifluoromethyl)phenyl]-2-hydroxybenzamide (Compound No. 109)

Using 5-bromosalicylic acid and 4-chloro-3-(trifluoromethyl)aniline as the raw materials, the same operation as the example 16 gave the title compound.

Yield: 37.4%. $^1$H-NMR (DMSO-$d_6$): δ 6.98 (1H, d, J=8.7 Hz), 7.59 (1H, dd, J=8.7, 2.4 Hz), 7.73 (1H, d, J=8.7 Hz), 7.98 (1H, d, J=2.4 Hz), 8.00 (1H, dd, J=8.7, 2.4 Hz), 8.31 (1H, d, J=2.4 Hz), 10.68 (1H, s), 11.52 (1H, brs).

Example 110

5-Chloro-N-[3-fluoro-5-(trifluoromethyl)phenyl]-2-hydroxybenzamide (Compound No. 110)

Using 5-chlorosalicylic acid and 3-fluoro-5-(trifluoromethyl)aniline as the raw materials, the same operation as the example 16 gave the title compound.

Yield: 62.0%. $^1$H-NMR (DMSO-$d_6$): δ 7.04 (1H, d, J=8.7 Hz), 7.42 (1H, d, J=8.4 Hz), 7.48 (1H, dd, J=9.0, 3.0 Hz), 7.85 (1H, d, J=2.4 Hz), 7.94 (1H, dd, J=11.4, 2.1 Hz), 7.99 (1H, s), 10.73 (1H, s), 11.46 (1H, s).

Example 111

5-Bromo-N-3-bromo-N-[3-bromo-5-(trifluoromethyl)phenyl]-2-hydroxybenzamide (Compound No. 111)

Using 5-bromosalicylic acid and 3-bromo-5-(trifluoromethyl)aniline as the raw materials, the same operation as the example 16 gave the title compound.

Yield: 73.3%. $^1$H-NMR (DMSO-$d_6$): δ 6.99 (1H, d, J=9.0 Hz), 7.60 (1H, dd, J=9.0, 2.4 Hz), 7.72 (1H, s), 7.97 (1H, d, J=2.7 Hz), 8.16 (1H, s), 8.28 (1H, s), 10.69 (1H, s), 11.45 (1H, s).

Example 112

5-Chloro-N-[2-fluoro-5-(trifluoromethyl)phenyl]-2-hydroxybenzamide (Compound No. 112)

Using 5-chlorosalicylic acid and 2-fluoro-5-(trifluoromethyl)aniline as the raw materials, the same operation as the example 16 gave the title compound.

Yield: 77.9%. $^1$H-NMR (DMSO-$d_6$): δ 7.07 (1H, d, J=9.0 Hz), 7.52 (1H, dd, J=9.0, 2.7 Hz), 7.58-7.61 (2H, m), 7.95 (1H, d, J=2.7 Hz), 8.71 (1H, d, J=7.5 Hz), 10.90 (1H, s), 12.23 (1H, s).

Example 113

5-Chloro-N-[2-chloro-5-(trifluoromethyl)phenyl]-2-hydroxybenzamide (Compound No. 113)

Using 5-chlorosalicylic acid and 2-chloro-5-(trifluoromethyl)aniline as the raw materials, the same operation as the example 16 gave the title compound.

Yield: 49.1%. $^1$H-NMR (DMSO-$d_6$): δ 7.09 (1H, d, J=9.0 Hz), 7.53 (1H, dd, J=9.0, 3.0 Hz), 7.55 (1H, dd, J=8.4, 2.7 Hz), 7.83 (1H, d, J=8.4 Hz), 7.98 (1H, d, J=3.0 Hz), 8.88 (1H, d, J=2.7 Hz), 11.14 (1H, s), 12.39 (1H, s).

Example 114

5-Bromo-N-[2-chloro-5-(trifluoromethyl)phenyl]-2-hydroxybenzamide (Compound No. 114)

Using 5-bromosalicylic acid and 2-chloro-5-(trifluoromethyl)aniline as the raw materials, the same operation as the example 16 gave the title compound.

Yield: 34.2%. $^1$H-NMR (DMSO-$d_6$): δ 7.04 (1H, d, J=8.7 Hz), 7.56 (1H, ddd, J=8.1, 2.4, 1.2 Hz), 7.64 (1H, dd, J=8.7, 2.7 Hz), 7.83 (1H, dd, J=8.1, 1.2 Hz), 8.11 (1H, d, J=2.7 Hz), 8.87 (1H, d, J=2.4 Hz), 11.12 (1H, s), 12.42 (1H, s).

Example 115

5-Chloro-2-hydroxy-N-[4-nitro-3-(trifluoromethyl)phenyl]benzamide (Compound No. 115)

Using 5-chlorosalicylic acid and 4-nitro-3-(trifluoromethyl)aniline as the raw materials, the same operation as the example 16 gave the title compound.

Yield: 44.8%. $^1$H-NMR (DMSO-d$_6$): δ 7.04 (1H, d, J=9.0 Hz), 7.49 (1H, dd, J=9.0, 2.7 Hz), 7.81 (1H, d, J=2.7 Hz), 8.23-8.24 (2H, m), 8.43 (1H, d, J=1.2 Hz), 11.02 (1H, s), 11.30 (1H, br).

Example 116

5-Chloro-2-hydroxy-N-[2-nitro-5-(trifluoromethyl)phenyl]benzamide (Compound No. 116)

Using 5-chlorosalicylic acid and 2-nitro-5-(trifluoromethyl)aniline as the raw materials, the same operation as the example 16 gave the title compound.
Yield: 8.1%. $^1$H-NMR (DMSO-d$_6$): δ 7.08 (1H, d, J=9.0 Hz), 7.53 (1H, dd, J=8.7, 2.7 Hz), 7.73 (1H, dd, J=8.4, 1.8 Hz), 7.95 (1H, d, J=3.0 Hz), 8.36 (1H, d, J=8.7 Hz), 9.01 (1H, d, J=1.8 Hz), 12.04 (1H, s), 12.20 (1H, s).

Example 117

5-Bromo-2-hydroxy-N-[4-nitro-3-(trifluoromethyl)phenyl]benzamide (Compound No. 117)

Using 5-bromosalicylic acid and 4-nitro-3-(trifluoromethyl)aniline as the raw materials, the same operation as the example 16 gave the title compound.
Yield: 49.7%. $^1$H-NMR (DMSO-d$_6$): δ 6.99 (1H, d, J=8.7 Hz), 7.60 (1H, dd, J=8.7, 2.4 Hz), 7.92 (1H, d, J=2.7 Hz), 8.16 (2H, s), 8.42 (1H, s), 10.93 (1H, s), 11.36 (1H, s).

Example 118

5-Chloro-2-hydroxy-N-[2-methyl-3-(trifluoromethyl)phenyl]benzamide (Compound No. 118)

Using 5-chlorosalicylic acid and 2-methyl-3-(trifluoromethyl)aniline as the raw materials, the same operation as the example 16 gave the title compound.
Yield: 14.5%. $^1$H-NMR (DMSO-d$_6$): δ 2.36 (3H, d, J=1.2 Hz), 7.05 (1H, d, J=8.7 Hz), 7.46 (1H, t, J=8.1 Hz), 7.50 (1H, dd, J=8.7, 2.7 Hz), 7.60 (1H, d, J=7.2 Hz), 7.99 (1H, d, J=7.2 Hz), 8.00 (1H, d, J=2.4 Hz), 10.43 (1H, s), 12.08 (1H, s).

Example 119

5-Chloro-2-hydroxy-N-[4-methyl-3-(trifluoromethyl)phenyl]benzamide (Compound No. 119)

Using 5-chlorosalicylic acid and 4-methyl-3-(trifluoromethyl)aniline as the raw materials, the same operation as the example 16 gave the title compound.
Yield: 80.2%. $^1$H-NMR (DMSO-d$_6$): δ 7.01 (1H, d, J=8.7 Hz), 7.44 (1H, d, J=8.4 Hz), 7.47 (1H, dd, J=9.0, 2.7 Hz), 7.84 (1H, dd, J=8.4, 2.1 Hz), 7.92 (1H, d, J=2.7 Hz), 8.13 (1H, d, J=2.1 Hz), 10.65 (1H, s), 11.68 (1H, br).

Example 120

5-Chloro-2-hydroxy-N-[2-methyl-5-(trifluoromethyl)phenyl]benzamide (Compound No. 120)

Using 5-chlorosalicylic acid and 2-methyl-5-(trifluoromethyl)aniline as the raw materials, the same operation as the example 16 gave the title compound.
Yield: 73.3%. $^1$H-NMR (DMSO-d$_6$): δ 2.39 (3H, s), 7.07 (1H, d, J=8.7 Hz), 7.44-7.54 (3H, m), 7.99 (1H, d, J=3.0 Hz), 8.43 (1H, s), 10.52 (1H, s), 12.17 (1H, brs).

Example 121

5-Chloro-2-hydroxy-N-[4-methoxy-3-(trifluoromethyl)phenyl]benzamide (Compound No. 121)

Using 5-chlorosalicylic acid and 4-methoxy-3-(trifluoromethyl)aniline as the raw materials, the same operation as the example 16 gave the title compound.
Yield: 79.1%. $^1$H-NMR (DMSO-d$_6$): δ 7.02 (1H, d, J=9.0 Hz), 7.30 (1H, d, J=9.00 Hz), 7.48 (1H, dd, J=9.0, 3.0 Hz), 7.92 (1H, dd, J=9.0, 2.4 Hz), 7.96 (1H, d, J=2.7 Hz), 8.04 (1H, d, J=2.4 Hz), 10.47 (1H, s), 11.78 (1H, s).

Example 122

5-Bromo-2-hydroxy-N-[3-methoxy-5-(trifluoromethyl)phenyl]benzamide (Compound No. 122)

Using 5-bromosalicylic acid and 3-methoxy-5-(trifluoromethyl)aniline as the raw materials, the same operation as the example 16 gave the title compound.
Yield: 58.8%. $^1$H-NMR (DMSO-d$_6$): δ 3.85 (3H, s), 6.98 (1H, d, J=8.7 Hz), 7.03 (1H, s), 7.57-7.61 (2H, m), 7.77 (1H, s), 8.00 (1H, d, J=2.4 Hz), 10.57 (1H, s), 11.56 (1H, s).

Example 123

5-Bromo-2-hydroxy-N-[2-methoxy 5-(trifluoromethyl)phenyl]benzamide (Compound No. 123)

Using 5-bromosalicylic acid and 2-methoxy-5-(trifluoromethyl)aniline as the raw materials, the same operation as the example 16 gave the title compound.
Yield: 71.3%. $^1$H-NMR (DMSO-d$_6$): δ 3.99 (3H, s), 7.03 (1H, d, J=9.0 Hz), 7.30 (1H, d, J=8.7 Hz), 7.47-7.51 (1H, m), 7.61 (1H, dd, J=9.0, 2.4 Hz), 8.10 (1H, d, J=2.4 Hz), 8.82 (1H, d, J=2.1 Hz), 11.03 (1H, s), 12.19 (1H, s).

Example 124

5-Chloro-hydroxy-N-[2-methoxy-5-(trifluoromethyl)phenyl]-2-benzamide (Compound No. 124)

Using 6-chlorosalicylic acid and 2-methoxy-5-(trifluoromethyl)aniline as the raw materials, the same operation as the example 16 gave the title compound.
Yield: 83.4%. $^1$H-NMR (DMSO-d$_6$): δ 4.00 (3H, s), 7.08 (1H, d, J=9.0 Hz), 7.30 (1H, d, J=8.7 Hz), 7.47-7.52 (2H, m), 7.97 (1H, d, J=2.7 Hz), 8.83 (1H, d, J=2.4 Hz), 11.05 (1H, s), 12.17 (1H, s).

Example 125

5-Chloro-2-hydroxy-N-[2-methylsulfanyl-5-(trifluoromethyl)-phenyl]benzamide (Compound No. 125)

Using 5-chlorosalicylic acid and 2-methyl-5-(trifluoromethyl)aniline as the raw materials, the same operation as the example 16 gave the title compound.
Yield: 79.2%. $^1$H-NMR (DMSO-d$_6$): δ 2.57 (3H, s), 7.07 (1H, d, J=8.7 Hz), 7.52 (1H, dd, J=8.7, 2.4 Hz), 7.55 (1H, dd, J=8.4, 1.5 Hz), 7.63 (1H, d, J=8.1 Hz), 8.00 (1H, d, J=2.4 Hz), 8.48 (1H, d, J=1.5 Hz), 10.79 (1H, s), 12.26 (1H, s).

Example 126

5-Bromo-2-hydroxy-N-[2-(1-pyrrolidinyl)-5-(trifluoromethyl)-phenyl]benzamide (Compound No. 126)

Using 5-bromosalicylic acid and 2-(1-pyrrolidinyl)-5-(trifluoromethyl)aniline as the raw materials, the same operation as the example 16 gave the title compound.

Yield: 44.5%. $^1$H-NMR (DMSO-$d_6$): δ 1.86-1.91 (4H, m), 3.20-3.26 (4H, m), 6.99 (1H, d, J=8.7 Hz), 7.07 (1H, d, J=8.7 Hz), 7.43 (1H, dd, J=8.7, 2.1 Hz), 7.62 (1H, dd, J=8.7, 2.4 Hz), 7.94 (1H, d, J=2.1 Hz), 8.17 (1H, d, J=2.4 Hz), 10.54 (1H, s), 12.21 (1H, s).

Example 127

5-Bromo-2-hydroxy-N-[2-morpholino-5-(trifluoromethyl)phenyl]-benzamide (Compound No. 127)

Using 5-bromosalicylic acid and 2-morpholino-5-(trifluoromethyl)aniline as the raw materials, the same operation as the example 16 gave the title compound.

Yield: 65.9%. $^1$H-NMR (DMSO-$d_6$): δ 2.90 (4H, dd, J=4.5, 4.2 Hz), 3.84 (4H, dd, J=4.8, 4.2 Hz), 7.09 (1H, d, J=8.4 Hz), 7.48 (2H, s), 7.61 (1H, dd, J=8.4, 2.7 Hz), 8.13 (1H, d, J=2.7 Hz), 8.90 (1H, s), 11.21 (1H, s), 12.04 (1H, s).

Example 128

5-Chloro-2-hydroxy-N-[4-(trifluoromethyl)phenyl]benzamide (Compound No. 128)

Using 5-chlorosalicylic acid and 4-(trifluoromethyl)aniline as the raw materials, the same operation as the example 16 gave the title compound.

Yield: 75.0%, white solid. $^1$H-NMR (DMSO-$d_6$): δ 7.04 (1H, d, J=9.0 Hz), 7.48 (1H, dd, J=8.7, 2.7 Hz), 7.74 (2H, d, J=8.7 Hz), 7.90 (1H, d, J=2.7 Hz), 7.95 (2H, d, J=9.0 Hz), 10.65 (1H, s), 11.59 (1H, s).

Example 129

5-Bromo-N-[2-chloro-4-(trifluoromethyl)phenyl]-2-hydroxybenzamide (Compound No. 129)

Using 5-bromosalicylic acid and 2-chloro-4-(trifluoromethyl)aniline as the raw materials, the same operation as the example 16 gave the title compound.

Yield: 34.9%.
$^1$H-NMR (DMSO-$d_6$): δ 7.04 (1H, d, J=8.7 Hz), 7.64 (1H, dd, J=8.7, 2.7 Hz), 7.79 (1H, dd, J=9.0, 2.1 Hz), 7.99 (1H, d, J=2.1 Hz), 8.11 (1H, d, J=2.4 Hz), 8.73 (1H, d, J=9.0 Hz), 11.15 (1H, s), 12.42 (1H, s).

Example 130

2-Acetoxy-5-chloro-N-[2-chloro-5-(trifluoromethyl)phenyl]benzamide (Compound No. 130)

Using 5-chloro-N-[2-chloro-5-(trifluoromethyl)phenyl]-2 hydroxybenzamide and acetyl chloride as the raw materials, the same operation as the example 96 gave the title compound.

Yield: 34.0%. $^1$H-NMR (CDCl$_3$): δ 2.39 (3H, s), 7.16 (1H, d, J=8.7 Hz), 7.37 (1H, ddd, J=8.7, 2.4, 0.6 Hz), 7.51-7.56 (2H, m), 7.97 (1H, d, J=3.0 Hz), 8.84 (1H, s), 8.94 (1H, d, J=1.8 Hz).

Example 131

N-[2-Chloro-5-(trifluoromethyl)phenyl]-2-hydroxy-5-nitrobenzamide (Compound No. 131)

Using 5-nitrosalicylic acid and 2-chloro-5-(trifluoromethyl)aniline as the raw materials, the same operation as the example 16 gave the title compound.

Yield: 31.1%. $^1$H-NMR (DMSO-$d_6$): δ 6.98 (1H, d, J=9.3 Hz), 7.52 (1H, dd, J=8.4, 2.1 Hz), 7.81 (1H, d, J=8.4 Hz), 8.21 (1H, dd, J=9.0, 3.3 Hz), 8.82 (1H, d, J=3.0 Hz), 8.93 (1H, d, J=2.4 Hz), 12.18 (1H, s).

Example 132

N-[2-Chloro-5-trifluoromethyl)phenyl]-2-hydroxy-5-methylbenzamide (Compound No. 132)

Using 5-methylsalicylic acid and 2-chloro-5-(trifluoromethyl)aniline as the raw materials, the same operation as the example 16 gave the title compound.

Yield: 15.8%. $^1$H-NMR (CDCl$_3$): δ 2.36 (3H, s), 6.95 (1H, d, J=8.1 Hz), 7.26-7.31 (2H, m), 7.37 (1H, dd, J=8.4, 1.8 Hz), 7.56 (1H, d, J=8.4 Hz), 8.65 (1H, brs), 8.80 (1H, d, J=1.8 Hz), 11.33 (1H, brs).

Example 133

N-[2-Chloro-5-(trifluoromethyl)phenyl]-2-hydroxy-5-methoxybenzamide (Compound No. 133)

Using 5-methoxysalicylic acid and 2-chloro-5-(trifluoromethyl)aniline as the raw materials, the same operation as the example 16 gave the title compound.

Yield: 56.4%. $^1$H-NMR (DMSO-$d_6$): δ 3.77 (3H, s), 6.91 (1H, d, J=9.0 Hz), 7.07 (1H, dd, J=8.7, 3.0 Hz), 7.20 (1H, t, J=1.8 Hz), 7.52-7.54 (3H, m), 10.33 (1H, s), 11.44 (1H, s).

Example 134

N-[4-Chloro-3-(trifluoromethyl)phenyl]-2-hydroxy-5-methylbenzamide (Compound No. 134)

Using 5-methylsalicylic acid and 4-chloro-3-(trifluoromethyl)aniline as the raw materials, the same operation as the example 16 gave the title compound.

Yield: 70.4%. $^1$H-NMR (DMSO-$d_6$): δ 2.29 (3H, s), 6.91 (1H, d, J=8.3 Hz), 7.27 (1H, ddd, J=8.3, 2.2, 0.6 Hz), 7.71 (1H, d, J=2.2 Hz), 7.72 (1H, d, J=8.5 Hz), 8.02 (1H, dd, J=8.5, 2.5 Hz), 8.33 (1H, d, J=2.5 Hz), 10.64 (1H, s), 11.25 (1H, s).

Example 135

2-Hydroxy-5 methyl-N-[4-methyl-3-(trifluoromethyl)phenyl]benzamide (Compound No. 135)

Using 5-methylsalicylic acid and 4-methyl-3-(trifluoromethyl)aniline as the raw materials, the same operation as the example 16 gave the title compound.

Yield: 63.7%. $^1$H-NMR (DMSO-$d_6$): δ 2.29 (3H, s), 2.42 (3H, s), 6.89 (1H, d, J=8.4 Hz), 7.26 (1H, ddd, J=8.4, 2.1, 0.6

Hz), 7.44 (1H, d, J=8.1 Hz), 7.75 (1H, d, J=2.1 Hz), 7.56 (1H, dd, J=8.4, 1.8 Hz), 8.13 (1H, d, J=2.1 Hz), 10.50 (1H, s), 11.42 (1H, s).

Example 136

2-Hydroxy-5-methyl-N-[2-methyl-5-(trifluoromethyl)phenyl]benzamide (Compound No. 136)

Using 5-methylsalicylic acid and 2-methyl-5-(trifluoromethyl)aniline as the raw materials, the same operation as the example 16 gave the title compound.
Yield: 14.2%, white solid. $^1$H-NMR (DMSO-$d_6$): δ 2.29 (3H, s), 2.33 (3H, s), 6.94 (1H, d, J=8.4 Hz), 7.27 (1H, ddd, J=8.4, 2.4, 0.6 Hz), 7.44 (1H, dd, J=8.1, 1.5 Hz), 7.52 (1H, d, J=7.8 Hz), 7.84 (1H, d, J=2.4 Hz), 8.46 (1H, d, J=1.5 Hz), 10.55 (1H, s), 11.72 (1H, s).

Example 137

2-Hydroxy-N-[4-methoxy-3-(trifluoromethyl)phenyl]-5-methylbenzamide (Compound No. 137)

Using 5-methylsalicylic acid and 4-methoxy-3-(trifluoromethyl)aniline as the raw materials, the same operation as the example 16 gave the title compound.
Yield: 65.1%, slight yellow solid. $^1$H-NMR (DMSO-$d_6$): δ 2.35 (3H, s), 3.89 (3H, s), 6.88 (1H, d, J=8.4 Hz), 7.26 (1H, dd, J=8.1, 1.8 Hz), 7.30 (1H, d, J=8.4 Hz), 7.77 (1H, d, J=2.1 Hz), 7.92 (1H, dd, J=9.0, 2.1 Hz), 8.04 (1H, d, J=2.7 Hz), 10.42 (1H, s), 11.54 (1H, s).

Example 138

2-Hydroxy-N-[2-methoxy-5-(trifluoromethyl)phenyl]-5-methylbenzamide (Compound No. 138)

Using 5-methylsalicylic acid and 2-methoxy-5-(trifluoromethyl)aniline as the raw materials, the same operation as the example 16 gave the title compound.
Yield: 77.9%. $^1$H-NMR (CDCl$_3$): δ 2.35 (3H, s), 4.02 (3H, s), 6.93 (1H, d, J=9.0 Hz), 6.98 (1H, d, J=8.4 Hz), 7.25-7.28 (2H, m), 7.36 (1H, ddd, J=8.4, 2.1, 0.9 Hz), 8.65 (1H, brs), 8.73 (1H, d, J=2.1 Hz), 11.69 (1H, s).

Example 139

5-Bromo-2-hydroxy-N-phenylbenzamide (Compound No. 139)

Using 5-bromosalicylic acid and aniline as the raw materials, the same operation as the example 16 gave the title compound.
Yield: 68.8%. mp 229-230° C. $^1$H-NMR (DMSO-$d_6$): δ 6.96 (1H, d, J=9.0 Hz), 7.12-7.18 (1H, m), 7.35-7.41 (2H, m), 7.58 (1H, dd, J=8.7, 2.7 Hz), 7.67-7.71 (2H, m), 8.08 (1H, d, J=2.7 Hz), 10.43 (1H, s), 11.87 (1H, s).

Example 140

5-Bromo-N-(3-chlorophenyl)-2-hydroxybenzamide (Compound No. 140)

Using 5-bromosalicylic acid and 3-chloroaniline as the raw materials, the same operation as the example 16 gave the title compound.
Yield: 63.1%. mp 231-232° C. $^1$H-NMR (DMSO-$d_6$): δ 6.97 (1H, d, J=3.7 Hz), 7.19-7.22 (1H, m), 7.38-7.43 (1H, m), 7.57-7.63 (2H, m), 7.91-7.92 (1H, m), 8.01 (1H, d, J=2.7 Hz), 10.49 (1H, s), 11.84 (1H, s).

Example 141

5-Bromo-N-(4-chlorophenyl)-2-hydroxybenzamide (Compound No. 141)

This compound is a commercially available compound.
Supplier: Tokyo Kasei.
Catalog code number: B0897.

Example 142

5-Chloro-N-(2,5-dichlorophenyl)-2-hydroxybenzamide (Compound No. 142)

Using 5-chlorosalicylic acid and 2,5-dichloroaniline as the raw materials, the same operation as the example 16 gave the title compound.
Yield: 10.8%. $^1$H-NMR (DMSO-$d_6$): δ 7.08 (1H, d, J=9.0 Hz), 7.24-7.28 (1H, m), 7.50-7.54 (1H, m), 7.61 (1H, dd, J=9.0, 3.0 Hz), 7.97 (1H, d, J=2.7 Hz), 8.58 (1H, d, J=2.4 Hz), 11.02 (1H, s), 12.35 (1H, brs).

Example 143

5-Bromo-N-(3,4-dichlorophenyl)-2-hydroxybenzamide (Compound No. 143)

Using 5-bromosalicylic acid and 3,4-dichloroaniline as the raw materials, the same operation as the example 16 gave the title compound.
Yield: 58.2%. mp 249-251° C. $^1$H-NMR (DMSO-$d_6$): δ 6.97 (1H, d, J=8.7 Hz), 7.57-7.70 (3H, m), 7.98 (1H, d, J=2.7 Hz), 8.10 (1H, d, J=2.4 Hz), 10.54 (1H, s), 11.55 (1H, s).

Example 144

5-Bromo-N-(3,5-difluorophenyl)-2-hydroxybenzamide (Compound No. 144)

Using 5-bromosalicylic acid and 3,5-difluoroaniline as the raw materials, the same operation as the example 16 gave the title compound.
Yield: 36.3%. mp 259-261° C. $^1$H-NMR (DMSO-$d_6$): δ 6.96-7.04 (2H, m), 7.45-7.54 (2H, m), 7.58 (1H, dd, J=8.7, 2.7 Hz), 7.94 (1H, d, J=2.7 Hz), 10.60 (1H, s), 11.48 (1H, s).

Example 145

2-Acetoxy-N-(3,5-dichlorophenyl)benzamide (Compound No. 172)

Using o-acetylsalicyloyl chloride and 3,5-dichloroaniline as the raw materials, the same operation as the example 2(1) gave the title compound.

Yield: 73.5%. mp 167-168° C. $^1$H-NMR (CDCl$_3$): δ 2.35 (3H, s), 7.14-7.18 (2H, m), 7.35-7.40 (1H, m), 7.52-7.57 (3H, m), 7.81 (1H, dd, J=7.8, 1.8 Hz), 8.05 (1H, brs).

Example 146

N-(3,5-Dichlorophenyl)-2-hydroxybenzamide (Compound No. 145)

Using 2-acetoxy-N-(3,5-dichlorophenyl)benzamide as the raw material, the same operation as the example 2(2) gave the title compound.
Yield: 60.3%. mp 218-219° C. $^1$H-NMR (DMSO-d$_6$): δ 6.95-7.02 (2H, m), 7.35-7.36 (1H, m), 7.42-7.47 (1H, m), 7.83-7.87 (3H, m), 10.54 (1H, s), 11.35 (1H, s).

Example 147

N-(3,5-Dichlorophenyl)-5-fluoro-2-hydroxybenzamide (Compound No. 146)

Using 5-fluorosalicylic acid and 3,5-dichloroaniline as the raw materials, the same operation as the example 16 gave the title compound.
Yield: 33.3%. mp 258-260° C. $^1$H-NMR (DMSO-d$_6$): δ 7.00-7.05 (1H, m), 7.28-7.37 (2H, m), 7.63 (1H, dd, J=9.3, 3.3 Hz), 7.84 (2H, d, J=2.1 Hz), 10.56 (1H, s), 11.23 (1H, s).

Example 148

5-Chloro-N-(3,5-dichlorophenyl)-2-hydroxybenzamide (Compound No. 147)

Using 5-chlorosalicylic acid and 3,5-dichloroaniline as the raw materials, the same operation as the example 16 gave the title compound.
Yield: 41.2%. $^1$H-NMR (DMSO-d$_6$): δ 7.03 (1H, d, J=9.0 Hz), 7.36-7.37 (1H, m), 7.48 (1H, dd, J=8.7, 2.7 Hz), 7.83-7.84 (3H, m), 10.56 (1H, s), 11.44 (1H, s).

Example 149

5-Bromo-N-(3,5-dichlorophenyl)-2-hydroxybenzamide (Compound No. 148)

Using 5-bromosalicylic acid and 3,5-dichloroaniline as the raw materials, the same operation as the example 16 gave the title compound.
Yield: 61.6%. mp 243-244° C. $^1$H-NMR (DMSO-d$_6$): δ 6.98 (1H, d, J=8.7 Hz), 7.36-7.37 (1H, m), 7.59 (1H, dd, J=9.0, 2.4 Hz), 7.83 (2H, d, J=1.8 Hz), 7.95 (1H, d, J=2.4 Hz), 10.56 (1H, s), 11.46 (1H, s).

Example 150

N-(3,5-Dichlorophenyl)-2-hydroxy-5-iodobenzamide (Compound No. 149)

Using 5-iodosalicylic acid and 3,5-dichloroaniline as the raw materials, the same operation as the example 16 gave the title compound.
Yield: 65.4%. mp 244-245° C. $^1$H-NMR (DMSO-d$_6$): δ 6.84 (1H, d, J=9.0 Hz), 7.35-7.37 (1H, m), 7.72 (1H, dd, J=9.0, 2.1 Hz), 7.83 (2H, d, J=1.8 Hz), 8.09 (1H, d, J=2.1 Hz), 10.55 (1H, s), 11.45 (1H, s).

Example 151

3,5-Dibromo-N-(3,5-dichlorophenyl)-2-hydroxybenzamide (Compound No. 150)

Using 3,5-dibromosalicylic acid and 3,5-dichloroaniline as the raw materials, the same operation as the example 16 gave the title compound.
Yield: 44.2%. mp 181-182° C. $^1$H-NMR (DMSO-d$_6$): δ 7.42-7.43 (1H, m), 7.80 (2H, d, J=1.8 Hz), 8.03 (1H, d, J=2.1 Hz), 8.17 (1H, d, J=2.1 Hz), 10.82 (1H, s).

Example 152

4-Chloro-N-(3,5-dichlorophenyl)-2-hydroxybenzamide (Compound No. 151)

Using 4-chlorosalicylic acid and 3,5-dichloroaniline as the raw materials, the same operation as the example 16 gave the title compound.
Yield: 57.2%. mp 255-256° C. $^1$H-NMR (DMSO-d$_6$): δ 7.03-7.06 (2H, m), 7.34-7.36 (1H, m), 7.82-7.85 (3H, m), 10.51 (1H, s), 11.70 (1H, brs).

Example 153

N-(3,5-Dichlorophenyl)-2-hydroxy-5-nitrobenzamide (Compound No. 152)

Using 5-nitrosalicylic acid and 3,5-dichloroaniline as the raw materials, the same operation as the example 16 gave the title compound.
Yield: 83.1%. mp 232-233.
$^1$H-NMR (DMSO-d$_6$): δ 7.16 (1H, d, J=9.6 Hz), 7.37-7.39 (1H, m), 7.84 (1H, d, J=2.1 Hz), 8.29 (1H, dd, J=9.0, 3.0 Hz), 8.65 (1H, d, J=3.0 Hz), 10.83 (1H, s).

Example 154

N-(3,5-Dichlorophenyl)-2-hydroxy-5-methylbenzamide (Compound No. 153)

Using 5-methylsalicylic acid and 3,5-dichloroaniline as the raw materials, the same operation as the example 16 gave the title compound.
Yield: 71.0%. mp 216-217° C. $^1$H-NMR (DMSO-d$_6$): δ 2.28 (3H, s), 6.90 (1H, d, J=8.4 Hz), 7.26 (1H, dd, J=8.7, 1.8 Hz), 7.34-7.36 (1H, m), 7.67 (1H, d, J=1.5 Hz), 7.85 (2H, d, J=1.8 Hz), 10.52 (1H, s), 11.15 (1H, s).

Example 155

N-(3,5-Dichlorophenyl)-2-hydroxy-5-methoxybenzamide (Compound No. 154)

Using 5-methoxysalicylic acid and 3,5-dichloroaniline as the raw materials, the same operation as the example 16 gave the title compound.
Yield: 29.8%. mp 230-232° C. $^1$H-NMR (DMSO-d$_6$): δ 3.76 (3H, s), 6.95 (1H, d, J=8.7 Hz), 7.08 (1H, dd, J=9.0, 3.0

Hz), 7.35-7.36 (1H, m), 7.40 (1H, d, J=3.0 Hz), 7.85 (2H, d, J=1.5 Hz), 10.55 (1H, s), 10.95 (1H, s).

Example 156

5-Bromo-2-hydroxy-N-(3,4,5-trichlorophenyl)benzamide (Compound No. 155)

Using 5-bromosalicylic acid and 3,4,5-trichloroaniline as the raw materials, the same operation as the example 16 gave the title compound.
Yield: 78.6%. mp 297-299° C. $^1$H-NMR (DMSO-d$_6$): δ 6.98 (1H, d, J=9.0 Hz), 7.58 (1H, dd, J=8.4, 2.4 Hz), 7.95 (1H, d, J=2.4 Hz), 8.03 (1H, s), 10.58 (1H, s), 11.49 (1H, s).

Example 157

5-Bromo-2-hydroxy-N-(3,5-dichloro-4-hydroxyphenyl)benzamide (Compound No. 156)

Using 5-bromosalicylic acid and 3,5-dichloro-4-hydroxyaniline as the raw materials, the same operation as the example 16 gave the title compound. 22.5%).
$^1$H-NMR (DMSO-d$_6$): δ 6.96 (1H, d, J=8.7 Hz), 7.58 (1H, dd, J=3.7, 2.4 Hz). 7.76 (2H, s), 8.01 (1H, d, J=2.4 Hz), 10.03 (1H, s), 10.36 (1H, s), 11.67 (1H, brs).

Example 158

5-Chloro-2-hydroxy-N-(2,3,4,5,6-pentafluorophenyl)benzamide (Compound No. 157)

Using 5-chlorosalicylic acid and 2,3,4,5,6-pentafluoroaniline as the raw materials, the same operation as the example 16 gave the title compound.
Yield: 58.6%. $^1$H-NMR (DMSO-d$_6$): δ 7.07 (1H, d, J=8.7 Hz), 7.53 (1H, dd, J=8.7, 2.7 Hz), 7.91 (1H, d, J=2.7 Hz), 10.38 (1H, brs), 11.74 (1H, brs).

Example 159

5-Bromo-N-(3,5-dinitrophenyl)-2-hydroxybenzamide (Compound No. 158)

Using 5-bromosalicylic acid and 3,5-dinitroaniline as the raw materials, the same operation as the example 16 gave the title compound.
Yield: 32.2%. mp 258-260° C. $^1$H-NMR (DMSO-d$_6$): δ 6.98-7.02 (1H, m), 7.59-7.63 (1H, m), 7.9-6.7.97 (1H, m), 8.56-8.58 (1H, m), 9.03-9.05 (2H, m), 11.04 (1H, s), 11.39 (1H, brs).

Example 160

N-{2,5-Bis[(1,1-dimethyl)ethyl]phenyl}-5-chloro-2-hydroxybenzamide (Compound No. 159)

Using 5-chlorosalicylic acid and 2,5-bis[(1,1-dimethyl)ethyl]aniline as the raw materials, the same operation as the example 16 gave the title compound.
Yield: 75.7%. $^1$H-NMR (DMSO-d$_6$): δ 1.27 (9H, s), 1.33 (9H, s), 7.04 (1H, d, J=9.0 Hz), 7.26 (1H, dd, J=8.4, 2.1 Hz), 7.35-7.38 (2H, m), 7.49 (1H, dd, J=8.7, 2.7 Hz), 8.07 (1H, d, J=2.4 Hz), 10.22 (1H, s), 12.38 (1H, brs).

Example 161

5-Chloro-N-[5-(1,1-dimethyl)ethyl-2-methoxyphenyl]-2-hydroxybenzamide (Compound No. 160)

Using 5-chlorosalicylic acid and 5-[(1,1-dimethyl)ethyl]-2-methoxyaniline as the raw materials, the same operation as the example 16 gave the title compound.
Yield: 89.5%. $^1$H-NMR (DMSO-d$_6$): δ 1.28 (9H, s), 3.33 (3H, s), 7.01 (1H, d, J=8.7 Hz), 7.05 (1H, d, J=9.0 Hz), 7.11 (1H, dd, J=8.7, 2.4 Hz), 7.47 (1H, dd, J=9.0, 3.0 Hz), 7.99 (1H, d, J=3.0 Hz), 8.49 (1H, d, J=2.4 Hz), 10.78 (1H, s), 12.03 (1H, s).

Example 162

5-Bromo-N-(3,5-dimethylphenyl)-2-hydroxybenzamide (Compound No. 161)

Using 5-bromosalicylic acid and 3,5-dimethylaniline as the raw materials, the same operation as the example 16 gave the title compound.
Yield: 58.1%. mp 188-190° C. $^1$H-NMR (DMSO-d$_6$): δ 2.28 (6H, s), 6.80 (1H, s), 6.96 (1H, d, J=8.7 Hz), 7.33 (2H, s), 7.58 (1H, dd, J=9.0, 2.4 Hz), 8.10 (1H, d, J=2.4 Hz), 10.29 (1H, s), 11.93 (1H, brs).

Example 163

N-{3,5-Bis[(1,1-dimethyl)ethyl]phenyl}-5-chloro-2-hydroxybenzamide (Compound No. 162)

Using 5-chlorosalicylic acid and 3,5-bis[(1,1-dimethyl)ethyl]aniline as the raw materials, the same operation as the example 16 gave the title compound.
Yield: 34.1%. $^1$H-NMR (CDCl$_3$): δ 1.26 (18H, s), 6.99 (1H, d, J=8.7 Hz), 7.29 (1H, t, J=1.8 Hz), 7.39 (1H, dd, J=9.0, 2.4 Hz), 7.41 (2H, d, J=1.5 Hz), 7.51 (1H, d, J=2.1 Hz), 7.81 (1H, brs), 12.01 (1H, s).

Example 164

N-{3,5-Bis[(1,1-dimethyl)ethyl]phenyl}-5-bromo-2-hydroxybenzamide (Compound No. 163)

Using 5-bromosalicylic acid and 3,5-bis[(1,1-dimethyl)ethyl]aniline as the raw materials, the same operation as the example 16 gave the title compound.
Yield: 45.2%. $^1$H-NMR (DMSO-d$_6$, δ): 1.30 (18H, s), 6.95 (1H, d, J=8.7 Hz), 7.20 (1H, t, J=1.5 Hz), 7.56 (2H, d, J=1.5 Hz), 7.58 (1H, dd, J=8.7, 2.4 Hz), 8.12 (1H, d, J=2.7 Hz), 10.39 (1H, s), 11.98 (1H, s).

Example 165

5-Chloro-2-hydroxy-(3,5,5,8,8-pentamethyl-5,6,7,8-tetrahydro-naphthalen-2-yl)benzamide (Compound No. 164)

Using 5-chlorosalicylic acid and 2-amino-3,5,5,8,8-pentamethyl-5,6,7,8-tetrahydronaphthalene as the raw materials, the same operation as the example 16 gave the title compound.

Yield: 77.5%. $^1$H-NMR (DMSO-d$_6$): δ 1.23 (6H, s), 1.24 (6H, s), 1.64 (4H, s), 2.19 (3H, s), 7.13 (1H, d, J=9.0 Hz), 7.20 (1H, s), 7.49 (1H, dd, J=8.7, 2.7 Hz), 7.67 (1H, s), 8.04 (1H, d, J=2.7 Hz), 10.23 (1H, s), 12.26 (1H, s).

Example 166

N-(Biphenyl-3-yl)-5-chloro-2-hydroxybenzamide (Compound No. 165)

Using 5-chlorosalicylic acid and 3-aminobiphenyl as the raw materials, the same operation as the example 16 gave the title compound.

Yield: 75.6%. $^1$H-NMR (DMSO-d$_6$): δ 7.04 (1H, d, J=8.7 Hz), 7.35-7.44 (1H, m), 7.45-7.54 (5H, m), 7.65-7.68 (2H, m), 7.72 (1H, dt, J=7.2, 2.1 Hz), 7.99 (1H, d, J=3.0 Hz), 8.03 (1H, m), 10.50 (1H, s), 11.83 (1H, brs).

Example 167

5-Chloro-2-hydroxy-N-(4-methoxybiphenyl-3-yl) benzamide (Compound No. 166)

Using 5-chlorosalicylic acid and 3-amino-4-methoxybiphenyl as the raw materials, the same operation as the example 16 gave the title compound.

Yield: 37.0%. $^1$H-NMR (DMSO-d$_6$): δ 3.95 (3H, s), 7.08 (1H, d, J=8.7 Hz), 7.20 (1H, d, J=8.4 Hz), 7.34 (1H, t, J=7.2 Hz), 7.40-7.50 (4H, m), 7.62 (1H, d, J=8.7 Hz), 8.00 (1H, d, J=3.0 Hz), 8.77 (1H, d, J=2.1 Hz), 10.92 (1H, s), 12.09 (1H, s).

Example 168

5-Bromo-N-(2,5-dimethoxyphenyl)-2-hydroxybenzamide (Compound No. 167)

Using 5-bromosalicylic acid and 2,5-dimethoxyaniline as the raw materials, the same operation as the example 16 gave the title compound.

Yield: 39.7%. $^1$H-NMR (DMSO-d$_6$): δ 3.72 (3H, s), 3.84 (3H, s), 6.66 (1H, ddd, J=9.0, 3.0, 0.6 Hz), 6.99-7.03 (2H, m), 7.58 (1H, ddd, J=9.0, 2.7, 0.6 Hz), 8.10 (1H, dd, J=2.4, 0.6 Hz), 8.12 (1H, d, J=3.0 Hz), 10.87 (1H, s), 12.08 (1H, s).

Example 169

5-Bromo-N-(3,5-dimethoxyphenyl)-2-hydroxybenzamide (Compound No. 168)

Using 5-bromosalicylic acid and 3,5-dimethoxyaniline as the raw materials, the same operation as the example 16 gave the title compound.

Yield: 40.3%. mp 207-209° C. $^1$H-NMR (DMSO-d$_6$): δ 3.75 (6H, s), 6.30-6.32 (1H, m), 6.94-6.97 (3H, m), 7.57 (1H, dd, J=8.7, 2.4 Hz), 8.04 (1H, d, J=2.4 Hz), 10.32 (1H, s), 11.78 (1H, s).

Example 170

5-Chloro-N-(3-acetylphenyl)-2-hydroxybenzamide (Compound No. 169)

Using 5-chlorosalicylic acid and 3-acetylaniline as the raw materials, the same operation as the example 16 gave the title compound.

Yield: 80.0%. $^1$H-NMR (DMSO-d$_6$): δ 2.60 (3H, s), 7.03 (1H, d, J=9.0 Hz), 7.49 (1H, dd, J=9.0, 3.0 Hz), 7.54 (1H, t, J=8.1 Hz), 7.76 (1H, dq, J=7.8, 0.9 Hz), 7.96-8.00 (2H, m), 8.30 (1H, t, J=1.8 Hz), 10.56 (1H, s), 11.75 (1H, s).

Example 171

5-{[(5-Bromo-2-hydroxy)benzoyl]amino}isophthalic acid dimethyl ester (Compound No. 170)

Using 5-bromosalicylic acid and 5-aminoisophthalic acid dimethyl ester as the raw materials, the same operation as the example 16 gave the title compound.

Yield: 74.1%. mp 254-256° C. $^1$H-NMR (DMSO-d$_6$): δ 3.92 (6H, s), 6.97 (1H, d, J=9.0 Hz), 7.60 (1H, dd, J=9.0, 2.4 Hz), 8.06 (1H, d, J=2.4 Hz), 8.24-8.25 (1H, m), 8.62 (2H, m), 10.71 (1H, s), 11.57 (1H, s).

Example 172

N-(4-{3-(2,3-Dichlorophenyl)thioureidolphenyl}-2-hydroxybenzamide (Compound No. 171)

This compound is a commercially available compound.
Seller: Maybridge.
Catalog code number: RDR 01434

Example 173

N-{2,5-Bis[(1,1-dimethyl)ethyl]phenyl}-2-hydroxy-5-methylbenzamide (Compound No. 173)

Using 5-methylsalicylic acid and 2,5-bis[(1,1-dimethyl)ethyl]aniline as the raw materials, the same operation as the example 16 gave the title compound.

Yield: 61.1%. $^1$H-NMR (DMSO-d$_6$): δ 1.27 (9H, s), 1.33 (9H, s), 2.28 (3H, s), 6.89 (1H, d, J=8.1 Hz), 7.24 (1H, d, J=2.1 Hz), 7.27 (1H, d, J=2.1 Hz), 7.32 (1H, d, J=2.4 Hz), 7.37 (1H, d, J=8.4 Hz), 7.88 (1H, d, J=1.5 Hz), 10.15 (1H, s), 11.98 (1H, brs).

Example 174

2-Acetoxy-N-{3,5-bis[(1,1-dimethyl)ethyl]phenyl}-5-chlorobenzamide (Compound No. 174)

Using N-{3,5-bis[(1,1-dimethyl)ethyl]phenyl}-5-chloro-2-hydroxybenzamide and acetyl chloride as the raw materials, the same operation as the example 96 gave the title compound.

Yield: 66.1%. $^1$H-NMR (CDCl$_3$): δ 1.34 (18H, s), 2.36 (3H, s), 7.12 (1H, d, J=8.4 Hz), 7.25 (1H, d, J=1.5 Hz), 7.44 (2H, d, J=1.2 Hz), 7.47 (1H, dd, J=8.7, 2.7 Hz), 7.87 (1H, d, J=2.4 Hz), 7.98 (1H, s).

Example 175

N-{3,5-Bis[(1,1-dimethyl)ethyl]phenyl}-2-hydroxy-5-nitrobenzamide (Compound No. 175)

Using 5-nitrosalicylic acid and 3,5-bis[(1,1-dimethyl)ethyl]aniline as the raw materials, the same operation as the example 16 gave the title compound.

Yield: 46.7%. $^1$H-NMR (CDCl$_3$): δ 1.37 (18H, s), 7.13 (1H, d, J=9.3 Hz), 7.32 (1H, t, J=1.8 Hz), 7.46 (2H, d, J=1.8 Hz), 8.07 (1H, s), 8.33 (1H, dd, J=9.3, 2.1 Hz), 8.59 (1H, d, J=2.4 Hz), 13.14 (1H, s).

Example 176

N-{3,5-Bis[(1,1-dimethyl)ethyl]phenyl}-2-hydroxy-5-methylbenzamide (Compound No. 176)

Using 5-methylsalicylic acid and 3,5-bis[(1,1-dimethyl)ethyl]aniline as the raw materials, the same operation as the example 16 gave the title compound.
Yield: 16.3%.
$^1$H-NMR (CDCl$_3$): δ 1.35 (18H, s), 2.35 (3H, s), 6.94 (1H, d, J=8.4 Hz), 7.23-7.28 (2H, m), 7.31 (1H, s), 7.42 (1H, d, J=1.8 Hz), 7.88 (1H, s), 11.86 (1H, s).

Example 177

N-{3,5-Bis[(1,1-dimethyl)ethyl]phenyl}-2-hydroxy-5-methoxybenzamide (Compound No. 177)

Using 5-methoxysalicylic acid and 3,5-bis[(1,1-dimethyl)ethyl]aniline as the raw materials, the same operation as the example 16 gave the title compound.
Yield: 12.7%. $^1$H-NMR (DMSO-d$_6$): δ 3.56 (3H, s), 7.01 (1H, d, J=9.0 Hz), 7.11 (1H, dd, J=9.0, 3.0 Hz), 7.52-7.56 (2H, m), 7.83 (1H, d, J=8.1 Hz), 8.95 (1H, d, J=1.5 Hz), 11.29 (1H, s), 11.63 (1H, s).

Example 178

2-Acetoxy-5-chloro-N-[5 (1,1-dimethyl)ethyl-2-methoxyphenyl]-benzamide (Compound No. 178)

Using 5-chloro-N-[5-(1,1-dimethyl)ethyl-2-methoxyphenyl]ethyl-2-hydroxybenzamide and acetyl chloride as the raw materials, the same operation as the example 96 gave the title compound.
Yield: 87.5%. $^1$H-NMR (CDCl$_3$): δ 1.35 (9H, s), 2.37 (3H, s), 3.91 (3H, s), 6.86 (1H, d, 8.7 Hz), 7.12 (1H, dd, J=8.7, 2.4 Hz), 7.13 (1H, d, J=9.0 Hz), 7.47 (1H, dd, J=9.0, 2.4 Hz), 8.02 (1H, d, J=2.7 Hz), 8.66 (1H, d, J=2.4 Hz), 8.93 (1H, s).

Example 179

N-[5-(1,1-Dimethyl)ethyl-2-methoxyphenyl]-2-hydroxy-5-methylbenzamide (Compound No. 178)

Using 5-methylsalicylic acid and 5-(1,1-dimethyl)ethyl-2-methoxyaniline as the raw materials, the same operation as the example 16 gave the title compound.
Yield: 84.7%. $^1$H-NMR (CDCl$_3$): δ 1.35 (9H, s), 2.34 (3H, s), 3.93 (3H, s), 6.86 (1H, d, J=8.7 Hz), 6.93 (1H, d, J=8.4 Hz). 7.12 (1H, dd, J=8.7, 2.4 Hz), 7.24 (1H, dd, J=8.4, 1.8 Hz), 7.27 (1H, brs), 8.48 (1H, d, J=2.4 Hz), 8.61 (1H, brs), 11.95 (1H, s).

Example 180

5-Bromo-2-hydroxy-N-(thiazol-2-yl)benzamide (Compound No. 180)

Using 5-bromosalicylic acid and 2-aminothiazole as the raw materials, the same operation as the example 16 gave the title compound.
Yield: 12.0%. mp 212° C. (dec.). $^1$H-NMR (DMSO-d$_6$): δ6.94 (1H, brd, J=8.0 Hz), 7.25 (1H, brd, J=3.2 Hz), 7.56 (2H, m), 8.05 (1H, d, J=2.8 Hz).

Example 181

5-Bromo-N-{4-[(1,1-dimethyl)ethyl]thiazol-2-yl}-2-hydroxybenzamide (Compound No. 186)

(1) 2-Amino-4-[(1,1-dimethyl)ethyl]thiazole
A mixture of 1-bromo-3,3-dimethyl-2-butanone (5.03 g, 28.1 mmol), thiourea (2.35 g, 30.9 mmol) and ethanol (30 mL) was refluxed for 1.5 hours. After cooling, the reaction mixture was poured into saturated aqueous sodium hydrogen carbonate and extracted with ethyl acetate. After the organic layer was washed with water and brine, dried over anhydrous sodium sulfate, the residue obtained by evaporation under reduced pressure was purified by chromatography on silica gel (hexane:ethyl acetate=2:1 →1:1) to give the title compound (3.99 g, 90.9%) as a yellowish white powder.
$^1$H-NMR (CDCl$_3$): δ 1.26 (9H, s), 4.96 (2H, brs), 6.09 (1H, s).
(2) 2-Acetoxy-5-bromo-N-{4-[(1,1-dimethyl)ethyl]thiazol-2-yl}benzamide
Using 2-acetoxy-5-bromobenzoic acid and 2-amino-4-[(1,1-dimethyl)-ethyl]thiazole as the raw materials, the same operation as the example 24 gave the title compound.
Yield: 59.4%. $^1$H-NMR (CDCl$_3$): δ 1.31 (9H, s), 2.44 (3H, s), 6.60 (1H, s), 7.13 (1H, d, J=8.4 Hz), 7.68 (1H, dd, J=8.7, 2.4 Hz), 8.17 (1H, d, J=2.4 Hz), 9.72 (1H, brs).
(3) 5-Bromo-N-{4-[(1,1-dimethyl)ethyl}thiazol-2-yl]-2-hydroxybenzamide
2-Acetoxy-5-bromo-N-{4-[(1,1-dimethyl)ethyl]thiazol-2-yl}benzamide (100.1 mg, 0.25 mmol) was dissolved in tetrahydrofuran (3 mL). 2 N sodium hydroxide (0.2 ml) was added, and the mixture was stirred at room temperature for 20 minutes. The reaction mixture was poured into diluted hydrochloric acid and extracted with ethyl acetate. After the organic layer was washed with brine, dried over anhydrous sodium sulfate, the residue obtained by evaporation under reduced pressure was crystallized (isopropyl ether/n-hexane) to give the title compound (70.1 mg, 78.9%) as a light gray solid.
$^1$H-NMR (DMSO-d$_6$): δ 1.30 (9H, s), 6.80 (1H, brs), 6.95 (1H, brs), 7.57 (1H, brs), 8.06 (1H, d, J=2.4 Hz), 11.82 (1H, brs), 13.27 (1H, brs).

Example 182

5-Bromo-N-{5-bromo-4-[(1,1-dimethyl)ethyl]thiazol-2-yl}-2-hydroxybenzamide (Compound No. 181)

(1) 2-Acetoxy-5-bromo-{5-bromo-4-[(1,1-dimethyl)ethyl]thiazol-2-yl}benzamide
2-Acetoxy-5-bromo-N-{4-[(1,1-dimethyl)ethyl]imidazol-2-yl}benzamide (0.20 g, 0.50 mmol) was dissolved in acetonitrile (10 mL). N-Bromosuccinimide (97.9 mg, 0.55 mmol) was added, and the mixture was stirred at room temperature for 1 hour. The reaction mixture was concentrated under reduced pressure, and the obtained residue was purified by chromatography on silica gel (n-hexane:ethyl acetate=3:1) to give the title compound as a crude product.
(2) 5-Bromo-N-{5-bromo-4-[(1,1-dimethyl)ethyl]thiazol-2-yl}-2-hydroxybenzamide
Using 2-acetoxy-5-bromo-N-{5-bromo-4-[(1,1-dimethyl)ethyl]thiazol-2-yl}benzamide as the raw material, the same operation as the example 2(2) gave the title compound.
Yield: 90.9% (2 steps). mp 212° C. (dec.). $^1$H-NMR (DMSO-d$_6$): δ 1.42 (9H, s), 6.99 (1H, d, J=8.7 Hz), 7.61 (1H, dd, J=8.7, 2.7 Hz), 8.02 (1H, d, J=2.4 Hz), 11.79 (1H, brs), 12.00 (1H, brs).

Example 183

5-Bromo-N-[5-bromo-4-(trifluoromethyl)thiazol-2-yl]-2-hydroxybenzamide (Compound No. 182)

Using 5-bromosalicylic acid and 2-amino-5-bromo-4-(trifluoromethyl)thiazole as the raw materials, the same operation as the example 16 gave the title compound. (2-Amino-5-bromo-4-(trifluoromethyl)thiazole: refer to J. Heterocycl. Chem., 1991, 28, 1017.)

Yield: 22.4%. mp 215° C. (dec.). $^1$H-NMR (DMSO-d$_6$): δ 7.00 (1H, d, J=8.8 Hz), 7.61 (1H, dd, J=8.8, 2.8 Hz), 7.97 (1H, d, J=2.4 Hz).

Example 184

5-Chloro-N-[5-cyano-4-[(1,1-dimethyl)ethyl]thiazol-2-yl]-2-hydroxybenzamide (1) α-Bromo-pivaloylacetonitrile Pivaloylacetonitrile (1.00 g, 7.99 mmol) was dissolved in carbon tetrachloride (15 mL). N-Bromosuccinimide (1.42 g, 7.99 mmol) was added, and the mixture was refluxed for 15 minutes. After cooling, the insoluble matter was filtered off, and the residue obtained by evaporation of the filtrate under reduced pressure was purified by chromatography on silica gel (n-hexane:ethyl acetate=4:1) to give the title compound (1.43 g, 87.9%) as a yellowish brown oil.

$^1$H-NMR (CDCl$_3$): δ 1.33 (9H, s), 5.10 (1H, s).

(2) 2-Amino-5-cyano {4-[(1,1-dimethyl)ethyl]thiazole

Using α-bromo-pivaloylacetonitrile and thiourea as the raw materials, the same operation as the example 181(1) gave the title compound.

Yield: 66.3%. $^1$H-NMR (CDCl$_3$) δ 1.41 (9H, s), 5.32 (2H, s).

(3) 5-Chloro-N-{5-cyano-4-[(1,1-dimethyl)ethyl]thiazol-2-yl}-2-hydroxybenzamide

Using 5-chlorosalicylic acid and 2-amino-5-cyano-{4-[(1,1-dimethyl)ethyl]-thiazole as the raw materials, the same operation as the example 16 gave the title compound.

Yield: 63.4%. $^1$H-NMR (DMSO-d$_6$): δ 1.43 (9H, s). 7.06 (1H, d, J=8.7 Hz), 7.51 (1H, dd, J=8.7, 3.0 Hz), 7.85 (1H, d, J=2.7 Hz), 12.31 (2H, br).

Example 185

5-Bromo-N-{5-cyano-4-[(1,1-dimethyl)ethyl]thiazol-2-yl}-2-hydroxybenzamide (Compound No. 184)

Using 5-bromosalicylic acid and 2-amino-5-cyano-{4-[(1,1-dimethyl)ethyl]thiazole as the raw materials, the same operation as the example 16 gave the title compound.

Yield: 61.3%. $^1$H-NMR (DMSO-d$_6$): δ 1.43 (9H, s), 7.00 (1H, d, J=8.7 Hz), 7.62 (1H, dd, J=8.7, 2.7 Hz), 7.97 (1H, d, J=2.7 Hz), 11.75 (1H, br), 12.43 (1H, br).

Example 186

5-Bromo-2-hydroxy-N-(5-methylthiazol-2-yl)benzamide (Compound No. 185)

Using 5-bromosalicylic acid and 2-amino-5-methylthiazole as the raw materials, the same operation as the example 16 gave the title compound.

Yield: 12.9%. $^1$H-NMR (DMSO-d$_6$): δ 2.33 (3H, s), 6.91 (1H, d, J=7.6 Hz), 7.26 (1H, s), 7.54 (1H, d, J=9.6 Hz), 8.03 (1H, d, J=2.8 Hz).

Example 187

5-Bromo-N-(4,5-dimethylthiazol-2-yl)-2-hydroxybenzamide (Compound No. 187)

Using 5-bromosalicylic acid and 2-amino-4,5-dimethylhiazole as the raw materials, the same operation as the example 16 gave the title compound.

Yield: 14.4%. $^1$H-NMR (DMSO-d$_6$): δ 2.18 (3H, s), 2.22 (3H, s), 6.89 (1H, d, J=8.8 Hz), 7.51 (1H, d, J=6.8 Hz), 8.02 (1H, d, J=2.8 Hz), 13.23 (1H, brs).

Example 188

5-Bromo-N-(5-methyl-4-phenylthiazol-2-yl)-2-hydroxybenzamide (Compound No. 188)

Using 5-bromosalicylic acid and 2-amino-5-methyl-4-phenylthiazole as the raw materials, the same operation as the example 16 gave the title compound. (2-Amino-5-methyl-4-phenylthiazole: refer to Yakugaku Zasshi, 1961, 81, 1456.)

Yield: 27.7%. mp 243-244° C. $^1$H-NMR (CD$_3$OD): δ 2.47 (3H, s), 6.92 (1H, d, J=8.7 Hz), 7.36-7.41 (1H, m), 7.44-7.50 (2H, m), 7.53 (1H, dd, J=9.0, 2.7 Hz), 7.57-7.6.1 (2H, m), 8.16 (1H, d, J=2.7 Hz).

Example 189

5-Bromo-[4-methyl-5-(4-fluorophenyl)thiazol-2-yl]-2-hydroxybenzamide (Compound No. 189)

Using (4-fluorophenyl)acetone as the raw material, the same operation as the examples 184(1)-(3) gave the title compound.

Yield: 28.8% (3 steps).

(1) α-Bromo-(4-fluorophenyl)acetone $^1$H-NMR (CDCl$_3$): δ 2.33 (3H, s), 5.41 (1H, s), 7.07 (2H, t, J=8.7 Hz), 7.43 (2H, dd, J=8.7, 5.1 Hz).

(2) 2-Amino-4-methyl-5-(4-fluorophenyl)thiazole $^1$H-NMR (CDCl$_3$): δ 2.27 (3H, s), 4.88 (2H, s), 7.07 (2H, t, J=8.7 Hz), 7.32 (2H, dd, J=8.7, 5.4 Hz).

(3) 5-Bromo-N-[4-methyl-5 (4-fluorophenyl)thiazol-2-yl]-2-hydroxybenzamide $^1$H-NMR (DMSO-d$_6$): δ 2.36 (3H, s), 6.95 (1H, d, J=8.4 Hz), 7.33 (2H, t, J=8.7 Hz), 7.52-7.59 (3H, m), 8.06 (1H, d, J=3.0 Hz), 12.01-13.65 (2H, br).

Example 190

5-Bromo-N-{4-methyl-5-[3-(trifluoromethyl)phenyl]thiazol-2-yl}-2-hydroxybenzamide (Compound No. 190)

Using 3-trifluoromethyl)phenylacetone as the raw material, the same operation as the examples 184(1)-(3) gave the title compound.

Yield: 39.8% (3 steps).

(1) α-Bromo-3-(trifluoromethyl)phenylacetone $^1$H-NMR (CDCl$_3$): δ 2.38 (3H, s), 5.43 (1H, s), 7.52 (1H, t, J=7.8 Hz), 7.61-7.66 (2H, m), 7.69-7.70 (1H, m).

(2) 2-Amino-4-methyl-5-[3-(trifluoro methyl)phenyl]thiazole $^1$H-NMR (CDCl$_3$): δ 2.32 (3H, s), 4.95 (2H, s), 7.46-7.56 (3H, m), 7.59-7.61 (1H, m).

(3) 5-Bromo-N-{4-methyl-5-[3-(trifluoromethy)phenyl]thiazol-2-yl}-2-hydroxybenzamide ¹H-NMR (DMSO-d₆): δ2.40 (3H, s), 6.97 (1H, d, J=8.7 Hz), 7.59 (1H, dd, J=8.7, 2.4 Hz), 7.71-7.84 (4H, m), (2H, m), 8.06 (1H, d, J=2.4 Hz), 12.09 (1H, br), 12.91-13.63 (1H, br).

Example 191

5-Bromo-N-{4-[(1,1-dimethyl)ethyl]-5-ethylthiazol-2-yl}-2-hydroxybenzamide (Compound No. 191)

Using 2,2-dimethyl-3-hexanone as the raw material, the same operation as the examples 184(1)-(3) gave the title compound.

Yield: 17.0% (3 steps).

(2) 2-Amino-4-[(1,1-dimethyl)ethyl]-5-ethylthiazole

¹H-NMR (CDCl₃): δ 1.21 (3H, t, J=7.5 Hz), 1.32 (9H, s), 2.79 (9H, q, J=7.5 Hz), 4.63 (2H, brs).

(3) 5-Bromo-N-{4-[(1,1-dimethyl)ethyl]-5-ethylthiazol-2-yl}-2-hydroxybenzamide

¹H-NMR (CDCl₃): δ 1.32 (3H, t, J=7.5 Hz), 1.41 (9H, s), 2.88 (2H, q, J=7.5 Hz), 6.84 (1H, d, J=9.0 Hz), 7.44 (1H, dd, J=8.7, 2.4 Hz), 8.05 (1H, d, J=2.7 Hz), 11.46 (2H, br).

Example 192

5-Bromo-N-(4-ethyl-5-phenylthiazol-2-yl)-2-hydroxybenzamide (Compound No. 192)

Using 5-bromosalicylic acid and 2-amino-4-ethyl-5-phenylthiazole as the raw materials, the same operation as the example 16 gave the title compound.

Yield: 17.4%. mp 224-225° C. ¹H-NMR (DMSO-d₆): δ1.24 (3H, t, J=7.6 Hz), 2.70 (2H, q, J=7.6 Hz), 6.95 (1H, brd, J=7.6 Hz), 7.39-7.42 (1H, m), 7.45-7.51 (4H, m), 7.56 (1H, brd, J=8.0 Hz), 8.06 (1H, d, J=2.8 Hz), 11.98 (1H, brs).

Example 193

5-Bromo-N-(4-ethyl-5-isopropylthiazol-2-yl)-2-hydroxybenzamide (Compound No. 193)

Using benzyl isopropyl ketone as the raw material, the same operation as the examples 184(1)-(3) gave the title compound.

Yield: 4.4% (3 steps).

(2) 2-Amino-4-ethyl-5-isopropylthiazole

¹H-NMR (CDCl₃): δ 1.23 (6H, d, J=6.6 Hz), 3.05 (1H, m), 4.94 (2H, s), 7.28-7.41 (5H, m).

(3) 5-Bromo-N-(4-ethyl-5-isopropylthiazol-2-yl)-2-hydroxybenzamide

¹H-NMR (DMSO-d₆): δ 1.26 (6H, d, J=6.0 Hz), 3.15 (1H, m), 6.98 (1H, brs), 7.43-7.53 (5H, m), 7.59 (1H, brs), 8.08 (1H, d, J=2.7 Hz), 11.90 (1H, brs), 13.33 (1H, brs).

Example 194

5-Bromo-N-(4 butyl-5-phenylthiazol-2-yl)-2-hydroxybenzamide (Compound No. 194)

Using 1-phenyl-2-hexanone as the raw material, the same operation as the examples 184(1)-(3) gave the title compound.

Yield: 52.6% (3 steps).

(1) α-Bromo-1-phenyl-2-hexanone

¹H-NMR (CDCl₃): δ 0.85 (3H, t, J=7.3 Hz), 1.19-1.32 (2H, m), 1.50-1.60 (2H, m), 2.59 (2H, td, J=7.5, 3.9 Hz), 5.44 (1H, s), 7.34-7.45 (5H, m).

(2) 2-Amino-4-butyl-5-phenylthiazole

¹H-NMR (CDCl₃, δ): 0.89 (3H, t, J=7.5 Hz), 1.28-1.41 (2H, m), 1.61-1.71 (2H, m), 2.56-2.61 (2H, m), 4.87 (2H, s), 7.25-7.40 (5H, m).

(3) 5-Bromo-N-(4-butyl-5-phenylthiazol-2-yl)-2-hydroxybenzamide

¹H-NMR (DMSO-d₆): δ 0.85 (3H, t, J=7.2 Hz), 1.23-1.35 (2H, m), 1.59-1.69 (2H, m), 2.70 (2H, t, J=7.2 Hz), 6.96 (1H, d, J=6.9 Hz), 7.39-7.59 (6H, m) 8.07 (1H, d, J=2.4 Hz), 11.93 (1H, br), 13.18-13.59 (1H, br).

Example 195

5-Chloro-N-{4-(1,1-dimethyl)ethyl-5-[(2,2-dimethyl)-propionyl]thiazol-2-yl}-2-hydroxybenzamide (Compound No. 195)

(1) α-Bromo-dipivaloylmethane

Dipivaloylmethane (1.00 g, 5.42 mmol) was dissolved in carbon tetrachloride (10 mL). N-Bromosuccinimide (965.8 mg, 5.42 mmol) was added, and the mixture was refluxed for 2 hours. After cooling, the insoluble matter was filtered off, and the filtrate was evaporated under reduced pressure to give the title compound (1.42 g, quant.) as a white crystal.

¹H-NMR (CDCl₃, δ): 1.27 (18H, s), 5.67 (1H, s).

(2) 2-Amino-4-[(1,1-dimethyl)ethyl]-5-[(2,2-dimethyl)propionyl]thiazole

A mixture of α-bromo-dipivaloylmethane (1.42 g), thiourea (451.8 mg) and ethanol (15 mL) was refluxed for 2 hours. After cooling, the reaction mixture was poured into saturated aqueous sodium hydrogen carbonate and extracted with ethyl acetate. After the organic layer was washed with water and brine, dried over anhydrous sodium sulfate, the residue obtained by evaporation under reduced pressure was crystallized (dichloromethane/hexane) to give the title compound (1.23 g, 94.5%) as a white crystal.

¹H-NMR (CDCl₃, δ): 1.26 (9H, s), 1.29 (9H, s), 5.03 (2H, s).

(3) 5-Chloro-N-{4-(1,1-dimethylethyl-5-[(2,2-dimethyl)propionyl]thiazol-2-yl}-2-hydroxybenzamide A mixture of 5-bromosalicylic acid (0.20 g, 0.92 mmol), 2-amino-4-[(1,1-dimethyl)ethyl]-5-[(2,2-dimethyl)propionyl]thiazole (221.5 mg, 0.92 mmol), phosphorus trichloride (40 μl, 0.46 mmol) and chlorobenzene (5 mL) was refluxed for 3 hours. The residue obtained by concentration of the reaction mixture under reduced pressure was purified by chromatography on silica gel (n-hexane:ethyl acetate=2:1) to give the title compound (96.2 mg, 23.8%) as a white powder.

¹H-NMR (CDCl₃, δ): 1.33 (9H, s), 1.35 (9H, s), 6.94 (1H, d, J=8.7 Hz), 7.55 (1H, dd, J=8.7, 2.1 Hz), 7.85 (1H, d, J=2.1 Hz), 10.51 (2H, br).

Example 196

5-Bromo-N-{4-(1,1-dimethyl)ethyl-5-[(2,2-dimethyl)propionyl]thiazol-2-yl}-2-hydroxybenzamide (Compound No. 196)

Using 5-bromosalicylic acid and 2-amino-4-[(1,1-dimethyl)ethyl]-5-[(2,2-dimethyl)propionyl]thiazole as the raw material, the same operation as the example 195(3) gave the title compound.

Yield: 23.8%. $^1$H-NMR (CDCl$_3$): δ 1.33 (9H, s), 1.35 (9H, s), 6.94 (1H, d, J=8.7 Hz), 7.55 (1H, dd, J=8.7, 2.1 Hz), 7.85 (1H, d, J=2.1 Hz), 10.51 (2H, br).

Example 197

2-(5-Bromo-2-hydroxybenzoyl)amino-4-[(1,1-dimethyl)ethyl]thiazole-5-carboxylic acid ethyl ester (Compound No. 197)

Using pivaloyl acetic acid ethyl ester as the raw material, the same operation as the examples 195(1)-(3) gave the title compound.
Yield: 45.7% (3 steps).
(1) α-Bromo-pivaloyl acetic acid ethyl ester
$^1$H-NMR (CDCl$_3$): δ 1.28 (9H, s), 1.29 (3H, t, J=7.2 Hz), 4.26 (2H, q, J=7.2 Hz), 5.24 (1H, 5).
(2) 2-Amino-4-[(1,1-dimethyl)ethyl]thiazole-5-carboxylic acid ethyl ester
$^1$H-NMR (CDCl$_3$, δ) 1.32 (3H, t, J=7.2 Hz), 1.43 (9H, s), 4.24 (2H, q, J=72 Hz), 5.18 (2H, s).
(3) 2-(5-Bromo-2-hydroxybenzoyl)amino-4-[(1,1-dimethyl)ethyl]thiazole-5-carboxylic acid ethyl ester
$^1$H-NMR (DMSO-d$_6$): δ 1.30 (3H, t, J=7.2 Hz), 1.44 (9H, s), 4.27 (2H, q, J=6.9 Hz), 7.00 (1H, d, J=8.7 Hz), 7.63 (1H, dd, J=8.7, 2.7 Hz), 8.02 (1H, d, J=2.4 Hz), 11.80 (1H, br), 12.12 (1H, br).

Example 198

5-Bromo-N-[4-(1,1-dimethyl)ethyl-5-piperidinothiazol-2-yl]-2-hydroxybenzamide (Compound No. 198)

(1) 2-Amino-5-bromo-4-[(1,1-dimethyl)ethyl]thiazole
2-Amino-4-[(1,1-dimethyl)ethyl]thiazole (0.87 g, 5.6 mmol) was dissolved in carbon tetrachloride (9 mL). N-Bromosuccinimide (1.00 g, 5.6 mmol) was added, and the mixture was stirred at room temperature for 1 hour. Hexane was added to the reaction mixture, the insoluble matter was filtered off, and the residue obtained by evaporation of the filtrate under reduced pressure was purified by chromatography on silica gel (hexane:ethyl acetate=2:1) to give the title compound (1.23 g, 93.7%) as a yellowish gray powder.
$^1$H-NMR (CDCl$_3$): δ 1.39 (9H, s), 4.81 (2H, brs).
(2) 2-Amino-4-[(1,1-dimethyl)ethyl]-5-piperidinothiazole
A mixture of 2-amino-5-bromo-4-[(1,1-dimethyl)ethyl]thiazole (0.10 g, 0.42 mmol), piperidine (0.1 mL), potassium carbonate (0.20 g) and acetonitrile (4 mL) was refluxed for 3 hours. The reaction mixture was poured into water and extracted with ethyl acetate. After the organic layer was washed with water and brine, dried over anhydrous sodium sulfate, the residue obtained by evaporation under reduced pressure was purified by chromatography on silica gel (n-hexane:ethyl acetate=2:1) to give the title compound (80.7 mg, 79.3%) as a yellow crystal.
$^1$H-NMR (CDCl$_3$): δ 1.32 (9H, s), 1.64 (4H, t, J=5.7 Hz), 1.71-1.77 (2H, m), 2.35 (2H, brs), 2.99 (21, brs), 4.68 (2H, s).
(3) 2-Acetoxy-5-bromo-N-[4-(1,1-dimethyl)ethyl-5-piperidinothiazol-2-yl]benzamide
Under argon atmosphere, phosphorus oxychloride (46 µl, 0.50 mmol) was added to a mixture of 2-acetoxy-5-bromo-beazoic acid (J. Med. Chem. 31, 861-874 1996)(90.3 mg, 0.35 mmol), the thiazole (80.7 mg, 0.34 mmol), pyridine (0.1 mL) and THF (3 mL), and the mixture was stirred at room temperature for 2 hours. The reaction mixture was poured into 2N hydrochloric acid and extracted with ethyl acetate. After the organic layer was washed with water and brine, dried over anhydrous sodium sulfate, the residue obtained by evaporation under reduced pressure was purified by chromatography on silica gel (n-hexane:ethyl acetate=3:1) to give the title compound (84.3 mg) as a crude product.
(4) 5-Bromo-N-[4-(1,1-dimethyl)ethyl)ethyl-5-piperidinothiazol-2-yl]-2-hydroxybenzamide
2-Acetoxy-5-bromo-N-[4-(1,1-dimethyl)ethyl)ethyl-5-piperidinothiazol-2-yl]benzamide (crude product, 84.3 mg) was dissolved in ethanol (3 mL). 2 N aqueous sodium hydroxide (0.1 mL) was added, and the mixture was stirred at room temperature for 1 hour. The reaction mixture was poured into 2 N hydrochloric acid and extracted with ethyl acetate. After the organic layer was washed with water and brine, dried over anhydrous sodium sulfate, the residue obtained by evaporation under reduced pressure was purified by chromatography on silica gel (n-hexane:ethyl acetate=4:1) to give the title compound (54.1 mg, 36.3%; 2 steps) as a white powder.
$^1$H-NMR (CDCl$_3$): δ 1.41 (9H, s), 1.56 (2H, brs), 1.67-1.74 (4H, m), 2.79 (4H, brs), 6.85 (1H, d, J=9.0 Hz), 7.45 (1H, dd, J=9.0, 2.4 Hz), 8.06 (1H, d, J=2.4 Hz), 11.70 (2H, br).

Example 199

5-Bromo-N-[4-(1,1-dimethyl)ethyl-5-morpholinothiazol-2-yl]-2-hydroxybenzamide (Compound No. 199)

Using morpholine as the raw material, the same operation as the examples 198(2)-(4) gave the title compound.
Yield: 17.1%.
(2) 2-Amino-4-[(1,1-dimethyl)ethyl]-5-morpholinothiazole
$^1$H-NMR (CDCl$_3$): δ 1.33 (9H, s), 2.76 (4H, brs), 3.79 (4H, brs), 4.66 (2H, s).
(3) 2 Acetoxy-5-bromo-N-[4-(1,1-dimethyl)ethyl-5-morpholinothiazol-2-yl]benzamide
The product was used for the next reaction as a crude product.
(4) 5-Bromo-N-[4-(1,1-dimethyl)ethyl-5-morpholinothiazol-2-yl]-2-hydroxybenzamide
$^1$H-NMR (CDCl$_3$): δ 1.24 (9H, s), 2.89 (4H, dd, J=4.8, 4.2 Hz), 3.83 (4H, dd, J=4.5, 4.2 Hz), 6.89 (1H, d, J=9.0 Hz), 7.49 (1H, dd, J=9.0, 2.4 Hz), 7.98 (1H, d, J=2.1 Hz), 11.20 (2H, br).

Example 200

5-Bromo-N-[4-(1,1-dimethyl)ethyl-5-(4-methylpiperazin-1-yl)thiazol-2-yl]-2-hydroxybenzamide (Compound No. 200)

Using 4-methylpiperazine as the raw material, the same operation as the examples 198(2)-(4) gave the title compound.
Yield: 6.9%.
(2) 2-Amino-4-(1,1-dimethyl)ethyl-5-(4-methylpiperazin-1-yl)thiazole
$^1$H-NMR (DMSO-d$_6$): δ 1.25 (9H, s), 2.12 (2H, brs), 2.19 (3H, s), 2.57 (2H, brs), 2.72 (4H, brs), 6.51 (2H, s).
(3) 2-Acetoxy-N-[4-(1,1-dimethyl)ethyl-5-(4-methylpiperazin-1-yl)thiazol-2-yl]benzamide
The product was used for the next reaction as a crude product.
(4) 5-Bromo-N-[4-(1,1 dimethyl)ethyl-5-(4-methylpiperazin-1-yl)thiazol-2-yl]-2-hydroxybenzamide
$^1$H-NMR (CD$_3$OD): δ 1.41 (9H, s), 2.55 (3H, s), 2.87 (4H, brs), 3.03 (4H, brs), 6.88 (1H, d, J=8.7 Hz), 7.49 (1H, dd, J=8.7, 2.7 Hz), 8.11 (1H, d, J=21 Hz).

Example 201

5-Bromo-N-[4-(1,1-dimethyl)ethyl-5-(4-phenylpip-erazin-1-yl)thiazol-2-yl]-2-hydroxybenzamide (Compound No. 201)

Using 4-phenylpiperazine as the raw material, the same operation as the examples 198(2)-(4) gave the title compound.
Yield: 6.9%.
(2) 2-Amino-4-(1,1-dimethyl)ethyl-5-(4-phenylpiperazin-1-yl)thiazole
$^1$H-NMR (CDCl$_3$): δ 1.34 (9H, s), 2.80 (2H, brs), 3.03 (4H, brs), 3.55 (2H, brs), 4.69 (2H, s), 6.88 (1H, tt, J=7.2, 1.2 Hz), 6.95 (2H, dd, J=9.0, 1.2 Hz), 7.28 (2H, dd, J=8.7, 7.2 Hz).
(3) 2-Acetoxy-5-bromo-N-[4-(1,1-dimethyl)ethyl-5-(4-phenylpiperazin-1-yl)thiazol-2-yl]benzamide
The product was used for the next reaction as a crude product.
(4) 5-Bromo-N-[4-(1,1-dimethyl)ethyl-5-(4-phenylpiperazin-1-yl)thiazol-2-yl]-2-hydroxybenzamide
$^1$H-NMR (DMSO-d$_6$): δ 1.39 (9H, s), 2.97 (4H, s), 3.30 (4H, s), 6.82 (1H, t, J=7.5 Hz), 6.97 (2H, brs), 6.99 (2H, t, J=7.5 Hz), 7.58 (1H, brs), 8.05 (1H, d, J=2.4 Hz), 11.69 (1H, brs), 11.82 (1H, brs).

Example 202

5-Bromo-N-(4-phenylthiazol-2-yl)-2-hydroxybenzamide (Compound No. 202)

Using 5-bromosalicylic acid and 2-amino-4-phenylthiazole as the raw materials, the same operation as the example 195(3) gave the title compound.
Yield: 16.0%. mp 239° C. (dec.). $^1$H-NMR (DMSO-d$_6$): δ 7.02 (1H, d, J=8.4 Hz), 7.34 (1H, t, J=7.6 Hz), 7.44 (2H, t, J=7.6 Hz), 7.62 (1H, dd, J=8.4, 2.8 Hz), 7.67 (1H, s), 7.92 (2H, d, J=7.2 Hz), 8.08 (1H, d, J=2.8 Hz), 11.88 (1H, brs), 12.05 (1H, brs).

Example 203

{2-[(5-Bromo-2-hydroxybenzoyl)amino]-4-phenylthiazol-5-yl}acetic acid (Compound No. 203)

(1) {2-[(5-Bromo-2-hydroxybenzoyl)amino]-4-phenylthiazol-5-yl}acetic acid methyl ester
Using 5-bromosalicylic acid and 2-amino-4-phenylthiazole-5-acetic acid methyl ester as the raw materials, the same operation as the example 195(3) gave the title compound.
Yield: 32.1%. mp 288.5-229.5° C. $^1$H-NMR (DMSO-d$_6$): δ 3.66 (3H, s), 3.95 (2H, s), 6.99 (1H, d, J=8.0 Hz), 7.42 (1H, d, J=6.0 Hz), 7.48 (2H, brt, J=7.6 Hz), 7.56-7.61 (3H, m), 8.07 (1H, d, J=2.4 Hz), 11.85 (1H, brs), 11.98 (1H, brs).
(2) {2-[(5-Bromo-2-hydroxybenzoyl)amino]-4-phenylthiazol-5-yl}acetic acid
{2-[(5-Bromo-2-hydroxybenzoyl)amino]-4-phenylthiazol-5-yl}acetic acid methyl ester (75 mg, 0.17 mmol) was dissolved in methanol (5 mL). 2 N sodium hydroxide (0.5 mL, 1 mmol) was added, and the mixture was stirred at room temperature for 12 hours. The reaction mixture was poured into 2 N hydrochloric acid and extracted with ethyl acetate. After the ethyl acetate layer was washed with water and brine one after another, dried over anhydrous sodium sulfate, the solvent was evaporated under reduced pressure. The obtained residue was suspended and washed with n-hexane-ethyl acetate under heating at reflux to give the title compound (56 mg, 77.3%) as a light yellow white crystal.
mp 284-286° C. $^1$H-NMR (DMSO-d$_6$): δ 3.84 (2H, s), 6.98 (1H, d, J=8.8 Hz), 7.42 (1H, d, J=6.8 Hz), 7.49 (2H, t, J=7.6 Hz), 7.58-7.61 (3H, m), 8.07 (1H, d, J=2.8 Hz), 12.25 (H, brs).

Example 204

5-Bromo-N-(4,5-diphenylthiazol-2-yl)-2-hydroxybenzamide (Compound No. 204)

Using 5-bromosalicylic acid and 2-amino-4,5-diphenylthiazole as the raw materials, the same operation as the example 195(3) gave the title compound. (2-Amino-4,5-diphenylthiazole: refer to Nihon Kagaku Zasshi, 1962, 33, 209.)
Yield: 25.9%. mp 262-263° C. $^1$H-NMR (DMSO-d$_6$): δ 7.02 (1H, d, J=8.1 Hz), 7.34-7.47 (10H, m), 7.63 (1H, d, J=6.9 Hz), 8.08 (1H, d, J=2.4 Hz), 11.88 (1H, brs), 12.08 (1H, brs).

Example 205

5-Bromo-N-(4-benzyl-5-phenylthiazol-2-yl)-2-hydroxybenzamide (Compound No. 205)

Using 5-bromosalicylic acid and 2-amino-4-benzyl-5-phenylthiazole as the raw materials, the same operation as the example 195(3) gave the title compound. (2-Amino-4-benzyl-5-phenylthiazole: refer to Chem. Pharm. Bull., 1962, 10, 376.)
Yield: 28.1%. mp 198-200° C. $^1$H-NMR (DMSO-d$_6$): δ 4.08 (2H, s), 6.95 (1H, d, J=8.8 Hz), 7.15-7.22 (3H, m), 7.30 (2H, t, J=7.6 Hz), 7.38-7.43 (1H, m), 7.47 (4H, d, J=4.4 Hz), 7.57 (1H, brd, J=8.8 Hz), 8.05 (1H, d, J=2.4 Hz), 11.98 (1H, brs).

Example 206

5-Bromo-N-[5-phenyl-4-(trifluoromethyl)thiazol-2-yl]-2-hydroxybenzamide (Compound No. 206)

Using 5-bromosalicylic acid and 2-amino-5-phenyl-4-(trifluoromethyl)thiazole as the raw materials, the same operation as the example 195(3) gave the title compound.
Yield: 33.2%. mp 250° C. (dec.). $^1$H-NMR (DMSO-d$_6$): δ 7.02 (1H, d, J=8.8 Hz), 7.51 (5H, s), 7.63 (1H, dd, J=8.8, 2.4 Hz), 8.02 (1H, d, J=2.8 Hz), 12.38 (1H, brs).

Example 207

5-Bromo-N-[5-acetyl-4-phenylthiazol-2-yl]-2-hydroxybenazamide (Compound No. 207)

Using 1-phenyl-1,3-butanedione as the raw material, the same operation as the examples 195(1)-(3) gave the title compound.
Yield: 8.9% (3 steps).
(1) α-Bromo-1-phenyl-1,3-butanedione
$^1$H-NMR (CDCl$_3$): δ 2.46 (3H, s), 5.62 (1H, s), 7.48-7.54 (2H, m), 7.64 (1H, tt, J=7.5, 2.1 Hz), 7.97-8.01 (2H, m).
(2) 2-Amino-5-acetyl-4-phenylthiazole
$^1$H-NMR (DMSO-d$_6$): δ 2.18 (3H, s), 7.50-7.53 (2H, m), 7.59-7.68 (3H, m), 8.69 (2H, brs).

(3) 5-Bromo-N-[5-acetyl-4-phenylthiazol-2-yl]-2-hydroxybenzamide

¹H-NMR (DMSO-d₆): δ 2.44 (3H, s), 6.99 (1H, d, J=9.0 Hz), 7.55-7.71 (4H, m), 7.76-7.80 (2H, m), 8.01 (1H, d, J=2.4 Hz), 12.36 (2H, br).

Example 208

5-Bromo-N-[5-benzoyl-4-phenylthiazol-2-yl]-2-hydroxybenzamide (Compound No. 208)

Using 1,3-diphenyl-1,3-propanedione as the raw material, the same operation as the examples 195(1)-(3) gave the title compound.

Yield: 49.7%.

(1) α-Bromo-1,3-diphenyl-1,3-propanedione

¹H-NMR (CDCl₃, δ): 6.55 (1H, s), 7.45-7.50 (4H, m), 7.61 (2H, tt, J=7.2, 2.1 Hz), 7.98-8.01 (4H, m).

(2) 2-Amino-5 benzoyl-4-phenylthiazole

¹H-NMR (DMSO-d₆): δ 7.04-7.18 (5H, m), 7.22-7.32 (3H, m), 7.35-7.38 (2H, m), 8.02 (2H, s).

(3) 5-Bromo-N-[5-benzoyl-4-phenylthiazol-2-yl]-2-hydroxybenzamide

¹H-NMR (DMSO-d₆): δ 7.03 (1H, d, J=8.7 Hz), 7.17-7.30 (5H, m), 7.39-7.47 (3H, m), 7.57-7.60 (2H, m), 7.64 (1H, dd, J=8.7, 2.7 Hz), 8.05 (1H, d, J=2.4 Hz), 11.82 (1H, brs), 12.35 (1H, brs).

Example 209

2-(5-Chloro-2-hydroxybenzoyl)amino-4-phenylthiazole-5-carboxylic acid ethyl ester (Compound No. 209)

Using 5-chlorosalicylic acid and 2-amino-4-phenylthiazole-5-carboxylic acid ethyl ester as the raw materials, the same operation as the example 195(3) gave the title compound.

Yield: 69.4%. ¹H-NMR (DMSO-d₆): δ 1.22 (3H, t, J=7.5 Hz), 4.21 (2H, q, J=7.5 Hz), 7.07 (1H, d, J=8.7 Hz), 7.43-7.47 (3H, m), 7.53 (1H, dd, J=8.7, 2.4 Hz), 7.70-7.74 (2H, m), 7.92 (1H, d, J=3.0 Hz), 11.88 (1H, br), 12.29 (1H, brs).

Example 210

2-(5-Bromo-2-hydroxybenzoyl)amino-4-phenylthiazole-5-carboxylic acid ethyl ester (Compound No. 210)

Using 5-bromosalicylic acid and 2-amino-4-phenylthiazole-5-carboxylic acid ethyl ester as the raw materials, the same operation as the example 195(3) gave the title compound.

Yield: 28.6%. mp 197-199° C. ¹H-NMR (DMSO-d₆): δ 1.21 (3H, t, J=6.8 Hz), 4.20 (2H, q, J=6.8 Hz), 7.01 (1H, d, J=8.8 Hz), 7.43-7.48 (3H, m), 7.63 (1H, dd, J=8.8, 2.4 Hz), 7.70-7.72 (2H, m), 8.04 (1H, d, J=2.4 Hz), 12.33 (1H, brs).

Example 211

2-(5-Bromo-2-hydroxybenzoyl)amino-4-(pentafluorophenyl)thiazole-5-carboxylic acid ethyl ester (Compound No. 211)

Using pentafluorobenzoylacetic acid as the raw material, the same operation as the examples 195(1)-(3) gave the title compound.

Yield: 40.0% (3 steps).

(1) α-Bromo-pentafluorobenzoylacetic acid ethyl ester

It was used for the next reaction as a crude product.

(2) 2-Amino-4-(pentafluorophenyl)thiazole-5-carboxylic acid ethyl ester

¹H-NMR (CDCl₃): δ 1.23 (3H, t, J=7.2 Hz), 4.21 (2H, q, J=7.2 Hz), 5.41 (2H, s).

(3) 2-(5-Bromo-2-hydroxybenzoyl)amino-4-(pentafluorophenyl)thiazole-5-carboxylic acid ethyl ester ¹H-NMR (DMSO-d₆): δ 1.20 (3H, t, J=7.2 Hz), 2.51 (2H, q, J=7.2 Hz), 7.02 (1H, d, J=8.7 Hz), 7.84 (1H, dd, J=8.7, 2.7 Hz), 7.90 (1H, d, J=3.0 Hz), 11.92 (1H, br), 12.58 (1H, br).

Example 212

[2-(5-Bromo-2-hydroxybenzoyl)amino-4-(pentafluorophenyl)thiazol-5-yl]-N-methylcarboxamide (Compound No. 212)

(1) 2-(5-Bromo-2-hydroxybenzoyl)amino-4-(pentafluorophenyl)thiazole-5-carboxylic acid Using 2-(5-bromo-2-hydroxybenzoyl)amino-4-(pentafluorophenyl)-thiazole-5-carboxylic acid ethyl ester as the raw material, the same operation as the example 82 gave the title compound.

(2) [2-(5-Bromo-2-hydroxybenzoyl)amino-4-(pentafluorophenyl)thiazol-5-yl]-N-methylcarboxamide A mixture of 2-(5-bromo-2-hydroxybenzoyl)amino-4-(pentafluorophenyl)-thiazole-5-carboxylic acid (0.20 g, 0.48 mmol), methylamine 40% methanol solution (0.2 ml), 1-hydroxybenzotriazole hydrate (96.7 mg, 0.72 mmol), WSC-HCl (137.2 mg, 0.72 mmol) and tetrahydrofuran (15 mL) was stirred at room temperature for 18 hours. The reaction mixture was poured into 2 N hydrochloric acid and extracted with ethyl acetate. After the organic layer was washed with water and brine, dried over anhydrous sodium sulfate, the residue obtained by evaporation under reduced pressure was purified by chromatography on silica gel (n-hexane:ethyl acetate=1: 2), and crystallized (dichloromethane/n-hexane) to give the title compound (87.9 mg, 42.6%) as a white powder.

¹H-NMR (DMSO-d₆): δ 2.70 (3H, d, J=4.5 Hz), 7.02 (1H, d, J=9.0 Hz), 7.40-7.48 (3H, m), 7.63 (1H, dd, J=9.0, 2.4 Hz), 7.68-7.71 (2H, m), 8.06 (1H, d, J=2.4 Hz), 8.16 (1H, t, J=4.5 Hz). 11.88 (1H, br), 12.15 (1H, brs).

Example 213

[2-(5-Bromo-2-hydroxybenzoyl)amino-4-(pentafluorophenyl)thiazol-5-yl]-N-ethylcarboxamide (Compound No. 213)

Using 2-(5-bromo-2-hydroxybenzoyl)amino-4-(pentafluorophenyl)thiazole-5-carboxylic acid and 70% aqueous ethylamine solution as the raw materials, the same operation as the example 212(2) gave the title compound.

Yield: 62.5%. ¹H-NMR (DMSO-d₆): δ 1.05 (3H, t, J=6.9 Hz), 3.15-3.24 (2H, m), 7.02 (1H, d, J=8.7 Hz), 7.40-7.47 (3H, m), 7.63 (1H, dd, J=3.7, 3.0 Hz), 7.69-7.72 (2H, m), 8.06 (1H, d, J=2.4 Hz), 8.20 (1H, t, J=5.4 Hz), 11.84 (1H, br), 12.14 (1H, brs).

Example 214

[2-(5-Bromo-2-hydroxybenzoyl)amino-4-(pentafluorophenyl)-thiazol-5-yl]-N-isopropylcarboxamide (Compound No. 214)

Using 2-(5-bromo-2-hydroxybenzoyl)amino-4-(pentafluorophenyl)-thiazole-5-carboxylic acid and isopropylamine as the raw materials, the same operation as the example 212(2) gave the title compound.

Yield: 23.9%. $^1$H-NMR (DMSO-d$_6$): δ 1.07 (6H, d, J=6.3 Hz), 4.02 (1H, m), 7.02 (1H, d, J=9.0 Hz), 7.40-7.52 (3H, m), 7.64 (1H, dd, J=8.7, 2.7 Hz), 7.69-7.73 (2H, m), 8.06 (1H, d, J=2.7 Hz), 11.89 (1H, br), 12.14 (1H, brs).

Example 215

[2-(5-Bromo-2-hydroxybenzoyl)amino-4-(pentafluorophenyl)thiazol-5-yl]-N-(2-phenethyl)carboxamide (Compound No. 215)

Using 2-(5-bromo-2-hydroxybenzoyl)amino-4-(pentafluorophenyl)-thiazole-5-carboxylic acid and 2-phenethylamine as the raw materials, the same operation as the example 212 gave the title compound.

Yield: 62.2%. $^1$H-NMR (DMSO-d$_6$): δ 2.78 (2H, t, J=7.5 Hz), 3.43 (2H, q, J=7.5 Hz), 7.02 (1H, d, J=9.0 Hz), 7.19-7.24 (3H, m), 7.27-7.33 (2H, m), 7.39-7.41 (3H, m), 7.61-7.65 (3H, m), 8.06 (1H, d, J=2.4 Hz), 8.25 (1H, t, J=6.0 Hz), 11.85 (1H, brs), 12.15 (1H, brs).

Example 216

2-(5-Bromo-2-hydroxybenzoyl)amino 4-(trifluoromethyl)thiazole-5-carboxylic acid ethyl ester (Compound No. 216)

Using 5-bromosalicylic acid and 2-amino-4-(trifluoromethyl)thiazole-5-carboxylic acid ethyl ester as the raw materials, the same operation as the example 195(3) gave the title compound.

Yield: 88.7%. $^1$H-NMR (DMSO-d$_6$): δ 1.32 (3H, t, J=7.2 Hz), 4.33 (2H, q, J=7.2 Hz), 7.01 (1H, d, J=8.7 Hz), 7.63 (1H, dd, J=8.7, 2.7 Hz), 7.98 (1H, d, J=2.4 Hz), 12.64 (1H, br).

Example 217

2-Acetoxy-5-chloro-N-{4-(1,1-dimethyl)ethyl-5-[(2,2-dimethyl)propionyl]thiazol-2-yl}benzamide Using 5-chloro-N {4-(1,1-dimethyl)ethyl-5-[(2,2-dimethyl)propionyl]thiazol-2-yl}-2-hydroxybenzamide and acetyl chloride as the raw materials, the same operation as the example 96 gave the title compound.

Yield: 65.3%. $^1$H-NMR (CDCl$_3$): δ 1.32 (9H, s), 1.33 (9H, s), 2.46 (3H, s), 7.22 (1H, d, J=8.4 Hz), 7.56 (1H, dd, J=8.7, 2.4 Hz), 8.05 (1H, d, J=2.7 Hz), 9.82 (1H, brs).

Example 218

2-[(4-Hydroxybiphenyl)-3-carbonyl]amino-4-phenylthiazole-5-carboxylic acid ethyl ester (Compound No. 218)

Using 4-hydroxybiphenyl-3-carboxylic acid and 2-amino-4-phenylthiazole-5-carboxylic acid ethyl ester as the raw materials, the same operation as the example 195(3) gave the title compound. (4-Hydroxybiphenyl-3-carboxylic acid: refer to Tetrahedron, 1997, 53, 11437.)

Yield: 61.7%. mp 207-208° C. $^1$H-NMR (DMSO-d$_6$): δ 1.23 (3H, t, J=7.2 Hz), 4.22 (2H, q, J=7.2 Hz), 7.16 (1H, d, J=8.7 Hz), 7.36 (1H, t, J=7.5 Hz), 7.45-7.50 (5H, m), 7.69-7.76 (4H, m), 7.85 (1H, dd, J=8.7, 2.4 Hz), 8.31 (1H, d, J=2.4 Hz), 11.73 (1H, brs), 12.60 (1H, brs).

Example 219

2-[(4'-Fluoro-4-hydroxybiphenyl)-3-carbonyl]amino-4-phenylthiazole-5-carboxylic acid ethyl ester (Compound No. 219)

Using (4'-fluoro-4-hydroxybiphenyl)-3-carboxylic acid and 2-amino-4-phenylthiazole-5-carboxylic acid ethyl ester as the raw materials, the same operation as the example 195 (3) gave the title compound. ((4'-Fluoro-4-hydroxybiphenyl)-3-carboxylic acid: refer to Tetrahedron, 1997, 53, 11437.)

Yield: 62.7%. mp 237-238° C. $^1$H-NMR (DMSO-d$_6$): δ 1.22 (3H, t, J=7.2 Hz), 4.21 (2H, q, J=7.2 Hz), 7.13 (1H, d, J=8.4 Hz), 7.28 (2H, t, J=8.8 Hz), 7.44-7.45 (3H, m), 7.71-7.75 (4H, m), 7.81 (1H, dd, J=8.8, 2.4 Hz), 8.27 (1H, d, J=2.4 Hz), 11.67 (1H, brs), 12.58 (1H, brs).

Example 220

2-[(2',4'-Difluoro-4-hydroxybiphenyl)-3-carbonyl] amino-4-phenylthiazole-5-carboxylic acid ethyl ester (Compound No. 220)

Using (2',4'-difluoro-4-hydroxybiphenyl)-3-carboxylic acid and 2-amino-4-phenylthiazole-5-carboxylic acid ethyl ester as the raw materials, the same operation as the example 195(3) gave the title compound.

Yield: 45.6%. mp 206-207° C. $^1$H-NMR (DMSO-d$_6$): δ 1.22 (3H, t, J=7.2 Hz), 4.22 (2H, q, J=7.2 Hz), 7.17 (1H, d, J=9.0 Hz), 7.21 (1H, td, J=8.7, 2.4 Hz), 7.38 (1H, ddd, J=11.7, 9.3, 2.4 Hz), 7.44-7.46 (3H, m), 7.60-7.75 (4H, m), 8.13-8.14 (1H, m), 11.86 (1H, brs), 12.46 (1H, brs).

Example 221

2-{[4-Hydroxy-4'-(trifluoromethy)biphenyl]-3-carbonyl}amino-4-phenylthiazole-5-carboxylic acid ethyl ester (Compound No. 221)

(1) [4'-(Trifluoromethyl)-4-hydroxybiphenyl]-3-carboxylic acid

A mixture of 5-bromosalicylic acid (500 mg, 2.30 mmol), dihydroxy-4-(trifluoromethyl)phenylborane (488 mg, 2.57 mmol), palladium acetate (10 mg, 0.040 mmol) and 1M sodium carbonate (7 mL) was stirred at 80° C. for 1 hour. The reaction mixture was poured into 2 N hydrochloric acid and extracted with ethyl acetate. After the ethyl acetate layer was washed with water and brine one after another, dried over anhydrous sodium sulfate, the solvent was evaporated under reduced pressure. According to the fixed procedure, the obtained residue was methyl-esterified by trimethylsilyldiazomethane and methanol, and purified by column chromatography on silica gel (n-hexane:ethyl acetate=5:1) to give a colourless liquid (563 mg). This liquid was dissolved in methanol (10 mL). 2 N sodium hydroxide (3 mL) was added, and the mixture was stirred at 60° C. for 1 hour. After the reaction mixture was cooled to room temperature, it was poured into 2 N hydrochloric acid and extracted with ethyl acetate. After the ethyl acetate layer was washed with water and saturated brine one after another, dried over MgSO$_4$, the solvent was evaporated under reduced pressure. The obtained residue was suspended and washed with n-hexane-dichloromethane under heating at reflux to give the title compound (458 mg, 70.4%) as a white crystal.

mp 185° C. (dec). $^1$H-NMR (DMSO-d$_6$): δ 7.09 (1H, d, J=8.8 Hz), 7.77 (2H, d, J=8.0 Hz), 7.85 (2H, d, J=8.0 Hz), 7.90 (1H, dd, J=8.8, 2.0 Hz), 8.10 (1H, d, J=2.4 Hz), 11.80 (brs).

(2) 2-{[4-Hydroxy-4'-(trifluoromethyl)biphenyl]-3-carbonyl}amino-4-phenylthiazole-5-carboxylic acid ethyl ester Using [4'-(trifluoromethyl)-4-hydroxybiphenyl]-3-carboxylic acid and 2-amino-4-phenylthiazole-5-carboxylic acid ethyl ester as the raw materials, the same operation as the example 195(3) gave the title compound.

Yield: 41.7%. mp 236-237° C. $^1$H-NMR (DMSO-d$_6$): δ 1.22 (3H, t, J=7.2 Hz), 4.21 (2H, q, J=7.2 Hz), 7.18 (1H, d, J=8.8 Hz), 7.44-7.45 (3H, m), 7.72-7.74 (2H, m), 7.81 (2H, d, J=8.4 Hz), 7.91 (1H, dd, J=8.8, 2.4 Hz), 7.93 (2H, d, J=8.4 Hz), 8.36 (1H, d, J=2.4 Hz), 11.78 (1H, brs), 12.62 (1H, brs).

Example 222

2-[2-Hydroxy-5-(1-pyrrolyl)benzoyl]amino-4-phenylthiazole-5-carboxylic acid ethyl ester (Compound No. 222)

Using 2-hydroxy-5-(1-pyrrolyl)benzoic acid and 2-amino-4-phenylthiazole-5-carboxylic acid ethyl ester as the raw materials, the same operation as the example 195(3) gave the title compound.

Yield: 55.0%. $^1$H-NMR (DMSO-d$_6$): δ 1.22 (3H, t, J=7.2 Hz), 4.22 (2H, q, J=7.2 Hz), 6.26 (2H, t, J=2.1 Hz), 7.13 (1H, d, J=8.7 Hz), 7.32 (2H, t, J=2.1 Hz), 7.43-7.47 (3H, m), 7.70-7.75 (3H, m), 8.09 (1H, d, J=2.7 Hz), 11.58 (1H, brs), 12.55 (1H, brs).

Example 223

2-[2-Hydroxy-5-(2-thienyl)benzoyl]amino 4-phenylthiazole-5-carboxylic acid ethyl ester (Compound No. 223)

(1) 2 Hydroxy-5-(2-thienyl)benzoic acid

5-Bromosalicylic acid (500 mg, 2.30 mmol) was dissolved in 1,2-dimethoxyethane (5 mL). Tetrakis(triphenylphosphine)palladium (80 mg, 0.07 mmol) was added under argon atmosphere, and the mixture was stirred at room temperature for 10 minutes. Then dihydroxy-2-thienylborane (324 mg, 2.53 mmol) and 1M sodium carbonate (7 mL) were added, and the mixture was refluxed for 2 hours. After the reaction mixture was cooled to room temperature, it was poured into 2 N hydrochloric acid and extracted with ethyl acetate. After the ethyl acetate layer was washed with water and brine one after another, dried over anhydrous sodium sulfate, the solvent was evaporated under reduced pressure. According to the fixed procedure, the obtained residue was methyl-esterified by trimethylsilyldiazosmethane and methanol, and purified by column chromatography on silica gel (n-hexane:ethyl acetate=5:1) to give a yellow liquid (277 mg). This was dissolved in methanol (5 mL). 2 N sodium hydroxide (1.5 mL) was added, and the mixture was stirred at 60° C. for 1 hour. After the reaction mixture was cooled to room temperature, it was poured into 2 N hydrochloric acid and extracted with ethyl acetate. After the ethyl acetate layer was washed with water and brine one after another, dried over anhydrous magnesium sulfate, the residue obtained by evaporating the solvent under reduced pressure was crystallized from n-hexane-dichloromethane to give the title compound (58 mg, 11.5%) as a white crystal.

$^1$H-NMR (DMSO-d$_6$): δ 6.95 (1H, d, J=8.8 Hz), 7.09 (1H, dd, J=4.8, 3.6 Hz), 7.37 (1H, dd, J=4.0, 1.2 Hz), 7.45 (1H, dd, J=5.2, 1.2 Hz), 7.74 (1H, dd, J=8.8, 2.8 Hz), 7.96 (1H, d, J=2.8 Hz).

(2) 2-[2-Hydroxy-5-(2-thienyl)benzoyl]amino-4-phenylthiazole-5-carboxylic acid ethyl ester Using 2-hydroxy-5-(2-thienyl)benzoic acid and 2-amino-4-phenylthiazole-5-carboxylic acid ethyl ester as the raw materials, the same operation as the example 195(3) gave the title compound.

Yield: 58.2%. mp 213-2149° C. $^1$H-NMR (DMSO-d$_6$): δ 1.22 (3H, t, J=7.2 Hz), 4.21 (2H, q, J=7.2 Hz), 7.10 (1H, d, J=9.2 Hz), 7.12 (1H, dd, J=4.8, 3.6 Hz), 7.44-7.46 (4H, m), 7.50 (1H, dd, J=4.8, 1.2 Hz), 7.71-7.74 (2H, m), 7.79 (1H, dd, J=8.8, 2.4 Hz), 8.21 (1H, d, J=2.4 Hz), 11.78 (1H, brs), 12.44 (1H, brs).

Test Example

Measurement of Inhibitory Activity of NF-κB Activation

Inhibitory activity of NF-κB activation was measured referring to the method of Hill et al. (Hill C. S., et al., Cell, 73, 395-406 (1993).). Using a transfection reagent (Effectene; QIAGEN), the human hepatoma cell strain HepG2 or the human hysterocarcinoma cell strain HeLa was transfected with the firefly luciferase gene (Luc) contained plasmid (pNFκB-Luc Reporter Plasmid; STRATAGENE) which contained oligonucleotide having five tandem copies of NF-κB binding sequences (TGGGGACTTTCCGC) on a upstream region of Luc, according to the QUAGEN's protocol and it was incuvated for 6-24 hours. After addition of TNF-α (40 ng/ml) with or without the test compound, the cells were incuvated for 4 hours, and intracellular luciferase activity was measured with PicaGene LT (TOYO INK MFG Co., Ltd.) and chemical luminescence measurement device (SPECTRAFluor Plus; TECAN). The inhibition ratio was measured as a ratio to the value of the luciferase activity without the test compound. The inhibition ratio of NF-κB activity with the test compound 10 μg/ml or 1 μg/ml were shown in the following table.

| Compound Number | The rate of inhibitory activity against NF·κB activation (%) | |
|---|---|---|
| | Concentration of the agent: 10 μg/mL | Concentration of the agent: 1 μg/mL |
| 1 | 54.4 | −33.6 |
| 2 | 83.2 | 18.6 |
| 3 | 68.4 | 54.2 |
| 4 | 94.1 | 42.9 |
| 5 | 98.0 | 33.3 |
| 6 | 61.9 | 27.8 |
| 7 | 68.7 | 30.4 |
| 8 | 59.9 | 35.3 |
| 9 | 99.2 | 21.9 |
| 10 | 78.6 | 7.1 |
| 11 | 44.1 | 28.4 |
| 12 | 87.3 | 68.6 |
| 13 | 63.8 | −7.1 |
| 14 | 98.9 | 21.7 |
| 15 | 70.4 | 15.2 |
| 16 | 91.6 | 36.4 |
| 17 | 96.5 | 19.9 |
| 18 | 90.2 | 85.3 |
| 19 | 95.1 | −55.4 |
| 20 | 86.8 | −12.1 |
| 21 | 95.0 | 89.6 |
| 22 | 92.9 | 37.0 |
| 23 | 96.6 | 75.7 |
| 24 | 82.2 | 58.1 |
| 25 | 86.9 | 85.4 |

| Compound Number | Concentration of the agent: 10 µg/mL | Concentration of the agent: 1 µg/mL | Compound Number | Concentration of the agent: 10 µg/mL | Concentration of the agent: 1 µg/mL |
|---|---|---|---|---|---|
| 27 | 47.3 | 68.5 | 107 | 95.0 | 92.3 |
| 28 | 41.7 | 16.3 | 108 | 97.6 | 94.7 |
| 29 | 73.0 | 46.3 | 109 | 88.8 | 83.0 |
| 30 | 98.1 | 76.5 | 110 | 98.9 | 94.7 |
| 31 | 93.2 | 13.3 | 111 | 98.7 | 96.7 |
| 32 | 96.3 | 89.3 | 112 | 95.9 | 93.1 |
| 33 | 99.5 | 95.1 | 113 | 97.1 | 94.8 |
| 34 | 98.5 | 90.5 | 114 | 94.1 | 88.9 |
| 35 | 85.4 | 88.2 | 115 | 94.3 | 89.0 |
| 36 | 84.7 | 26.6 | 116 | 96.7 | 86.3 |
| 37 | 63.1 | 29.1 | 117 | 93.0 | 89.2 |
| 38 | 81.8 | −10.1 | 118 | 96.3 | 94.1 |
| 39 | 56.0 | 21.4 | 119 | 91.7 | 88.1 |
| 40 | 81.9 | 3.9 | 120 | 97.9 | 93.8 |
| 41 | 90.3 | 26.1 | 121 | 96.5 | 85.5 |
| 42 | 92.3 | 14.3 | 122 | 97.2 | 84.5 |
| 43 | 78.9 | 25.5 | 123 | 93.4 | 76.6 |
| 44 | 65.8 | 36.7 | 125 | 99.1 | 94.6 |
| 45 | 91.3 | 61.7 | 126 | 97.8 | 95.8 |
| 46 | 85.7 | −43.7 | 127 | 86.4 | 81.8 |
| 47 | 99.4 | 91.3 | 128 | 95.0 | 87.2 |
| 48 | 95.6 | 93.3 | 129 | 85.8 | 75.4 |
| 49 | 94.3 | 81.5 | 139 | 60.2 | −48.2 |
| 50 | 99.5 | 96.3 | 140 | 96.7 | 94.2 |
| 51 | 98.6 | 94.9 | 141 | 96.4 | 83.3 |
| 52 | 85.4 | 86.6 | 142 | 96.9 | 95.1 |
| 53 | 99.2 | 92.0 | 143 | 93.8 | 91.6 |
| 54 | 99.6 | 92.2 | 144 | 96.8 | 91.8 |
| 55 | 99.4 | 95.8 | 145 | 95.5 | 92.9 |
| 56 | 98.3 | 92.9 | 146 | 97.0 | 94.2 |
| 57 | 96.0 | 76.8 | 147 | 96.8 | 84.5 |
| 58 | 98.3 | 94.7 | 148 | 92.8 | 77.1 |
| 59 | 99.2 | 94.5 | 149 | 97.1 | 85.4 |
| 60 | 99.4 | 42.7 | 150 | 95.1 | 91.4 |
| 61 | 98.5 | 59.7 | 151 | 71.8 | −42.8 |
| 62 | 99.1 | 74.9 | 152 | 70.6 | −56.8 |
| 63 | 96.9 | 95.5 | 153 | 88.7 | 49.1 |
| 64 | 90.1 | 53.3 | 154 | 48.2 | −31.0 |
| 65 | 97.1 | 83.9 | 155 | 94.1 | 85.6 |
| 66 | 94.9 | 91.1 | 156 | 74.9 | 7.3 |
| 67 | 96.8 | 91.8 | 157 | 98.1 | 86.2 |
| 68 | 98.3 | 92.3 | 158 | 95.6 | 91.0 |
| 69 | 99.6 | 96.4 | 159 | 96.3 | 89.1 |
| 70 | 95.4 | 93.3 | 160 | 99.2 | 86.2 |
| 71 | 97.9 | 93.8 | 161 | 92.6 | 86.3 |
| 72 | 97.8 | 79.5 | 163 | 82.0 | 70.9 |
| 73 | 92.9 | 81.7 | 164 | 98.6 | 94.9 |
| 74 | 95.3 | 82.1 | 165 | 95.1 | 88.2 |
| 76 | 99.0 | 90.4 | 166 | 97.9 | 82.4 |
| 77 | 97.0 | 30.7 | 167 | 95.7 | 32.4 |
| 78 | 99.2 | 86.3 | 168 | 96.8 | 38.3 |
| 79 | 98.7 | 90.7 | 169 | 88.1 | 14.5 |
| 81 | 96.4 | 88.2 | 170 | 56.4 | −40.0 |
| 82 | 94.5 | −8.7 | 171 | 95.8 | 33.7 |
| 83 | 87.1 | 16.0 | 172 | 97.5 | 88.6 |
| 84 | 82.2 | 23.7 | 180 | 42.8 | −23.1 |
| 85 | 96.0 | 44.9 | 181 | 98.7 | 96.5 |
| 86 | 95.9 | 42.2 | 182 | 94.4 | 85.3 |
| 87 | 98.1 | 84.4 | 183 | 92.4 | 92.6 |
| 89 | 67.5 | −21.6 | 184 | 93.8 | 20.0 |
| 90 | 63.4 | 1.0 | 185 | 69.7 | −1.5 |
| 91 | 88.4 | 20.5 | 186 | 95.2 | 88.4 |
| 92 | 97.2 | 51.8 | 187 | 67.2 | 4.6 |
| 93 | 98.7 | 96.2 | 188 | 94.4 | 83.6 |
| 94 | 89.1 | 19.4 | 189 | 82.0 | −8.4 |
| 95 | 97.1 | 90.9 | 190 | 71.7 | −32.4 |
| 96 | 99.2 | 96.5 | 191 | 98.1 | 90.5 |
| 97 | 96.0 | 69.9 | 192 | 87.6 | 28.8 |
| 98 | 98.2 | 90.5 | 193 | 96.1 | 70.1 |
| 101 | 98.3 | 95.7 | 194 | 88.7 | 46.1 |
| 104 | 96.9 | 76.2 | 195 | 98.3 | 95.7 |
| 105 | 93.9 | 89.6 | 196 | 97.5 | 86.8 |
| 106 | 93.3 | 80.7 | 197 | 92.4 | 84.5 |

-continued

| Compound Number | The rate of inhibitory activity against NF·κB activation (%) | |
|---|---|---|
| | Concentration of the agent: 10 μg/mL | Concentration of the agent: 1 μg/mL |
| 198 | 97.8 | 93.6 |
| 199 | 96.8 | 87.8 |
| 200 | 89.6 | 36.3 |
| 201 | 95.9 | 92.5 |
| 202 | 78.8 | −41.8 |
| 203 | 72.1 | 2.4 |
| 204 | 67.0 | −5.3 |
| 205 | 95.0 | 79.7 |
| 206 | 89.4 | 85.1 |
| 207 | 95.9 | 70.2 |
| 208 | 97.3 | 90.7 |
| 209 | 82.8 | 55.8 |
| 210 | 94.2 | 80.7 |
| 211 | 96.0 | 82.2 |
| 212 | 58.6 | 50.8 |
| 213 | 84.0 | 51.9 |
| 214 | 91.3 | 49.6 |
| 215 | 60.4 | 33.3 |
| 216 | 96.5 | 87.6 |
| 217 | 97.7 | 95.0 |
| 218 | 78.6 | 34.6 |
| 219 | 85.8 | 45.0 |
| 220 | 90.3 | 31.8 |
| 221 | 90.0 | 66.9 |
| 222 | 90.1 | 74.0 |
| 223 | 84.8 | 40.8 |

INDUSTRIAL APPLICABILITY

The medicaments of the present invention have inhibitory activity against the activation of transcription factor NF-κB, furthermore they have suppressing activity against the production and release of inflammatory cytokines. Therefore, the medicaments of the present invention are useful as preventive and/or therapeutic agent for treatment of diseases caused by activation of NF-κB and for diseases caused by overproduction of inflammatory cytokines.

What is claimed is:

1. A compound represented by the following formula or a salt thereof:

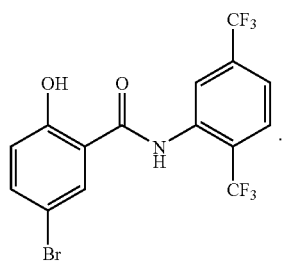

2. A medicament comprising the compound according to claim 1 or a pharmacologically acceptable salt thereof, and at least one pharmacologically acceptable pharmaceutical additive.

3. An NF-κB inhibitor comprising the compound according to claim 1 or a salt thereof.

* * * * *